US012165759B2

United States Patent
Abraham et al.

(10) Patent No.: US 12,165,759 B2
(45) Date of Patent: Dec. 10, 2024

(54) CLASSIFYING AN ENTITY FOR FOLFOX TREATMENT

(71) Applicant: CARIS MPI, INC., Irving, TX (US)

(72) Inventors: Jim Abraham, Gilbert, AZ (US); David Spetzler, Paradise Valley, AZ (US); Anthony Helmstetter, Gilbert, AZ (US); Wolfgang Michael Korn, Mill Valley, CA (US); Daniel Magee, Phoenix, AZ (US)

(73) Assignee: Caris MPI, Inc., Irving, TX (US)

( * ) Notice: Subject to any disclaimer, the term of this patent is extended or adjusted under 35 U.S.C. 154(b) by 0 days.

(21) Appl. No.: 17/727,681

(22) Filed: Apr. 22, 2022

(65) Prior Publication Data
US 2022/0262494 A1 Aug. 18, 2022

Related U.S. Application Data

(63) Continuation of application No. 17/334,483, filed on May 28, 2021, now Pat. No. 11,315,673, which is a (Continued)

(51) Int. Cl.
*G06N 20/20* (2019.01)
*G06N 20/00* (2019.01)
(Continued)

(52) U.S. Cl.
CPC ............. *G16H 20/40* (2018.01); *G06N 20/00* (2019.01); *G06N 20/20* (2019.01); *G16B 20/10* (2019.02); *G16B 40/00* (2019.02)

(58) Field of Classification Search
CPC ........ G16H 20/40; G16H 20/10; G16H 50/20; G16H 10/40; G16H 20/70; G16H 50/70;
(Continued)

(56) References Cited

U.S. PATENT DOCUMENTS

| 3,817,837 A | 6/1974 | Rubenstein et al. |
| 3,850,752 A | 11/1974 | Schuurs et al. |
(Continued)

FOREIGN PATENT DOCUMENTS

| EP | 0332435 | 9/1989 |
| JP | 2014503222 | 2/2014 |
(Continued)

OTHER PUBLICATIONS

Bauer et al., "An Empirical Comparison of Voting Classification Algorithms: Bagging, Boosting, and Variants," Machine Learning, 1999, 36:105-139.
(Continued)

*Primary Examiner* — Luis A Sitiriche
(74) *Attorney, Agent, or Firm* — Kilpatrick Townsend & Stockton LLP

(57) ABSTRACT

Comprehensive molecular profiling provides a wealth of data concerning the molecular status of patient samples. Such data can be compared to patient response to treatments to identify biomarker signatures that predict response or non-response to such treatments. This approach has been applied to identify biomarker signatures that strongly correlate with response of colorectal cancer patients to FOLFOX. Described herein are data structures, data processing, and machine learning models to predict effectiveness of a treatment for a disease or disorder of a subject having a particular set of biomarkers, as well as an exemplary application of such a model to precision medicine, e.g., to methods for selecting a treatment based on a molecular profile, e.g., a treatment comprising administration of 5-fluorouracil/leucovorin combined with oxaliplatin (FOLFOX) or with irinotecan (FOLFIRI).

31 Claims, 34 Drawing Sheets

Related U.S. Application Data continuation of application No. PCT/US2019/064078, filed on Dec. 2, 2019.

(60) Provisional application No. 62/789,495, filed on Jan. 7, 2019, provisional application No. 62/788,689, filed on Jan. 4, 2019, provisional application No. 62/774,082, filed on Nov. 30, 2018.

(51) Int. Cl.
*G16B 20/10* (2019.01)
*G16B 40/00* (2019.01)
*G16H 20/40* (2018.01)

(58) Field of Classification Search
CPC ........ G16H 10/60; G16H 30/40; G16H 40/67; G16H 50/30; G16H 50/50; G16H 30/20; G16H 10/20; G16H 15/00; G16H 20/00; G16H 20/60; G16H 40/20; G16H 20/30; G16H 40/63; G16H 70/00; G16H 80/00; G16H 40/40; G16H 50/80; G16H 70/20; G16H 70/60; G06N 20/00; G06N 20/20; G06N 3/084; G06N 20/10; G06N 5/003; G06N 5/01; G06N 3/045; G06N 3/044; G06N 3/08; G06N 7/01; G06N 3/047; G06N 3/088; G06N 5/04; G06N 3/04; G06N 3/0464; G06N 3/0455; G06N 5/045; G06N 5/048; G06N 3/006; G06N 3/048; G06N 3/086; G06N 3/09; G06N 5/02; G16B 20/10; G16B 40/00; G16B 20/00; G16B 40/20; G16B 20/40; G16B 40/30; G16B 5/00; Y02A 90/10; A61B 5/7267; A61B 5/4836; A61B 5/7264; A61B 5/055; A61B 5/4842; A61B 5/7275; A61B 6/032; A61B 5/14546; A61B 5/4839; A61B 6/5205; A61B 6/5211; A61B 6/5217; A61B 6/5258; A61B 6/563; A61B 8/4416; A61B 8/5207; A61B 8/5215; A61B 8/5269; A61B 2576/026; A61B 5/0035; A61B 5/0042; A61B 5/0077; A61B 5/1473; A61B 5/207; A61B 5/4088; A61B 5/42; A61B 5/4833; A61B 5/4848; A61B 5/486; C12Q 1/6886; C12Q 2600/106; C12Q 2600/156; C12Q 2600/158; C12Q 1/6883

See application file for complete search history.

(56) References Cited

U.S. PATENT DOCUMENTS

| | | |
|---|---|---|
| 3,939,350 A | 2/1976 | Kronick et al. |
| 3,996,345 A | 12/1976 | Ullman et al. |
| 4,016,043 A | 4/1977 | Schuurs et al. |
| 4,018,653 A | 4/1977 | Mennen |
| 4,275,149 A | 6/1981 | Litman et al. |
| 4,277,437 A | 7/1981 | Maggio |
| 4,366,241 A | 12/1982 | Tom et al. |
| 4,376,110 A | 3/1983 | David et al. |
| 4,424,279 A | 1/1984 | Bohn et al. |
| 4,437,975 A | 3/1984 | Gillespie et al. |
| 4,486,530 A | 12/1984 | David et al. |
| 4,656,127 A | 4/1987 | Mundy |
| 4,666,828 A | 5/1987 | Gusella |
| 4,683,195 A | 7/1987 | Mullis et al. |
| 4,683,202 A | 7/1987 | Mullis |
| 4,800,159 A | 1/1989 | Mullis et al. |
| 4,801,531 A | 1/1989 | Frossard |
| 4,851,331 A | 7/1989 | Vary et al. |
| 4,965,188 A | 10/1990 | Mullis et al. |
| 4,988,617 A | 1/1991 | Landegren et al. |
| 5,137,765 A | 8/1992 | Farnsworth |
| 5,143,854 A | 9/1992 | Pirrung et al. |
| 5,192,659 A | 3/1993 | Simons |
| 5,242,794 A | 9/1993 | Whiteley et al. |
| 5,242,974 A | 9/1993 | Holmes |
| 5,252,743 A | 10/1993 | Barrett et al. |
| 5,266,222 A | 11/1993 | Willis et al. |
| 5,272,057 A | 12/1993 | Smulson et al. |
| 5,324,633 A | 6/1994 | Fodor et al. |
| 5,333,675 A | 8/1994 | Mullis et al. |
| 5,384,261 A | 1/1995 | Winkler et al. |
| 5,405,783 A | 4/1995 | Pirrung et al. |
| 5,409,818 A | 4/1995 | Davey et al. |
| 5,412,087 A | 5/1995 | McGall et al. |
| 5,413,909 A | 5/1995 | Bassam et al. |
| 5,424,186 A | 6/1995 | Fodor et al. |
| 5,451,683 A | 9/1995 | Barrett et al. |
| 5,482,867 A | 1/1996 | Barrett et al. |
| 5,491,074 A | 2/1996 | Aldwin et al. |
| 5,494,810 A | 2/1996 | Barany et al. |
| 5,527,681 A | 6/1996 | Holmes |
| 5,547,835 A | 8/1996 | Koster |
| 5,547,839 A | 8/1996 | Dower et al. |
| 5,550,215 A | 8/1996 | Holmes |
| 5,554,517 A | 9/1996 | Davey et al. |
| 5,571,639 A | 11/1996 | Hubbell et al. |
| 5,578,832 A | 11/1996 | Trulson et al. |
| 5,593,839 A | 1/1997 | Hubbell et al. |
| 5,599,695 A | 2/1997 | Pease et al. |
| 5,605,798 A | 2/1997 | Koster |
| 5,624,711 A | 4/1997 | Sundberg et al. |
| 5,631,734 A | 5/1997 | Stern et al. |
| 5,656,493 A | 8/1997 | Mullis et al. |
| 5,679,524 A | 10/1997 | Nikiforov et al. |
| 5,691,141 A | 11/1997 | Koster |
| 5,733,729 A | 3/1998 | Lipshutz et al. |
| 5,786,146 A | 7/1998 | Herman et al. |
| 5,795,716 A | 8/1998 | Chee |
| 5,800,992 A | 9/1998 | Fodor et al. |
| 5,831,070 A | 11/1998 | Pease et al. |
| 5,834,189 A | 11/1998 | Stevens et al. |
| 5,834,758 A | 11/1998 | Trulson et al. |
| 5,837,832 A | 11/1998 | Chee et al. |
| 5,849,542 A | 12/1998 | Reeve et al. |
| 5,851,770 A | 12/1998 | Babon et al. |
| 5,856,092 A | 1/1999 | Dale et al. |
| 5,856,101 A | 1/1999 | Hubbell et al. |
| 5,858,659 A | 1/1999 | Sapolsky et al. |
| 5,861,245 A | 1/1999 | McClelland et al. |
| 5,869,242 A | 2/1999 | Kamb |
| 5,871,928 A | 2/1999 | Fodor et al. |
| 5,874,219 A | 2/1999 | Rava et al. |
| 5,876,934 A | 3/1999 | Duthie et al. |
| 5,889,165 A | 3/1999 | Fodor et al. |
| 5,891,625 A | 4/1999 | Buchardt et al. |
| 5,902,723 A | 5/1999 | Dower et al. |
| 5,908,755 A | 6/1999 | Kumar et al. |
| 5,912,118 A | 6/1999 | Ansorge et al. |
| 5,925,525 A | 7/1999 | Fodor et al. |
| 5,928,906 A | 7/1999 | Koster et al. |
| 5,936,324 A | 8/1999 | Montagu |
| 5,952,174 A | 9/1999 | Nokoforov et al. |
| 5,958,692 A | 9/1999 | Cotton et al. |
| 5,959,098 A | 9/1999 | Goldberg et al. |
| 5,968,740 A | 10/1999 | Fodor et al. |
| 5,974,164 A | 10/1999 | Chee |
| 5,976,802 A | 11/1999 | Ansorge et al. |
| 5,981,185 A | 11/1999 | Matson et al. |
| 5,981,186 A | 11/1999 | Gabe et al. |
| 5,981,956 A | 11/1999 | Stern |
| 5,998,143 A | 12/1999 | Ellis et al. |
| 6,004,744 A | 12/1999 | Goelet et al. |
| 6,013,431 A | 1/2000 | Soderlund |
| 6,013,499 A | 1/2000 | Narumiya et al. |
| 6,017,702 A | 1/2000 | Lee et al. |
| 6,025,601 A | 2/2000 | Trulson et al. |
| 6,033,860 A | 3/2000 | Lockhart et al. |

(56) References Cited

U.S. PATENT DOCUMENTS

| | | | |
|---|---|---|---|
| 6,040,193 A | 3/2000 | Winkler et al. |
| 6,043,031 A | 3/2000 | Koster et al. |
| 6,045,996 A | 4/2000 | Cronin et al. |
| 6,046,005 A | 4/2000 | Ju et al. |
| 6,063,603 A | 5/2000 | Davey et al. |
| 6,066,454 A | 5/2000 | Lipshutz et al. |
| 6,087,095 A | 7/2000 | Rosenthal et al. |
| 6,090,555 A | 7/2000 | Fiekowsky et al. |
| 6,110,684 A | 8/2000 | Kemper et al. |
| 6,136,269 A | 10/2000 | Winkler et al. |
| 6,140,054 A | 10/2000 | Wittwer et al. |
| 6,141,096 A | 10/2000 | Stern et al. |
| 6,147,205 A | 11/2000 | McGall et al. |
| 6,183,958 B1 | 2/2001 | Stanton |
| 6,185,030 B1 | 2/2001 | Overbeck |
| 6,185,561 B1 | 2/2001 | Balaban et al. |
| 6,188,783 B1 | 2/2001 | Balaban et al. |
| 6,194,144 B1 | 2/2001 | Koster |
| 6,201,639 B1 | 3/2001 | Overbeck |
| 6,210,891 B1 | 4/2001 | Nyren et al. |
| 6,218,803 B1 | 4/2001 | Montagu et al. |
| 6,223,127 B1 | 4/2001 | Berno |
| 6,225,625 B1 | 5/2001 | Pirrung et al. |
| 6,229,911 B1 | 5/2001 | Balaban et al. |
| 6,258,538 B1 | 7/2001 | Koster et al. |
| 6,262,216 B1 | 7/2001 | McGall |
| 6,269,846 B1 | 8/2001 | Overbeck et al. |
| 6,300,070 B1 | 10/2001 | Boles et al. |
| 6,308,170 B1 | 10/2001 | Balaban |
| 6,310,189 B1 | 10/2001 | Fodor et al. |
| 6,335,167 B1 | 1/2002 | Pinkel et al. |
| 6,361,947 B1 | 3/2002 | Dong et al. |
| 6,386,749 B1 | 5/2002 | Watts et al. |
| 6,391,592 B1 | 5/2002 | Su et al. |
| 6,391,623 B1 | 5/2002 | Besemer et al. |
| 6,410,276 B1 | 6/2002 | Burg et al. |
| 6,420,108 B2 | 7/2002 | Mack et al. |
| 6,428,752 B1 | 8/2002 | Montagu |
| 6,649,348 B2 | 11/2003 | Bass et al. |
| 6,723,513 B2 | 4/2004 | Lexow |
| 7,118,661 B2 | 10/2006 | Surh et al. |
| 7,118,910 B2 | 10/2006 | Unger et al. |
| 7,125,711 B2 | 10/2006 | Pugia et al. |
| 7,135,147 B2 | 11/2006 | Cox et al. |
| 7,138,062 B2 | 11/2006 | Yin et al. |
| 7,141,978 B2 | 11/2006 | Peck et al. |
| 7,169,314 B2 | 1/2007 | Unger et al. |
| 7,189,368 B2 | 3/2007 | Andersson et al. |
| 7,189,580 B2 | 3/2007 | Beebe et al. |
| 7,189,581 B2 | 3/2007 | Beebe et al. |
| 7,195,986 B1 | 3/2007 | Bousse et al. |
| 7,201,881 B2 | 4/2007 | Cox et al. |
| 7,229,538 B2 | 6/2007 | Tseng et al. |
| 7,233,865 B2 | 6/2007 | Chien |
| 7,238,255 B2 | 7/2007 | Derand et al. |
| 7,238,324 B2 | 7/2007 | Ko et al. |
| 7,253,003 B2 | 8/2007 | Beebe et al. |
| 7,258,837 B2 | 8/2007 | Yager et al. |
| 7,261,824 B2 | 8/2007 | Schlautmann |
| 7,323,140 B2 | 1/2008 | Handique et al. |
| 7,329,391 B2 | 2/2008 | Cox |
| 7,338,637 B2 | 3/2008 | Pease et al. |
| 7,351,380 B2 | 4/2008 | Simmons et al. |
| 7,351,592 B2 | 4/2008 | Storek et al. |
| 7,357,864 B2 | 4/2008 | Takada et al. |
| 7,381,471 B2 | 6/2008 | Augustine et al. |
| 7,390,463 B2 | 6/2008 | He et al. |
| 7,399,600 B2 | 7/2008 | Jeffrey et al. |
| 7,402,229 B2 | 7/2008 | Sibbett et al. |
| 7,411,184 B2 | 8/2008 | Sarrut |
| 7,413,709 B2 | 8/2008 | Roitman et al. |
| 7,419,639 B2 | 9/2008 | Osterfeld et al. |
| 7,419,822 B2 | 9/2008 | Jeon et al. |
| 7,422,669 B2 | 9/2008 | Jacobson et al. |
| 7,422,725 B2 | 9/2008 | Kimizuka |
| 7,431,887 B2 | 10/2008 | Storek et al. |
| 7,449,096 B2 | 11/2008 | Berndt |
| 7,452,509 B2 | 11/2008 | Cox et al. |
| 7,452,713 B2 | 11/2008 | Barlocchi et al. |
| 7,467,928 B2 | 12/2008 | Fakunle et al. |
| 7,485,214 B2 | 2/2009 | Palmieri |
| 7,488,596 B2 | 2/2009 | Lee et al. |
| 7,518,726 B2 | 4/2009 | Rulison et al. |
| 7,541,578 B2 | 6/2009 | Weng |
| 7,544,506 B2 | 6/2009 | Breidford et al. |
| 7,552,741 B2 | 6/2009 | Yamada et al. |
| 7,568,399 B2 | 8/2009 | Sparks et al. |
| 7,575,722 B2 | 8/2009 | Arnold |
| 7,579,136 B2 | 8/2009 | Shim et al. |
| 7,581,429 B2 | 9/2009 | Sparks et al. |
| 7,591,936 B2 | 9/2009 | Sarrut |
| 7,640,947 B2 | 1/2010 | Fernandes et al. |
| 7,655,479 B2 | 2/2010 | Zhukov et al. |
| 7,666,361 B2 | 2/2010 | McBride et al. |
| 7,704,735 B2 | 4/2010 | Facer et al. |
| 7,745,150 B2 | 6/2010 | Liang et al. |
| 7,751,053 B2 | 7/2010 | Carr |
| 7,888,035 B2 | 2/2011 | Klass et al. |
| 7,897,356 B2 | 3/2011 | Klass et al. |
| 10,734,096 B1 | 8/2020 | Neumann |
| 11,120,364 B1 * | 9/2021 | Gokalp ................ G06N 20/00 |
| 11,250,345 B1 * | 2/2022 | Rabbani ............... G06F 16/353 |
| 11,315,673 B2 | 4/2022 | Abraham et al. |
| 11,392,827 B1 * | 7/2022 | Rubin .................. G06N 3/042 |
| 11,527,323 B2 | 12/2022 | Michuda et al. |
| 2002/0183936 A1 | 12/2002 | Kulp et al. |
| 2003/0082543 A1 | 5/2003 | Su et al. |
| 2003/0096235 A1 | 5/2003 | Dong |
| 2004/0096915 A1 | 5/2004 | Diamandis |
| 2005/0124071 A1 | 6/2005 | Kraus |
| 2006/0003465 A1 | 1/2006 | Zhukov et al. |
| 2006/0035243 A1 | 2/2006 | Wenz et al. |
| 2007/0117164 A1 | 5/2007 | Raskov et al. |
| 2008/0213907 A1 | 9/2008 | Lomnytska et al. |
| 2008/0233576 A1 * | 9/2008 | Weston ................. G16B 25/10<br>707/999.005 |
| 2008/0261258 A1 | 10/2008 | Smith et al. |
| 2009/0004687 A1 | 1/2009 | Mansfield et al. |
| 2009/0061422 A1 | 3/2009 | Linke |
| 2009/0111121 A1 | 4/2009 | Rosiers et al. |
| 2009/0226937 A1 | 9/2009 | Liang et al. |
| 2009/0239246 A1 | 9/2009 | Pemberton et al. |
| 2009/0291932 A1 | 11/2009 | White et al. |
| 2010/0144543 A1 | 6/2010 | Witcher et al. |
| 2010/0144836 A1 | 6/2010 | Engeland et al. |
| 2010/0151468 A1 | 6/2010 | Esteller et al. |
| 2010/0173788 A1 | 7/2010 | Goncalves et al. |
| 2010/0184027 A1 | 7/2010 | Lofton-Day et al. |
| 2010/0203566 A1 | 8/2010 | Liang et al. |
| 2010/0222230 A1 | 9/2010 | Iliopoulos et al. |
| 2010/0248290 A1 | 9/2010 | Lam et al. |
| 2010/0330683 A1 | 12/2010 | Rosiers et al. |
| 2011/0008808 A1 | 1/2011 | Pemberton et al. |
| 2011/0078099 A1 * | 3/2011 | Weston ................. G16B 40/20<br>706/12 |
| 2011/0119212 A1 | 5/2011 | De Bruin et al. |
| 2014/0024553 A1 * | 1/2014 | Michalek ............... G16Z 99/00<br>702/19 |
| 2014/0172319 A1 | 6/2014 | Von Hoff et al. |
| 2015/0186748 A1 * | 7/2015 | Cootes ............. G06F 18/24323<br>382/201 |
| 2016/0034809 A1 * | 2/2016 | Trenholm .............. G06F 18/00<br>706/20 |
| 2017/0132362 A1 * | 5/2017 | Skinner ................. G16B 30/00 |
| 2017/0175169 A1 | 6/2017 | Lee |
| 2017/0283884 A1 | 10/2017 | Knudsen |
| 2018/0011966 A1 * | 1/2018 | Vaske .................... G16B 5/20 |
| 2018/0068083 A1 * | 3/2018 | Cohen ................. G16B 50/30 |
| 2018/0085447 A1 | 3/2018 | Chaudhuri et al. |
| 2018/0089373 A1 | 3/2018 | Matsuguchi et al. |
| 2019/0106732 A1 * | 4/2019 | Spurlock, III ....... C12Q 1/6883 |
| 2019/0233895 A1 | 8/2019 | Kurzrock |
| 2019/0317079 A1 * | 10/2019 | Trenholm ............ G01N 21/783 |
| 2019/0360059 A1 | 11/2019 | Adams et al. |

(56) References Cited

U.S. PATENT DOCUMENTS

| | | |
|---|---|---|
| 2019/0360060 A1 | 11/2019 | Lee et al. |
| 2020/0185063 A1 | 6/2020 | Narain |
| 2020/0285939 A1* | 9/2020 | Baker .................. G06N 3/04 |
| 2022/0108771 A1* | 4/2022 | Steingrimsson ....... G16B 40/20 |
| 2022/0319658 A1 | 10/2022 | Abraham et al. |
| 2023/0187028 A1* | 6/2023 | Ma ..................... G16H 20/10 |
| | | 702/19 |

FOREIGN PATENT DOCUMENTS

| | | |
|---|---|---|
| WO | WO88/10315 | 12/1988 |
| WO | WO90/06995 | 6/1990 |
| WO | WO99/36760 | 7/1999 |
| WO | WO99/47964 | 9/1999 |
| WO | WO00/26401 | 5/2000 |
| WO | WO00/58516 | 10/2000 |
| WO | WO01/20039 | 3/2001 |
| WO | WO01/27326 | 4/2001 |
| WO | WO01/27327 | 4/2001 |
| WO | WO01/27329 | 4/2001 |
| WO | WO01/58593 | 8/2001 |
| WO | WO01/85341 | 11/2001 |
| WO | WO2004/011666 | 2/2004 |
| WO | WO2006/084132 | 8/2006 |
| WO | 2006093507 A2 | 9/2006 |
| WO | WO2007/088537 | 8/2007 |
| WO | WO2007/121489 | 10/2007 |
| WO | WO2007/137187 | 11/2007 |
| WO | WO2010/045318 | 4/2010 |
| WO | WO2010/072410 | 7/2010 |
| WO | WO2010/093465 | 8/2010 |
| WO | 2010147601 | 12/2010 |
| WO | WO2011/056688 | 5/2011 |
| WO | WO2011/066589 | 6/2011 |
| WO | WO2011/088226 | 7/2011 |
| WO | WO2011/109440 | 9/2011 |
| WO | WO2011/127219 | 10/2011 |
| WO | WO2012/074085 | 6/2012 |
| WO | WO2012/092336 | 7/2012 |
| WO | WO2012/170715 | 12/2012 |
| WO | WO2014/089241 | 6/2014 |
| WO | WO2015/116868 | 8/2015 |
| WO | WO2016/141169 | 9/2016 |
| WO | WO2017/053915 | 3/2017 |
| WO | WO-2018078142 A1 * | 5/2018 |
| WO | WO2018/160675 | 9/2018 |
| WO | WO2018/175501 | 9/2018 |

OTHER PUBLICATIONS

Dietterich, Thomas G., "Ensemble Learning," Department of Computer Science, Oregon State University, Sep. 4, 2002, 9 pages.
Jalali et al., "Interpretable per case weighted ensemble method for cancer associations," BMC Genomics, 2016, 17:501 (10 pages).
Schapire et al., "Improved Boosting Algorithms Using Confidence-rated Predictions," Proceedings of the eleventh annual conference on Computational learning theory, 1998, pp. 80-91.
Yousefnezhad et al., "Wisdom of Crowds Cluster Ensemble Selection," 2014 International Academic Conference of Postgraduates, NUAA, Dec. 2014, 13 pages.
U.S. Appl. No. 09/916,135, filed Jul. 25, 2001, Matsuzaki et al.
U.S. Appl. No. 09/854,317, filed May 11, 2001, Su et al.
U.S. Appl. No. 11/950,395, filed Dec. 4, 2007, Van Den Boom.
U.S. Appl. No. 10/423,403, filed Apr. 25, 2003, Loraine et al.
U.S. Appl. No. 10/389,194, filed Mar. 14, 2003, Weiner et al.
U.S. Appl. No. 10/328,872, filed Dec. 23, 2002, Cheng et al.
U.S. Appl. No. 10/328,818, filed Dec. 23, 2002, Kulp et al.
U.S. Appl. No. 10/197,621, filed Jul. 17, 2002, Craford et al.
U.S. Appl. No. 60/804,818, filed Jun. 14, 2006, Stoughton et al.
U.S. Appl. No. 60/493,495, filed Aug. 8, 2003, Kaiser.
U.S. Appl. No. 10/065,868, filed Nov. 26, 2002, Zhou et al.
U.S. Appl. No. 10/065,856, filed Nov. 26, 2002, Loraine et al.
U.S. Appl. No. 10/063,559, filed May 2, 2002, Kulp et al.
U.S. Appl. No. 10/013,598, filed Dec. 10, 20001, Su.
U.S. Appl. No. 61/021,871, filed Jan. 17, 2008, Cantor et al.
Ahmadian et al., "Single-nucleotide polymorphism analysis by pyrosequencing," Anal. Biochem., Apr. 2000, 280(1):103-110.
Ahmed et al., "Proteomic-based identification of haptoglobin-1 precursor as a novel circulating biomarker of ovarian cancer," Br. J. Cancer, 2004, 91:129-140.
Al-Batran et al., "Phase III trial in metastatic gastroesophageal adenocarcinoma with fluorouracil, leucovorin plus either oxaliplatin or cisplatin: A study of the Arbeitsgemeinschaft Intemistische Onkologie," J Clin Oncol., Mar. 20, 2008, 26(9):1435-1442.
Amado et al., "Wild-type KRAS is required for panitumumab efficacy in patients with metastatic colorectal cancer," Journal of Clinical Oncology, Apr. 2008, 26(10):1626-1634.
Angerer et al., "Demonstration of Tissue-Specific Gene Expression by in Situ Hybridization," Methods Enzymol., Jan. 1987, 152:649-660 (1987).
Argüello et al., "Mutation detection and typing of polymorphic loci through double-strand conformation analysis," Nat. Genet., Feb. 1998, 18(2):192-194.
Ashktorab et al., "Distinct genetic alterations in colorectal cancer," PLoS One, Jan. 26, 2010, 5(1):e8879, 7 pages.
Aurekari, "Methylation of tumor suppressor genes p16(INK4a), p27(Kip1) and E-cadherin in carcinogenesis," Oral Oncology, Jan. 2006, 42(1)5-13.
Barringer et al., "Blunt-end and single-strand ligations by *Escherichia coli* ligase: influence on an in vitro amplication scheme," Gene, Apr. 1990, 89(1):117-122.
Bartsch et al., "Trastuzumab in the management of early and advanced stage breast cancer," Biologics, Mar. 2007, 1(1): 19-31.
Batzer et al., "Enhanced evolutionary PCR using oligonucleotides with inosine at the 3'-terminus," Nucleic Acid Res., Sep. 25, 1991, 19(18):5081.
Behjati et al., "What is next generation sequencing?," Arch Dis Child Educ Pract Ed., Aug. 28, 2013, 98:236-238.
Braslavsky et al., "Sequence information can be obtained from single DNA molecules," PNAS, Apr. 2003, 100(7):3960-3964.
Brenner et al., "Gene expression analysis by massively parallel signature sequencing (MPSS) on microbead arrays," Nature Biotechnology, Jun. 2000,18(6):630-634.
Brownie et al., "The elimination of primer-dimer accumulation in PCR," Nucleic Acids Res., Aug. 1997, 25(16):3235-3241.
Cardullo et al., "Detection of Nucleic Acid Hybridization by Nonradiative Fluorescence Resonance Energy Transfer," Proc. Nat. Acad. Sci. USA, Dec. 1988, 85(23):8790-8794.
Cariello et al., "Resolution of a missense mutant in human genomic DNA by denaturing gradient gel electrophoresis and direct sequencing using in vitro DNA amplification: HPRT Munich," American Journal of Human Genetics, May 1988, 42(5):726-734.
Carney, "Circulating oncoproteins HER2/neu, EGFR and CAIX (MN) as novel cancer biomarkers," Expert Rev Mol Diagn, May 2007, 7(3):309-19.
Chang et al., "Practice parameters for the management of colon cancer," Dis Colon Rectum., Aug. 2012; 55(8):831-43.
Charras et al., "Blebs lead the way: how to migrate without lamellipodia," Nature Reviews Molecular and Cell Biology, 2008, vol. 9(9):730-736.
Chee et al., "Accessing genetic information with high-density DNA arrays," Science., Oct. 1996, 274(5287):610-614.
Chen & Kwok, "Template-directed dye-terminator incorporation (TDI) assay: a homogeneous DNA diagnostic method based on fluorescence resonance energy transfer," Nucleic Acids Research, Jan. 1997, 25(2):347-353.
Chen et al., "A homogeneous, ligase-mediated DNA diagnostic test," Genome Res., May 1998, 8(5):549-556.
Chen et al., "Microfluidic isolation and transcriptome analysis of serum microvesicles," Lab on a Chip, Feb. 2010, 10(4):505-511.
Chen et al., "A Microsphere-Based Assay for Multiplexed Single Nucleotide Polymorphism Analysis Using Single Base Chain Extension," Genome Res., Apr. 2000, 10:549-557.

(56) References Cited

OTHER PUBLICATIONS

Chen et al., "Fluorescence energy transfer detection as a homogeneous DNA diagnostic method," Proc. Natl. Acad. Sci. USA, Sep. 1997, 94(20):10756-10761.
Collins et al., "A branched DNA signal amplification assay for quantification of nucleic acid targets below 100 molecules/ml," Nucleic Acids Res., Aug. 1997, 25(15):2979-2984.
Conner et al., "Detection of sickle cell beta S-globin allele by hybridization with synthetic oligonucleotides," Proc. Natl. Acad. Sci. USA, Jan. 1983, 80(1):278-282.
Conroy et al., "FOLFIRINOX versus gemcitabine for metastatic pancreatic cancer," N Engl J Med., May 12, 2011, 364(19):1817-1825.
Cooksey et al., "Evaluation of the invader assay, a linear signal amplification method, for identification of mutations associated with resistance to rifampin and isoniazid in *Mycobacterium tuberculosis*," Antimicrobial Agents and Chemotherapy, May 2000, 44(5):1296-1301.
De la Roche et al., "The function of BCL9 in Wnt/p. catenin signaling and colorectal cancer cells," BMC Cancer, Jul. 15, 2008, 8:199, pp. 1-13.
Dear, "One by one: single molecule tools for genomics," Brief Funct. Genomic., Jan. 2003, 1(4):397-416.
Deka et al., "Bc19/Bc191 are critical for Wnt-mediated regulation of stem cell traits in colon epithelium and adenocarcinomas," Caner Res., Aug. 15, 2010, 70(16):6619-6628.
DeRisi et al., "Use of a cDNA microarray to analyse gene expression," Nat. Genet., Dec. 1996, 14(4):457-460.
Detmer et al., "Accurate quantification of hepatitis C virus (HCV) RNA from all HCV genotypes by using branched-DNA technology," J. Clin. Microbial., Apr. 1996, 34(4):901-907.
Dong et al., "Flexible use of high-density oligonucleotide arrays for single-nucleotide polymorphism discovery and validation," Genome Research, Aug. 2001, 11(8):1418-1424.
Drmanac et al., "Accurate sequencing by hybridization for DNA diagnostics and individual genomics," Nat. Biotechnol., Jan. 1998, 16(1):54-58.
Drobyshev et al., "Sequence analysis by hybridization with oligonucleotide microchip: identification of β-thalassemia mutations," Gene, Mar. 1997, 188(1):45-52.
Eads et al., "CpG island hypermethylation in human colorectal tumors is not associated with DNA methyltransferase overexpression," Cancer Res., May 1999, 59(10):2302-2306.
Eckert et al., "DNA polymerase fidelity and the polymerase chain reaction," PCR Methods and Applications, Aug. 1991, 1(1):17-24.
Egger et al., "Epigenetics in human disease and prospects for epigenetic therapy," Nature, May 2004, 429(6990):457-463.
Eigen et al., "Sorting single molecules: application to diagnostics and evolutionary biotechnology," Proc. Natl. Acad. Sci. USA, Jun. 1994, 91(13):5740-5747.
Extended European Search Report in European Appln. No. 19888693.9, dated Jul. 13, 2022, 8 pages.
Fabbri, "miRNAs as molecular biomarkers of cancer," Expert Rev Mol Diagn., May 2010, 10(4):435-444.
Ferracin et al., "Micromarkers: miRNAs in cancer diagnosis and prognosis," Expert Rev Mol Diagn., Apr. 2010, 10(3):297-308.
Ferry, "Burkitt's lymphoma: clinicopathologic features and differential diagnosis," Oncologist, Apr. 2006, 11(4):375-383.
Finkelstein et al., "Use of denaturing gradient gel electrophoresis for detection of mutation and prospective diagnosis in late onset ornithine transcarbamylase deficiency," Genomics, Jun. 1990, 7(2):167-172.
Fiorini and Chiu, "Disposable microfluidic devices: fabrication, function, and application," Bio. Techniques, Mar. 2005, 38(3):429-446.
Fitzmaurice et al., "Global, Regional, and National Cancer Incidence, Mortality, Years of Life Lost, Years Lived With Disability, and Disability-Adjusted Life-years for 32 Cancer Groups, 1990 to 2015: A Systematic Analysis for the Global Burden of Disease Study," Global Burden of Disease Cancer Collaboration, JAMA Oncol., Apr. 2017, 3(4):524-548.
Fleming et al., "Colorectal carcinoma: Pathologic aspects," J Gastrointest Oncol., Sep. 2012, 3(3): 153-173.
Fox et al., "The detection of K-ras mutations in colorectal cancer using the amplification-refractory mutation system," Br. J. Cancer, Apr. 1998, 77(8): 1267-1274.
Furuichi et al., "Chemical modification of tRNA-Tyr-yeast with bisulfite. A new method to modify isopentenyladenosine residue," Biochem Biophys. Res. Commun., Dec. 1970, 41(5):1185-1191.
Gagnon et al., "Discovery and application of protein biomarkers for ovarian cancer," Curr Opin Obstet Gynecol, Feb. 2008, 20(1):9-13.
Gatlin et al., "Automated identification of amino acid sequence variations in proteins by HPLC/microspray tandem mass spectrometry," Anal. Chem., Feb. 2000, 72(4):757-763.
Gibson et al., "A homogeneous method for genotyping with fluorescence polarization," Clin. Chem., Aug. 1997, 43(8):1336-1341.
Gingeras et al., "Simultaneous genotyping and species identification using hybridization pattern recognition analysis of generic *Mycobacterium* DNA arrays," Genome Res., May 1998, 8(5):435-448.
Giunta et al., "Rapid diagnosis of germline p53 mutation using the enzyme mismatch cleavage method," Diagn. Mol. Path., Dec. 1996, 5(4):265-270.
Gonzalgo & Jones, "Rapid quantitation of methylation differences at specific sites using methylation-sensitive single nucleotide primer extension (Ms-SNuPE)," Nucleic Acids Res., Jun. 1997, 25(12):2529-2531.
Gonzalgo et al., "Identification and characterization of differentially methylated regions of genomic DNA by methylation-sensitive arbitrarily primed PCR," Cancer Research, Feb. 1997, 57(4):594-599.
Graber et al., "Advances in DNA diagnostics," Curr. Opin. Biotechnol., Feb. 1998, 9(1):14-18.
Graham et al., "Selective detection of deoxyribonucleic acid at ultralow concentrations by SERRS," Anal. Chem., Nov. 1997, 69(22):4703-4707.
Griffiths-Jones et al., "miRBase: tools for microRNA genomics," NAR 2008, 36(Database Issue):D154-D158.
Griffiths-Jones et al., miRBase:microRNA sequences, targets and gene nomenclature, NAR 2006, 34(Database Issue):D140-D144.
Griffiths-Jones, Sam, "The microRNA Registry," NAR 2004, 32(Database Issue):D109-D111.
Grompe et al., "Scanning detection of mutations in human ornithine transcarbamoylase by chemical mismatch cleavage," Proc. Natl. Acad. Sci. USA, Aug. 1989, 86(15):5888-5892.
Grompe, "The rapid detection of unknown mutations in nucleic acids" Nature Genetics 5(2):111-117.
Guatelli et al., "Isothermal, in vitro amplification of nucleic acids by a multienzyme reaction modeled after retroviral replication," Proc. Nat. Acad. Sci. USA, Mar. 1990, 87(5):1874-1878.
Guo et al., "Direct fluorescence analysis of genetic polymorphisms by hybridization with oligonucleotide arrays on glass supports," Nucleic Acids Res., Dec. 1994, 22(24):5456-5465.
Haase et al., "Detection of viral nucleic acids by in situ hybridization," Methods in Virology, Jan. 1984, 7:189-226.
Hacia et al., "Detection of heterozygous mutations in BRCA1 using high density oligonucleotide arrays and two-colour fluorescence analysis," Nat. Genet., Dec. 1996, 14(4):441-447.
Haimovich, "Methods, challenges, and promise of nextgeneration sequencing in cancer biology," Yale J. Biol Med., Dec. 2011, 84(4):439-446.
Harris et al., "Single-molecule DNA sequencing of a viral genome," Science, Apr. 2008, 320(5872):106-109.
Hawkins et al., "Rapid DNA mutation identification and fingerprinting using base excision sequence scanning," Electrophoresis, Jun. 1999, 20(6):1171-1176.
Heid et al., "Real time quantitative PCR," Genome Research, Oct. 1996, 6:986-994.
Herman et al., "Methylation-specific PCR: a novel PCR assay for methylation status of CpG islands," Proc. Natl. Acad. Sci. USA, Sep. 1996, 93(18):9821-9826.

(56) References Cited

OTHER PUBLICATIONS

Holland et al., "Detection of specific polymerase chain reaction product by utilizing the 5'—3'exonuclease activity of Thermus aquaticus DNA polymerase," Proc. Natl. Acad. Sci. USA, Aug. 1991, 88(16):7276-7280.

Horn et al., "An improved divergent synthesis of comb-type branched oligodeoxyribonucleotides (bDNA) containing multiple secondary sequences," Nucleic Acids Res., Dec. 1997, 25(23):4835-4841.

Horn et al., "Chemical synthesis and characterization of branched oligodeoxyribonucleotides (bDNA) for use as signal amplifiers in nucleic acid quantification assays," Nucleic Acids Res., 1997, 25(23):4842-4849.

Iannone et al., "Multiplexed single nucleotide polymorphism genotyping by oligonucleotide ligation and flow cytometry," Cytometry, Feb. 2000, 39(2):131-140.

Jablonski et al., "Preparation of oligodeoxynucleotide-alkaline phosphatase conjugates and their use hybridization probes," Nucleic Acids Res., Aug. 1986, 14:6115-6128.

Jiang et al., "BCL9 provides multi-cellular communication properties in colorectal cancer by interacting with paraspeckle proteins," Nat Commun., Jan. 2020, 11(1):19, pp. 1-16.

Kaissis et al., "A machine learning algorithm predicts molecular subtypes in pancreatic ductal adenocarcinoma with differential response to gemcitabine-based versus FOLFIRINOX chemotherapy," PLoS One, Oct. 2, 2019, 14(10):1-16.

Kalinina et al., "Nanoliter scale PCR with TaqMan detection," Nucleic Acids Res., May 1997, 25(10):1999-2004.

Kantarjian et al., "Important therapeutic targets in chronic myelogenous leukemia," Clinical Cancer Research, Feb. 2007, 13(4):1089-1097.

Kaplan & Meier, "Nonparametric estimation from incomplete observations," J. Amer. Statist. Assoc., Jun. 1958, 53(282):457-481.

Karlin et al., "Applications and statistics for multiple high-scoring segments in molecular sequences," Proc. Natl. Acad. Sci. USA, Jun. 1993, 90:5873-5877.

Kartalov & Quake, "Microfluidic device reads up to four consecutive base pairs in DNA sequencing-by-synthesis," Nucl. Acids Res., May 2004, 32(9):2873-2879.

Keller et al., "Exosomes: from biogenesis and secretion to biological function," Immunol. Lett., Nov. 15, 2006, 107(2): 102-8.

Kinzler et al., "Identification of a gene located at chromosome 5q21 that is mutated in colorectal cancers," Science, Mar. 1991, 251(4999):1366-1370.

Kopetz S, et al., "Encorafenib, binimetinib, and cetuximab in BRAF V600E-mutated colorectal cancer," N Engl J Med., Oct. 24, 2019, 381: 1632-1643.

Kozal et al., "Extensive polymorphisms observed in HIV-1 clade B protease gene using high-density oligonucleotide arrays," Nat. Med., Jul. 1996, 2(7):753-759.

Kurzrock et al., "Philadelphia chromosomepositive leukemias: from basic mechanisms to molecular therapeutics," Annals of Internal Medicine, May 2003, 138(10):819-830.

Kwoh et al., "Transcription-based amplification system and detection of amplified human immunodeficiency virus type 1 with a bead-based sandwich hybridization format," Proc. Natl. Acad. Sci. USA, Feb. 1989, 86(4):1173-1177.

Laird, "The power and the promise of DNA methylation markers," Nature Reviews, Apr. 2003, 3(4):253-266.

Landegren et al., "A ligase-mediated gene detection technique," Science, Aug. 1989, 241(4869):1077-1080.

Landgren et al., "Reading bits of genetic information: methods for single-nucleotide polymorphism analysis," Genome Research, Aug. 1998, 8(8):769-776.

Le et al., "PD-1 Blockade in Tumors with Mismatch-Repair Deficiency," N Engl J Med, Jun. 25, 2015, 372(26):2509-2520.

Lenz et al., "Impact of consensus molecular subtype on survival in patients with metastatic colorectal cancer: Results from CALGB/SWOG 80405 (Alliance)," J Clin Oncol., Aug. 2019, 37(22):1876-1885.

Levy & Myers, "Advancements in Next-Generation Sequencing," Annu. Rev. Genomics Hum. Genet., Aug. 2016, 17:95-115.

Liu et al., "TiIGER: a database for tissue-specific gene expression and regulation," BMC Bioinformatics, Jun. 2008, 9:271, 7 pages.

Lizardi et al., "Mutation detection and single-molecule counting using isothermal rolling-circle amplification," Nature Genetics, Jul. 1998, 19(3):225-232.

Lockhart et al., "Expression monitoring by hybridization to high-density oligonucleotide arrays," Nat. Bio., Dec. 1996, 14(13):675-680.

Lyamichev et al., "Polymorphism identification and quantitative detection of genomic DNA by invasive cleavage of oligonucleotide probes," Nat. Biotechnol., Mar. 1999, 17(3):292-296.

Margulies et al., "Genome sequencing in microfabricated high-density picolitre reactors," Nature, Sep. 2005, 437(7057):376-380.

Maskos & Southern, "Oligonucleotide hybridisations on glass supports: a novel linker for oligonucleotide synthesis and hybridisation properties of oligonucleotides synthesised in situ," Nucleic Acids Res, Apr. 1992, 20(7):1679-1684.

Mathelin et al., "Circulating proteinic biomarkers and breast cancer," Gynecol Obstet Fertil., Jul. 2006, 34(7-8):638-646.

Mattila et al., "Fidelity of DNA synthesis by the Thermococcus litoralis DNA polymerase—an extremely heat stable enzyme with proofreading activity," Nucleic Acids Res., Sep. 1991, 19(18):4967-4973.

Metzker, "Sequencing technologies—the next generation," Nat. Rev. Genet., Jan. 2010, 11(1):31-46.

Meyers et al., "Criteria for annotation of plant MicroRNAs," Plant Cell., Dec. 2008, 20(12):3186-3190.

Mittleman et al., "The impact of translocations and gene fusions on cancer causation," Nature Reviews Cancer, Apr. 2007, 7(4):233-245.

Modrich et al., "Mechanisms and biological effects of mismatch repair," Ann. Rev. Genet., Dec. 1991, 25(1):229-253.

Mohelnikova-Duchonova et al., "FOLFOX/FOLFIRI pharmacogenetics: The call for a personalized approach in colorectal cancer therapy," World J. Gastroenterol., Aug. 14, 2014, 20(30): 10316-10330.

Monforte & Becker, "High-throughput DNA analysis by time-of-flight mass spectrometry," Nat. Med., Mar. 1997, 3(3):360-362.

Mucaki et al., "Predicting responses to platin chemotherapy agents with biochemically-inspired machine learning," Signal Transduction and Targeted Therapy, Jan. 11, 2019, 4:1 (12 pages).

Muzny et al., "Comprehensive molecular characterization of human colon and rectal cancer," Nature, Jul. 18, 2012, 487(7407):330-337.

Nakano et al., "Single-molecule PCR using water-in-oil emulsion;" Journal of Biotechnology, Apr. 2003, 102(2): 117-124.

Nazarenko et al., "A closed tube format for amplification and detection of DNA based on energy transfer," Nucleic Acids Res., Jun. 1997, 25(12):2516-2521.

Nelson et al., "Detection of all single-base mismatches in solution by chemiluminescence," Nucleic Acids Res., Dec. 1996, 24(24):4998-5003.

Newton et al., "Analysis of any point mutation in DNA. The amplification refractory mutation system (ARMS)," Nucleic Acids Res., Apr. 1989, 17:2503-2515.

Ohtsuka et al., "An Alternative Approach to Deoxyoligonucleotides as Hybridization Probes by Insertion of Deoxyinosine at Ambiguous Codon Positions," J. Biol. Chem., Mar. 1985, 260:2605-2608.

Orita et al., "Detection of polymorphisms of human DNA by gel electrophoresis as single-strand conformation polymorphisms," Proc. Natl. Acad. Sci. U.S.A., Apr. 1989, 86(8): 27776-2770.

Oun et al., "The side effects of platinum-based chemotherapy drugs: a review for chemists," Dalton Trans., May 15, 2018, 47(19):6645-6653. doi: 10.1039/c8dt00838h.

Parikh et al., "MAVERICC, a randomized, biomarker-stratified, phase II study of mFOLFOX6-Bevacizumab versus FOLFIRI-bevacizumab as first-line chemotherapy in metastatic colorectal cancer," Clin Canc Res., May 15, 2019, 25(10):2988-2995.

Parker et al., "mRNA: detection by in Situ and northern hybridization," Methods in Molecular Biology, 1999, 106:247-283.

Pasterkamp et al., "Immune regulatory cells: circulating biomarker factories in cardiovascular disease," Clin Sci (Lond)., Aug. 2008, 115(4): 129-31.

(56) References Cited

OTHER PUBLICATIONS

PCT International Preliminary Report on Patentability in International Application No. PCT/US2019/064078, dated Jun. 10, 2021, 22 pages.
PCT International Preliminary Report on Patentability in International Appln. No. PCT/US2020/035990, mailed on Jun. 16, 2022 11 pages.
PCT International Search Report and Written Opinion in International Application No. PCT/US19/64078, dated Apr. 21, 2020, 22 pages.
PCT International Search Report and Written Opinion in International Appln. No. PCT/US2020/035990, mailed on Feb. 19, 2021, 14 pages.
PCT Invitation to Pay Additional Fees in International Application No. PCT/US 19/64078, dated Feb. 20, 2020, 4 pages.
PCT Invitation to Pay Additional Fees in International Application No. PCT/US2020/035990, dated Sep. 4, 2020, 2 pages.
Pedregosa et al., "Scikitleam: Machine Learning in Python," JMLR, Nov. 2011, 12:2825-2830.
Rein et al., "Identifying 5-methylcytosine and Related Modifications in DNA Genomes," Nucleic Acids Research, May 1998, 26(10):2255-2264.
Rigby et al., "Labeling deoxyribonucleic acid to high specific activity in vitro by nick translation with DNA polymerase I," J. Mol. Biol., Jun. 1977, 113(1):237-251.
Roberts et al., "Potassium permanganate and tetraethylammonium chloride are a safe and effective substitute for osmium tetroxide in solid-phase fluorescent chemical cleavage of mismatch," Nucleic Acids Res., Aug. 1997, 25(16):3377-3378.
Robertson et al., "Development and validation of a screening test for 12 common mutations of the cystic fibrosis CFTR gene," Eur. Respir. J., Aug. 1998, 12(2):477-482.
Roever, "Endpoints in Clinical Trials: Advantages and Limitations," Evidence Based Medicine and Practice, Dec. 2015, 1(2):1000e111, 2 pages.
Rossolini et al., "Use of deoxyinosine-containing primers vs degenerate primers for polymerase chain reaction based on ambiguous sequence information," Mol. Cell Probes., Apr. 1994, 8(2):91-98.
Rychlik et al., "A computer program for choosing optimal oligonudeotides for filter hybridization, sequencing and in vitro amplification of DNA," Nucleic Acids Res., Nov. 1989, 17(21):8543-8551.
Saiki et al., "Genetic analysis of amplified DNA with immobilized sequence-specific oligonucleotide probes," Proc. Natl. Acad. Sci. USA, Aug. 1989, 86(16):6230-6234.
Salem et al., "Comparative molecular analyses of left-sided colon, right-sided colon, and rectal cancers," Oncotarget, Sep. 21, 2017, 8(49): 86356-86368.
Salem et al., "Landscape of tumor mutation load, mismatch repair deficiency, and PD-LI expression in a large patient cohort of gastrointestinal cancers," Mol Cane Res., May 2018, 16(5):805-812.
Sashegy et al., "On the Interpretation of the Hazard Ratio and Communication of Survival Benefit," Oncologist., Apr. 2017, 22(4): 484-486.
Schena et al., "Parallel human genome analysis: microarray-based expression monitoring of 1000 genes," Proc. Natl. Acad. Sci. USA, Oct. 1996, 93(2):10614-10619).
Schuster, "Next-generation sequencing transforms today's biology," Nature Methods, Jan. 2008, 5(1):16-18.
Sharkey et al., "Antibodies as thermolabile switches: high temperature triggering for the polymerase chain reaction," Bio/Technology, May 1994, 12(5):506-509.
Sheffield et al., "Attachment of a 40-base-pair G+ C-rich sequence (GC-clamp) to genomic DNA fragments by the polymerase chain reaction results in improved detection of single-base changes," Proc. Natl. Acad. Sci. USA, Jan. 1989, 86(1):232-236.
Sheffield et al., "Identification of novel rhodopsin mutations associated with retinitis pigmentosa by GC-clamped denaturing gradient gel electrophoresis," Am. J. Hum, Genet., Oct. 1991, 49(4):699-706.
Shen et al., "Deep Learning to Improve Breast Cancer Detection on Screening Mammography," Sci Rep., Aug. 29, 2019, 9(1):12495, 12 pages.
Shendure et al., Accurate Multiplex Polony Sequencing of an Evolved Bacterial Genome, Science, Sep. 2005, 309(5741):1728-1732.
Shoemaker et al., "Quantitative phenotypic analysis of yeast deletion mutants using a highly parallel molecular bar-coding strategy," Nat. Genet., Dec. 1996, 14(4):450-456.
Shumaker et al., "Mutation detection by solid phase primer extension," Hum. Mutat., Jan. 1996, 7(4):346-354.
Somashekhar et al., "Watson for Oncology and breast cancer treatment recommendations: agreement with an expert multidisciplinary tumor board," Annals Oncol., Feb. 2018, 29(2):418-423.
Soni & Meller, "Progress toward ultrafast DNA sequencing using solid-state nanopores," Clinical Chemistry, Nov. 2007, 53(11):1996-2001.
Southern et al., "Arrays of complementary oligonucleotides for analysing the hybridisation behaviour of nucleic acids," Nucleic Acids Res., Apr. 1994, 22(8):1368-1373.
Stintzing et al., "Consensus molecular subgroups (CMS) of colorectal cancer (CRC) and first-line efficacy of FOLFIRI plus cetuximab or bevacizumab in the FIRE3 (AIO KRK-0306) trial," Annals of oncology: official journal of the European Society for Medical Oncology, Nov. 2019, 30(11):1796-1803.
Syvanen et al., "A primer-guided nucleotide incorporation assay in the genotyping of apolipoprotein E," Genomics, Dec. 1990, 8(4):684-692.
Tatusova et al., "BLAST 2 Sequences, a new tool for comparing protein and nucleotide sequences," FEMS Microbial. Lett., May 1, 1999, 174(2):247-250.
Thery et al., "Membrane vesicles as conveyors of immune responses," Nat Rev Immunol., Aug. 2009, 9(8):581-93.
Tost et al., "Molecular haplotyping at high throughput," Nucleic Acids Res., Oct. 2002, 30(19):e96.
Tournigand et al., "FOLFIRI followed by FOLFOX6 or the reverse sequence in advanced colorectal cancer: a randomized GERCOR study," J. Clin. Oncol., Jan. 2004, 22(2):229-237.
Toyota et al., "Identification of differentially methylated sequences in colorectal cancer by methylated CpG island amplification," Cancer Res., May 1999, 59(10):2307-2312.
Tyagi et al., "Molecular beacons: probes that fluoresce upon hybridization," Nat. Biotechnol., Mar. 1996, 14(3):303-308.
Tyagi et al., "Multicolor molecular beacons for allele discrimination," Nat. Biotechnol., Nature Biotechnology, Jan. 1998, 16(1):49-53.
Velculescu et al., "Characterization of the yeast transcriptome," Cell, Jan. 1997, 88(2):243-251.
Velculescu et al., "Serial analysis of gene expression," Science, Oct. 1995, 270(5235):484-487.
Venook et al., "Effect of First-Line Chemotherapy Combined With Cetuximab or Bevacizumab on Overall Survival in Patients With KRAS Wild-Type Advanced or Metastatic Colorectal Cancer: A Randomized Clinical Trial," JAMA. Jun. 2017, 317(23):2392-2401.
Venter et al., "The sequence of the human genome," Science, Feb. 2001, 291(5507):1304-1351.
Von Hoff et al., "Increased survival in pancreatic cancer with nab-paclitaxel plus gemcitabine," N Engl J Med., Oct. 31, 2013, 369(18):1691-1703.
Von Hoff et al., "Pilot Study Using Molecular Profiling of Patients' Tumors to Find Potential Targets and Select Treatments for Their Refractory Cancers," J. Clin. Oncol., Nov. 20, 2010, 28(33):4877-83.
Wartell et al., "Detecting base pair substitutions in DNA fragments by temperature-gradient gel electrophoresis," Nucleic Acids Res., May 1990, 18(9):2699-2705.
Weis et al., "Detection of rare mRNAs via quantitative RT-PCR," Trends in Genetics, Aug. 1992, 8(8):263-264.

(56) References Cited

OTHER PUBLICATIONS

Whitcombe et al., "A homogeneous fluorescence assay for PCR amplicons: its application to real-time, single-tube genotyping," Clin. Chem., May 1998, 44(5):918-923.

White et al., "Detecting single base substitutions as heteroduplex polymorphisms," Genomics, Feb. 1992, 12(2):301-306.

Wilgenbus et al., "DNA chip technology ante portas," J. Mol. Med., Nov. 1999, 77(11):761-768.

Wu & Wallace, "The ligation amplification reaction (LAR)—amplification of specific DNA sequences using sequential rounds of template-dependent ligation," Genomics, May 1989, 4(4):560-569.

Xiong & Laird, "COBRA: a sensitive and quantitative DNA methylation assay," Nucleic Acids Res., Jun. 1997, 25(12):2532-2534.

Ye et al., "Recent technical strategies to identify diagnostic biomarkers for ovarian cancer," Expert Rev. Proteomics., Feb. 2007, 4(1):121-31.

Young & Davis, "Efficient isolation of genes by using antibody probes," P.N.A.S, Mar. 1983, 80(5):1194-1198.

Zhang et al., "BCL9 promotes epithelial mesenchymal transition and invasion in cisplatin resistant NSCLC cells via β-catenin pathway," Life Sciences, Sep. 2018, 208:284-294.

U.S. Appl. No. 17/334,483, Non-Final Office Action mailed on Sep. 3, 2021, 17 pages.

Extended European Search Report dated Jun. 26, 2024 in EP Patent Application No. 24154019.4. 13 pages.

Lin, Hengjun et al.; "Identification of the predictive genes for the response of colorectal cancer patients to FOLFOX therapy"; Onco Targets and Therapy; 2018; vol. 11; pp. 5943-5955.

Tsuji, S. et al.; "Potential responders to FOLFOX therapy for colorectal cancer by Random Forests analysis"; British Journal of Cancer; published online Nov. 17, 2011; vol. 106; pp. 126-132.

Examination Report No. 1 dated Jul. 5, 2024 in AU Patent Application No. 2019389175. 4 pages.

\* cited by examiner

| | | | SP<br>Chemo+MEKi+EGFRi<br>(BRAF mut) |
|---|---|---|---|
| 1st Line | FOLFOX | FOLFIRI | SP<br>Bevacizumab<br>Anti-EGFR (KRAS WT) |
| 2nd Line | Irinotecan/FOLFIRI | FOLFOX | SP<br>Bevacizumab<br>Anti-EGFR (KRAS WT) |
| | | | SP<br>Anti-PD-L1<br>(MSI-H) |
| 3rd Line | Regorafenib /Lonsurf | | |
| >3 Line | Clinical Trials<br>More chemotherapy (?) | | |

SP-Small Panel: KRAS, NRAS, BRAF, MSI

FIG. 4A

| Characteristics | Responder N=63 (%) | Non-Responder N=42 (%) | p |
|---|---|---|---|
| Age | 58 | 58 | 0.95 |
| Female/Male | 40/60 | 40/60 | 1 |
| Colon/Rectal | 86/14 | 83/17 | 0.96 |
| Left/Right/unknown | 32/27/41 | 33/36/31 | 0.55 |
| Bevacizumab | 84 | 88 | 0.78 |
| Cetuximab | 88 | 17 | 0.29 |

FIG. 4E

CLASSIFYING AN ENTITY FOR FOLFOX TREATMENT

CLAIM OF PRIORITY

This application is a continuation of U.S. application Ser. No. 17/334,483, filed on May 28, 2021, which is a continuation of International Application Serial No. PCT/US2019/064078, filed on Dec. 2, 2019, which claims the benefit of U.S. Provisional Patent Application Serial Nos. 62/774,082, filed on Nov. 30, 2018; 62/788,689, filed on Jan. 4, 2019; and 62/789,495, filed on Jan. 7, 2019. The entire contents of the foregoing are hereby incorporated by reference.

TECHNICAL FIELD

The present disclosure relates to the fields of data structures, data processing, and machine learning, and their use in precision medicine, e.g., the use of molecular profiling to guide personalized treatment recommendations for victims of various diseases and disorders, including without limitation cancer.

BACKGROUND

Drug therapy for cancer patients has long been a challenge. Traditionally, when a patient was diagnosed with cancer, a treating physician would typically select from a defined list of therapy options conventionally associated with the patient's observable clinical factors, such as type and stage of cancer. As a result, cancer patients generally received the same treatment as others who had the same type and stage of cancer. Efficacy of such treatment would be determined through trial and error because patients with the same type and stage of cancer often respond differently to the same therapy. Moreover, when patients failed to respond to any such "one-size-fits-all" treatment, either immediately or when a previously successful treatment began to fail, a physician's treatment choice would often be based on anecdotal evidence at best.

Until the late 2000s, limited molecular testing was available to aid the physician in making a more informed selection from the list of conventional therapies associated with the patient's type of cancer, also known as "cancer lineage." For example, a physician with a breast cancer patient, presented with a list of conventional therapy options including Herceptin®, could have tested the patient's tumor for overexpression of the gene HER2/neu. HER2/neu was known at that time to be associated with breast cancer and responsiveness to Herceptin®. About one third of breast cancer patients whose tumor was found to overexpress the HER2/neu gene would have an initial response to treatment with Herceptin®, although most of those would begin to progress within a year. See, e.g., Bartsch, R. et al., Trastuzumab in the management of early and advanced stage breast cancer, Biologics. 2007 March; 1(1): 19-31. While this type of molecular testing helped explain why a known treatment for a particular type of cancer was more effective in treating some patients with that type of cancer than others, this testing did not identify or exclude any additional therapy options for patients.

Dissatisfied with the one-size-fits-all approach to treating cancer patients, and faced with the reality that many patients' tumors progress and eventually exhaust all conventional therapies, Dr. Daniel Von Hoff, an oncologist, sought to identify additional, unconventional treatment options for his patients. Recognizing the limitations of making treatment decisions based on clinical observation and the limitations of the lineage-specific molecular testing, and believing that effective treatment options were overlooked because of these limitations, Dr. Von Hoff and colleagues developed a system and methods for determining individualized treatment regimens for cancers based on comprehensive assessment of a tumor's molecular characteristics. Their approach to such "molecular profiling" used various testing techniques to gather molecular information from a patient's tumor to create a unique molecular profile independent of the type of cancer. A physician can then use the results of the molecular profile to aid in selection of a candidate treatment for the patient regardless of the stage, anatomical location, or anatomical origin of the cancer cells. See Von Hoff D D, et al., Pilot study using molecular profiling of patients' tumors to find potential targets and select treatments for their refractory cancers. J Clin Oncol. 2010 Nov. 20; 28(33):4877-83. Such a molecular profiling approach may suggest likely benefit of therapies that would otherwise be overlooked by the treating physician, but may likewise suggest unlikely benefit of certain therapies and thereby avoid the time, expense, disease progression and side effects associated with ineffective treatment. Molecular profiling may be particularly beneficial in the "salvage therapy" setting wherein patients have failed to respond to or developed resistance to multiple treatment regimens. In addition, such an approach can also be used to guide decision making for front-line and other standard-of-care treatment regimens.

Colorectal carcinoma (CRC) is the second most common cancer in women and the third most common in men; worldwide there were 835,000 deaths attributable to CRC in 2015 (see Global Burden of Disease Cancer Collaboration, JAMA Oncol. 2017; 3(4):524). While surgery is the first line of treatment, systemic therapy including the administration of 5-fluorouracil/leucovorin combined with oxaliplatin (FOLFOX) or with irinotecan (FOLFIRI) has been shown to be effective in some patients, particularly in colorectal carcinoma patients with distant metastases (Mohelnikova-Duchonova et al., World J Gastroenterol. 2014 Aug. 14; 20(30): 10316-10330).

Although FOLFOX has become a standard of care for CRC in the metastatic and adjuvant settings, only about half of patients respond to the therapy. In addition, 20-100% of patients on FOLFOX will experience at least one of hair loss, pain or peeling of palms and soles, rash, diarrhea, nausea, vomiting, constipation, loss of appetite, difficulty swallowing, mouth sores, heartburn, infection with low white blood cell count, anemia, bruising or bleeding, headache, malaise, numbness, tingling or pain in the extremities, difficulty breathing, cough, and fever; from 4-20% will experience at least one of chest pain, abnormal heartbeat, fainting, reaction to the infusion site, hives, weight gain, weight loss, belly pain, internal bleeding (including black stool, blood in vomit or urine, coughing up blood, vaginal or testicular bleeding, bleeding of the brain), changes in taste, blood clots, liver damage, yellowing of eyes and skin, allergic reactions, change in voice, confusion, dizziness, weakness, blurred vision, light sensitivity, tics or twitches, difficultly with motor skills (walking, using hands, opening mouth, talking, balance and hearing, smelling, eating, sleeping, emptying the bladder), and hearing loss; and up to 3% will experience severe side effects including at least one of heart damage and treatment induced onset of another cancer.

Machine learning models can be configured to analyze labeled training data and then draw inferences from the training data. Once the machine learning model has been trained, sets of data that are not labeled may be provided to the machine learning model as an input. The machine learning model may process the input data, e.g., molecular profiling data, and make predictions about the input based on inferences learned during training. The present disclosure provides a "voting" methodology to combine multiple classifier models to achieve more accurate classification than that achieved by use a single model.

Comprehensive molecular profiling provides a wealth of data concerning the molecular status of patient samples. We have performed such profiling on well over 100,000 tumor patients from practically all cancer lineages and have tracked patient outcomes and responses to treatments in thousands of these patients. For example, our molecular profiling data can be compared to patient benefit or lack of benefit to treatments and processed using machine learning algorithms, e.g., the "voting" methodology, to identify additional biomarker signatures that predict to the effectiveness of various treatments. Here, this "next generation profiling" (NGP) approach has been applied to identify biomarker signatures that predict benefit of the FOLFOX treatment regimen in colorectal cancer patients.

SUMMARY

Comprehensive molecular profiling provides a wealth of data concerning the molecular status of patient samples. Such data can be compared to patient response to treatments to identify biomarker signatures that predict response or non-response to such treatments. This approach has been applied to identify biomarker signatures that correlate with benefit or lack of benefit of the FOLFOX treatment regimen in colorectal cancer patients.

Described herein are methods for training a machine learning model to predict effectiveness of a treatment for a disease or disorder of a subject having a particular set of biomarkers.

Provided herein is a data processing apparatus for generating input data structure for use in training a machine learning model to predict an effectiveness of a treatment of a disease or disorder for a subject, the data processing apparatus including one or more processors and one or more storage devices storing instructions that when executed by the one or more processors cause the one or more processors to perform operations, the operations comprising: obtaining, by the data processing apparatus one or more biomarker data structures and one or more outcome data structures; extracting, by the data processing apparatus, first data representing one or more biomarkers associated with the subject from the one or more biomarker data structures, second data representing the disease or disorder and the treatment from the one or more outcome data structures, and third data representing an outcome of the treatment for the disease or disorder; generating, by the data processing apparatus, a data structure, for input to a machine learning model, based on the first data representing the one or more biomarkers and the second data representing the disease or disorder and the treatment; providing, by the data processing apparatus, the generated data structure as an input to the machine learning model; obtaining, by the data processing apparatus, an output generated by the machine learning model based on the machine learning model's processing of the generated data structure; determining, by the data processing apparatus, a difference between the third data representing an outcome of the treatment for the disease or disorder and the output generated by the machine learning model; and adjusting, by the data processing apparatus, one or more parameters of the machine learning model based on the difference between the third data representing an outcome of the treatment for the disease or disorder and the output generated by the machine learning model.

In some embodiments, the set of one or more biomarkers include one or more biomarkers listed in any one of Tables 2-8. In some embodiments, the set of one or more biomarkers include each of the biomarkers in Tables 2-8. In some embodiments, the set of one or more biomarkers includes at least one of the biomarkers in Tables 2-8, optionally wherein the set of one or more biomarkers comprises the markers in Table 5, Table 6, Table 7, Table 8, or any combination thereof.

Also provided herein is a data processing apparatus for generating input data structure for use in training a machine learning model to predict treatment responsiveness of a subject to a particular treatment, the data processing apparatus including one or more processors and one or more storage devices storing instructions that when executed by the one or more processors cause the one or more processors to perform operations, the operations comprising: obtaining, by the data processing apparatus, a first data structure that structures data representing a set of one or more biomarkers associated with a subject from a first distributed data source, wherein the first data structure includes a key value that identifies the subject; storing, by the data processing apparatus, the first data structure in one or more memory devices; obtaining, by the data processing apparatus, a second data structure that structures data representing outcome data for the subject having the one or more biomarkers from a second distributed data source, wherein the outcome data includes data identifying a disease or disorder, a treatment, and an indication of the effectiveness of the treatment, wherein second data structure also includes a key value that identifies the subject; storing, by the data processing apparatus, the second data structure in the one or more memory devices; generating, by the data processing apparatus and using the first data structure and the second data structure stored in the memory devices, a labeled training data structure that includes (i) data representing the set of one or more biomarkers, the disease or disorder, and the treatment and (ii) a label that provides an indication of the effectiveness of the treatment for the disease or disorder, wherein generating, by the data processing apparatus and using the first data structure and the second data structure includes correlating, by the data processing apparatus, the first data structure that structures the data representing the set of one or more biomarkers associated with the subject with the second data structure representing outcome data for the subject having the one or more biomarkers based on the key value that identifies the subject; and training, by the data processing apparatus, a machine learning model using the generated label training data structure, wherein training the machine learning model using the generated labeled training data structure includes providing, by the data processing apparatus and to the machine learning model, the generated label training data structure as an input to the machine learning model.

In some embodiments, the operations further comprise: obtaining, by the data processing apparatus and from the machine learning model, an output generated by the machine learning model based on the machine learning model's processing of the generated labeled training data structure; and determining, by the data processing apparatus, a difference between the output generated by the machine learning model and the label that provides an indication of the effectiveness of the treatment for the disease or disorder.

In some embodiments, the operations further comprise: adjusting, by the data processing apparatus, one or more parameters of the machine learning model based on the determined difference between the output generated by the machine learning model and the label that provides an indication of the effectiveness of the treatment for the disease or disorder.

In some embodiments, the set of one or more biomarkers include one or more biomarkers listed in any one of Tables 2-8. In some embodiments, the set of one or more biomarkers include each of the biomarkers in Tables 2-8. In some embodiments, the set of one or more biomarkers includes at least one of the biomarkers in Tables 2-8, optionally wherein the set of one or more biomarkers comprises the markers in Table 5, Table 6, Table 7, Table 8, or any combination thereof.

Relatedly, provided herein is a method comprising steps that correspond to each of the operations of the data processing apparatus described above. Still further, provided herein is a system comprising one or more computers and one or more storage media storing instructions that, when executed by the one or more computers, cause the one or more computers to perform each of the operations described with reference to the data processing apparatus described above. Yet further still, provided herein is a non-transitory computer-readable medium storing software comprising instructions executable by one or more computers which, upon such execution, cause the one or more computers to perform the operations described with reference to the data processing apparatus described above.

In another aspect, provided herein is a method for classification of an entity, the method comprising: for each particular machine learning model of a plurality of machine learning models: i) providing, to the particular machine learning model that has been trained to determine an prediction or classification, input data representing a description of an entity to be classified; and ii) obtaining output data, generated by the particular machine learning model based on the particular machine learning model's processing the input data, that represents an entity classification into an initial entity class of multiple candidate entity classes; providing, to a voting unit, the output data obtained for each of the plurality of machine learning models, wherein the provided output data includes data representing an initial entity class determined by each of the plurality of machine learning models; and determining, by the voting unit and based on the provided output data, an actual entity class for the entity.

In some embodiments, the actual entity class for the entity is determined by applying a majority rule to the provided output data.

In some embodiments, determining, by the voting unit and based on the provided output data, an actual entity class for the entity comprises: determining, by the voting unit, a number of occurrences of each initial entity class of the multiple candidate entity classes; and selecting, by the voting unit, the initial entity class of the multiple candidate entity classes having the highest number of occurrences.

In some embodiments, each machine learning model of the plurality of machine learning models comprises a random forest classification algorithm, support vector machine, logistic regression, k-nearest neighbor model, artificial neural network, naïve Bayes model, quadratic discriminant analysis, or Gaussian processes model.

In some embodiments, each machine learning model of the plurality of machine learning models comprises a random forest classification algorithm.

In some embodiments, the plurality of machine learning models includes multiple representations of a same type of classification algorithm.

In some embodiments, the input data represents a description of (i) entity attributes and (ii) a treatment for a disease or disorder.

In some embodiments, the multiple candidate entity classes include a responsive class or a non-responsive class.

In some embodiments, the entity attributes includes one or more biomarkers for the entity.

In some embodiments, the one or more biomarkers includes a panel of genes that is less than all known genes of the entity.

In some embodiments, the one or more biomarkers includes a panel of genes that comprises all known genes for the entity.

In some embodiments, the input data further includes data representing a description of the disease or disorder.

Relatedly, provided herein is a system comprising one or more computers and one or more storage media storing instructions that, when executed by the one or more computers, cause the one or more computers to perform each of the operations described with reference to the method for classification of an entity described above. Further still, provided herein is a non-transitory computer-readable medium storing software comprising instructions executable by one or more computers which, upon such execution, cause the one or more computers to perform the operations described with reference to the method for classification of an entity described above.

In still another aspect, provided herein is a method comprising: obtaining a biological sample comprising cells from a cancer in a subject; and performing an assay to assess at least one biomarker in the biological sample, wherein the biomarkers comprise at least one of the following: (a) Group 1 comprising 1, 2, 3, 4, 5 or all 6 of MYC, EP300, U2AF1, ASXL1, MAML2, and CNTRL; (b) Group 2 comprising 1, 2, 3, 4, 5, 6, 7, or all 8 of MYC, EP300, U2AF1, ASXL1, MAML2, CNTRL, WRN, and CDX2; (c) Group 3 comprising 1, 2, 3, 4, 5, 6, 7, 8, 9, 10, 11, 12, 13, or all 14 of BCL9, PBX1, PRRX1, INHBA, YWHAE, GNAS, LHFPL6, FCRL4, HOXA11, AURKA, BIRC3, IKZF1, CASP8, and EP300; (d) Group 4 comprising 1, 2, 3, 4, 5, 6, 7, 8, 9, 10, 11, 12, or all 13 of PBX1, BCL9, INHBA, PRRX1, YWHAE, GNAS, LHFPL6, FCRL4, AURKA, IKZF1, CASP8, PTEN, and EP300; (e) Group 5 comprising 1, 2, 3, 4, 5, 6, 7, 8, 9, 10, 11, or all 12 of BCL9, PBX1, PRRX1, INHBA, GNAS, YWHAE, LHFPL6, FCRL4, PTEN, HOXA11, AURKA, and BIRC3; (f) Group 6 comprising 1, 2, 3, 4, or all 5 of BCL9, PBX1, PRRX1, INHBA, and YWHAE; (g) Group 7 comprising 1, 2, 3, 4, 5, 6, 7, 8, 9, 10, 11, 12, 13, 14 or all 15 of BCL9, PBX1, GNAS, LHFPL6, CASP8, ASXL1, FH, CRKL, MLF1, TRRAP, AKT3, ACKR3, MSI2, PCM1, and MNX1; (h) Group 8 comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or all 45 of BX1, GNAS, AURKA, CASP8, ASXL1, CRKL, MLF1, GAS7, MN1, SOX10, TCL1A, LMO1, BRD3, SMARCA4, PER1, PAX7, SBDS, SEPT5, PDGFB, AKT2, TERT, KEAP1, ETV6, TOP1, TLX3, COX6C, NFIB, ARFRP1, ARID1A, MAP2K4, NFKBIA, WWTR1, ZNF217, IL2, NSD3, CREB1, BRIP1, SDC4, EWSR1, FLT3, FLT1, FAS, CCNE1, RUNX1T1, and EZR; and (i) Group 9 comprising 1, 2, 3, 4, 5, 6, 7, 8, 9, 10, or all 11 of BCL9, PBX1, PRRX1, INHBA, YWHAE, GNAS, LHFPL6, FCRL4, BIRC3, AURKA, and HOXA11.

In some embodiments, the biological sample comprises formalin-fixed paraffin-embedded (FFPE) tissue, fixed tissue, a core needle biopsy, a fine needle aspirate, unstained slides, fresh frozen (FF) tissue, formalin samples, tissue comprised in a solution that preserves nucleic acid or protein molecules, a fresh sample, a malignant fluid, a bodily fluid, a tumor sample, a tissue sample, or any combination thereof.

In some embodiments, the biological sample comprises cells from a solid tumor.

In some embodiments, the biological sample comprises a bodily fluid.

In some embodiments, the bodily fluid comprises a malignant fluid, a pleural fluid, a peritoneal fluid, or any combination thereof.

In some embodiments, the bodily fluid comprises peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid, pre-ejaculatory fluid, female ejaculate, sweat, fecal matter, tears, cyst fluid, pleural fluid, peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyst cavity fluid, or umbilical cord blood.

In some embodiments, the assessment comprises determining a presence, level, or state of a protein or nucleic acid for each biomarker, optionally wherein the nucleic acid comprises deoxyribonucleic acid (DNA), ribonucleic acid (RNA), or a combination thereof. In some embodiments: (a) the presence, level or state of the protein is determined using immunohistochemistry (IHC), flow cytometry, an immunoassay, an antibody or functional fragment thereof, an aptamer, or any combination thereof; and/or (b) the presence, level or state of the nucleic acid is determined using polymerase chain reaction (PCR), in situ hybridization, amplification, hybridization, microarray, nucleic acid sequencing, dye termination sequencing, pyrosequencing, next generation sequencing (NGS; high-throughput sequencing), or any combination thereof.

In some embodiments, the state of the nucleic acid comprises a sequence, mutation, polymorphism, deletion, insertion, substitution, translocation, fusion, break, duplication, amplification, repeat, copy number, copy number variation (CNV; copy number alteration; CNA), or any combination thereof.

In some embodiments, the state of the nucleic acid comprises a copy number.

In some embodiments, the method comprises performing an assay to determine a copy number of all of members of Group 1 (i.e., MYC, EP300, U2AF1, ASXL1, MAML2, and CNTRL), or proximate genomic regions thereto.

In some embodiments, the method comprises performing an assay to determine a copy number of all members of Group 2 (i.e., MYC, EP300, U2AF1, ASXL1, MAML2, CNTRL, WRN, and CDX2), or proximate genomic regions thereto.

In some embodiments, the method comprises performing an assay to determine a copy number of all members of Group 3 (i.e., BCL9, PBX1, PRRX1, INHBA, YWHAE, GNAS, LHFPL6, FCRL4, HOXA11, AURKA, BIRC3, IKZF1, CASP8, and EP300), or proximate genomic regions thereto.

In some embodiments, the method comprises performing an assay to determine a copy number of all members of Group 4 (i.e., PBX1, BCL9, INHBA, PRRX1, YWHAE, GNAS, LHFPL6, FCRL4, AURKA, IKZF1, CASP8, PTEN, and EP300), or proximate genomic regions thereto.

In some embodiments, the method comprises performing an assay to determine a copy number of all members of Group 5 (i.e., BCL9, PBX1, PRRX1, INHBA, GNAS, YWHAE, LHFPL6, FCRL4, PTEN, HOXA11, AURKA, and BIRC3), or proximate genomic regions thereto.

In some embodiments, the method comprises performing an assay to determine a copy number of all members of Group 6 (i.e., BCL9, PBX1, PRRX1, INHBA, and YWHAE), or proximate genomic regions thereto.

In some embodiments, the method comprises performing an assay to determine a copy number of all members of Group 7 (i.e., BCL9, PBX1, GNAS, LHFPL6, CASP8, ASXL1, FH, CRKL, MLF1, TRRAP, AKT3, ACKR3, MSI2, PCM1, and MNX1), or proximate genomic regions thereto.

In some embodiments, the method comprises performing an assay to determine a copy number of all members of Group 8 (i.e., BX1, GNAS, AURKA, CASP8, ASXL1, CRKL, MLF1, GAS7, MN1, SOX10, TCL1A, LMO1, BRD3, SMARCA4, PER1, PAX7, SBDS, SEPT5, PDGFB, AKT2, TERT, KEAP1, ETV6, TOP1, TLX3, COX6C, NFIB, ARFRP1, ARID1A, MAP2K4, NFKBIA, WWTR1, ZNF217, IL2, NSD3, CREB1, BRIP1, SDC4, EWSR1, FLT3, FLT1, FAS, CCNE1, RUNX1T1, and EZR), or proximate genomic regions thereto.

In some embodiments, the method comprises performing an assay to determine a copy number of all members of Group 9 (i.e., BCL9, PBX1, PRRX1, INHBA, YWHAE, GNAS, LHFPL6, FCRL4, BIRC3, AURKA, and HOXA11), or proximate genomic regions thereto.

In some embodiments, the method comprises performing an assay to determine a copy number of: (a) at least one or all members of Group 1 and Group 2, or proximate genomic regions thereto; (b) at least one or all members of Group 3, or proximate genomic regions thereto; or (c) at least one or all members of Group 2, Group 6, Group 7, Group 8, and Group 9, or proximate genomic regions thereto.

In some embodiments, the method further comprises comparing the copy number of the biomarkers to a reference copy number (e.g., diploid), and identifying biomarkers that have a copy number variation (CNV).

In some embodiments, the method further comprises generating a molecular profile that identifies the genes or proximate regions thereto that have a CNV.

In some embodiments, a presence or level of PTEN protein is determined, optionally wherein the PTEN protein presence or level is determined using immunohistochemistry (IHC).

In some embodiments, the method further comprises determining a level of proteins comprising TOPO1 and one or more mismatch repair proteins (e.g., MLH1, MSH2, MSH6, and PMS2), optionally wherein the PTEN protein presence or level is determined using immunohistochemistry (IHC).

In some embodiments, the method further comprises comparing the level of the protein or proteins to a reference level for the protein or each of the proteins.

In some embodiments, the method further comprises generating a molecular profile that identifies the proteins that have a level that differs from the reference level, e.g., that is significantly different from the reference level.

In some embodiments, the method further comprises selecting a treatment of likely benefit based on the biomarkers assessed, optionally wherein the treatment comprises 5-fluorouracil/leucovorin combined with oxaliplatin (FOLFOX) or an alternate treatment thereto, wherein optionally the alternate treatment comprises 5-fluorouracil/leucovorin combined with irinotecan (FOLFIRI).

In some embodiments, selecting a treatment of likely benefit is based on: (a) the copy number determined for the Groups described above; and/or (b) the molecular profile determined as described above.

In some embodiments, selecting a treatment of likely benefit based on the copy number determined for the Groups described above comprises use of a voting module.

In some embodiments, the voting module is as provided herein.

In some embodiments, the voting module comprises use of at least one random forest model.

In some embodiments, use of the voting module comprises applying a machine learning classification model to the copy numbers obtained for each of Group 2, Group 6, Group 7, Group 8, and Group 9 (see above), optionally wherein each machine learning classification model is a random forest model, optionally wherein the random forest models are as described in Table 10 below.

In some embodiments, the subject has not previously been treated with the treatment of likely benefit.

In some embodiments, the cancer comprises a metastatic cancer, a recurrent cancer, or a combination thereof.

In some embodiments, the subject has not previously been treated for the cancer.

In some embodiments, the method further comprises administering the treatment of likely benefit to the subject.

In some embodiments, progression free survival (PFS), disease free survival (DFS), or lifespan is extended by the administration.

In some embodiments, the cancer comprises an acute lymphoblastic leukemia; acute myeloid leukemia; adrenocortical carcinoma; AIDS-related cancer; AIDS-related lymphoma; anal cancer; appendix cancer; astrocytomas; atypical teratoid/rhabdoid tumor; basal cell carcinoma; bladder cancer; brain stem glioma; brain tumor, brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma; breast cancer; bronchial tumors; Burkitt lymphoma; cancer of unknown primary site (CUP); carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor.

In some embodiments, the cancer comprises an acute myeloid leukemia (AML), breast carcinoma, cholangiocarcinoma, colorectal adenocarcinoma, extrahepatic bile duct adenocarcinoma, female genital tract malignancy, gastric adenocarcinoma, gastroesophageal adenocarcinoma, gastrointestinal stromal tumor (GIST), glioblastoma, head and neck squamous carcinoma, leukemia, liver hepatocellular carcinoma, low grade glioma, lung bronchioloalveolar carcinoma (BAC), non-small cell lung cancer (NSCLC), lung small cell cancer (SCLC), lymphoma, male genital tract malignancy, malignant solitary fibrous tumor of the pleura (MSFT), melanoma, multiple myeloma, neuroendocrine tumor, nodal diffuse large B-cell lymphoma, non epithelial ovarian cancer (non-EOC), ovarian surface epithelial carcinoma, pancreatic adenocarcinoma, pituitary carcinomas, oligodendroglioma, prostatic adenocarcinoma, retroperitoneal or peritoneal carcinoma, retroperitoneal or peritoneal sarcoma, small intestinal malignancy, soft tissue tumor, thymic carcinoma, thyroid carcinoma, or uveal melanoma.

In some embodiments, the cancer comprises a colorectal cancer.

Further provided herein is a method of selecting a treatment for a subject who has a colorectal cancer, the method comprising: obtaining a biological sample comprising cells from the colorectal cancer; performing next generation sequencing on genomic DNA from the biological sample to determine a copy number for each of the following groups of genes or proximate genomic regions thereto: (a) Group 2 comprising 1, 2, 3, 4, 5, 6, 7, or all 8 of MYC, EP300, U2AF1, ASXL1, MAML2, CNTRL, WRN, and CDX2; (b) Group 6 comprising 1, 2, 3, 4, or all 5 of BCL9, PBX1, PRRX1, INHBA, and YWHAE; (c) Group 7 comprising 1, 2, 3, 4, 5, 6, 7, 8, 9, 10, 11, 12, 13, 14 or all 15 of BCL9, PBX1, GNAS, LHFPL6, CASP8, ASXL1, FH, CRKL, MLF1, TRRAP, AKT3, ACKR3, MSI2, PCM1, and MNX1; (d) Group 8 comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or all 45 of BX1, GNAS, AURKA, CASP8, ASXL1, CRKL, MLF1, GAS7, MN1, SOX10, TCL1A, LMO1, BRD3, SMARCA4, PER1, PAX7, SBDS, SEPT5, PDGFB, AKT2, TERT, KEAP1, ETV6, TOP1, TLX3, COX6C, NFIB, ARFRP1, ARID1A, MAP2K4, NFKBIA, WWTR1, ZNF217, IL2, NSD3, CREB1, BRIP1, SDC4, EWSR1, FLT3, FLT1, FAS, CCNE1, RUNX1T1, and EZR; and (e) Group 9 comprising 1, 2, 3, 4, 5, 6, 7, 8, 9, 10, or all 11 of BCL9, PBX1, PRRX1, INHBA, YWHAE, GNAS, LHFPL6, FCRL4, BIRC3, AURKA, and HOXA11; applying a machine learning classification model to the copy numbers obtained for each of Group 2, Group 6, Group 7, Group 8, and Group 9, optionally wherein each machine learning classification model is a random forest model, optionally wherein the random forest models are as described in Table 10; obtaining an indication from each machine learning classification model whether the subject is likely to benefit from treatment with 5-fluorouracil/leucovorin combined with oxaliplatin (FOLFOX); and selecting FOLFOX if the majority of the machine learning classification models indicate that the subject is likely to benefit from the treatment and selecting an alternate treatment to FOLFOX if the majority of the machine learning classification models indicate that the subject is not likely to benefit from the FOLFOX, optionally wherein the alternate treatment is 5-fluorouracil/leucovorin combined with irinotecan (FOLFIRI). In some embodiments, the method further comprises administering the selected treatment to the subject.

Still further provided herein is a method for generating a molecular profiling report comprising preparing a report summarizing results of performing the methods described above. In some embodiments, the report comprises: (a) the treatment of likely benefit determined as disclosed above; or (b) the selected treatment determined as disclosed above. In some embodiments, the report is computer generated; is a printed report or a computer file; or is accessible via a web portal.

Relatedly, provided herein are systems for identifying a therapy for a cancer in a subject, the system comprising: (a) at least one host server; (b) at least one user interface for accessing the at least one host server to access and input data; (c) at least one processor for processing the inputted data; (d) at least one memory coupled to the processor for storing the processed data and instructions for: (1) accessing results of analyzing the biological sample as described above; and (2) determining the treatment of likely benefit as described above or the selected treatment as described above; and (e) at least one display for displaying the treatment of the cancer, wherein the treatment is FOLFOX or an alternative thereto, e.g., FOLFIRI.

In some embodiments, the at least one display comprises a report comprising the results of analyzing the biological sample and the treatment with likely benefit for or selected for treatment of the cancer.

In addition, provided herein are methods of providing recommendations for treating a cancer to provide longer progression free survival, longer disease free survival, longer overall survival, or an extended lifespan comprising: obtaining a biological sample comprising a nucleic acid and/or a protein from an individual diagnosed with a cancer; performing a molecular test on the biological sample to determine one or more molecular characteristics selected from the group consisting of: nucleic acid sequence of a set of target genes or portions thereof; presence of a copy number variation of a set of target genes; presence of a gene fusion or other genomic alteration; level of one or more of a set of proteins and/or transcripts; and or epigenetic status of a set of target genes, e.g., as described herein, thereby generating a molecular profile for the cancer; comparing the molecular profile of the cancer to a reference molecular profile for the cancer type; generating a list of molecular characteristics that exhibit a difference, e.g., a significant difference, as compared to the reference molecular profile; and generating a list of one or more therapeutic recommendations for the individual based on the list of molecular characteristics that exhibit a difference as compared to the reference sequence profile of the target gene.

In some embodiments, the molecular test is at least one of NextGen sequencing, Sanger sequencing, ISH, fragment analysis, PCR, IHC, and immunoassay.

In some embodiments, the biological sample comprises cells, a tissue sample, a blood sample or a combination thereof.

In some embodiments, the molecular test detects at least one of a mutation, polymorphism, deletion, insertion, substitution, translocation, fusion, break, duplication, amplification or repeat.

In some embodiments, the nucleic acid sequence comprises a deoxyribonucleic acid sequence.

In some embodiments, the nucleic acid sequence comprises a ribonucleic acid sequence.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
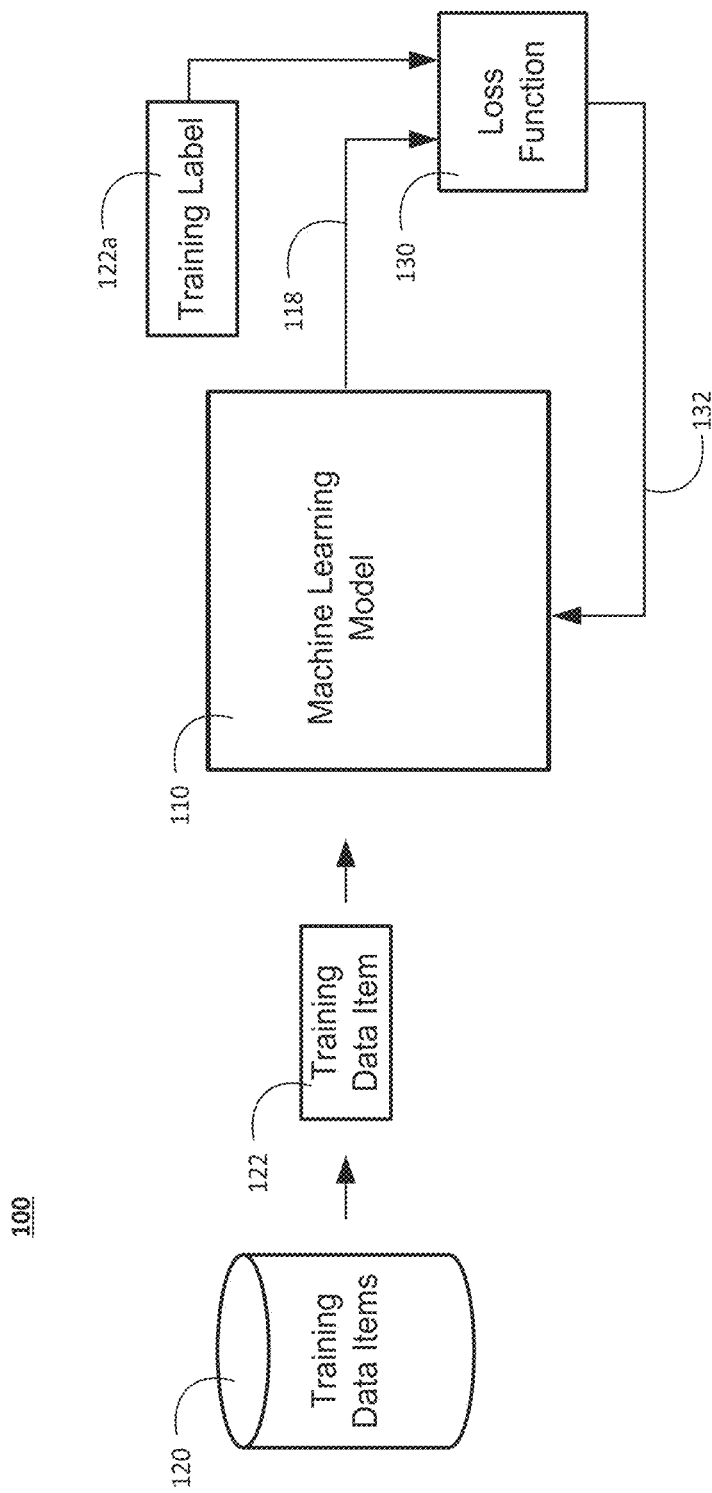
FIG. 1A is a block diagram of an example of a prior art system for training a machine learning model.

Described herein are methods and systems for identifying therapeutic agents for use in treatments on an individualized basis by using molecular profiling, including systems, methods, apparatuses, and computer programs for training a machine learning model, and then using the trained machine learning model, to predict the effectiveness of a treatment for a disease or disorder of a subject. In some implementations, the systems can include one or more computer programs on one or more computers in one or more locations, e.g., configured for use in a method described herein.

Aspects of the present disclosure are directed towards a system that generates a set of one or more training data structures that can be used to train a machine learning model to provide various classifications, such as characterizing a phenotype of a biological sample. Characterizing a phenotype can include providing a diagnosis, prognosis, theranosis or other relevant classification. For example, the classification can be predicting a disease state or effectiveness of a treatment for a disease or disorder of a subject having a particular set of biomarkers. Once trained, the trained machine learning model can then be used to process input data provided by the system and make predictions based on the processed input data. The input data may include a set of features related to a subject such data representing one or more subject biomarkers and data representing a disease or disorder, In some embodiments, the input data may further include features representing a proposed treatment type and make a prediction describing the subject's likely responsive to the treatment. The prediction may include data that is output by the machine learning model based on the machine learning model's processing of a specific set of features provided as an input to the machine learning model. The data may include data representing one or more subject biomarkers, data representing a disease or disorder, and data representing a proposed treatment type as desired.

Innovative aspects of the present disclosure include the extraction of specific data from incoming data streams for use in generating training data structures. Of critical importance is the selection of a specific set of one or more biomarkers for inclusions in the training data structure. This is because the presence, absence or state of particular biomarkers may be indicative of the desired classification. For example, certain biomarkers may be selected to determine whether a treatment for a disease or disorder will be effective or not effective. By way of example, in the present disclosure, the Applicant puts forth specific sets of biomarkers that, when used to train a machine learning model, result in a trained model that can more accurately predict treatment efficiency than using a different set of biomarkers. See Examples 2-4.

The system is configured to obtain output data generated by the trained machine learning model based on the machine learning model's processing of the data. In various embodiments, the data comprises biological data representing one or more biomarkers, data representing a disease or disorder, and data representing a treatment type. The system may then predict effectiveness of a treatment for a subject having a particular set of biomarkers. In some implementations, the disease or disorder may include a type of cancer and the treatment for the subject may include one or more therapeutic agents, e.g., small molecule drugs, biologics, and various combinations thereof. In this setting, output of the trained machine learning model that is generated based on trained machine learning model processing of the input data that includes the set of biomarkers, the disease or disorder and the treatment type includes data representing the level of responsiveness that the subject will be have to the treatment for the disease or disorder.

In some implementations, the output data generated by the trained machine learning model may include a probability of the desired classification. By way of illustration, such probability may be a probability that the subject will favorably respond to the treatment for the disease or disorder. In other implementations, the output data may include any output data generated by the trained machine learning model based on the trained machine learning model's processing of the input data. In some embodiments, the input data comprising set of biomarkers, data representing the disease or disorder, and data representing the treatment type.

In some implementations, the training data structures generated by the present disclosure may include a plurality of training data structures that each include fields representing feature vector corresponding to a particular training sample. The feature vector includes a set of features derived from, and representative of, a training sample. The training sample may include, for example, one or more biomarkers of a subject, a disease or disorder of the subject, and a proposed treatment for the disease or disorder. The training data structures are flexible because each respective training data structure may be assigned a weight representing each respective feature of the feature vector. Thus, each training data structure of the plurality of training data structures can be particularly configured to cause certain inferences to be made by a machine learning model during training.

Consider a non-limiting example wherein the model is trained to make a prediction of likely benefit of a certain treatment for a disease or disorder. As a result, the novel training data structures that are generated in accordance with this specification are designed to improve the performance of a machine learning model because they can be used to train a machine learning model to predict effectiveness of the treatment for a disease or disorder of a subject having a particular set of biomarkers. By way of example, a machine learning model that could not perform predictions regarding the effectiveness of a treatment for a disease or disorder of a subject having a particular set of biomarkers prior to being trained using the training data structures, system, and operations described by this disclosure can learn to make predictions regarding the effectiveness of a treatment for a disease or disorder of a subject by being trained using the training data structures, systems and operations described by the present disclosure. Accordingly, this process takes an otherwise general purpose machine learning model and changes the general purpose machine leaning model into a specific computer for perform a specific task of performing predicting the effectiveness of a treatment for a disease or disorder of a subject having a particular set of biomarkers.

FIG. 1A is a block diagram of an example of a prior art system 100 for training a machine learning model 110. In some implementations, the machine learning model may be, for example, a support vector machine. Alternatively, the machine learning model may include a neural network model, a linear regression model, a random forest model, a logistic regression model, a naive Bayes model, a quadratic discriminant analysis model, a K-nearest neighbor model, a support vector machine, or the like. The machine learning model training system 100 may be implemented as computer programs on one or more computers in one or more locations, in which the systems, components, and techniques described below can be implemented. The machine learning model training system 100 trains the machine learning model 110 using training data items from a database (or data set) 120 of training data items. The training data items may include a plurality of feature vectors. Each training vector may include a plurality of values that each correspond to a particular feature of a training sample that the training vector represents. The training features may be referred to as independent variables. In addition, the system 100 maintains a respective weight for each feature that is included in the feature vectors.

The machine learning model 110 is configured to receive an input training data item 122 and to process the input training data item 122 to generate an output 118. The input training data item may include a plurality of features (or independent variables "X") and a training label (or dependent variable "Y"). The machine learning model may be trained using the training items, and once trained, is capable of predicting X=f(Y).

To enable machine learning model 110 to generate accurate outputs for received data items, the machine learning model training system 100 may train the machine learning model 110 to adjust the values of the parameters of the machine learning model 110, e.g., to determine trained values of the parameters from initial values. These parameters derived from the training steps may include weights that can be used during the prediction stage using the fully trained machine learning model 110.

In training, the machine learning model 110, the machine learning model training system 100 uses training data items stored in the database (data set) 120 of labeled training data items. The database 120 stores a set of multiple training data items, with each training data item in the set of multiple training items being associated with a respective label. Generally, the label for the training data item identifies a correct classification (or prediction) for the training data item, i.e., the classification that should be identified as the classification of the training data item by the output values generated by the machine learning model 110. With reference to FIG. 1A, a training data item 122 may be associated with a training label 122a.

The machine learning model training system 100 trains the machine learning model 110 to optimize an objective function. Optimizing an objective function may include, for example, minimizing a loss function 130. Generally, the loss function 130 is a function that depends on the (i) output 118 generated by the machine learning model 110 by processing a given training data item 122 and (ii) the label 122a for the training data item 122, i.e., the target output that the machine learning model 110 should have generated by processing the training data item 122.

Conventional machine learning model training system 100 can train the machine learning model 110 to minimize the (cumulative) loss function 130 by performing multiple iterations of conventional machine learning model training techniques on training data items from the database 120, e.g., hinge loss, stochastic gradient methods, stochastic gradient descent with backpropagation, or the like, to iteratively adjust the values of the parameters of the machine learning model 110. A fully trained machine learning model 110 may then be deployed as a predicting model that can be used to make predictions based on input data that is not labeled.

Figure 1B:
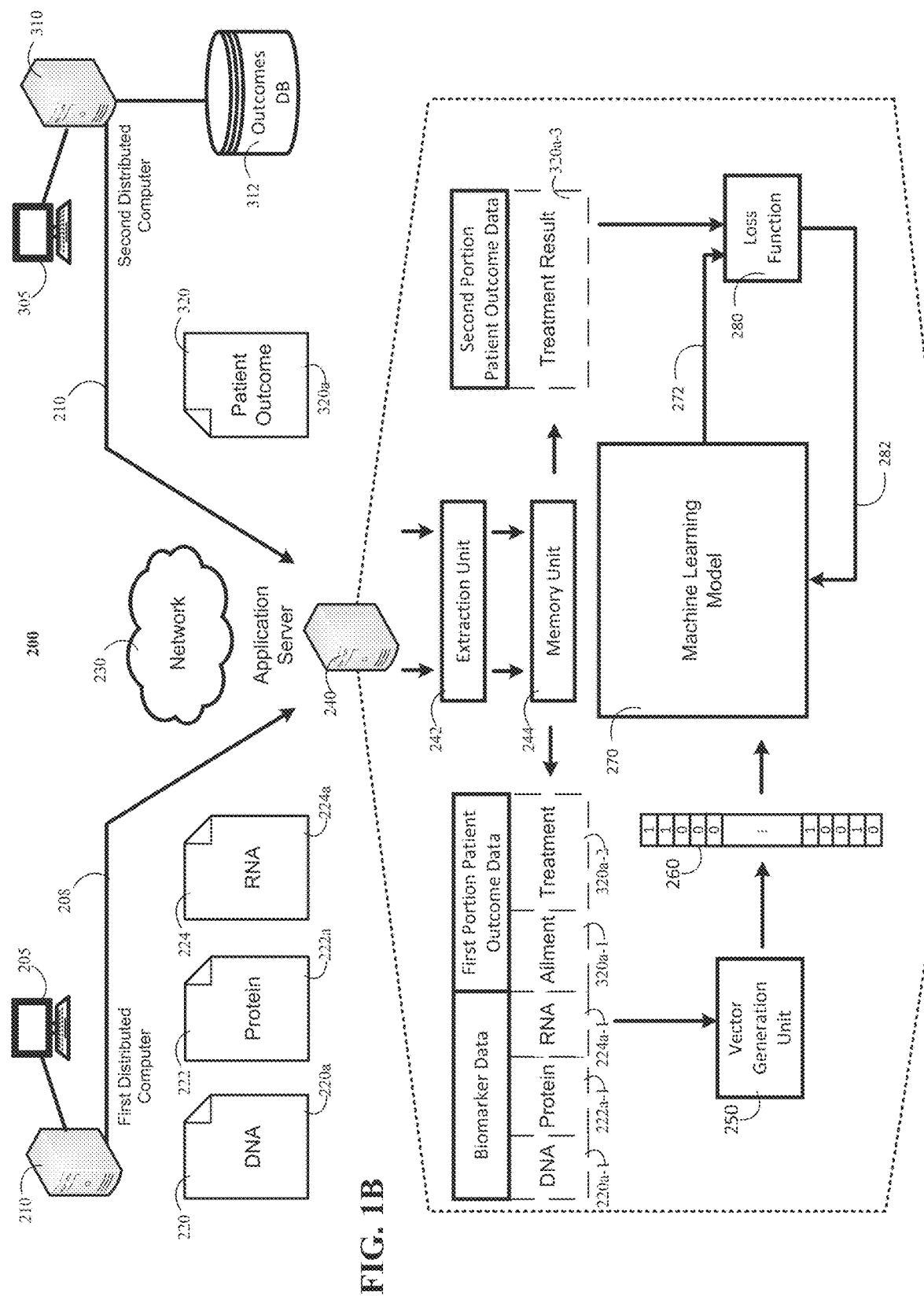
FIG. 1B is a block diagram of a system that generates training data structures for training a machine learning model to predict effectiveness of a treatment for a disease or disorder of a subject having a particular set of biomarkers.

FIG. 1B is a block diagram of a system 200 that generates training data structures for training a machine learning model to predict effectiveness of a treatment for a disease or disorder of a subject having a particular set of biomarkers.

The system 200 includes two or more distributed computers 210, 310, a network 230, and an application server 240. The application server 240 includes an extraction unit 242, a memory unit 244, a vector generation unit 250, and a machine learning model 270. The machine learning model 270 may include one or more of a vector support machine, a neural network model, a linear regression model, a random forest model, a logistic regression model, a naive Bayes model, a quadratic discriminant analysis, model, a K-nearest neighbor model, a support vector machine, or the like. Each distributed computer 210, 310 may include a smartphone, a tablet computer, laptop computer, or a desktop computer, or the like. Alternatively, the distributed computers 210, 310 may include server computers that receive data input by one or more terminals 205, 305, respectively. The terminal computers 205, 305 may include any user device including a smartphone, a tablet computer, a laptop computer, a desktop computer or the like. The network 230 may include one or more networks 230 such as a LAN, a WAN, a wired Ethernet network, a wireless network, a cellular network, the Internet, or any combination thereof.

The application server 240 is configured to obtain, or otherwise receive, data records 220, 222, 224, 320 provided by one or more distributed computers such as the first distributed computer 210 and the second distributed computer 310 using the network 230. In some implementations, each respective distributed computer 210, 310 may provide different types of data records 220, 222, 224, 320. For example, the first distributed computer 210 may provide biomarker data records 220, 222, 224 representing biomarkers for a subject and the second distributed computer 310 may provide outcome data 320 representing outcome data for a subject obtained from the outcomes database 312.

The biomarker data records 220, 222, 224 may include any type of biomarker data that describes a biometric attributes of a subject. By way of example, the example of FIG. 1B shows the biomarker data records as including data records representing DNA biomarkers 220, protein biomarkers 222, and RNA data biomarkers 224. These biomarker data records may each include data structures having fields that structure information 220a, 222a, 224a describing biomarkers of a subject such as a subject's DNA biomarkers 220a, protein biomarkers 222a, or RNA biomarkers 224a. However, the present disclosure need not be so limited. For example, the biomarker data records 220, 222, 224 may include next generation sequencing data such as DNA alterations. Such next generation sequencing data may include single variants, insertions and deletions, substitution, translocation, fusion, break, duplication, amplification, loss, copy number, repeat, total mutational burden, microsatellite instability, or the like. Alternatively, or in addition, the biomarker data records 220, 222, 224 may also include in situ hybridization data such as DNA copies. Such in situ hybridization data may include gene copies, gene translocations, or the like. Alternatively, or in addition, the biomarker data records 220, 222, 224 may include RNA data such as gene expression or gene fusion, including without limitation whole transcriptome sequencing. Alternatively, or in addition, the biomarker data records 220, 222, 224 may include protein expression data such as obtained using immunohistochemistry (IHC). Alternatively, or in addition, the biomarker data records 220, 222, 224 may include ADAPT data such as complexes.

In some implementations, the set of one or more biomarkers include one or more biomarkers listed in any one of Tables 2-8. However, the present disclosure need not be so limited, and other types of biomarkers may be used instead. For example, the biomarker data may be obtained by whole exome sequencing, whole transcriptome sequencing, or a combination thereof.

The outcome data records 320 may describe outcomes of a treatment for a subject. For example, the outcome data records 320 obtained from the outcome database 312 may include one or more data structures having fields that structure data attributes of a subject such as a disease or disorder 320a, a treatment 320a the subject received for the disease or disorder, a treatment results 320a, or a combination of both. In addition, the outcome data records 320 may also include fields that structure data attributes describing details of the treatment and a subject's response to the treatment. An example of a disease or disorder may include, for example, a type of cancer. A type of treatment may include, for example, a type of drug, biologic, or other treatment that the subject has received for the disease or disorder included in the outcome data records 320. A treatment result may include data representing a subject's outcome of a treatment regimen such as beneficial, moderately beneficial, not beneficial, or the like. In some implementations, the treatment result may include descriptions of a cancerous tumor at the end of treatment such as an amount that the tumor was reduced, an overall size of the tumor after treatment, or the like. Alternatively, or in addition, the treatment result may include a number or ratio of white blood cells, red blood cells, or the like. Details of the treatment may include dosage amounts such as an amount of drug taken, a drug regimen, number of missed doses, or the like. Accordingly, though the example of FIG. 1B shows that outcome data may include a disease or disorder, a treatment, and a treatment result, the outcome data may include other types of information, as described herein. Moreover, there is no requirements that the outcome data be limited to human "patients." Instead, the outcome data records 220, 222, 224 and biometric data records 320 may be associated with any desired subject including any non-human organism.

In some implementations, each of the data records 220, 222, 224, 320 may include keyed data that enables the data records from each respective distributed computer to be correlated by application server 240. The keyed data may include, for example, data representing a subject identifier. The subject identifier may include any form of data that identifies a subject and that can associate biomarker for the subject with outcome data for the subject.

The first distributed computer 210 may provide 208 the biomarker data records 220, 222, 224 to the application server 240. The second distributed compute 310 may provide 210 the outcome data records 320 to the application server 240. The application server 240 can provide the biomarker data records 220 and the outcome data records 220, 222, 224 to the extraction unit 242.

The extraction unit 242 can process the received biomarker data 220, 222, 224 and outcome data records 320 in order to extract data 220a-1, 222a-1, 224a-1, 320a-1, 320a-2, 320a-3 that can be used to train the machine learning model. For example, the extraction unit 242 can obtain data structured by fields of the data structures of the biometric data records 220, 222, 224, obtain data structured by fields of the data structures of the outcome data records 320, or a combination thereof. The extraction unit 242 may perform one or more information extraction algorithms such as keyed data extraction, pattern matching, natural language processing, or the like to identify and obtain data 220a-1, 222a-1, 224a-1, 320a-1, 320a-2, 320a-3 from the biometric data records 220, 222, 224 and outcome data records 320, respectively. The extraction unit 242 may provide the extracted data to the memory unit 244. The extracted data unit may be stored in the memory unit 244 such as flash memory (as opposed to a hard disk) to improve data access times and reduce latency in accessing the extracted data to improve system performance. In some implementations, the extracted data may be stored in the memory unit 244 as an in-memory data grid.

In more detail, the extraction unit 242 may be configured to filter a portion of the biomarker data records 220, 222, 224 and the outcome data records 320 that will be used to generate an input data structure 260 for processing by the machine learning model 270 from the portion of the outcome data records 320 that will be used as a label for the generated input data structure 260. Such filtering includes the extraction unit 242 separating the biomarker data and a first portion of the outcome data that includes a disease or disorder, treatment, treatment details, or a combination thereof, from the treatment result. The application server 240 can then use the biomarker data 220a-1, 222a-1, 224a-1, 320a-1, 320a-2 and the first portion of the outcome data that includes the disease or disorder 320a-1, treatment 320a-2, treatment details (not shown in FIG. 1B), or a combination thereof, to generate the input data structure 260. In addition, the application server 240 can use the second portion of the outcome data describing the treatment result 320a-3 as the label for the generated data structure.

The application server 240 may process the extracted data stored in the memory unit 244 correlate the biomarker data 220a-1, 222a-1, 224a-1 extracted from biomarker data records 220, 222, 224 with the first portion of the outcome data 320a-1, 320a-2. The purpose of this correlation is to cluster biomarker data with outcome data so that the outcome data for the subject is clustered with the biomarker data for the subject. In some implementations, the correlation of the biomarker data and the first portion of the outcome data may be based on keyed data associated with each of the biomarker data records 220, 222, 224 and the outcome data records 320. For example, the keyed data may include a subject identifier.

The application server 240 provides the extracted biomarker data 220a-1, 222a-1, 224a-1 and the extracted first portion of the outcome data 320a-1, 320a-2 as an input to a vector generation unit 250. The vector generation unit 250 is used to generate a data structure based on the extracted biomarker data 220a-1, 222a-1, 224a-1 and the extracted first portion of the outcome data 320a-1, 320a-2. The generated data structure is a feature vector 260 that includes a plurality of values that numerical represents the extracted biomarker data 220a-1, 222a-1, 224a-1 and the extracted first portion of the outcome data 320a-1, 320a-2. The feature vector 260 may include a field for each type of biomarker and each type of outcome data. For example, the feature vector 260 may include one or more fields corresponding to (i) one or more types of next generation sequencing data such as single variants, insertions and deletions, substitution, translocation, fusion, break, duplication, amplification, loss, copy number, repeat, total mutational burden, microsatellite instability, (ii) one or more types of in situ hybridization data such as DNA copies, gene copies, gene translocations, (iii) one or more types of RNA data such as gene expression or gene fusion, (iv) one or more types of protein data such as obtained using immunohistochemistry, (v) one or more types of ADAPT data such as complexes, and (vi) one or more types of outcomes data such as disease or disorder, treatment type, each type of treatment details, or the like.

The vector generation unit 250 is configured to assign a weight to each field of the feature vector 260 that indicates an extent to which the extracted biomarker data 220a-1, 222a-1, 224a-1 and the extracted first portion of the outcome data 320a-1, 320a-2 includes the data represented by each field. In one implementation, for example, the vector generation unit 250 may assign a '1' to each field of the feature vector that corresponds to a feature found in the extracted biomarker data 220a-1, 222a-1, 224a-1 and the extracted first portion of the outcome data 320a-1, 320a-2. In such implementations, the vector generation unit 250 may, for example, also assign a '0' to each field of the feature vector that corresponds to a feature not found in the extracted biomarker data 220a-1, 222a-1, 224a-1 and the extracted first portion of the outcome data 320a-1, 320a-2. The output of the vector generation unit 250 may include a data structures such as a feature vector 260 that can be used to train the machine learning model 270.

The application server 240 can label the training feature vector 260. Specifically, the application server can use the extracted second portion of the patient outcome data 320a-3 to label the generated feature vector 260 with a treatment result 320a-3. The label of the training feature vector 260 generated based on the treatment result 320a-3 can provide an indication of an effectiveness of the treatment 320a-2 for a disease or disorder 320a-1 of a subject defined by the specific set of biomarkers 220a-1, 222a-1, 224a-1, each of which is described by described in the training data structure 260.

The application server 240 can train the machine learning model 270 by providing the feature vector 260 as an input to the machine learning model 270. The machine learning model 270 may process the generated feature vector 260 and generate an output 272. The application server 240 can use a loss function 280 to determine the amount of error between the output 272 of the machine learning model 280 and the value specified by the training label, which is generated based on the second portion of the extracted patient outcome data describing the treatment result 320a-3. The output 282 of the loss function 280 can be used to adjust the parameters of the machine learning model 282.

In some implementations, adjusting the parameters of the machine learning model 270 may include manually tuning of the machine learning model parameters model parameters. Alternatively, in some implementations, the parameters of the machine learning model 270 may be automatically tuned by one or more algorithms of executed by the application server 242.

The application server 240 may perform multiple iterations of the process described above with reference to FIG. 1B for each outcome data record 320 stored in the outcomes database that correspond to a set of biomarker data for a subject. This may include hundreds of iterations, thousands of iterations, tens of thousands of iterations, hundreds of thousands of iterations, millions of iterations, or more, until each of the outcomes data records 320 stored in the outcomes database 312 and having a corresponding set of biomarker data for a subject are exhausted, until the machine learning model 270 is trained to within a particular margin of error, or a combination thereof. A machine learning model 270 is trained within a particular margin of error when, for example, the machine learning model 270 is able to predict, based upon a set of unlabeled biomarker data, disease or disorder data, and treatment data, an effectiveness of the treatment for the subject having the biomarker data. The effectiveness may include, for example, a probability, a general indication of the treatment being successful or unsuccessful, or the like.

Figure 1C:
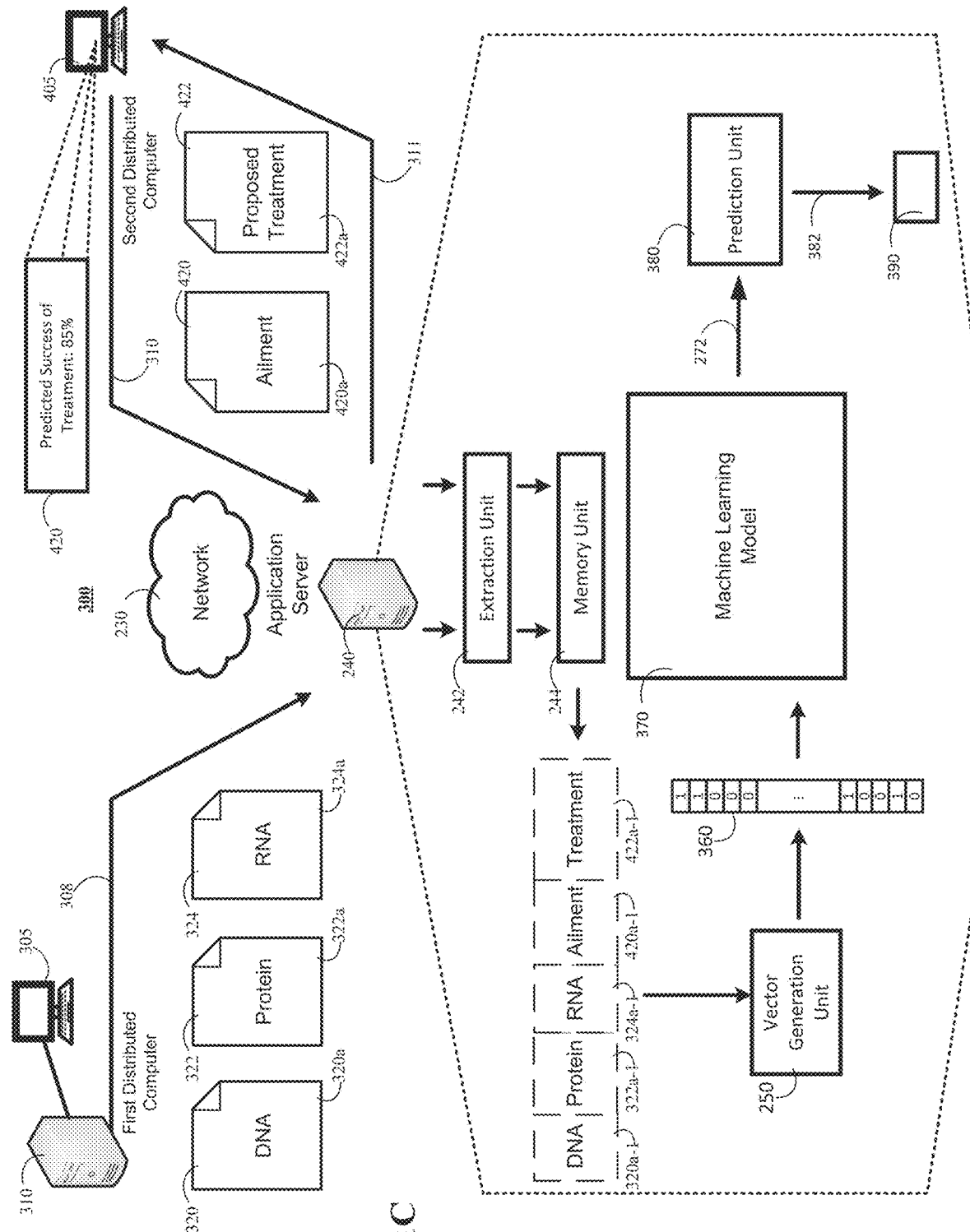
FIG. 1C is a block diagram of a system for using a machine learning model that has been trained to predict effectiveness of a treatment for a disease or disorder of a subject having a particular set of biomarkers.

FIG. 1C is a block diagram of a system for using a machine learning model that has been trained to predict effectiveness of a treatment for a disease or disorder of a subject having a particular set of biomarkers.

The machine learning model 370 includes a machine learning model that has been trained using the process described with reference to the system of FIG. 1B above. The trained machine learning model 370 is capable of predicting, based on an input feature vector representative of a set of one or more biomarkers, a disease or disorder, and a treatment, a level of effectiveness for the treatment in treating the disease or disorder for the subject having the biomarkers. In some implementations, the "treatment" may include a drug, treatment details (e.g., dosage, regiment, missed doses, etc), or any combination thereof.

The application server 240 hosting the machine learning model 370 is configured to receive unlabeled biomarker data records 320, 322, 324. The biomarker data records 320, 322, 324 include one or more data structures that have fields structuring data that represents one or more particular biomarkers such as DNA biomarkers 320a, protein biomarkers 322a, RNA biomarkers 324a, or any combination thereof. As discussed above, the received biomarker data records may include types of biomarkers not depicted by FIG. 1C such as (i) one or more types of next generation sequencing data such as single variants, insertions and deletions, substitution, translocation, fusion, break, duplication, amplification, loss, copy number, repeat, total mutational burden, microsatellite instability, (ii) one or more types of in situ hybridization data such as DNA copies, gene copies, gene translocations, (iii) one or more types of RNA data such as gene expression or gene fusion, (iv) one or more types of protein data such as obtained using immunohistochemistry, or (v) one or more types of ADAPT data such as complexes.

The application server 240 hosting the machine learning model 370 is also configured to receive data representing a proposed treatment data 422a for a disease or disorder described by the disease or disorder data 420*a* of the subject having biomarkers represented by the received biomarker data records 320, 322, 324. The proposed treatment data 422*a* for the disease or disorder 422*a* are also unlabeled and merely a suggestion for treating a subject having biomarkers representing by biomarker data records 320, 322, 324.

In some implementations, the disease or disorder data 420*a* and the proposed treatment 422*a* is provided 305 by a terminal 405 over the network 230 and the biomarker data is obtained from a second distributed computer 310. The biomarker data may be derived from laboratory machinery used to perform various assays. In other implementations, the disease or disorder data 420*a*, the proposed treatment 422*a*, and the biomarker data 320, 322, 324 may each be received from the terminal 405. For example, the terminal 405 may be user device of a doctor, an employee or agent of the doctor working at the doctor's office, or other human entity that inputs data representing a disease or disorder, data representing a proposed treatment, and a data representing one or more biomarkers for a subject having the disease or disorder. In some implementations, the treatment data 422 may include data structures structuring fields of data representing a proposed treatment described by a drug name. In other implementations, the treatment data 422 may include data structures structuring fields of data representing more complex treatment data such as dosage amounts, a drug regimen, number of allowed missed doses, or the like.

The application server 240 receives the biomarker data records 320, 322, 324, the disease or disorder data 420, and the treatment data 422. The application server 240 provides the biomarker data records 320, 322, 324, the disease or disorder data 420, and the treatment data 422 to an extraction unit 242 that is configured to extract (i) particular biomarker data such as DNA biomarker data 320*a*-1, protein expression data 322*a*-1, 324*a*-1, (ii) disease or disorder data 420*a*-1, and (iii) proposed treatment data 420*a*-1 from the fields of the biomarker data records 320, 322, 324 and the outcome data records 420, 422. In some implementations, the extracted data is stored in the memory unit 244 as a buffer, cache or the like, and then provided as an input to the vector generation unit 250 when the vector generation unit 250 has bandwidth to receive an input for processing. In other implementations, the extracted data is provided directly to a vector generation unit 250 for processing. For example, in some implementations, multiple vector generation units 250 may be employed to enable parallel processing of inputs to reduce latency.

The vector generation unit 250 can generate a data structure such as a feature vector 360 that includes a plurality of fields and includes one or more fields for each type of biomarker data and one or more fields for each type of outcome data. For example, each field of the feature vector 360 may correspond to (i) each type of extracted biomarker data that can be extracted from the biomarker data records 320, 322, 324 such as each type of next generation sequencing data, each type of in situ hybridization data, each type of RNA data, each type of immunohistochemistry data, and each type of ADAPT data and (ii) each type of outcome data that can be extracted from the outcome data records 420, 422 such as each type of disease or disorder, each type of treatment, and each type of treatment details.

The vector generation unit 250 is configured to assign a weight to each field of the feature vector 360 that indicates an extent to which the extracted biomarker data 320*a*-1, 322*a*-1, 324*a*-1, the extracted disease or disorder 420*a*-1, and the extracted treatment 422*a*-1 includes the data represented by each field. In one implementation, for example, the vector generation unit 250 may assign a '1' to each field of the feature vector 360 that corresponds to a feature found in the extracted biomarker data 320*a*-1, 322*a*-1, 324*a*-1, the extracted disease or disorder 420*a*-1, and the extracted treatment 422*a*-1. In such implementations, the vector generation unit 250 may, for example, also assign a '0' to each field of the feature vector that corresponds to a feature not found in the extracted biomarker data 320*a*-1, 322*a*-1, 324*a*-1, the extracted disease or disorder 420*a*-1, and the extracted treatment 422*a*-1. The output of the vector generation unit 250 may include a data structure such as a feature vector 360 that can be provided as an input to the trained machine learning model 370.

The trained machine learning model 370 process the generated feature vector 360 based on the adjusted parameters that were determining during the training stage and described with reference to FIG. 1B. The output 272 of the trained machine learning model provides an indication of the effectiveness of the treatment 422*a*-1 of the disease or disorder 420*a*-1 for the subject having biomarkers 320*a*-1, 322*a*-1, 324*a*-1. In some implementations, the output 272 may include a probability that is indicative of the effectiveness of the treatment 422*a*-1 of the disease or disorder 420*a*-1 for the subject having biomarkers 320*a*-1, 322*a*-1, 324*a*-1. In such implementations, the output 272 may be provided 311 to the terminal 405 using the network 230. The terminal 405 may then generate output on a user interface 420 that indicates a predicted level of effectiveness of a treatment of the disease or disorder for a person having the biomarkers represented by the feature vector 360.

In other implementations, the output 272 may be provided to a prediction unit 380 that is configured to decipher the meaning of the output 272. For example, the prediction unit 380 can be configured to map the output 272 to one or more categories of effectiveness. Then, the output of the prediction unit 328 can be used as part of message 390 that is provided 311 to the terminal 305 using the network 230 for review by the subject, a guardian of the subject, a nurse, a doctor, or the like.

Figure 1D:
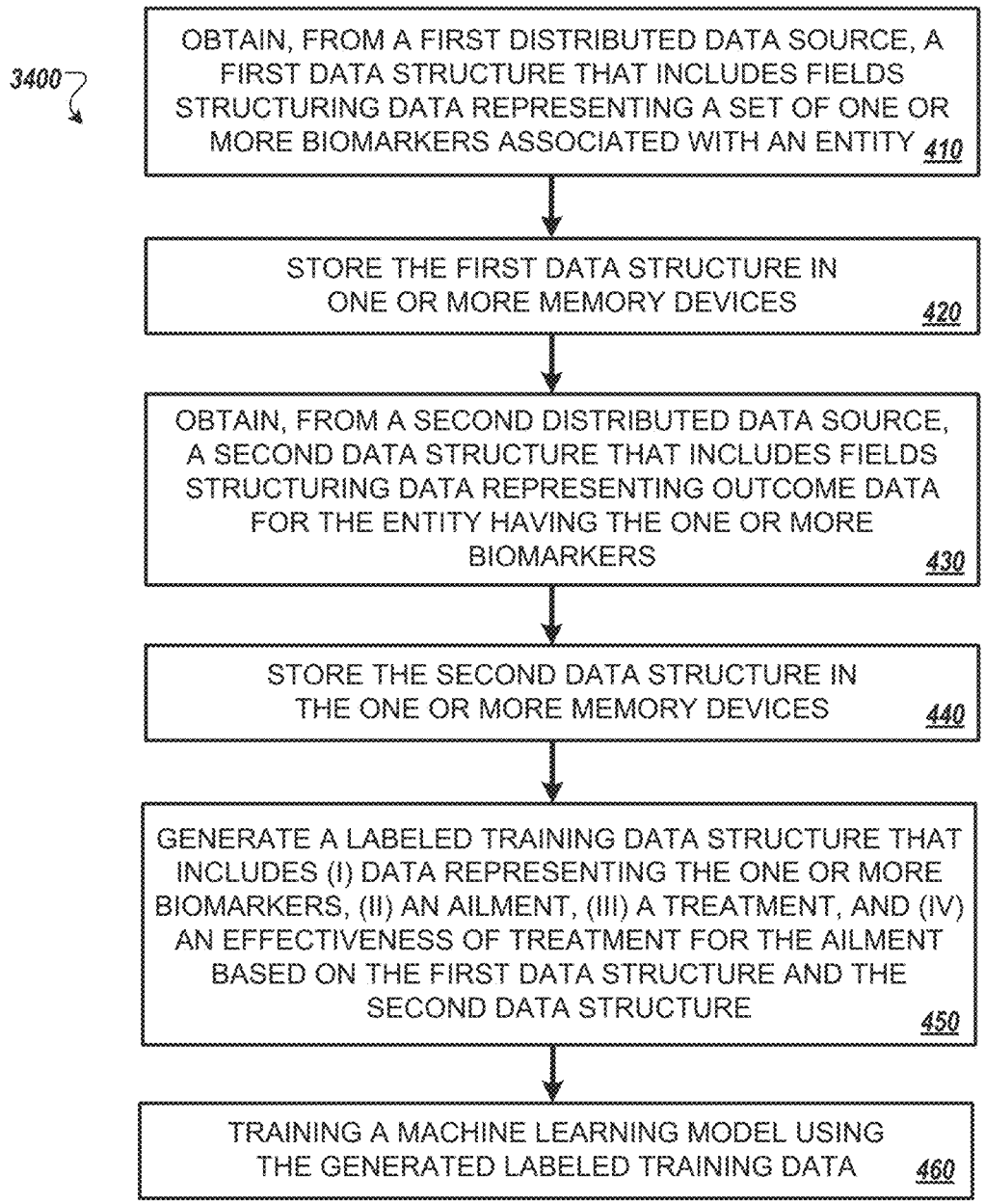
FIG. 1D is a flowchart of a process for generating training data for training a machine learning model to predict effectiveness of a treatment for a disease or disorder of a subject having a particular set of biomarkers.

FIG. 1D is a flowchart of a process 400 for generating training data for training a machine learning model to predict effectiveness of a treatment for a disease or disorder of a subject having a particular set of biomarkers. In one aspect, the process 400 may include obtaining, from a first distributed data source, a first data structure that includes fields structuring data representing a set of one or more biomarkers associated with a subject (410), storing the first data structure in one or more memory devices (420), obtaining from a second distributed data source, a second data structure that includes fields structuring data representing outcome data for the subject having the one or more biomarkers (430), storing the second data structure in the one or more memory devices (440), generating a labeled training data structure that includes (i) data representing the one or more biomarkers, (ii) a disease or disorder, (iii) a treatment, and (iv) an effectiveness of treatment for the disease or disorder based on the first data structure and the second data structure (450), and training a machine learning model using the generated labeled training data (460).

Figure 1E:
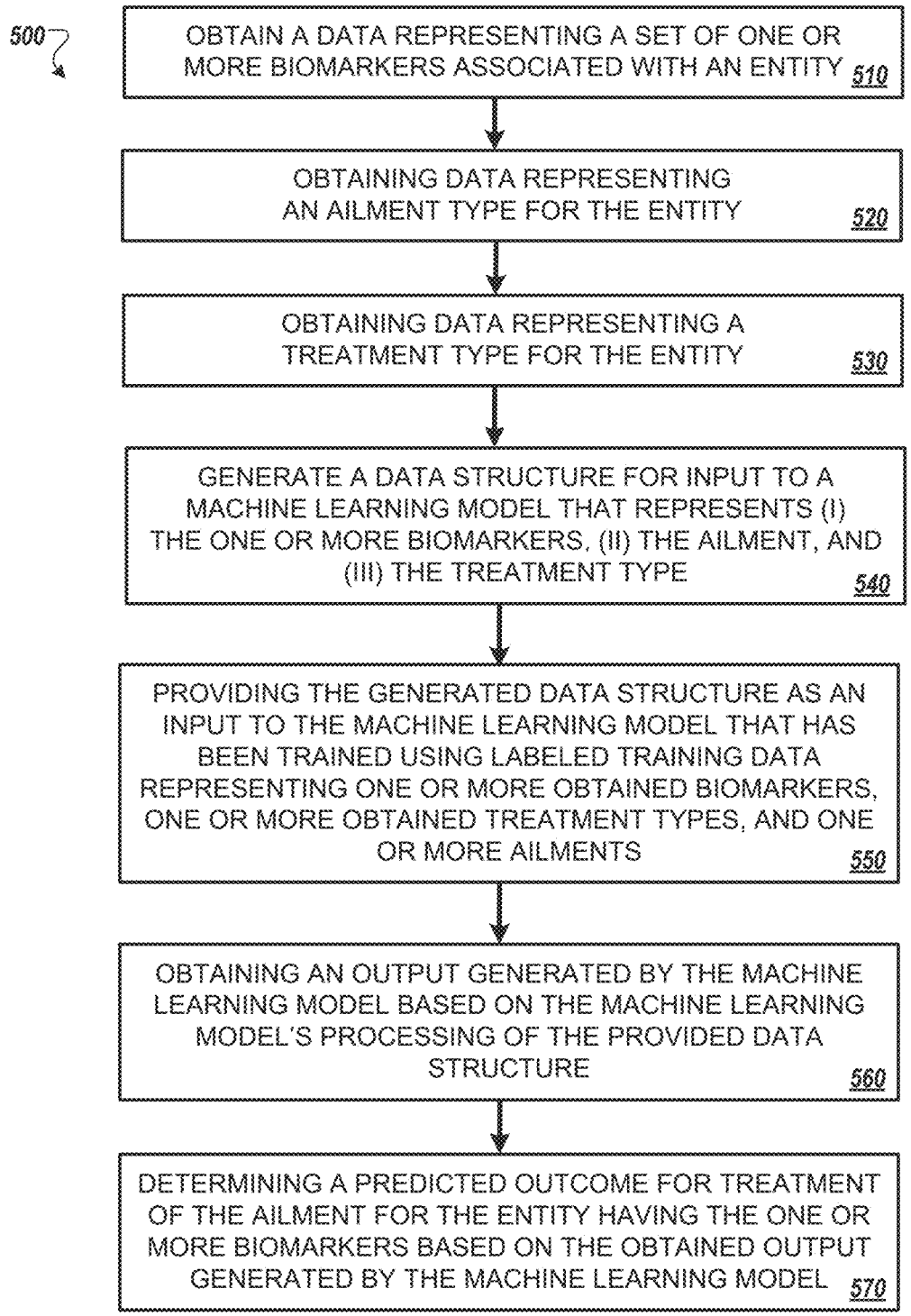
FIG. 1E is a flowchart of a process for using a machine learning model that has been trained to predict effectiveness of a treatment for a disease or disorder of a subject having a particular set of biomarkers.

FIG. 1E is a flowchart of a process 500 for using a machine learning model that has been trained to predict effectiveness of a treatment for a disease or disorder of a subject having a particular set of biomarkers. In one aspect, the process 500 may include obtaining a data structure representing a set of one or more biomarkers associated with a subject (510), obtaining data representing a disease or disorder type for the subject (520), obtaining data representing a treatment type for the subject (530), generating a data structure for input to a machine learning model that represents (i) the one or more biomarkers, (ii) the disease or disorder, and (iii) the treatment type (540), providing the generated data structure as an input to the machine learning model that has been trained using labeled training data representing one or more obtained biomarkers, one or more treatment types, and one or more diseases or disorders (550), and obtaining an output generated by the machine learning model based on the machine learning model processing of the provided data structure (560), and determining a predicted outcome for treatment of the disease or disorder for the subject having the one or more biomarkers based on the obtained output generated by the machine learning model (570).

Provided herein are methods of employing multiple machine learning models to improve classification performance. Conventionally, a single model is chosen to perform a desired prediction/classification. For example, one may compare different model parameters or types of models, e.g., random forests, support vector machines, logistic regression, k-nearest neighbors, artificial neural network, naïve Bayes, quadratic discriminant analysis, or Gaussian processes models, during the training stage in order to identify the model having the optimal desired performance. Applicant realized that selection of a single model may not provide optimal performance in all settings. Instead, multiple models can be trained to perform the prediction/classification and the joint predictions can be used to make the classification. In this scenario, each model is allowed to "vote" and the classification receiving the majority of the votes is deemed the winner.

This voting scheme disclosed herein can be applied to any machine learning classification, including both model building (e.g., using training data) and application to classify naïve samples. Such settings include without limitation data in the fields of biology, finance, communications, media and entertainment. In some preferred embodiments, the data is highly dimensional "big data." In some embodiments, the data comprises biological data, including without limitation biological data obtained via molecular profiling such as described herein. See, e.g., Example 1. The molecular profiling data can include without limitation highly dimensional next-generation sequencing data, e.g., for particular biomarker panels (see, e.g., Example 1) or whole exome and/or whole transcriptome data. The classification can be any useful classification, e.g., to characterize a phenotype. For example, the classification may provide a diagnosis (e.g., disease or healthy), prognosis (e.g., predict a better or worse outcome) or theranosis (e.g., predict or monitor therapeutic efficacy or lack thereof). Application of the voting scheme is provided herein in Examples 2-4.

Figure 1F:
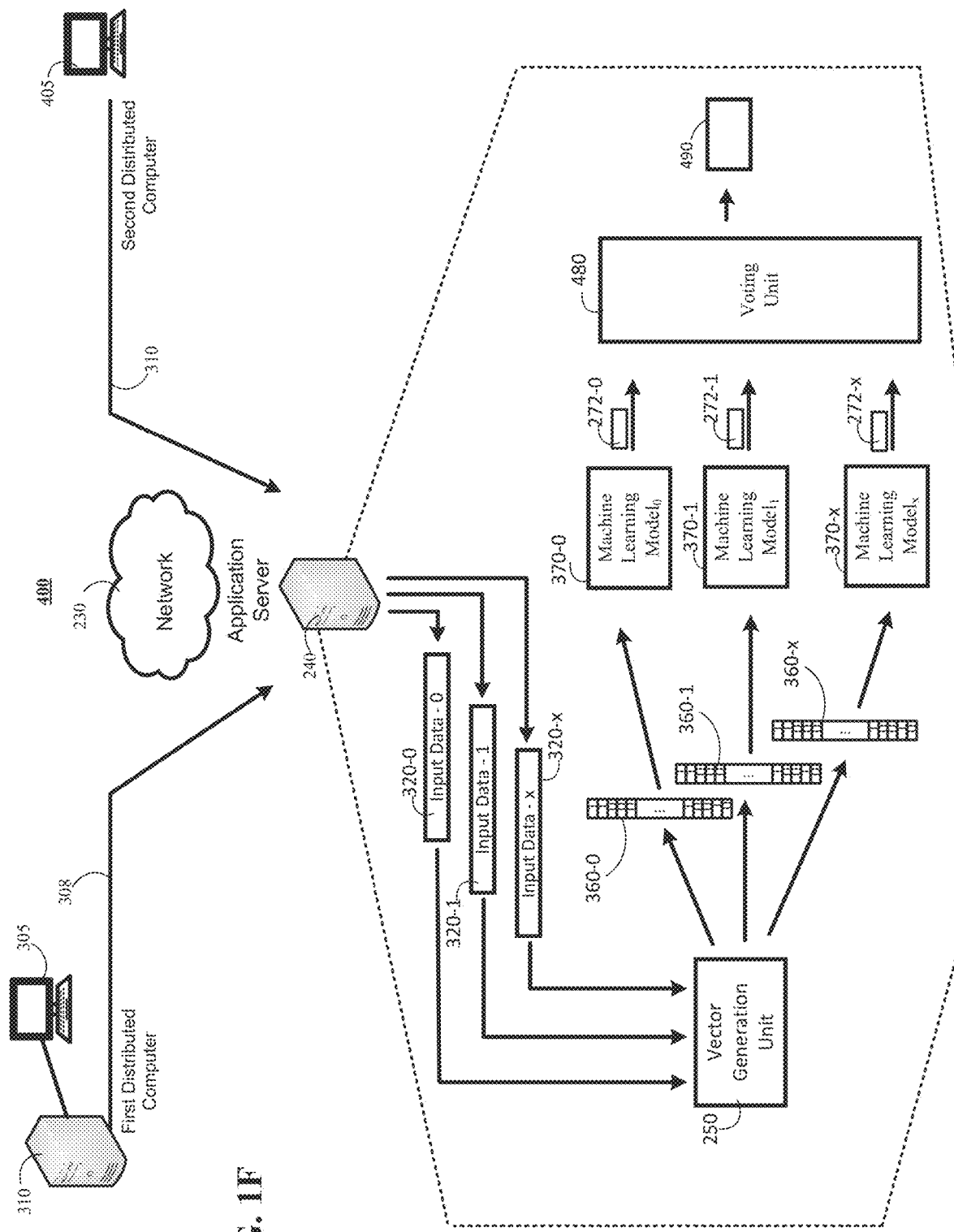
FIG. 1F is a block diagram of a system for predicting effectiveness of a treatment for a disease or disorder of a subject having a particular set of biomarkers by using voting unit to interpret output generated by multiple machine learning models.

FIG. 1F is a block diagram of a system 600 using a voting unit to interpret output generated by multiple machine learning models. The system 600 is similar to the system 300 of FIG. 1C. However, instead of a single machine learning model 370, the system 600 includes multiple machine learning models 370-0, 370-1 . . . 370-x, where x is any non-zero integer greater than 1. In addition, the system 600 also include a voting unit 480

As a non-limiting example, system 600 can be used for predicting effectiveness of a treatment for a disease or disorder of a subject having a particular set of biomarkers. See Examples 2-4.

Each machine learning model 370-0, 370-1, 370-x can include a machine learning model that has been trained to classify a particular type of input data 320-0, 320-1 . . . 320-x, wherein x is any non-zero integer greater than 1 and equal to the number x of machine learning models. In some implementations, each of the machine learning models 370-0, 370-1, 370-x can be of the same type. For example, each of the machine learning models 370-0, 370-1, 370-x can be a random forest classification algorithm, e.g., trained using differing parameters. In other implementations, the machine learning models 370-0, 370-1, 370-x can be of different types. For example, there can be one or more random forest classifiers, one or more neural networks, one or more K-nearest neighbor classifiers, other types of machine learning models, or any combination thereof.

Input data such as input data-0 320-0, input data-1 320-1, input data-x 320-x can be obtained by the application server 240. In some implementations, the input data 320-0, 320-1, 320-x is obtained across the network 230 from one or more distributed computers 310, 405. By way of example, one or more of the input data items 320-0, 320-1, 320-x can be generated by correlating data from multiple different data sources 210, 405. In such an implementation, (i) first data describing biomarkers for a subject can be obtained from the first distributed computer 310 and (ii) second data describing a disease or disorder and related treatment can be obtained from the second computer 405. The application server 240 can correlate the first data and the second data to generate an input data structure such as input data structure 320-0. This process is described in more detail in FIG. 1C. The input data items 320-0, 320-1, 320-x can be provided as respective inputs one-at-a-time, in series, for example, to the vector generation unit. The vector generation unit can generate input vectors 360-0, 360-1, 360-x that corresponding to each respective input data 320-0, 320-1, 320-x. While some implementations may generate vectors 360-0, 360-1, 360-x serially, the present disclosure need not be so limited.

Instead, in some implementations, the vector generation unit 250 can be configured to operate multiple parallel vector generation units that can parallelize the vector generation process. In such implementations, the vector generation unit 250 can receive input data 320-0, 320-1, 320-x in parallel, process the input data 320-0, 320-1, 320-x in parallel, and generate respective vectors 360-0, 360-1, 360-x that each correspond to one of the input data 320-0, 320-1, 320-x in parallel.

In some implementations, the vectors 360-0, 360-1, 360-x can each be generated based on corresponding input data such as input data 320-0, 320-1, 320-x, respectively. That is, vector 360-0 is generated based on, and represents, input data 320-0. Similarly, vector 360-1 is generated based on, and represents, input data 320-1. Similarly, vector 360-x is generated based on, and represents, input data 320-x.

In some implementations, each input data structure 320-0, 320-1, 320-x can include data representing biomarkers of a subject, data describing a disease or disorder associated with the subject, data describing a proposed treatment for the subject, or any combination thereof. The data representing the biomarkers of a subject can include data describing a specific subset or panel of genes from a subject. Alternatively, in some implementations, the data representing biomarkers of the subject can include data representing complete set of known genes for a subject. The complete set of known genes for a subject can include all of the genes of the subject. In some implementations, each of the machine learning models 370-0, 370-1, 370-x are the same type machine learning model such as a neural network trained to classify the input data vectors as corresponding to a subject that is likely to be responsive or likely to be non-responsive to a treatment identified associated by the vector processed by the machine learning model. In such implementations, though each of the machine learning models 370-0, 370-1, 370-x is the same type of machine learning model, each of the machine learning models 370-0, 370-1, 370-x may be trained in different ways. The machine learning models 370-1, 370-1, 370-x can generate output data 272-0, 272-1, 272-x, respectively, representing whether a subject associated with input vectors 360-0, 360-1, 360-x is likely to be responsive or is likely to be unresponsive to a treatment associated with the input vectors 360-0, 360-1, 360-x. In this example, the input data sets, and their corresponding input vectors, are the same—e.g., each set of input data has the same biomarkers, same disease or disorder, same treatment, or any combination. Nonetheless, given the different training methods used to train each respective machine learning model 370-0, 370-1, 370-x may generate different outputs 272-0, 272-1, 272-x, respectively, based on each machine learning model 370-0, 370-1, 370-x processing the input vector 360-0, 361-1, 361-x, as shown in FIG. 1F.

Alternatively, each of the machine learning models 370-0, 370-1, 370-x can be a different type of machine learning model that has been trained, or otherwise configured, to classify input data as representing a subject that is likely to be responsive or is likely to be non-responsive to a treatment for a disease or disorder. For example, the first machine learning model 370-1 can include a neural network, the machine learning model 370-1 can include a random forest classification algorithm, and the machine learning model 370-x can include a K-nearest neighbor algorithm. In this example, each of these different types of machine learning models 370-0, 370-1, 370-x can be trained, or otherwise configured, to receive and process an input vector and determine whether the input vector is associated with a subject that is likely to be responsive or likely to be non-responsive to a treatment also associated with the input vector. In this example, the input data sets, and their corresponding input vectors, can be the same—e.g., each set of input data has the same biomarkers, same disease or disorder, same treatment, or any combination. Accordingly, the machine learning model 370-0 can be a neural network trained to process input vector 360-0 and generate output data 272-0 indicating whether the subject associated with the input vector 360-0 is likely to be responsive or non-responsive to the treatment also associated with input vector 360-0. In addition, the machine learning model 370-1 can be a random forest classification algorithm trained to process input vector 360-1, which for purposes of this example is the same as input vector 360-0, and generate output data 272-1 indicating whether the subject associated with the input vector 360-1 is likely to be responsive or non-responsive to the treatment also associated with the input vector 360-1. This method of input vector analysis can continue for each of the x inputs, x input vectors, and x machine learning models. Continuing with this example with reference to FIG. 1F the machine learning model 370-x can be a K-nearest neighbor algorithm trained to process input vector 360-x, which for purposes of this example is the same as input vector 360-0 and 360-1, and generate output data 272-x indicating whether the subject associated with the input vector 360-x is likely to be responsive or non-responsive to the treatment also associated with the input vector 360-x.

Alternatively, each of the machine learning models 370-0, 370-1, 370-x can be the same type of machine learning models or different type of machine learning models that are each configured to receive different inputs. For example, the input to the first machine learning model 370-0 can include a vector 360-0 that includes data representing a first subset or first panel of genes of a subject and then predict, based on the machine learning models 370-0 processing of vector 360-0 whether the subject is likely to be responsive or likely to be non-responsive to a treatment. In addition, in this example, an input to the second machine learning model 370-1 can include a vector 360-1 that includes data representing a second subset or second panel of genes of a subject that is different than the first subset or first panel of genes. Then, the second machine learning model can generate second output data 272-1 that is indicative of whether the subject associated with the input vector 360-1 is likely to be responsive or likely to be non-responsive to the treatment associated with the input vector 360-2. This method of input vector analysis can continue for each of the x inputs, x input vectors, and x machine learning models. The input to the xth machine learning model 370-x can include a vector 360-x that includes data representing an xth subset or xth panel of genes of a subject that is different than (i) at least one, (i) two or more, or (iii) each of the other x-1 input data vectors 370-0 to 370-x-1. In some implementations, at least one of the x input data vectors can include data representing a complete set of genes from a subject. Then, the xth machine learning model 370-x can generate second output data 272-x, the second output data 272-x being indicative of whether the subject associated with the input vector 360-x is likely to be responsive or likely to be non-responsive to the treatment associated with the input vector 360-x.

Multiple implementations of system 400 described above are not intended to be limiting, and instead, are merely examples of configurations of the multiple machine learning models 370-0, 370-1, 370-x, and their respective inputs, that can be employed using the present disclosure. With reference to these examples, the subject can be any human, non-human animal, plant, or other subject. As described above, the input feature vectors can be generated, based on the input data, and represent the input data. Accordingly, each input vector can represent data that includes one or more biomarkers, a disease or disorder, and a treatment, a level of effectiveness for the treatment in treating the disease or disorder for the subject having the biomarkers. The "treatment" can include data describing any therapeutic agent, e.g., small molecule drugs or biologics, treatment details (e.g., dosage, regiment, missed doses, etc), or any combination thereof.

In the implementation of FIG. 1F, the output data 272-0, 272-1, 272-x can be analyzed using a voting unit 480. For example, the output data 272-0, 272-1, 272-x can be input into the vote unit 480. In some implementations, the output data 272-0, 272-1, 272-x can be data indicating whether the subject associated with the input vector processed by the machine learning model is likely to be responsive or non-responsive to treatment associated with the vector processed by the machine learning model. Data indicating whether the subject associated with the input vector, and generated by each machine learning model, can include a "0" or a "1." A "0," produced by a machine learning model 370-0 based on the machine learning model's 370-0 processing of an input vector 360-0, can indicate that the subject associated with the input vector 360-0 is likely to be non-responsive to the treatment associated with input vector 360-0. Similarity, as "1," produced by a machine learning model 360-0 based on the machine learning models' 370-0 processing of an input vector 360-0, can indicate that the subject associated with the input vector 360-0 is likely to be responsive to the treatment associated with the input vector 360-0. Though the example uses "0" as non-responsive and "1" as responsive, the present disclosure is not so limited. Instead, any value can be generated as output data to represent the "responsive" and "non-responsive" classes. For example, in some implementations "1" can be used to represent the "non-responsive" class and "0" to represent the "responsive" class. In yet other implementations, the output data 272-0, 272-1, 272-$x$ can include probabilities that indicate a likelihood that the subject associated with an input vector processed by a machine learning model is associated with a "responsive" or "non-responsive" class. In such implementations, for example, the generated probability can be applied to a threshold, and if the threshold is satisfied, then the subject associated with an input vector processed by the machine learning model can be determined to be in a "responsive" class.

The voting unit 480 can evaluate the received output data 270-0, 272-1, 272-$x$ and determine whether the subject associated with the processed input vectors 360-0, 360-1, 360-$x$ is likely to be responsive or unresponsive to a treatment associated with the processed input vectors 360-0, 360-1, 360-$x$. The voting unit 480 can then determine, based on the set of received output data 270-0, 272-1, 272-$x$, whether the subject associated with input vectors 360-0, 360-1, 360-$x$ is likely to be responsive to the treatment associated with the input vectors 360-0, 360-2, 360-$x$. In some implementations, the voting unit 480 can apply a "majority rule." Applying a majority rule, the voting unit 480 can tally the outputs 272-0, 272-1, and 272-$x$ indicating that the subject is responsive and outputs 272-0, 272-1, 272-$x$ indicating that the subject is non-responsive. Then, the class—e.g., responsive or non-responsive—having the majority predictions or votes is selected as the appropriate classification for the subject associated with the input vector 360-0, 360-1, 360-$x$. This selected class can be referred to as an actual class of the entity, with each of the predictions or votes output by the machine learning models 370-0, 370-1, 370-$x$ being referred to as initial entity classes.

Accordingly, in some implementations, determining a majority of predictions or votes can be achieved by the voting unit 480 tallying the number of occurrences of predictions or votes for each initial entity class. For example, the system 600 can determine a number of times each initial entity class is predicted or voted for by the machine learning models 370-0, 370-1, 370-$x$ and then select the entity class that is associated with the highest amount of occurrences of predictions or votes.

In some implementations, the voting unit 480 can complete a more nuanced analysis. For example, in some implementations, the voting unit 480 can store a confidence score for each machine learning model 370-0, 370-1, 370-$x$. This confidence score, for each machine learning model 370-0, 370-1, 370-$x$, can be initially set to a default value such as 0, 1, or the like. Then, with each round of processing of input vectors, the voting unit 480, or other module of the application server 240, can adjust the confidence score for the machine learning model 370-0, 370-1, 370-$x$ based on whether the machine learning model accurately predicted the subject classification selected by the voting unit 480 during a previous iteration. Accordingly, the stored confidence score, for each machine learning model, can provide an indication of the historical accuracy for each machine learning model.

In the more nuanced approached, the voting unit 480 can adjust output data 272-0, 272-0, 272-$x$ produced by each machine learning model 370-0, 370-1, 370-$x$, respectively, based on the confidence score calculated for the machine learning model. Accordingly, a confidence score indicating that a machine learning mode is historically accurate can be used to boost a value of output data generated by the machine learning model. Similarly, a confidence score indicating that a machine learning model is historically inaccurate can be used to reduce a value of output data generated by the machine learning model. Such boosting or reducing of the value of output data generated by a machine learning model can be achieved, for example, by using the confidence score as a multiplier of less than one for reduction and more than 1 for boosting. Other operations can also be used to adjust the value of output data such as subtracting a confidence score from the value of the output data to reduce the value of the output data or adding the confidence score to the value of the output data to boost the value of the output data. Use of confidence scores to boost or reduce the value of output data generated by the machine learning models is particularly useful when the machine learning models are configured to output probabilities that will be applied to one or more thresholds to determine whether a subject is responsive or non-responsive to a treatment. This is because using the confidence score to adjust the output of a machine learning model can be used to move a generated output value above or below a class threshold, thereby altering a prediction by a machine learning model based on its historical accuracy.

Use of the voting unit 480 to evaluate outputs of multiple machine learning models can lead to greater accuracy in prediction of the effectiveness of a treatment for a particular set of subject biomarkers, as the consensus amongst multiple machine learning models can be evaluated instead of the output of only a single machine learning model.

Figure 1G:
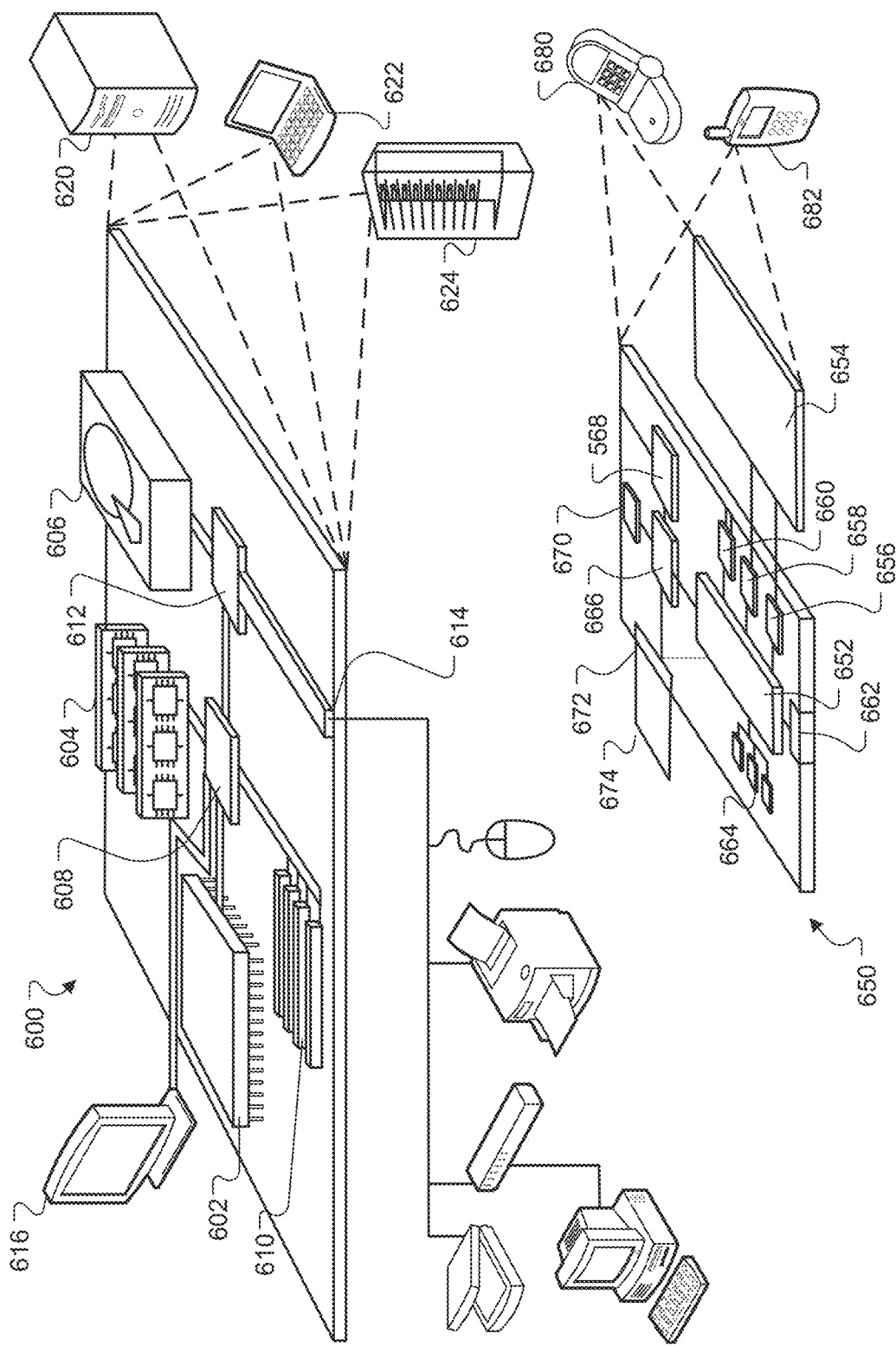
FIG. 1G is a block diagram of system components that can be used to implement systems of FIGS. 2-5.
Figure 1H:
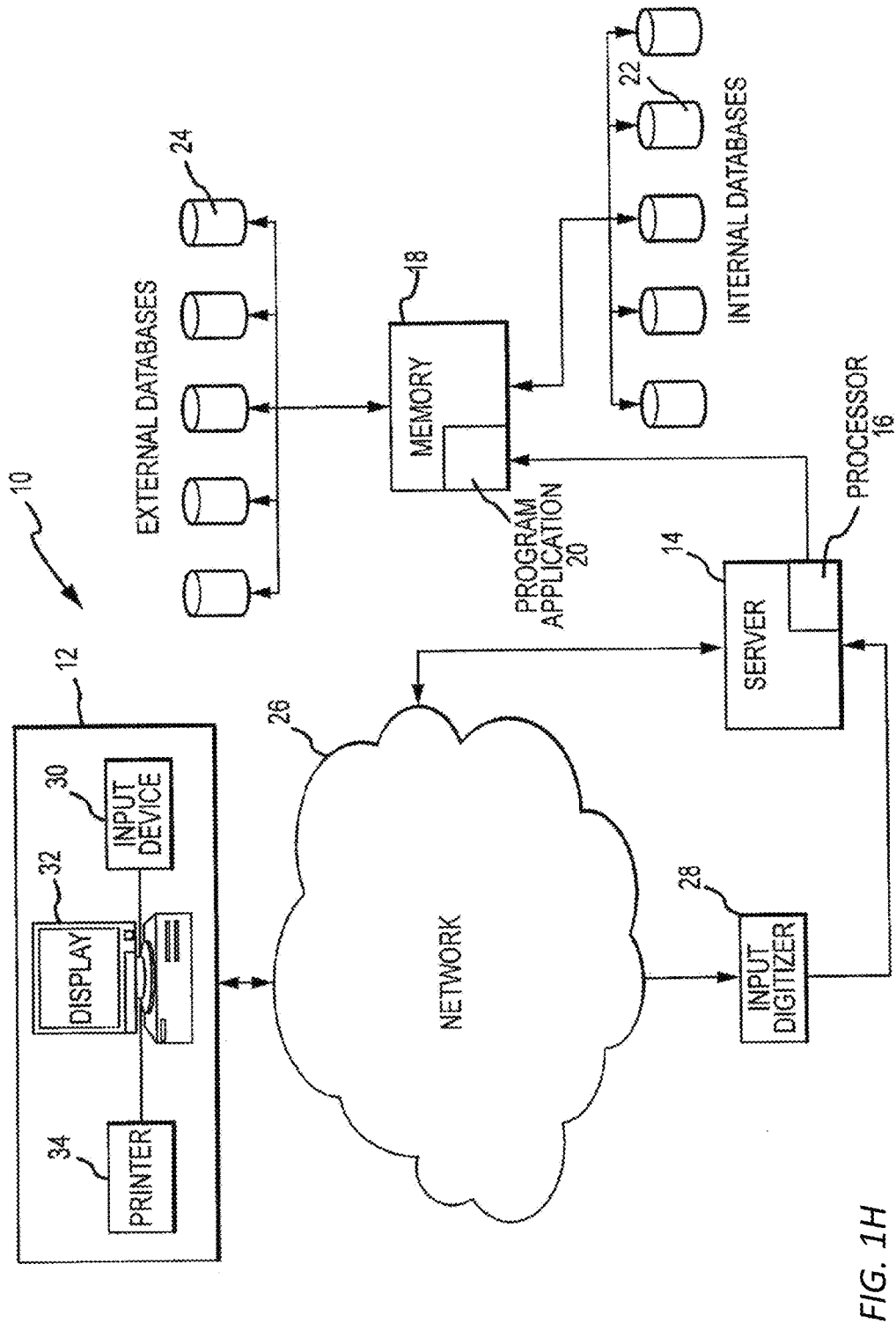
FIG. 1H illustrates a block diagram of an exemplary embodiment of a system for determining individualized medical intervention for cancer that utilizes molecular profiling of a patient's biological specimen.
Figure 2A:
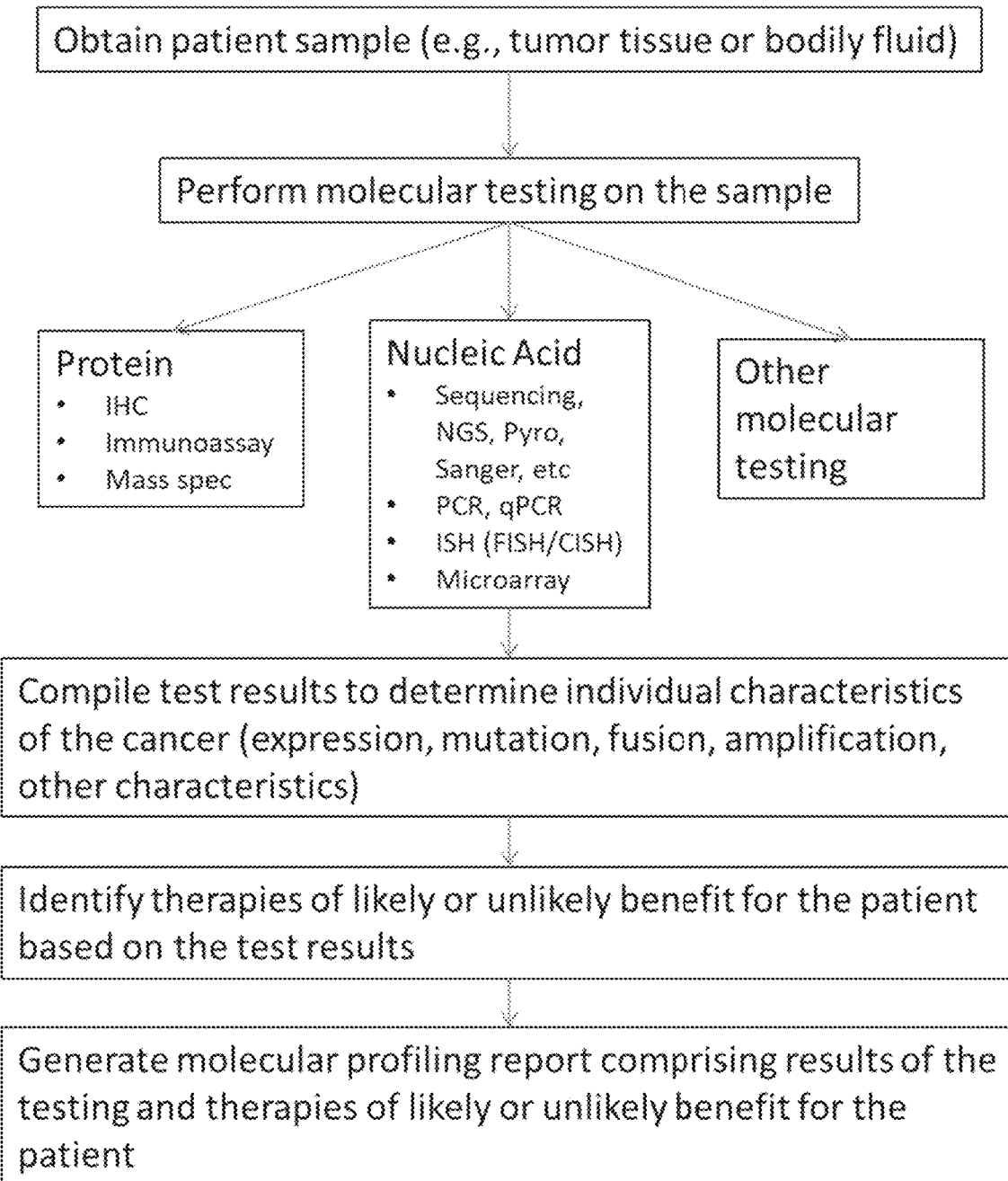
FIGS. 2A-C are flowcharts of exemplary embodiments of (A) a method for determining individualized medical intervention for cancer that utilizes molecular profiling of a patient's biological specimen, (B) a method for identifying signatures or molecular profiles that can be used to predict benefit from therapy, and (C) an alternate version of (B).
Figure 2B:
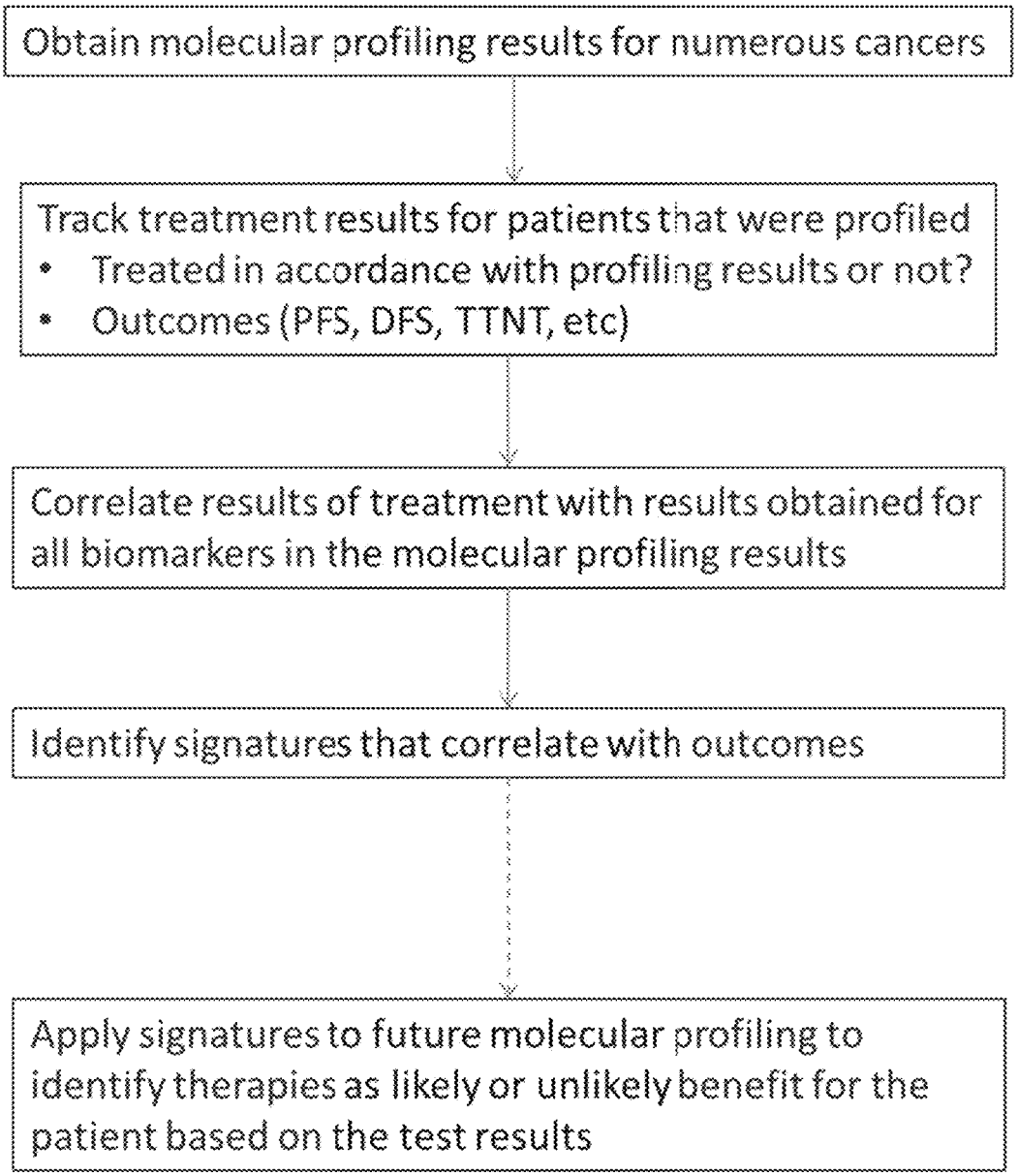
Figure 2C:
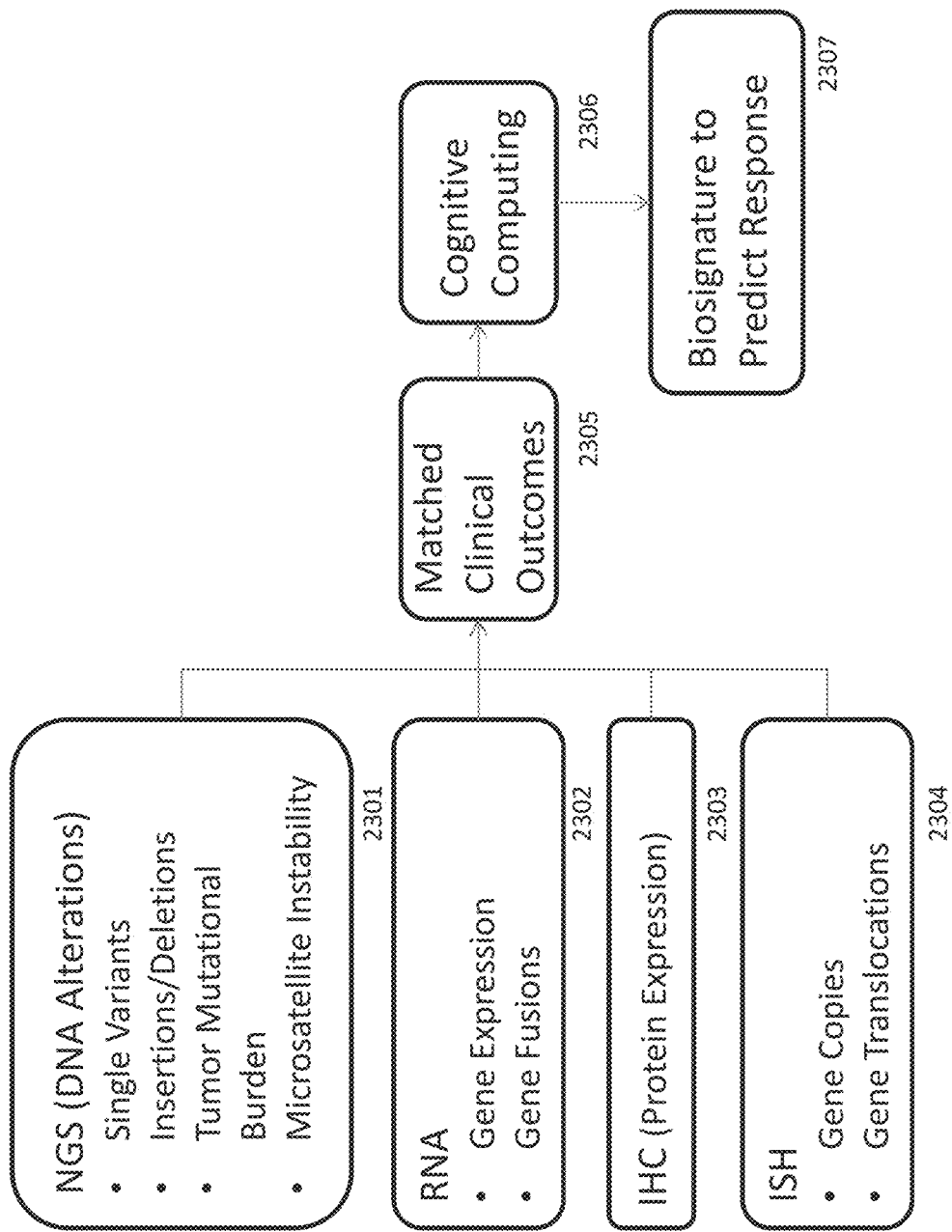

FIG. 1G is a block diagram of system components that can be used to implement a systems of FIGS. 2 and 3.

Computing device 600 is intended to represent various forms of digital computers, such as laptops, desktops, workstations, personal digital assistants, servers, blade servers, mainframes, and other appropriate computers. Computing device 650 is intended to represent various forms of mobile devices, such as personal digital assistants, cellular telephones, smartphones, and other similar computing devices. Additionally, computing device 600 or 650 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be exemplary only, and are not meant to limit implementations of the inventions described and/or claimed in this document.

Computing device 600 includes a processor 602, memory 604, a storage device 608, a high-speed interface 608 connecting to memory 604 and high-speed expansion ports 610, and a low speed interface 612 connecting to low speed bus 614 and storage device 608. Each of the components 602, 604, 608, 608, 610, and 612, are interconnected using various busses, and can be mounted on a common motherboard or in other manners as appropriate. The processor 602 can process instructions for execution within the computing device 600, including instructions stored in the memory 604 or on the storage device 608 to display graphical information for a GUI on an external input/output device, such as display 616 coupled to high speed interface 608. In other implementations, multiple processors and/or multiple buses can be used, as appropriate, along with multiple memories and types of memory. Also, multiple computing devices 600 can be connected, with each device providing portions of the necessary operations, e.g., as a server bank, a group of blade servers, or a multi-processor system.

The memory 604 stores information within the computing device 600. In one implementation, the memory 604 is a volatile memory unit or units. In another implementation, the memory 604 is a non-volatile memory unit or units. The memory 604 can also be another form of computer-readable medium, such as a magnetic or optical disk.

The storage device 608 is capable of providing mass storage for the computing device 600. In one implementation, the storage device 608 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 604, the storage device 608, or memory on processor 602.

The high speed controller 608 manages bandwidth-intensive operations for the computing device 600, while the low speed controller 612 manages lower bandwidth intensive operations. Such allocation of functions is exemplary only. In one implementation, the high-speed controller 608 is coupled to memory 604, display 616, e.g., through a graphics processor or accelerator, and to high-speed expansion ports 610, which can accept various expansion cards (not shown). In the implementation, low-speed controller 612 is coupled to storage device 608 and low-speed expansion port 614. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 600 can be implemented in a number of different forms, as shown in the figure. For example, it can be implemented as a standard server 620, or multiple times in a group of such servers. It can also be implemented as part of a rack server system 624. In addition, it can be implemented in a personal computer such as a laptop computer 622. Alternatively, components from computing device 600 can be combined with other components in a mobile device (not shown), such as device 650. Each of such devices can contain one or more of computing device 600, 650, and an entire system can be made up of multiple computing devices 600, 650 communicating with each other.

The computing device 600 can be implemented in a number of different forms, as shown in the figure. For example, it can be implemented as a standard server 620, or multiple times in a group of such servers. It can also be implemented as part of a rack server system 624. In addition, it can be implemented in a personal computer such as a laptop computer 622. Alternatively, components from computing device 600 can be combined with other components in a mobile device (not shown), such as device 650. Each of such devices can contain one or more of computing device 600, 650, and an entire system can be made up of multiple computing devices 600, 650 communicating with each other.

Computing device 650 includes a processor 652, memory 664, and an input/output device such as a display 654, a communication interface 666, and a transceiver 668, among other components. The device 650 can also be provided with a storage device, such as a micro-drive or other device, to provide additional storage. Each of the components 650, 652, 664, 654, 666, and 668, are interconnected using various buses, and several of the components can be mounted on a common motherboard or in other manners as appropriate.

The processor 652 can execute instructions within the computing device 650, including instructions stored in the memory 664. The processor can be implemented as a chipset of chips that include separate and multiple analog and digital processors. Additionally, the processor can be implemented using any of a number of architectures. For example, the processor 610 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 650, such as control of user interfaces, applications run by device 650, and wireless communication by device 650.

Processor 652 can communicate with a user through control interface 658 and display interface 656 coupled to a display 654. The display 654 can be, for example, a TFT (Thin-Film-Transistor Liquid Crystal Display) display or an OLED (Organic Light Emitting Diode) display, or other appropriate display technology. The display interface 656 can comprise appropriate circuitry for driving the display 654 to present graphical and other information to a user. The control interface 658 can receive commands from a user and convert them for submission to the processor 652. In addition, an external interface 662 can be provide in communication with processor 652, so as to enable near area communication of device 650 with other devices. External interface 662 can provide, for example, for wired communication in some implementations, or for wireless communication in other implementations, and multiple interfaces can also be used.

The memory 664 stores information within the computing device 650. The memory 664 can be implemented as one or more of a computer-readable medium or media, a volatile memory unit or units, or a non-volatile memory unit or units. Expansion memory 674 can also be provided and connected to device 650 through expansion interface 672, which can include, for example, a SIMM (Single In Line Memory Module) card interface. Such expansion memory 674 can provide extra storage space for device 650, or can also store applications or other information for device 650. Specifically, expansion memory 674 can include instructions to carry out or supplement the processes described above, and can include secure information also. Thus, for example, expansion memory 674 can be provide as a security module for device 650, and can be programmed with instructions that permit secure use of device 650. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 664, expansion memory 674, or memory on processor 652 that can be received, for example, over transceiver 668 or external interface 662.

Device 650 can communicate wirelessly through communication interface 666, which can include digital signal processing circuitry where necessary. Communication interface 666 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 668. In addition, short-range communication can occur, such as using a Bluetooth, Wi-Fi, or other such transceiver (not shown). In addition, GPS (Global Positioning System) receiver module 670 can provide additional navigation- and location-related wireless data to device 650, which can be used as appropriate by applications running on device 650.

Device 650 can also communicate audibly using audio codec 660, which can receive spoken information from a user and convert it to usable digital information. Audio codec 660 can likewise generate audible sound for a user, such as through a speaker, e.g., in a handset of device 650. Such sound can include sound from voice telephone calls, can include recorded sound, e.g., voice messages, music files, etc. and can also include sound generated by applications operating on device 650.

The computing device 650 can be implemented in a number of different forms, as shown in the figure. For example, it can be implemented as a cellular telephone 680. It can also be implemented as part of a smartphone 682, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Computer Systems

The practice of the present methods may also employ computer related software and systems. Computer software products as described herein typically include computer readable medium having computer-executable instructions for performing the logic steps of the method as described herein. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2.sup.nd ed., 2001). See U.S. Pat. No. 6,420,108.

The present methods may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present methods relates to embodiments that include methods for providing genetic information over networks such as the Internet as shown in U.S. Ser. Nos. 10/197,621, 10/063,559 (U.S. Publication Number 20020183936), U.S. Ser. Nos. 10/065,856, 10/065,868, 10/328,818, 10/328,872, 10/423,403, and 60/482,389. For example, one or more molecular profiling techniques can be performed in one location, e.g., a city, state, country or continent, and the results can be transmitted to a different city, state, country or continent. Treatment selection can then be made in whole or in part in the second location. The methods as described herein comprise transmittal of information between different locations.

Conventional data networking, application development and other functional aspects of the systems (and components of the individual operating components of the systems) may not be described in detail herein but are part as described herein. Furthermore, the connecting lines shown in the various figures contained herein are intended to represent illustrative functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: patient data such as family history, demography and environmental data, biological sample data, prior treatment and protocol data, patient clinical data, molecular profiling data of biological samples, data on therapeutic drug agents and/or investigative drugs, a gene library, a disease library, a drug library, patient tracking data, file management data, financial management data, billing data and/or like data useful in the operation of the system. As those skilled in the art will appreciate, user computer may include an operating system (e.g., Windows NT, 95/98/2000, OS2, UNIX, Linux, Solaris, MacOS, etc.) as well as various conventional support software and drivers typically associated with computers. The computer may include any suitable personal computer, network computer, workstation, minicomputer, mainframe or the like. User computer can be in a home or medical/business environment with access to a network. In an illustrative embodiment, access is through a network or the Internet through a commercially-available web-browser software package.

As used herein, the term "network" shall include any electronic communications means which incorporates both hardware and software components of such. Communication among the parties may be accomplished through any suitable communication channels, such as, for example, a telephone network, an extranet, an intranet, Internet, point of interaction device, personal digital assistant (e.g., Palm Pilot®, Blackberry®), cellular phone, kiosk, etc.), online communications, satellite communications, off-line communications, wireless communications, transponder communications, local area network (LAN), wide area network (WAN), networked or linked devices, keyboard, mouse and/or any suitable communication or data input modality. Moreover, although the system is frequently described herein as being implemented with TCP/IP communications protocols, the system may also be implemented using IPX, Appletalk, IP-6, NetBIOS, OSI or any number of existing or future protocols. If the network is in the nature of a public network, such as the Internet, it may be advantageous to presume the network to be insecure and open to eavesdroppers. Specific information related to the protocols, standards, and application software used in connection with the Internet is generally known to those skilled in the art and, as such, need not be detailed herein. See, for example, Dilip Naik, Internet Standards and Protocols (1998); Java 2 Complete, various authors, (Sybex 1999); Deborah Ray and Eric Ray, Mastering HTML 4.0 (1997); and Loshin, TCP/IP Clearly Explained (1997) and David Gourley and Brian Tatty, HTTP, The Definitive Guide (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish networks, ISDN, Digital Subscriber Line (DSL), or various wireless communication methods, see, e.g., Gilbert Held, Understanding Data Communications (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

As used herein, "transmit" may include sending electronic data from one system component to another over a network connection. Additionally, as used herein, "data" may include encompassing information such as commands, queries, files, data for storage, and the like in digital or any other form.

The system contemplates uses in association with web services, utility computing, pervasive and individualized computing, security and identity solutions, autonomic computing, commodity computing, mobility and wireless solutions, open source, biometrics, grid computing and/or mesh computing.

Any databases discussed herein may include relational, hierarchical, graphical, or object-oriented structure and/or any other database configurations. Common database products that may be used to implement the databases include DB2 by IBM (White Plains, NY), various database products available from Oracle Corporation (Redwood Shores, CA), Microsoft Access or Microsoft SQL Server by Microsoft Corporation (Redmond, Washington), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be used to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed vione or more keys, numeric, alphabetical by first tuple, etc.); Binary Large Object (BLOB); stored as ungrouped data elements encoded using ISO/IEC 7816-6 data elements; stored as ungrouped data elements encoded using ISO/IEC Abstract Syntax Notation (ASN.1) as in ISO/IEC 8824 and 8825; and/or other proprietary techniques that may include fractal compression methods, image compression methods, etc.

In one illustrative embodiment, the ability to store a wide variety of information in different formats is facilitated by storing the information as a BLOB. Thus, any binary information can be stored in a storage space associated with a data set. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data by multiple and unrelated owners of the data sets. For example, a first data set which may be stored may be provided by a first party, a second data set which may be stored may be provided by an unrelated second party, and yet a third data set which may be stored, may be provided by a third party unrelated to the first and second party. Each of these three illustrative data sets may contain different information that is stored using different data storage formats and/or techniques. Further, each data set may contain subsets of data that also may be distinct from other subsets.

As stated above, in various embodiments, the data can be stored without regard to a common format. However, in one illustrative embodiment, the data set (e.g., BLOB) may be annotated in a standard manner when provided for manipulating the data. The annotation may comprise a short header, trailer, or other appropriate indicator related to each data set that is configured to convey information useful in managing the various data sets. For example, the annotation may be called a "condition header", "header", "trailer", or "status", herein, and may comprise an indication of the status of the data set or may include an identifier correlated to a specific issuer or owner of the data. Subsequent bytes of data may be used to indicate for example, the identity of the issuer or owner of the data, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, issuer or owner of data, user or the like. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate. The data, including the header or trailer may be received by a standalone interaction device configured to add, delete, modify, or augment the data in accordance with the header or trailer.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

The computing unit of the web client may be further equipped with an Internet browser connected to the Internet or an intranet using standard dial-up, cable, DSL or any other Internet protocol known in the art. Transactions originating at a web client may pass through a firewall in order to prevent unauthorized access from users of other networks. Further, additional firewalls may be deployed between the varying components of CMS to further enhance security.

Firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based and Packet Filtering among others. Firewall may be integrated within an web server or any other CMS components or may further reside as a separate entity.

The computers discussed herein may provide a suitable website or other Internet-based graphical user interface which is accessible by users. In one embodiment, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, Interbase, etc., may be used to provide an Active Data Object (ADO) compliant database management system.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, Java applets, JavaScript, active server pages (ASP), common gateway interface scripts (CGI), extensible markup language (XML), dynamic HTML, cascading style sheets (CSS), helper applications, plug-ins, and the like. A server may include a web service that receives a request from a web server, the request including a URL (http://yahoo.com/stockquotes/ge) and an IP address (123.56.789.234). The web server retrieves the appropriate web pages and sends the data or applications for the web pages to the IP address. Web services are applications that are capable of interacting with other applications over a communications means, such as the internet. Web services are typically based on standards or protocols such as XML, XSLT, SOAP, WSDL and UDDI. Web services methods are well known in the art, and are covered in many standard texts. See, e.g., Alex Nghiem, IT Web Services: A Roadmap for the Enterprise (2003), hereby incorporated by reference.

The web-based clinical database for the system and method of the present methods preferably has the ability to upload and store clinical data files in native formats and is searchable on any clinical parameter. The database is also scalable and may use an EAV data model (metadata) to enter clinical annotations from any study for easy integration with other studies. In addition, the web-based clinical database is flexible and may be XML and XSLT enabled to be able to add user customized questions dynamically. Further, the database includes exportability to CDISC ODM.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, Macromedia Cold Fusion, Microsoft Active Server Pages, Java, COBOL, assembler, PERL, Visual Basic, SQL Stored Procedures, extensible markup language (XML), with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JavaScript, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "Java Cryptography" by Jonathan Knudson, published by O'Reilly & Associates (1998); (3) "Cryptography & Network Security: Principles & Practice" by William Stallings, published by Prentice Hall; all of which are hereby incorporated by reference.

As used herein, the term "end user", "consumer", "customer", "client", "treating physician", "hospital", or "business" may be used interchangeably with each other, and each shall mean any person, entity, machine, hardware, software or business. Each participant is equipped with a computing device in order to interact with the system and facilitate online data access and data input. The customer has a computing unit in the form of a personal computer, although other types of computing units may be used including laptops, notebooks, hand held computers, set-top boxes, cellular telephones, touch-tone telephones and the like. The owner/operator of the system and method of the present methods has a computing unit implemented in the form of a computer-server, although other implementations are contemplated by the system including a computing center shown as a main frame computer, a minicomputer, a PC server, a network of computers located in the same of different geographic locations, or the like. Moreover, the system contemplates the use, sale or distribution of any goods, services or information over any network having similar functionality described herein.

In one illustrative embodiment, each client customer may be issued an "account" or "account number". As used herein, the account or account number may include any device, code, number, letter, symbol, digital certificate, smart chip, digital signal, analog signal, biometric or other identifier/indicia suitably configured to allow the consumer to access, interact with or communicate with the system (e.g., one or more of an authorization/access code, personal identification number (PIN), Internet code, other identification code, and/or the like). The account number may optionally be located on or associated with a charge card, credit card, debit card, prepaid card, embossed card, smart card, magnetic stripe card, bar code card, transponder, radio frequency card or an associated account. The system may include or interface with any of the foregoing cards or devices, or a fob having a transponder and RFID reader in RF communication with the fob. Although the system may include a fob embodiment, the methods is not to be so limited. Indeed, system may include any device having a transponder which is configured to communicate with RFID reader via RF communication. Typical devices may include, for example, a key ring, tag, card, cell phone, wristwatch or any such form capable of being presented for interrogation. Moreover, the system, computing unit or device discussed herein may include a "pervasive computing device," which may include a traditionally non-computerized device that is embedded with a computing unit. The account number may be distributed and stored in any form of plastic, electronic, magnetic, radio frequency, wireless, audio and/or optical device capable of transmitting or downloading data from itself to a second device.

As will be appreciated by one of ordinary skill in the art, the system may be embodied as a customization of an existing system, an add-on product, upgraded software, a standalone system, a distributed system, a method, a data processing system, a device for data processing, and/or a computer program product. Accordingly, the system may take the form of an entirely software embodiment, an entirely hardware embodiment, or an embodiment combining aspects of both software and hardware. Furthermore, the system may take the form of a computer program product on a computer-readable storage medium having computer-readable program code means embodied in the storage medium. Any suitable computer-readable storage medium may be used, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, web pages, websites, web forms, prompts, etc. Practitioners will appreciate that the illustrated steps described herein may comprise in any number of configurations including the use of windows, web pages, web forms, popup windows, prompts and the like. It should be further appreciated that the multiple steps as illustrated and described may be combined into single web pages and/or windows but have been expanded for the sake of simplicity. In other cases, steps illustrated and described as single process steps may be separated into multiple web pages and/or windows but have been combined for simplicity.

Molecular Profiling

The molecular profiling approach provides a method for selecting a candidate treatment for an individual that could favorably change the clinical course for the individual with a condition or disease, such as cancer. The molecular profiling approach provides clinical benefit for individuals, such as identifying therapeutic regimens that provide a longer progression free survival (PFS), longer disease free survival (DFS), longer overall survival (OS) or extended lifespan. Methods and systems as described herein are directed to molecular profiling of cancer on an individual basis that can identify optimal therapeutic regimens. Molecular profiling provides a personalized approach to selecting candidate treatments that are likely to benefit a cancer. The molecular profiling methods described herein can be used to guide treatment in any desired setting, including without limitation the front-line/standard of care setting, or for patients with poor prognosis, such as those with metastatic disease or those whose cancer has progressed on standard front line therapies, or whose cancer has progressed on previous chemotherapeutic or hormonal regimens.

The systems and methods of the invention may be used to classify patients as more or less likely to benefit or respond to various treatments. Unless otherwise noted, the terms "response" or "non-response," as used herein, refer to any appropriate indication that a treatment provides a benefit to a patient (a "responder" or "benefiter") or has a lack of benefit to the patient (a "non-responder" or "non-benefiter"). Such an indication may be determined using accepted clinical response criteria such as the standard Response Evaluation Criteria in Solid Tumors (RECIST) criteria, or other useful patient response criteria such as progression free survival (PFS), time to progression (TTP), disease free survival (DFS), time-to-next treatment (TNT, TTNT), tumor shrinkage or disappearance, or the like. RECIST is a set of rules published by an international consortium that define when tumors improve ("respond"), stay the same ("stabilize"), or worsen ("progress") during treatment of a cancer patient. As used herein and unless otherwise noted, a patient "benefit" from a treatment may refer to any appropriate measure of improvement, including without limitation a RECIST response or longer PFS/TTP/DFS/TNT/TTNT, whereas "lack of benefit" from a treatment may refer to any appropriate measure of worsening disease during treatment. Generally disease stabilization is considered a benefit, although in certain circumstances, if so noted herein, stabilization may be considered a lack of benefit. A predicted or indicated benefit may be described as "indeterminate" if there is not an acceptable level of prediction of benefit or lack of benefit. In some cases, benefit is considered indeterminate if it cannot be calculated, e.g., due to lack of necessary data.

Personalized medicine based on pharmacogenetic insights, such as those provided by molecular profiling as described herein, is increasingly taken for granted by some practitioners and the lay press, but forms the basis of hope for improved cancer therapy. However, molecular profiling as taught herein represents a fundamental departure from the traditional approach to oncologic therapy where for the most part, patients are grouped together and treated with approaches that are based on findings from light microscopy and disease stage. Traditionally, differential response to a particular therapeutic strategy has only been determined after the treatment was given, i.e., a posteriori. The "standard" approach to disease treatment relies on what is generally true about a given cancer diagnosis and treatment response has been vetted by randomized phase III clinical trials and forms the "standard of care" in medical practice. The results of these trials have been codified in consensus statements by guidelines organizations such as the National Comprehensive Cancer Network and The American Society of Clinical Oncology. The NCCN Compendium™ contains authoritative, scientifically derived information designed to support decision-making about the appropriate use of drugs and biologics in patients with cancer. The NCCN Compendium™ is recognized by the Centers for Medicare and Medicaid Services (CMS) and United Healthcare as an authoritative reference for oncology coverage policy. On-compendium treatments are those recommended by such guides. The biostatistical methods used to validate the results of clinical trials rely on minimizing differences between patients, and are based on declaring the likelihood of error that one approach is better than another for a patient group defined only by light microscopy and stage, not by individual differences in tumors. The molecular profiling methods described herein exploit such individual differences. The methods can provide candidate treatments that can be then selected by a physician for treating a patient.

Molecular profiling can be used to provide a comprehensive view of the biological state of a sample. In an embodiment, molecular profiling is used for whole tumor profiling. Accordingly, a number of molecular approaches are used to assess the state of a tumor. The whole tumor profiling can be used for selecting a candidate treatment for a tumor. Molecular profiling can be used to select candidate therapeutics on any sample for any stage of a disease. In embodiment, the methods as described herein are nused to profile a newly diagnosed cancer. The candidate treatments indicated by the molecular profiling can be used to select a therapy for treating the newly diagnosed cancer. In other embodiments, the methods as described herein are used to profile a cancer that has already been treated, e.g., with one or more standard-of-care therapy. In embodiments, the cancer is refractory to the prior treatment/s. For example, the cancer may be refractory to the standard of care treatments for the cancer. The cancer can be a metastatic cancer or other recurrent cancer. The treatments can be on-compendium or off-compendium treatments.

Molecular profiling can be performed by any known means for detecting a molecule in a biological sample. Molecular profiling comprises methods that include but are not limited to, nucleic acid sequencing, such as a DNA sequencing or RNA sequencing; immunohistochemistry (IHC); in situ hybridization (ISH); fluorescent in situ hybridization (FISH); chromogenic in situ hybridization (CISH); PCR amplification (e.g., qPCR or RT-PCR); various types of microarray (mRNA expression arrays, low density arrays, protein arrays, etc); various types of sequencing (Sanger, pyrosequencing, etc); comparative genomic hybridization (CGH); high throughput or next generation sequencing (NGS); Northern blot; Southern blot; immunoassay; and any other appropriate technique to assay the presence or quantity of a biological molecule of interest. In various embodiments, any one or more of these methods can be used concurrently or subsequent to each other for assessing target genes disclosed herein.

Molecular profiling of individual samples is used to select one or more candidate treatments for a disorder in a subject, e.g., by identifying targets for drugs that may be effective for a given cancer. For example, the candidate treatment can be a treatment known to have an effect on cells that differentially express genes as identified by molecular profiling techniques, an experimental drug, a government or regulatory approved drug or any combination of such drugs, which may have been studied and approved for a particular indication that is the same as or different from the indication of the subject from whom a biological sample is obtain and molecularly profiled.

When multiple biomarker targets are revealed by assessing target genes by molecular profiling, one or more decision rules can be put in place to prioritize the selection of certain therapeutic agent for treatment of an individual on a personalized basis. Rules as described herein aide prioritizing treatment, e.g., direct results of molecular profiling, anticipated efficacy of therapeutic agent, prior history with the same or other treatments, expected side effects, availability of therapeutic agent, cost of therapeutic agent, drug-drug interactions, and other factors considered by a treating physician. Based on the recommended and prioritized therapeutic agent targets, a physician can decide on the course of treatment for a particular individual. Accordingly, molecular profiling methods and systems as described herein can select candidate treatments based on individual characteristics of diseased cells, e.g., tumor cells, and other personalized factors in a subject in need of treatment, as opposed to relying on a traditional one-size fits all approach that is conventionally used to treat individuals suffering from a disease, especially cancer. In some cases, the recommended treatments are those not typically used to treat the disease or disorder inflicting the subject. In some cases, the recommended treatments are used after standard-of-care therapies are no longer providing adequate efficacy.

The treating physician can use the results of the molecular profiling methods to optimize a treatment regimen for a patient. The candidate treatment identified by the methods as described herein can be used to treat a patient; however, such treatment is not required of the methods. Indeed, the analysis of molecular profiling results and identification of candidate treatments based on those results can be automated and does not require physician involvement.

Biological Entities

Nucleic acids include deoxyribonucleotides or ribonucleotides and polymers thereof in either single- or double-stranded form, or complements thereof. Nucleic acids can contain known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Nucleic acid sequence can encompass conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell Probes 8:91-98 (1994)). The term nucleic acid can be used interchangeably with gene, cDNA, mRNA, oligonucleotide, and polynucleotide.

A particular nucleic acid sequence may implicitly encompass the particular sequence and "splice variants" and nucleic acid sequences encoding truncated forms. Similarly, a particular protein encoded by a nucleic acid can encompass any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or created using recombinant techniques.

The terms "genetic variant" and "nucleotide variant" are used herein interchangeably to refer to changes or alterations to the reference human gene or cDNA sequence at a particular locus, including, but not limited to, nucleotide base deletions, insertions, inversions, and substitutions in the coding and non-coding regions. Deletions may be of a single nucleotide base, a portion or a region of the nucleotide sequence of the gene, or of the entire gene sequence. Insertions may be of one or more nucleotide bases. The genetic variant or nucleotide variant may occur in transcriptional regulatory regions, untranslated regions of mRNA, exons, introns, exon/intron junctions, etc. The genetic variant or nucleotide variant can potentially result in stop codons, frame shifts, deletions of amino acids, altered gene transcript splice forms or altered amino acid sequence.

An allele or gene allele comprises generally a naturally occurring gene having a reference sequence or a gene containing a specific nucleotide variant.

A haplotype refers to a combination of genetic (nucleotide) variants in a region of an mRNA or a genomic DNA on a chromosome found in an individual. Thus, a haplotype includes a number of genetically linked polymorphic variants which are typically inherited together as a unit.

As used herein, the term "amino acid variant" is used to refer to an amino acid change to a reference human protein sequence resulting from genetic variants or nucleotide variants to the reference human gene encoding the reference protein. The term "amino acid variant" is intended to encompass not only single amino acid substitutions, but also amino acid deletions, insertions, and other significant changes of amino acid sequence in the reference protein.

The term "genotype" as used herein means the nucleotide characters at a particular nucleotide variant marker (or locus) in either one allele or both alleles of a gene (or a particular chromosome region). With respect to a particular nucleotide position of a gene of interest, the nucleotide(s) at that locus or equivalent thereof in one or both alleles form the genotype of the gene at that locus. A genotype can be homozygous or heterozygous. Accordingly, "genotyping" means determining the genotype, that is, the nucleotide(s) at a particular gene locus. Genotyping can also be done by determining the amino acid variant at a particular position of a protein which can be used to deduce the corresponding nucleotide variant(s).

The term "locus" refers to a specific position or site in a gene sequence or protein. Thus, there may be one or more contiguous nucleotides in a particular gene locus, or one or more amino acids at a particular locus in a polypeptide. Moreover, a locus may refer to a particular position in a gene where one or more nucleotides have been deleted, inserted, or inverted.

Unless specified otherwise or understood by one of skill in art, the terms "polypeptide," "protein," and "peptide" are used interchangeably herein to refer to an amino acid chain in which the amino acid residues are linked by covalent peptide bonds. The amino acid chain can be of any length of at least two amino acids, including full-length proteins. Unless otherwise specified, polypeptide, protein, and peptide also encompass various modified forms thereof, including but not limited to glycosylated forms, phosphorylated forms, etc. A polypeptide, protein or peptide can also be referred to as a gene product.

Lists of gene and gene products that can be assayed by molecular profiling techniques are presented herein. Lists of genes may be presented in the context of molecular profiling techniques that detect a gene product (e.g., an mRNA or protein). One of skill will understand that this implies detection of the gene product of the listed genes. Similarly, lists of gene products may be presented in the context of molecular profiling techniques that detect a gene sequence or copy number. One of skill will understand that this implies detection of the gene corresponding to the gene products, including as an example DNA encoding the gene products. As will be appreciated by those skilled in the art, a "biomarker" or "marker" comprises a gene and/or gene product depending on the context.

The terms "label" and "detectable label" can refer to any composition detectable by spectroscopic, photochemical, biochemical, immunochemical, electrical, optical, chemical or similar methods. Such labels include biotin for staining with labeled streptavidin conjugate, magnetic beads (e.g., DYNABEADS™), fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. Labels can include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden Introduction to Immunocytochemistry, 2nd ed., Springer Verlag, N Y (1997); and in Haugland Handbook of Fluorescent Probes and Research Chemicals, a combined handbook and catalogue Published by Molecular Probes, Inc. (1996).

Detectable labels include, but are not limited to, nucleotides (labeled or unlabelled), compomers, sugars, peptides, proteins, antibodies, chemical compounds, conducting polymers, binding moieties such as biotin, mass tags, calorimetric agents, light emitting agents, chemiluminescent agents, light scattering agents, fluorescent tags, radioactive tags, charge tags (electrical or magnetic charge), volatile tags and hydrophobic tags, biomolecules (e.g., members of a binding pair antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) and the like.

The terms "primer", "probe," and "oligonucleotide" are used herein interchangeably to refer to a relatively short nucleic acid fragment or sequence. They can comprise DNA, RNA, or a hybrid thereof, or chemically modified analog or derivatives thereof. Typically, they are single-stranded. However, they can also be double-stranded having two complementing strands which can be separated by denaturation. Normally, primers, probes and oligonucleotides have a length of from about 8 nucleotides to about 200 nucleotides, preferably from about 12 nucleotides to about 100 nucleotides, and more preferably about 18 to about 50 nucleotides. They can be labeled with detectable markers or modified using conventional manners for various molecular biological applications.

The term "isolated" when used in reference to nucleic acids (e.g., genomic DNAs, cDNAs, mRNAs, or fragments thereof) is intended to mean that a nucleic acid molecule is present in a form that is substantially separated from other naturally occurring nucleic acids that are normally associated with the molecule. Because a naturally existing chromosome (or a viral equivalent thereof) includes a long nucleic acid sequence, an isolated nucleic acid can be a nucleic acid molecule having only a portion of the nucleic acid sequence in the chromosome but not one or more other portions present on the same chromosome. More specifically, an isolated nucleic acid can include naturally occurring nucleic acid sequences that flank the nucleic acid in the naturally existing chromosome (or a viral equivalent thereof). An isolated nucleic acid can be substantially separated from other naturally occurring nucleic acids that are on a different chromosome of the same organism. An isolated nucleic acid can also be a composition in which the specified nucleic acid molecule is significantly enriched so as to constitute at least 10%, 20%, 30%, 40%, 50%, 60%, 70%, 80%, 90%, 95%, or at least 99% of the total nucleic acids in the composition.

An isolated nucleic acid can be a hybrid nucleic acid having the specified nucleic acid molecule covalently linked to one or more nucleic acid molecules that are not the nucleic acids naturally flanking the specified nucleic acid. For example, an isolated nucleic acid can be in a vector. In addition, the specified nucleic acid may have a nucleotide sequence that is identical to a naturally occurring nucleic acid or a modified form or mutein thereof having one or more mutations such as nucleotide substitution, deletion/insertion, inversion, and the like.

An isolated nucleic acid can be prepared from a recombinant host cell (in which the nucleic acids have been recombinantly amplified and/or expressed), or can be a chemically synthesized nucleic acid having a naturally occurring nucleotide sequence or an artificially modified form thereof.

The term "high stringency hybridization conditions," when used in connection with nucleic acid hybridization, includes hybridization conducted overnight at 42° C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 0.1×SSC at about 65° C. The term "moderate stringent hybridization conditions," when used in connection with nucleic acid hybridization, includes hybridization conducted overnight at 37° C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 1×SSC at about 50° C. It is noted that many other hybridization methods, solutions and temperatures can be used to achieve comparable stringent hybridization conditions as will be apparent to skilled artisans.

For the purpose of comparing two different nucleic acid or polypeptide sequences, one sequence (test sequence) may be described to be a specific percentage identical to another sequence (comparison sequence). The percentage identity can be determined by the algorithm of Karlin and Altschul, Proc. Natl. Acad. Sci. USA, 90:5873-5877 (1993), which is incorporated into various BLAST programs. The percentage identity can be determined by the "BLAST 2 Sequences" tool, which is available at the National Center for Biotechnology Information (NCBI) website. See Tatusova and Madden, FEMS Microbiol. Lett., 174(2):247-250 (1999). For pairwise DNA-DNA comparison, the BLASTN program is used with default parameters (e.g., Match: 1; Mismatch: −2; Open gap: 5 penalties; extension gap: 2 penalties; gap x_dropoff: 50; expect: 10; and word size: 11, with filter). For pairwise protein-protein sequence comparison, the BLASTP program can be employed using default parameters (e.g., Matrix: BLOSUM62; gap open: 11; gap extension: 1; x_dropoff: 15; expect: 10.0; and wordsize: 3, with filter). Percent identity of two sequences is calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence. When BLAST is used to compare two sequences, it aligns the sequences and yields the percent identity over defined, aligned regions. If the two sequences are aligned across their entire length, the percent identity yielded by the BLAST is the percent identity of the two sequences. If BLAST does not align the two sequences over their entire length, then the number of identical amino acids or nucleotides in the unaligned regions of the test sequence and comparison sequence is considered to be zero and the percent identity is calculated by adding the number of identical amino acids or nucleotides in the aligned regions and dividing that number by the length of the comparison sequence. Various versions of the BLAST programs can be used to compare sequences, e.g., BLAST 2.1.2 or BLAST+ 2.2.22.

A subject or individual can be any animal which may benefit from the methods described herein, including, e.g., humans and non-human mammals, such as primates, rodents, horses, dogs and cats. Subjects include without limitation a eukaryotic organisms, most preferably a mammal such as a primate, e.g., chimpanzee or human, cow; dog; cat; a rodent, e.g., guinea pig, rat, mouse; rabbit; or a bird; reptile; or fish. Subjects specifically intended for treatment using the methods described herein include humans. A subject may also be referred to herein as an individual or a patient. In the present methods the subject has colorectal cancer, e.g., has been diagnosed with colorectal cancer. Methods for identifying subjects with colorectal cancer are known in the art, e.g., using a biopsy. See, e.g., Fleming et al., J Gastrointest Oncol. 2012 September; 3(3): 153-173; Chang et al., Dis Colon Rectum. 2012; 55(8):831-43.

Treatment of a disease or individual according to the methods described herein is an approach for obtaining beneficial or desired medical results, including clinical results, but not necessarily a cure. For purposes of the methods described herein, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. Treatment also includes prolonging survival as compared to expected survival if not receiving treatment or if receiving a different treatment. A treatment can include administration of either the FOLFOX or FOLFIRI regimen. A biomarker refers generally to a molecule, including without limitation a gene or product thereof, nucleic acids (e.g., DNA, RNA), protein/peptide/polypeptide, carbohydrate structure, lipid, glycolipid, characteristics of which can be detected in a tissue or cell to provide information that is predictive, diagnostic, prognostic and/or theranostic for sensitivity or resistance to candidate treatment.

Biological Samples

A sample as used herein includes any relevant biological sample that can be used for molecular profiling, e.g., sections of tissues such as biopsy or tissue removed during surgical or other procedures, bodily fluids, autopsy samples, and frozen sections taken for histological purposes. Such samples include blood and blood fractions or products (e.g., serum, buffy coat, plasma, platelets, red blood cells, and the like), sputum, malignant effusion, cheek cells tissue, cultured cells (e.g., primary cultures, explants, and transformed cells), stool, urine, other biological or bodily fluids (e.g., prostatic fluid, gastric fluid, intestinal fluid, renal fluid, lung fluid, cerebrospinal fluid, and the like), etc. The sample can comprise biological material that is a fresh frozen & formalin fixed paraffin embedded (FFPE) block, formalin-fixed paraffin embedded, or is within an RNA preservative+ formalin fixative. More than one sample of more than one type can be used for each patient. In a preferred embodiment, the sample comprises a fixed tumor sample.

The sample used in the systems and methods of the invention can be a formalin fixed paraffin embedded (FFPE) sample. The FFPE sample can be one or more of fixed tissue, unstained slides, bone marrow core or clot, core needle biopsy, malignant fluids and fine needle aspirate (FNA). In an embodiment, the fixed tissue comprises a tumor containing formalin fixed paraffin embedded (FFPE) block from a surgery or biopsy. In another embodiment, the unstained slides comprise unstained, charged, unbaked slides from a paraffin block. In another embodiment, bone marrow core or clot comprises a decalcified core. A formalin fixed core and/or clot can be paraffin-embedded. In still another embodiment, the core needle biopsy comprises 1, 2, 3, 4, 5, 6, 7, 8, 9, 10 or more, e.g., 3-4, paraffin embedded biopsy samples. An 18 gauge needle biopsy can be used. The malignant fluid can comprise a sufficient volume of fresh pleural/ascitic fluid to produce a 5×5×2 mm cell pellet. The fluid can be formalin fixed in a paraffin block. In an embodiment, the core needle biopsy comprises 1, 2, 3, 4, 5, 6, 7, 8, 9, 10 or more, e.g., 4-6, paraffin embedded aspirates.

A sample may be processed according to techniques understood by those in the art. A sample can be without limitation fresh, frozen or fixed cells or tissue. In some embodiments, a sample comprises formalin-fixed paraffin-embedded (FFPE) tissue, fresh tissue or fresh frozen (FF) tissue. A sample can comprise cultured cells, including primary or immortalized cell lines derived from a subject sample. A sample can also refer to an extract from a sample from a subject. For example, a sample can comprise DNA, RNA or protein extracted from a tissue or a bodily fluid. Many techniques and commercial kits are available for such purposes. The fresh sample from the individual can be treated with an agent to preserve RNA prior to further processing, e.g., cell lysis and extraction. Samples can include frozen samples collected for other purposes. Samples can be associated with relevant information such as age, gender, and clinical symptoms present in the subject; source of the sample; and methods of collection and storage of the sample. A sample is typically obtained from a subject.

A biopsy comprises the process of removing a tissue sample for diagnostic or prognostic evaluation, and to the tissue specimen itself. Any biopsy technique known in the art can be applied to the molecular profiling methods of the present disclosure. The biopsy technique applied can depend on the tissue type to be evaluated (e.g., colon, prostate, kidney, bladder, lymph node, liver, bone marrow, blood cell, lung, breast, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. Molecular profiling can use a "core-needle biopsy" of the tumor mass, or a "fine-needle aspiration biopsy" which generally obtains a suspension of cells from within the tumor mass. Biopsy techniques are discussed, for example, in Harrison's Principles of Internal Medicine, Kasper, et al., eds., 16th ed., 2005, Chapter 70, and throughout Part V.

Unless otherwise noted, a "sample" as referred to herein for molecular profiling of a patient may comprise more than one physical specimen. As one non-limiting example, a "sample" may comprise multiple sections from a tumor, e.g., multiple sections of an FFPE block or multiple core-needle biopsy sections. As another non-limiting example, a "sample" may comprise multiple biopsy specimens, e.g., one or more surgical biopsy specimen, one or more core-needle biopsy specimen, one or more fine-needle aspiration biopsy specimen, or any useful combination thereof. As still another non-limiting example, a molecular profile may be generated for a subject using a "sample" comprising a solid tumor specimen and a bodily fluid specimen. In some embodiments, a sample is a unitary sample, i.e., a single physical specimen.

Standard molecular biology techniques known in the art and not specifically described are generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) can be carried out generally as in PCR Protocols: A Guide to Methods and Applications, Academic Press, San Diego, Calif. (1990).

Vesicles

The sample can comprise vesicles. Methods as described herein can include assessing one or more vesicles, including assessing vesicle populations. A vesicle, as used herein, is a membrane vesicle that is shed from cells. Vesicles or membrane vesicles include without limitation: circulating microvesicles (cMVs), microvesicle, exosome, nanovesicle, dexosome, bleb, blebby, prostasome, microparticle, intralumenal vesicle, membrane fragment, intralumenal endosomal vesicle, endosomal-like vesicle, exocytosis vehicle, endosome vesicle, endosomal vesicle, apoptotic body, multivesicular body, secretory vesicle, phospholipid vesicle, liposomal vesicle, argosome, texasome, secresome, tolerosome, melanosome, oncosome, or exocytosed vehicle. Furthermore, although vesicles may be produced by different cellular processes, the methods as described herein are not limited to or reliant on any one mechanism, insofar as such vesicles are present in a biological sample and are capable of being characterized by the methods disclosed herein. Unless otherwise specified, methods that make use of a species of vesicle can be applied to other types of vesicles. Vesicles comprise spherical structures with a lipid bilayer similar to cell membranes which surrounds an inner compartment which can contain soluble components, sometimes referred to as the payload. In some embodiments, the methods as described herein make use of exosomes, which are small secreted vesicles of about 40-100 nm in diameter. For a review of membrane vesicles, including types and characterizations, see Thery et al., Nat Rev Immunol. 2009

August; 9(8):581-93. Some properties of different types of vesicles include those in Table 1:

TABLE 1

Vesicle Properties

| Feature | Exosomes | Micro-vesicles | Ectosomes | Membrane particles | Exosome-like vesicles | Apoptotic vesicles |
|---|---|---|---|---|---|---|
| Size | 50-100 nm | 100-1,000 nm | 50-200 nm | 50-80 nm | 20-50 nm | 50-500 nm |
| Density in sucrose | 1.13-1.19 g/ml | | | 1.04-1.07 g/ml | 1.1 g/ml | 1.16-1.28 g/ml |
| EM appearance | Cup shape | Irregular shape, electron dense | Bilamellar round structures | Round | Irregular shape | Hetero-geneous |
| Sedimentation | 100,000 g | 10,000 g | 160,000-200,000 g | 100,000-200,000 g | 175,000 g | 1,200 g, 10,000 g, 100,000 g |
| Lipid composition | Enriched in cholesterol, sphingomyelin and ceramide; contains lipid rafts; expose PPS | Expose PPS | Enriched in cholesterol and diacylglycerol; expose PPS | | No lipid rafts | |
| Major protein markers | Tetraspanins (e.g., CD63, CD9), Alix, TSG101 | Integrins, selectins and CD40 ligand | CR1 and proteolytic enzymes; no CD63 | CD133; no CD63 | TNFRI | Histones |
| Intra-cellular origin | Internal compartments (endosomes) | Plasma membrane | Plasma membrane | Plasma membrane | | |

Abbreviations: Phosphatidylserine (PPS); Electron Microscopy (EM)

Vesicles include shed membrane bound particles, or "microparticles," that are derived from either the plasma membrane or an internal membrane. Vesicles can be released into the extracellular environment from cells. Cells releasing vesicles include without limitation cells that originate from, or are derived from, the ectoderm, endoderm, or mesoderm. The cells may have undergone genetic, environmental, and/or any other variations or alterations. For example, the cell can be tumor cells. A vesicle can reflect any changes in the source cell, and thereby reflect changes in the originating cells, e.g., cells having various genetic mutations. In one mechanism, a vesicle is generated intracellularly when a segment of the cell membrane spontaneously invaginates and is ultimately exocytosed (see for example, Keller et al., Immunol. Lett. 107 (2): 102-8 (2006)). Vesicles also include cell-derived structures bounded by a lipid bilayer membrane arising from both herniated evagination (blebbing) separation and sealing of portions of the plasma membrane or from the export of any intracellular membrane-bounded vesicular structure containing various membrane-associated proteins of tumor origin, including surface-bound molecules derived from the host circulation that bind selectively to the tumor-derived proteins together with molecules contained in the vesicle lumen, including but not limited to tumor-derived microRNAs or intracellular proteins. Blebs and blebbing are further described in Charras et al., Nature Reviews Molecular and Cell Biology, Vol. 9, No. 11, p. 730-736 (2008). A vesicle shed into circulation or bodily fluids from tumor cells may be referred to as a "circulating tumor-derived vesicle." When such vesicle is an exosome, it may be referred to as a circulating-tumor derived exosome (CTE). In some instances, a vesicle can be derived from a specific cell of origin. CTE, as with a cell-of-origin specific vesicle, typically have one or more unique biomarkers that permit isolation of the CTE or cell-of-origin specific vesicle, e.g., from a bodily fluid and sometimes in a specific manner. For example, a cell or tissue specific markers are used to identify the cell of origin. Examples of such cell or tissue specific markers are disclosed herein and can further be accessed in the Tissue-specific Gene Expression and Regulation (TiGER) Database, available at bioinfo.wilmer.jhu.edu/tiger; Liu et al. (2008) TiGER: a database for tissue-specific gene expression and regulation. BMC Bioinformatics. 9:271; TissueDistributionDBs, available at genome.dkfz-heidelberg.de/menu/tissue_db/index.html.

A vesicle can have a diameter of greater than about 10 nm, 20 nm, or 30 nm. A vesicle can have a diameter of greater than 40 nm, 50 nm, 100 nm, 200 nm, 500 nm, 1000 nm or greater than 10,000 nm. A vesicle can have a diameter of about 30-1000 nm, about 30-800 nm, about 30-200 nm, or about 30-100 nm. In some embodiments, the vesicle has a diameter of less than 10,000 nm, 1000 nm, 800 nm, 500 nm, 200 nm, 100 nm, 50 nm, 40 nm, 30 nm, 20 nm or less than 10 nm. As used herein the term "about" in reference to a numerical value means that variations of 10% above or below the numerical value are within the range ascribed to the specified value. Typical sizes for various types of vesicles are shown in Table 1. Vesicles can be assessed to measure the diameter of a single vesicle or any number of vesicles. For example, the range of diameters of a vesicle population or an average diameter of a vesicle population can be determined. Vesicle diameter can be assessed using methods known in the art, e.g., imaging technologies such as electron microscopy. In an embodiment, a diameter of one or more vesicles is determined using optical particle detection. See, e.g., U.S. Pat. No. 7,751,053, entitled "Optical Detection and Analysis of Particles" and issued Jul. 6, 2010; and U.S. Pat. No. 7,399,600, entitled "Optical Detection and Analysis of Particles" and issued Jul. 15, 2010.

In some embodiments, vesicles are directly assayed from a biological sample without prior isolation, purification, or concentration from the biological sample. For example, the amount of vesicles in the sample can by itself provide a biosignature that provides a diagnostic, prognostic or theranostic determination. Alternatively, the vesicle in the sample may be isolated, captured, purified, or concentrated from a sample prior to analysis. As noted, isolation, capture or purification as used herein comprises partial isolation, partial capture or partial purification apart from other components in the sample. Vesicle isolation can be performed using various techniques as described herein or known in the art, including without limitation size exclusion chromatography, density gradient centrifugation, differential centrifugation, nanomembrane ultrafiltration, immunoabsorbent capture, affinity purification, affinity capture, immunoassay, immunoprecipitation, microfluidic separation, flow cytometry or combinations thereof.

Vesicles can be assessed to provide a phenotypic characterization by comparing vesicle characteristics to a reference. In some embodiments, surface antigens on a vesicle are assessed. A vesicle or vesicle population carrying a specific marker can be referred to as a positive (biomarker+) vesicle or vesicle population. For example, a DLL4+ population refers to a vesicle population associated with DLL4. Conversely, a DLL4− population would not be associated with DLL4. The surface antigens can provide an indication of the anatomical origin and/or cellular of the vesicles and other phenotypic information, e.g., tumor status. For example, vesicles found in a patient sample can be assessed for surface antigens indicative of colorectal origin and the presence of cancer, thereby identifying vesicles associated with colorectal cancer cells. The surface antigens may comprise any informative biological entity that can be detected on the vesicle membrane surface, including without limitation surface proteins, lipids, carbohydrates, and other membrane components. For example, positive detection of colon derived vesicles expressing tumor antigens can indicate that the patient has colorectal cancer. As such, methods as described herein can be used to characterize any disease or condition associated with an anatomical or cellular origin, by assessing, for example, disease-specific and cell-specific biomarkers of one or more vesicles obtained from a subject.

In embodiments, one or more vesicle payloads are assessed to provide a phenotypic characterization. The payload with a vesicle comprises any informative biological entity that can be detected as encapsulated within the vesicle, including without limitation proteins and nucleic acids, e.g., genomic or cDNA, mRNA, or functional fragments thereof, as well as microRNAs (miRs). In addition, methods as described herein are directed to detecting vesicle surface antigens (in addition or exclusive to vesicle payload) to provide a phenotypic characterization. For example, vesicles can be characterized by using binding agents (e.g., antibodies or aptamers) that are specific to vesicle surface antigens, and the bound vesicles can be further assessed to identify one or more payload components disclosed therein. As described herein, the levels of vesicles with surface antigens of interest or with payload of interest can be compared to a reference to characterize a phenotype. For example, overexpression in a sample of cancer-related surface antigens or vesicle payload, e.g., a tumor associated mRNA or microRNA, as compared to a reference, can indicate the presence of cancer in the sample. The biomarkers assessed can be present or absent, increased or reduced based on the selection of the desired target sample and comparison of the target sample to the desired reference sample. Non-limiting examples of target samples include: disease; treated/not-treated; different time points, such as in a longitudinal study; and non-limiting examples of reference sample: non-disease; normal; different time points; and sensitive or resistant to candidate treatment(s).

In an embodiment, molecular profiling as described herein comprises analysis of microvesicles, such as circulating microvesicles.

MicroRNA

Various biomarker molecules can be assessed in biological samples or vesicles obtained from such biological samples. MicroRNAs comprise one class biomarkers assessed via methods as described herein. MicroRNAs, also referred to herein as miRNAs or miRs, are short RNA strands approximately 21-23 nucleotides in length. MiRNAs are encoded by genes that are transcribed from DNA but are not translated into protein and thus comprise non-coding RNA. The miRs are processed from primary transcripts known as pri-miRNA to short stem-loop structures called pre-miRNA and finally to the resulting single strand miRNA. The pre-miRNA typically forms a structure that folds back on itself in self-complementary regions. These structures are then processed by the nuclease Dicer in animals or DCL1 in plants. Mature miRNA molecules are partially complementary to one or more messenger RNA (mRNA) molecules and can function to regulate translation of proteins. Identified sequences of miRNA can be accessed at publicly available databases, such as www.microRNA.org, www.mirbase.org, or www.mirz.unibas.ch/cgi/miRNA.cgi.

miRNAs are generally assigned a number according to the naming convention "mir-[number]." The number of a miRNA is assigned according to its order of discovery relative to previously identified miRNA species. For example, if the last published miRNA was mir-121, the next discovered miRNA will be named mir-122, etc. When a miRNA is discovered that is homologous to a known miRNA from a different organism, the name can be given an optional organism identifier, of the form [organism identifier]-mir-[number]. Identifiers include hsa for *Homo sapiens* and mmu for *Mus Musculus*. For example, a human homolog to mir-121 might be referred to as hsa-mir-121 whereas the mouse homolog can be referred to as mmu-mir-121.

Mature microRNA is commonly designated with the prefix "miR" whereas the gene or precursor miRNA is designated with the prefix "mir." For example, mir-121 is a precursor for miR-121. When differing miRNA genes or precursors are processed into identical mature miRNAs, the genes/precursors can be delineated by a numbered suffix. For example, mir-121-1 and mir-121-2 can refer to distinct genes or precursors that are processed into miR-121. Lettered suffixes are used to indicate closely related mature sequences. For example, mir-121a and mir-121b can be processed to closely related miRNAs miR-121a and miR-121b, respectively. In the context of the present disclosure, any microRNA (miRNA or miR) designated herein with the prefix mir-* or miR-* is understood to encompass both the precursor and/or mature species, unless otherwise explicitly stated otherwise.

Sometimes it is observed that two mature miRNA sequences originate from the same precursor. When one of the sequences is more abundant that the other, a "*" suffix can be used to designate the less common variant. For example, miR-121 would be the predominant product whereas miR-121* is the less common variant found on the opposite arm of the precursor. If the predominant variant is not identified, the miRs can be distinguished by the suffix "5p" for the variant from the 5' arm of the precursor and the suffix "3p" for the variant from the 3' arm. For example, miR-121-5p originates from the 5' arm of the precursor whereas miR-121-3p originates from the 3' arm. Less commonly, the 5p and 3p variants are referred to as the sense ("s") and anti-sense ("as") forms, respectively. For example, miR-121-5p may be referred to as miR-121-s whereas miR-121-3p may be referred to as miR-121-as.

The above naming conventions have evolved over time and are general guidelines rather than absolute rules. For example, the let- and lin-families of miRNAs continue to be referred to by these monikers. The mir/miR convention for precursor/mature forms is also a guideline and context should be taken into account to determine which form is referred to. Further details of miR naming can be found at www.mirbase.org or Ambros et al., A uniform system for microRNA annotation, RNA 9:277-279 (2003).

Plant miRNAs follow a different naming convention as described in Meyers et al., Plant Cell. 2008 20(12):3186-3190.

A number of miRNAs are involved in gene regulation, and miRNAs are part of a growing class of non-coding RNAs that is now recognized as a major tier of gene control. In some cases, miRNAs can interrupt translation by binding to regulatory sites embedded in the 3'-UTRs of their target mRNAs, leading to the repression of translation. Target recognition involves complementary base pairing of the target site with the miRNA's seed region (positions 2-8 at the miRNA's 5' end), although the exact extent of seed complementarity is not precisely determined and can be modified by 3' pairing. In other cases, miRNAs function like small interfering RNAs (siRNA) and bind to perfectly complementary mRNA sequences to destroy the target transcript.

Characterization of a number of miRNAs indicates that they influence a variety of processes, including early development, cell proliferation and cell death, apoptosis and fat metabolism. For example, some miRNAs, such as lin-4, let-7, mir-14, mir-23, and bantam, have been shown to play critical roles in cell differentiation and tissue development. Others are believed to have similarly important roles because of their differential spatial and temporal expression patterns.

The miRNA database available at miRBase (www.mirbase.org) comprises a searchable database of published miRNA sequences and annotation. Further information about miRBase can be found in the following articles, each of which is incorporated by reference in its entirety herein: Griffiths-Jones et al., miRBase: tools for microRNA genomics. NAR 2008 36(Database Issue):D154-D158; Griffiths-Jones et al., miRBase: microRNA sequences, targets and gene nomenclature. NAR 2006 34(Database Issue):D140-D144; and Griffiths-Jones, S. The microRNA Registry. NAR 2004 32(Database Issue):D109-D111. Representative miR-NAs contained in Release 16 of miRBase, made available September 2010.

As described herein, microRNAs are known to be involved in cancer and other diseases and can be assessed in order to characterize a phenotype in a sample. See, e.g., Ferracin et al., Micromarkers: miRNAs in cancer diagnosis and prognosis, Exp Rev Mol Diag, April 2010, Vol. 10, No. 3, Pages 297-308; Fabbri, miRNAs as molecular biomarkers of cancer, Exp Rev Mol Diag, May 2010, Vol. 10, No. 4, Pages 435-444.

In an embodiment, molecular profiling as described herein comprises analysis of microRNA.

Techniques to isolate and characterize vesicles and miRs are known to those of skill in the art. In addition to the methodology presented herein, additional methods can be found in U.S. Pat. No. 7,888,035, entitled "METHODS FOR ASSESSING RNA PATTERNS" and issued Feb. 15, 2011; and U.S. Pat. No. 7,897,356, entitled "METHODS AND SYSTEMS OF USING EXOSOMES FOR DETERMINING PHENOTYPES" and issued Mar. 1, 2011; and International Patent Publication Nos. WO/2011/066589, entitled "METHODS AND SYSTEMS FOR ISOLATING, STORING, AND ANALYZING VESICLES" and filed Nov. 30, 2010; WO/2011/088226, entitled "DETECTION OF GASTROINTESTINAL DISORDERS" and filed Jan. 13, 2011; WO/2011/109440, entitled "BIOMARKERS FOR THERANOSTICS" and filed Mar. 1, 2011; and WO/2011/127219, entitled "CIRCULATING BIOMARKERS FOR DISEASE" and filed Apr. 6, 2011, each of which applications are incorporated by reference herein in their entirety.

Circulating Biomarkers

Circulating biomarkers include biomarkers that are detectable in body fluids, such as blood, plasma, serum. Examples of circulating cancer biomarkers include cardiac troponin T (cTnT), prostate specific antigen (PSA) for prostate cancer and CA125 for ovarian cancer. Circulating biomarkers according to the present disclosure include any appropriate biomarker that can be detected in bodily fluid, including without limitation protein, nucleic acids, e.g., DNA, mRNA and microRNA, lipids, carbohydrates and metabolites. Circulating biomarkers can include biomarkers that are not associated with cells, such as biomarkers that are membrane associated, embedded in membrane fragments, part of a biological complex, or free in solution. In one embodiment, circulating biomarkers are biomarkers that are associated with one or more vesicles present in the biological fluid of a subject.

Circulating biomarkers have been identified for use in characterization of various phenotypes, such as detection of a cancer. See, e.g., Ahmed N, et al., Proteomic-based identification of haptoglobin-1 precursor as a novel circulating biomarker of ovarian cancer. Br. J. Cancer 2004; Mathelin et al., Circulating proteinic biomarkers and breast cancer, Gynecol Obstet Fertil. 2006 July-August; 34(7-8):638-46. Epub 2006 Jul. 28; Ye et al., Recent technical strategies to identify diagnostic biomarkers for ovarian cancer. Expert Rev Proteomics. 2007 February; 4(1):121-31; Carney, Circulating oncoproteins HER2/neu, EGFR and CAIX (MN) as novel cancer biomarkers. Expert Rev Mol Diagn. 2007 May; 7(3):309-19; Gagnon, Discovery and application of protein biomarkers for ovarian cancer, Curr Opin Obstet Gynecol. 2008 February; 20(1):9-13; Pasterkamp et al., Immune regulatory cells: circulating biomarker factories in cardiovascular disease. Clin Sci (Lond). 2008 August; 115(4):129-31; Fabbri, miRNAs as molecular biomarkers of cancer, Exp Rev Mol Diag, May 2010, Vol. 10, No. 4, Pages 435-444; PCT Patent Publication WO/2007/088537; U.S. Pat. Nos. 7,745,150 and 7,655,479; U.S. Patent Publications 20110008808, 20100330683, 20100248290, 20100222230, 20100203566, 20100173788, 20090291932, 20090239246, 20090226937, 20090111121, 20090004687, 20080261258, 20080213907, 20060003465, 20050124071, and 20040096915, each of which publication is incorporated herein by reference in its entirety. In an embodiment, molecular profiling as described herein comprises analysis of circulating biomarkers.

Gene Expression Profiling

The methods and systems as described herein comprise expression profiling, which includes assessing differential expression of one or more target genes disclosed herein. Differential expression can include overexpression and/or underexpression of a biological product, e.g., a gene, mRNA or protein, compared to a control (or a reference). The control can include similar cells to the sample but without the disease (e.g., expression profiles obtained from samples from healthy individuals). A control can be a previously determined level that is indicative of a drug target efficacy associated with the particular disease and the particular drug target. The control can be derived from the same patient, e.g., a normal adjacent portion of the same organ as the diseased cells, the control can be derived from healthy tissues from other patients, or previously determined thresholds that are indicative of a disease responding or not-responding to a particular drug target. The control can also be a control found in the same sample, e.g. a housekeeping gene or a product thereof (e.g., mRNA or protein). For example, a control nucleic acid can be one which is known not to differ depending on the cancerous or non-cancerous state of the cell. The expression level of a control nucleic acid can be used to normalize signal levels in the test and reference populations. Illustrative control genes include, but are not limited to, e.g., β-actin, glyceraldehyde 3-phosphate dehydrogenase and ribosomal protein P1. Multiple controls or types of controls can be used. The source of differential expression can vary. For example, a gene copy number may be increased in a cell, thereby resulting in increased expression of the gene. Alternately, transcription of the gene may be modified, e.g., by chromatin remodeling, differential methylation, differential expression or activity of transcription factors, etc. Translation may also be modified, e.g., by differential expression of factors that degrade mRNA, translate mRNA, or silence translation, e.g., microRNAs or siRNAs. In some embodiments, differential expression comprises differential activity. For example, a protein may carry a mutation that increases the activity of the protein, such as constitutive activation, thereby contributing to a diseased state. Molecular profiling that reveals changes in activity can be used to guide treatment selection.

Methods of gene expression profiling include methods based on hybridization analysis of polynucleotides, and methods based on sequencing of polynucleotides. Commonly used methods known in the art for the quantification of mRNA expression in a sample include northern blotting and in situ hybridization (Parker & Barnes (1999) Methods in Molecular Biology 106:247-283); RNAse protection assays (Hod (1992) Biotechniques 13:852-854); and reverse transcription polymerase chain reaction (RT-PCR) (Weis et al. (1992) Trends in Genetics 8:263-264). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), gene expression analysis by massively parallel signature sequencing (MPSS) and/or next generation sequencing.

RT-PCR

Reverse transcription polymerase chain reaction (RT-PCR) is a variant of polymerase chain reaction (PCR). According to this technique, a RNA strand is reverse transcribed into its DNA complement (i.e., complementary DNA, or cDNA) using the enzyme reverse transcriptase, and the resulting cDNA is amplified using PCR. Real-time polymerase chain reaction is another PCR variant, which is also referred to as quantitative PCR, Q-PCR, qRT-PCR, or sometimes as RT-PCR. Either the reverse transcription PCR method or the real-time PCR method can be used for molecular profiling according to the present disclosure, and RT-PCR can refer to either unless otherwise specified or as understood by one of skill in the art.

RT-PCR can be used to determine RNA levels, e.g., mRNA or miRNA levels, of the biomarkers as described herein. RT-PCR can be used to compare such RNA levels of the biomarkers as described herein in different sample populations, in normal and tumor tissues, with or without drug treatment, to characterize patterns of gene expression, to discriminate between closely related RNAs, and to analyze RNA structure.

The first step is the isolation of RNA, e.g., mRNA, from a sample. The starting material can be total RNA isolated from human tumors or tumor cell lines, and corresponding normal tissues or cell lines, respectively. Thus RNA can be isolated from a sample, e.g., tumor cells or tumor cell lines, and compared with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al. (1997) Current Protocols of Molecular Biology, John Wiley and Sons. Methods for RNA extraction from paraffin embedded tissues are disclosed, for example, in Rupp & Locker (1987) Lab Invest. 56:A67, and De Andres et al., BioTechniques 18:42044 (1995). In particular, RNA isolation can be performed using purification kit, buffer set and protease from commercial manufacturers, such as Qiagen, according to the manufacturer's instructions (QIAGEN Inc., Valencia, CA). For example, total RNA from cells in culture can be isolated using Qiagen RNeasy mini-columns. Numerous RNA isolation kits are commercially available and can be used in the methods as described herein.

In the alternative, the first step is the isolation of miRNA from a target sample. The starting material is typically total RNA isolated from human tumors or tumor cell lines, and corresponding normal tissues or cell lines, respectively. Thus RNA can be isolated from a variety of primary tumors or tumor cell lines, with pooled DNA from healthy donors. If the source of miRNA is a primary tumor, miRNA can be extracted, for example, from frozen or archived paraffin-embedded and fixed (e.g. formalin-fixed) tissue samples.

General methods for miRNA extraction are well known in the art and are disclosed in standard textbooks of molecular biology, including Ausubel et al. (1997) Current Protocols of Molecular Biology, John Wiley and Sons. Methods for RNA extraction from paraffin embedded tissues are disclosed, for example, in Rupp & Locker (1987) Lab Invest. 56:A67, and De Andres et al., BioTechniques 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Numerous miRNA isolation kits are commercially available and can be used in the methods as described herein.

Whether the RNA comprises mRNA, miRNA or other types of RNA, gene expression profiling by RT-PCR can include reverse transcription of the RNA template into cDNA, followed by amplification in a PCR reaction. Commonly used reverse transcriptases include, but are not limited to, avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. TaqMan PCR typically uses the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan™ RT-PCR can be performed using commercially available equipment, such as, for example, ABI PRISM 7700™ Sequence Detection System™ (Perkin-Elmer-Applied Biosystems, Foster City, Calif., USA), or LightCycler (Roche Molecular Biochemicals, Mannheim, Germany). In one specific embodiment, the 5' nuclease procedure is run on a real-time quantitative PCR device such as the ABI PRISM 7700 Sequence Detection System. The system consists of a thermocycler, laser, charge-coupled device (CCD), camera and computer. The system amplifies samples in a 96-well format on a thermocycler. During amplification, laser-induced fluorescent signal is collected in real-time through fiber optic cables for all 96 wells, and detected at the CCD. The system includes software for running the instrument and for analyzing the data.

TaqMan data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

Real time quantitative PCR (also quantitative real time polymerase chain reaction, QRT-PCR or Q-PCR) is a more recent variation of the RT-PCR technique. Q-PCR can measure PCR product accumulation through a dual-labeled fluorigenic probe (i.e., TaqMan probe). Real time PCR is compatible both with quantitative competitive PCR, where internal competitor for each target sequence is used for normalization, and with quantitative comparative PCR using a normalization gene contained within the sample, or a housekeeping gene for RT-PCR. See, e.g. Held et al. (1996) Genome Research 6:986-994.

Protein-based detection techniques are also useful for molecular profiling, especially when the nucleotide variant causes amino acid substitutions or deletions or insertions or frame shift that affect the protein primary, secondary or tertiary structure. To detect the amino acid variations, protein sequencing techniques may be used. For example, a protein or fragment thereof corresponding to a gene can be synthesized by recombinant expression using a DNA fragment isolated from an individual to be tested. Preferably, a cDNA fragment of no more than 100 to 150 base pairs encompassing the polymorphic locus to be determined is used. The amino acid sequence of the peptide can then be determined by conventional protein sequencing methods. Alternatively, the HPLC-microscopy tandem mass spectrometry technique can be used for determining the amino acid sequence variations. In this technique, proteolytic digestion is performed on a protein, and the resulting peptide mixture is separated by reversed-phase chromatographic separation. Tandem mass spectrometry is then performed and the data collected is analyzed. See Gatlin et al., Anal. Chem., 72:757-763 (2000).

Microarray

The biomarkers as described herein can also be identified, confirmed, and/or measured using the microarray technique. Thus, the expression profile biomarkers can be measured in cancer samples using microarray technology. In this method, polynucleotide sequences of interest are plated, or arrayed, on a microchip substrate. The arrayed sequences are then hybridized with specific DNA probes from cells or tissues of interest. The source of mRNA can be total RNA isolated from a sample, e.g., human tumors or tumor cell lines and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

The expression profile of biomarkers can be measured in either fresh or paraffin-embedded tumor tissue, or body fluids using microarray technology. In this method, polynucleotide sequences of interest are plated, or arrayed, on a microchip substrate. The arrayed sequences are then hybridized with specific DNA probes from cells or tissues of interest. As with the RT-PCR method, the source of miRNA typically is total RNA isolated from human tumors or tumor cell lines, including body fluids, such as serum, urine, tears, and exosomes and corresponding normal tissues or cell lines. Thus RNA can be isolated from a variety of sources. If the source of miRNA is a primary tumor, miRNA can be extracted, for example, from frozen tissue samples, which are routinely prepared and preserved in everyday clinical practice.

Also known as biochip, DNA chip, or gene array, cDNA microarray technology allows for identification of gene expression levels in a biologic sample. cDNAs or oligonucleotides, each representing a given gene, are immobilized on a substrate, e.g., a small chip, bead or nylon membrane, tagged, and serve as probes that will indicate whether they are expressed in biologic samples of interest. The simultaneous expression of thousands of genes can be monitored simultaneously.

In a specific embodiment of the microarray technique, PCR amplified inserts of cDNA clones are applied to a substrate in a dense array. In one aspect, at least 100, 200, 300, 400, 500, 600, 700, 800, 900, 1,000, 1,500, 2,000, 3000, 4000, 5000, 6000, 7000, 8000, 9000, 10,000, 15,000, 20,000, 25,000, 30,000, 35,000, 40,000, 45,000 or at least 50,000 nucleotide sequences are applied to the substrate. Each sequence can correspond to a different gene, or multiple sequences can be arrayed per gene. The microarrayed genes, immobilized on the microchip, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al. (1996) Proc. Natl. Acad. Sci. USA 93(2):106-149). Microarray analysis can be performed by commercially available equipment following manufacturer's protocols, including without limitation the Affymetrix GeneChip technology (Affymetrix, Santa Clara, CA), Agilent (Agilent Technologies, Inc., Santa Clara, CA), or Illumina (Illumina, Inc., San Diego, CA) microarray technology.

The development of microarray methods for large-scale analysis of gene expression makes it possible to search systematically for molecular markers of cancer classification and outcome prediction in a variety of tumor types.

In some embodiments, the Agilent Whole Human Genome Microarray Kit (Agilent Technologies, Inc., Santa Clara, CA). The system can analyze more than 41,000 unique human genes and transcripts represented, all with public domain annotations. The system is used according to the manufacturer's instructions.

In some embodiments, the Illumina Whole Genome DASL assay (Illumina Inc., San Diego, CA) is used. The system offers a method to simultaneously profile over 24,000 transcripts from minimal RNA input, from both fresh frozen (FF) and formalin-fixed paraffin embedded (FFPE) tissue sources, in a high throughput fashion.

Microarray expression analysis comprises identifying whether a gene or gene product is up-regulated or down-regulated relative to a reference. The identification can be performed using a statistical test to determine statistical significance of any differential expression observed. In some embodiments, statistical significance is determined using a parametric statistical test. The parametric statistical test can comprise, for example, a fractional factorial design, analysis of variance (ANOVA), a t-test, least squares, a Pearson correlation, simple linear regression, nonlinear regression, multiple linear regression, or multiple nonlinear regression. Alternatively, the parametric statistical test can comprise a one-way analysis of variance, two-way analysis of variance, or repeated measures analysis of variance. In other embodiments, statistical significance is determined using a nonparametric statistical test. Examples include, but are not limited to, a Wilcoxon signed-rank test, a Mann-Whitney test, a Kruskal-Wallis test, a Friedman test, a Spearman ranked order correlation coefficient, a Kendall Tau analysis, and a nonparametric regression test. In some embodiments, statistical significance is determined at a p-value of less than about 0.05, 0.01, 0.005, 0.001, 0.0005, or 0.0001. Although the microarray systems used in the methods as described herein may assay thousands of transcripts, data analysis need only be performed on the transcripts of interest, thereby reducing the problem of multiple comparisons inherent in performing multiple statistical tests. The p-values can also be corrected for multiple comparisons, e.g., using a Bonferroni correction, a modification thereof, or other technique known to those in the art, e.g., the Hochberg correction, Holm-Bonferroni correction, Šidák correction, or Dunnett's correction. The degree of differential expression can also be taken into account. For example, a gene can be considered as differentially expressed when the fold-change in expression compared to control level is at least 1.2, 1.3, 1.4, 1.5, 1.6, 1.7, 1.8, 1.9, 2.0, 2.2, 2.5, 2.7, 3.0, 4, 5, 6, 7, 8, 9 or 10-fold different in the sample versus the control. The differential expression takes into account both overexpression and underexpression. A gene or gene product can be considered up or down-regulated if the differential expression meets a statistical threshold, a fold-change threshold, or both. For example, the criteria for identifying differential expression can comprise both a p-value of 0.001 and fold change of at least 1.5-fold (up or down). One of skill will understand that such statistical and threshold measures can be adapted to determine differential expression by any molecular profiling technique disclosed herein.

Various methods as described herein make use of many types of microarrays that detect the presence and potentially the amount of biological entities in a sample. Arrays typically contain addressable moieties that can detect the presence of the entity in the sample, e.g., via a binding event. Microarrays include without limitation DNA microarrays, such as cDNA microarrays, oligonucleotide microarrays and SNP microarrays, microRNA arrays, protein microarrays, antibody microarrays, tissue microarrays, cellular microarrays (also called transfection microarrays), chemical compound microarrays, and carbohydrate arrays (glycoarrays). DNA arrays typically comprise addressable nucleotide sequences that can bind to sequences present in a sample. MicroRNA arrays, e.g., the MMChips array from the University of Louisville or commercial systems from Agilent, can be used to detect microRNAs. Protein microarrays can be used to identify protein-protein interactions, including without limitation identifying substrates of protein kinases, transcription factor protein-activation, or to identify the targets of biologically active small molecules. Protein arrays may comprise an array of different protein molecules, commonly antibodies, or nucleotide sequences that bind to proteins of interest. Antibody microarrays comprise antibodies spotted onto the protein chip that are used as capture molecules to detect proteins or other biological materials from a sample, e.g., from cell or tissue lysate solutions. For example, antibody arrays can be used to detect biomarkers from bodily fluids, e.g., serum or urine, for diagnostic applications. Tissue microarrays comprise separate tissue cores assembled in array fashion to allow multiplex histological analysis. Cellular microarrays, also called transfection microarrays, comprise various capture agents, such as antibodies, proteins, or lipids, which can interact with cells to facilitate their capture on addressable locations. Chemical compound microarrays comprise arrays of chemical compounds and can be used to detect protein or other biological materials that bind the compounds. Carbohydrate arrays (glycoarrays) comprise arrays of carbohydrates and can detect, e.g., protein that bind sugar moieties. One of skill will appreciate that similar technologies or improvements can be used according to the methods as described herein.

Certain embodiments of the current methods comprise a multi-well reaction vessel, including without limitation, a multi-well plate or a multi-chambered microfluidic device, in which a multiplicity of amplification reactions and, in some embodiments, detection are performed, typically in parallel. In certain embodiments, one or more multiplex reactions for generating amplicons are performed in the same reaction vessel, including without limitation, a multi-well plate, such as a 96-well, a 384-well, a 1536-well plate, and so forth; or a microfluidic device, for example but not limited to, a TaqMan™ Low Density Array (Applied Biosystems, Foster City, CA). In some embodiments, a massively parallel amplifying step comprises a multi-well reaction vessel, including a plate comprising multiple reaction wells, for example but not limited to, a 24-well plate, a 96-well plate, a 384-well plate, or a 1536-well plate; or a multi-chamber microfluidics device, for example but not limited to a low density array wherein each chamber or well comprises an appropriate primer(s), primer set(s), and/or reporter probe(s), as appropriate. Typically such amplification steps occur in a series of parallel single-plex, two-plex, three-Alex, four-plex, five-plex, or six-plex reactions, although higher levels of parallel multiplexing are also within the intended scope of the current teachings. These methods can comprise PCR methodology, such as RT-PCR, in each of the wells or chambers to amplify and/or detect nucleic acid molecules of interest.

Low density arrays can include arrays that detect 10s or 100s of molecules as opposed to 1000s of molecules. These arrays can be more sensitive than high density arrays. In embodiments, a low density array such as a TaqMan™ Low Density Array is used to detect one or more gene or gene product in any of Tables 5-12 of WO2018175501. For example, the low density array can be used to detect at least 1, 2, 3, 4, 5, 6, 7, 8, 9, 10, 15, 20, 25, 30, 40, 50, 60, 70, 80, 90 or 100 genes or gene products selected from any of Tables 5-12 of WO2018175501.

In some embodiments, the disclosed methods comprise a microfluidics device, "lab on a chip," or micrototal analytical system (pTAS). In some embodiments, sample preparation is performed using a microfluidics device. In some embodiments, an amplification reaction is performed using a microfluidics device. In some embodiments, a sequencing or PCR reaction is performed using a microfluidic device. In some embodiments, the nucleotide sequence of at least a part of an amplified product is obtained using a microfluidics device. In some embodiments, detecting comprises a microfluidic device, including without limitation, a low density array, such as a TaqMan™ Low Density Array. Descriptions of exemplary microfluidic devices can be found in, among other places, Published PCT Application Nos. WO/0185341 and WO 04/011666; Kartalov and Quake, Nucl. Acids Res. 32:2873-79, 2004; and Fiorini and Chiu, Bio Techniques 38:429-46, 2005.

Any appropriate microfluidic device can be used in the methods as described herein. Examples of microfluidic devices that may be used, or adapted for use with molecular profiling, include but are not limited to those described in U.S. Pat. Nos. 7,591,936, 7,581,429, 7,579,136, 7,575,722, 7,568,399, 7,552,741, 7,544,506, 7,541,578, 7,518,726, 7,488,596, 7,485,214, 7,467,928, 7,452,713, 7,452,509, 7,449,096, 7,431,887, 7,422,725, 7,422,669, 7,419,822, 7,419,639, 7,413,709, 7,411,184, 7,402,229, 7,390,463, 7,381,471, 7,357,864, 7,351,592, 7,351,380, 7,338,637, 7,329,391, 7,323,140, 7,261,824, 7,258,837, 7,253,003, 7,238,324, 7,238,255, 7,233,865, 7,229,538, 7,201,881, 7,195,986, 7,189,581, 7,189,580, 7,189,368, 7,141,978, 7,138,062, 7,135,147, 7,125,711, 7,118,910, 7,118,661, 7,640,947, 7,666,361, 7,704,735; U.S. Patent Application Publication 20060035243; and International Patent Publication WO 2010/072410; each of which patents or applications are incorporated herein by reference in their entirety. Another example for use with methods disclosed herein is described in Chen et al., "Microfluidic isolation and transcriptome analysis of serum vesicles," Lab on a chip, Dec. 8, 2009 DOI: 10.1039/b916199f.

Gene Expression Analysis by Massively Parallel Signature Sequencing (MPSS)

This method, described by Brenner et al. (2000) Nature Biotechnology 18:630-634, is a sequencing approach that combines non-gel-based signature sequencing with in vitro cloning of millions of templates on separate microbeads. First, a microbead library of DNA templates is constructed by in vitro cloning. This is followed by the assembly of a planar array of the template-containing microbeads in a flow cell at a high density. The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a cDNA library.

MPSS data has many uses. The expression levels of nearly all transcripts can be quantitatively determined; the abundance of signatures is representative of the expression level of the gene in the analyzed tissue. Quantitative methods for the analysis of tag frequencies and detection of differences among libraries have been published and incorporated into public databases for SAGE™ data and are applicable to MPSS data. The availability of complete genome sequences permits the direct comparison of signatures to genomic sequences and further extends the utility of MPSS data. Because the targets for MPSS analysis are not pre-selected (like on a microarray), MPSS data can characterize the full complexity of transcriptomes. This is analogous to sequencing millions of ESTs at once, and genomic sequence data can be used so that the source of the MPSS signature can be readily identified by computational means.

Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (e.g., about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. See, e.g. Velculescu et al. (1995) Science 270:484-487; and Velculescu et al. (1997) Cell 88:243-51.

DNA Copy Number Profiling

Any method capable of determining a DNA copy number profile of a particular sample can be used for molecular profiling according to the methods described herein as long as the resolution is sufficient to identify a copy number variation in the biomarkers as described herein. The skilled artisan is aware of and capable of using a number of different platforms for assessing whole genome copy number changes at a resolution sufficient to identify the copy number of the one or more biomarkers of the methods described herein. Some of the platforms and techniques are described in the embodiments below. In some embodiments as described herein, next generation sequencing or ISH techniques as described herein or known in the art are used for determining copy number/gene amplification.

In some embodiments, the copy number profile analysis involves amplification of whole genome DNA by a whole genome amplification method. The whole genome amplification method can use a strand displacing polymerase and random primers.

In some aspects of these embodiments, the copy number profile analysis involves hybridization of whole genome amplified DNA with a high density array. In a more specific aspect, the high density array has 5,000 or more different probes. In another specific aspect, the high density array has 5,000, 10,000, 20,000, 50,000, 100,000, 200,000, 300,000, 400,000, 500,000, 600,000, 700,000, 800,000, 900,000, or 1,000,000 or more different probes. In another specific aspect, each of the different probes on the array is an oligonucleotide having from about 15 to 200 bases in length. In another specific aspect, each of the different probes on the array is an oligonucleotide having from about 15 to 200, 15 to 150, 15 to 100, 15 to 75, 15 to 60, or 20 to 55 bases in length.

In some embodiments, a microarray is employed to aid in determining the copy number profile for a sample, e.g., cells from a tumor. Microarrays typically comprise a plurality of oligomers (e.g., DNA or RNA polynucleotides or oligonucleotides, or other polymers), synthesized or deposited on a substrate (e.g., glass support) in an array pattern. The support-bound oligomers are "probes", which function to hybridize or bind with a sample material (e.g., nucleic acids prepared or obtained from the tumor samples), in hybridization experiments. The reverse situation can also be applied: the sample can be bound to the microarray substrate and the oligomer probes are in solution for the hybridization. In use, the array surface is contacted with one or more targets under conditions that promote specific, high-affinity binding of the target to one or more of the probes. In some configurations, the sample nucleic acid is labeled with a detectable label, such as a fluorescent tag, so that the hybridized sample and probes are detectable with scanning equipment. DNA array technology offers the potential of using a multitude (e.g., hundreds of thousands) of different oligonucleotides to analyze DNA copy number profiles. In some embodiments, the substrates used for arrays are surface-derivatized glass or silica, or polymer membrane surfaces (see e.g., in Z. Guo, et al., Nucleic Acids Res, 22, 5456-65 (1994); U. Maskos, E. M. Southern, Nucleic Acids Res, 20, 1679-84 (1992), and E. M. Southern, et al., Nucleic Acids Res 22, 1368-73 (1994), each incorporated by reference herein). Modification of surfaces of array substrates can be accomplished by many techniques. For example, siliceous or metal oxide surfaces can be derivatized with bifunctional silanes, i.e., silanes having a first functional group enabling covalent binding to the surface (e.g., Si-halogen or Si-alkoxy group, as in —SiCl$_3$ or —Si(OCH$_3$)$_3$, respectively) and a second functional group that can impart the desired chemical and/or physical modifications to the surface to covalently or non-covalently attach ligands and/or the polymers or monomers for the biological probe array. Silylated derivatizations and other surface derivatizations that are known in the art (see for example U.S. Pat. No. 5,624,711 to Sundberg, U.S. Pat. No. 5,266,222 to Willis, and U.S. Pat. No. 5,137,765 to Farnsworth, each incorporated by reference herein). Other processes for preparing arrays are described in U.S. Pat. No. 6,649,348, to Bass et. al., assigned to Agilent Corp., which disclose DNA arrays created by in situ synthesis methods.

Polymer array synthesis is also described extensively in the literature including in the following: WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, 5,412,087, 6,147,205, 6,262,216, 6,310,189, 5,889,165, and 5,959,098 in PCT Applications Nos. PCT/US99/00730 (International Publication No. WO 99/36760) and PCT/US01/04285 (International Publication No. WO 01/58593), which are all incorporated herein by reference in their entirety for all purposes.

Nucleic acid arrays that are useful in the present disclosure include, but are not limited to, those that are commercially available from Affymetrix (Santa Clara, Calif.) under the brand name GeneChip™ Example arrays are shown on the website at affymetrix.com. Another microarray supplier is Illumina, Inc., of San Diego, Calif. with example arrays shown on their website at illumina.com.

In some embodiments, the inventive methods provide for sample preparation. Depending on the microarray and experiment to be performed, sample nucleic acid can be prepared in a number of ways by methods known to the skilled artisan. In some aspects as described herein, prior to or concurrent with genotyping (analysis of copy number profiles), the sample may be amplified any number of mechanisms. The most common amplification procedure used involves PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Manila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159, 4,965,188, and 5,333,675, and each of which is incorporated herein by reference in their entireties for all purposes. In some embodiments, the sample may be amplified on the array (e.g., U.S. Pat. No. 6,300,070 which is incorporated herein by reference).

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. Nos. 6,361,947, 6,391,592 and U.S. Ser. Nos. 09/916,135, 09/920,491 (U.S. Patent Application Publication 20030096235), U.S. Ser. No. 09/910,292 (U.S. Patent Application Publication 20030082543), and U.S. Ser. No. 10/013,598.

Methods for conducting polynucleotide hybridization assays are well developed in the art. Hybridization assay procedures and conditions used in the methods as described herein will vary depending on the application and are selected in accordance with the general binding methods known including those referred to in: Maniatis et al. Molecular Cloning: A Laboratory Manual (2.sup.nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The methods as described herein may also involve signal detection of hybridization between ligands in after (and/or during) hybridization. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

Immuno-Based Assays

Protein-based detection molecular profiling techniques include immunoaffinity assays based on antibodies selectively immunoreactive with mutant gene encoded protein according to the present methods. These techniques include without limitation immunoprecipitation, Western blot analysis, molecular binding assays, enzyme-linked immunosorbent assay (ELISA), enzyme-linked immunofiltration assay (ELIFA), fluorescence activated cell sorting (FACS) and the like. For example, an optional method of detecting the expression of a biomarker in a sample comprises contacting the sample with an antibody against the biomarker, or an immunoreactive fragment of the antibody thereof, or a recombinant protein containing an antigen binding region of an antibody against the biomarker; and then detecting the binding of the biomarker in the sample. Methods for producing such antibodies are known in the art. Antibodies can be used to immunoprecipitate specific proteins from solution samples or to immunoblot proteins separated by, e.g., polyacrylamide gels. Immunocytochemical methods can also be used in detecting specific protein polymorphisms in tissues or cells. Other well-known antibody-based techniques can also be used including, e.g., ELISA, radioimmunoassay (RIA), immunoradiometric assays (IRMA) and immunoenzymatic assays (IEMA), including sandwich assays using monoclonal or polyclonal antibodies. See, e.g., U.S. Pat. Nos. 4,376,110 and 4,486,530, both of which are incorporated herein by reference.

In alternative methods, the sample may be contacted with an antibody specific for a biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labelled antibody to a target biomarker.

A number of variations of the sandwich assay technique exist, and all are intended to be encompassed by the present methods. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labelled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the target biomarkers in the sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

Immunohistochemistry (IHC)

IHC is a process of localizing antigens (e.g., proteins) in cells of a tissue binding antibodies specifically to antigens in the tissues. The antigen-binding antibody can be conjugated or fused to a tag that allows its detection, e.g., via visualization. In some embodiments, the tag is an enzyme that can catalyze a color-producing reaction, such as alkaline phosphatase or horseradish peroxidase. The enzyme can be fused to the antibody or non-covalently bound, e.g., using a biotin-avadin system. Alternatively, the antibody can be tagged with a fluorophore, such as fluorescein, rhodamine, DyLight Fluor or Alexa Fluor. The antigen-binding antibody can be directly tagged or it can itself be recognized by a detection antibody that carries the tag. Using IHC, one or more proteins may be detected. The expression of a gene product can be related to its staining intensity compared to control levels. In some embodiments, the gene product is considered differentially expressed if its staining varies at least 1.2, 1.3, 1.4, 1.5, 1.6, 1.7, 1.8, 1.9, 2.0, 2.2, 2.5, 2.7, 3.0, 4, 5, 6, 7, 8, 9 or 10-fold in the sample versus the control.

IHC comprises the application of antigen-antibody interactions to histochemical techniques. In an illustrative example, a tissue section is mounted on a slide and is incubated with antibodies (polyclonal or monoclonal) specific to the antigen (primary reaction). The antigen-antibody signal is then amplified using a second antibody conjugated to a complex of peroxidase antiperoxidase (PAP), avidin-biotin-peroxidase (ABC) or avidin-biotin alkaline phosphatase. In the presence of substrate and chromogen, the enzyme forms a colored deposit at the sites of antibody-antigen binding. Immunofluorescence is an alternate approach to visualize antigens. In this technique, the primary antigen-antibody signal is amplified using a second antibody conjugated to a fluorochrome. On UV light absorption, the fluorochrome emits its own light at a longer wavelength (fluorescence), thus allowing localization of antibody-antigen complexes.

Epigenetic Status

Molecular profiling methods according to the present disclosure also comprise measuring epigenetic change, i.e., modification in a gene caused by an epigenetic mechanism, such as a change in methylation status or histone acetylation. Frequently, the epigenetic change will result in an alteration in the levels of expression of the gene which may be detected (at the RNA or protein level as appropriate) as an indication of the epigenetic change. Often the epigenetic change results in silencing or down regulation of the gene, referred to as "epigenetic silencing." The most frequently investigated epigenetic change in the methods as described herein involves determining the DNA methylation status of a gene, where an increased level of methylation is typically associated with the relevant cancer (since it may cause down regulation of gene expression). Aberrant methylation, which may be referred to as hypermethylation, of the gene or genes can be detected. Typically, the methylation status is determined in suitable CpG islands which are often found in the promoter region of the gene(s). The term "methylation," "methylation state" or "methylation status" may refers to the presence or absence of 5-methylcytosine at one or a plurality of CpG dinucleotides within a DNA sequence. CpG dinucleotides are typically concentrated in the promoter regions and exons of human genes.

Diminished gene expression can be assessed in terms of DNA methylation status or in terms of expression levels as determined by the methylation status of the gene. One method to detect epigenetic silencing is to determine that a gene which is expressed in normal cells is less expressed or not expressed in tumor cells. Accordingly, the present disclosure provides for a method of molecular profiling comprising detecting epigenetic silencing.

Various assay procedures to directly detect methylation are known in the art, and can be used in conjunction with the present methods. These assays rely onto two distinct approaches: bisulphite conversion based approaches and non-bisulphite based approaches. Non-bisulphite based methods for analysis of DNA methylation rely on the inability of methylation-sensitive enzymes to cleave methylation cytosines in their restriction. The bisulphite conversion relies on treatment of DNA samples with sodium bisulphite which converts unmethylated cytosine to uracil, while methylated cytosines are maintained (Furuichi Y, Wataya Y, Hayatsu H, Ukita T. Biochem Biophys Res Commun. 1970 Dec. 9; 41(5):1185-91). This conversion results in a change in the sequence of the original DNA. Methods to detect such changes include MS AP-PCR (Methylation-Sensitive Arbitrarily-Primed Polymerase Chain Reaction), a technology that allows for a global scan of the genome using CG-rich primers to focus on the regions most likely to contain CpG dinucleotides, and described by Gonzalgo et al., Cancer Research 57:594-599, 1997; MethyLight™, which refers to the art-recognized fluorescence-based real-time PCR technique described by Eads et al., Cancer Res. 59:2302-2306, 1999; the Heavy Methyl™ assay, in the embodiment thereof implemented herein, is an assay, wherein methylation specific blocking probes (also referred to herein as blockers) covering CpG positions between, or covered by the amplification primers enable methylation-specific selective amplification of a nucleic acid sample; HeavyMethyl™ MethyLight™ is a variation of the MethyLight™ assay wherein the MethyLight™ assay is combined with methylation specific blocking probes covering CpG positions between the amplification primers; Ms-SNuPE (Methylation-sensitive Single Nucleotide Primer Extension) is an assay described by Gonzalgo & Jones, Nucleic Acids Res. 25:2529-2531, 1997; MSP (Methylation-specific PCR) is a methylation assay described by Herman et al. Proc. Natl. Acad. Sci. USA 93:9821-9826, 1996, and by U.S. Pat. No. 5,786,146; COBRA (Combined Bisulfite Restriction Analysis) is a methylation assay described by Xiong & Laird, Nucleic Acids Res. 25:2532-2534, 1997; MCA (Methylated CpG Island Amplification) is a methylation assay described by Toyota et al., Cancer Res. 59:2307-12, 1999, and in WO 00/26401A1.

Other techniques for DNA methylation analysis include sequencing, methylation-specific PCR (MS-PCR), melting curve methylation-specific PCR (McMS-PCR), MLPA with or without bisulfite treatment, QAMA, MSRE-PCR, MethyLight, ConLight-MSP, bisulfite conversion-specific methylation-specific PCR (BS-MSP), COBRA (which relies upon use of restriction enzymes to reveal methylation dependent sequence differences in PCR products of sodium bisulfite-treated DNA), methylation-sensitive single-nucleotide primer extension conformation (MS-SNuPE), methylation-sensitive single-strand conformation analysis (MS-SSCA), Melting curve combined bisulfite restriction analysis (McCOBRA), PyroMethA, HeavyMethyl, MALDI-TOF, MassARRAY, Quantitative analysis of methylated alleles (QAMA), enzymatic regional methylation assay (ERMA), QBSUPT, MethylQuant, Quantitative PCR sequencing and oligonucleotide-based microarray systems, Pyrosequencing, Meth-DOP-PCR. A review of some useful techniques is provided in Nucleic acids research, 1998, Vol. 26, No. 10, 2255-2264; Nature Reviews, 2003, Vol. 3, 253-266; Oral Oncology, 2006, Vol. 42, 5-13, which references are incorporated herein by reference in their entirety. Any of these techniques may be used in accordance with the present methods, as appropriate. Other techniques are described in U.S. Patent Publications 20100144836; and 20100184027, which applications are incorporated herein by reference in their entirety.

Through the activity of various acetylases and deacetylylases the DNA binding function of histone proteins is tightly regulated. Furthermore, histone acetylation and histone deactelyation have been linked with malignant progression. See Nature, 429: 457-63, 2004. Methods to analyze histone acetylation are described in U.S. Patent Publications 20100144543 and 20100151468, which applications are incorporated herein by reference in their entirety.

Sequence Analysis

Molecular profiling according to the present disclosure comprises methods for genotyping one or more biomarkers by determining whether an individual has one or more nucleotide variants (or amino acid variants) in one or more of the genes or gene products. Genotyping one or more genes according to the methods as described herein in some embodiments, can provide more evidence for selecting a treatment.

The biomarkers as described herein can be analyzed by any method useful for determining alterations in nucleic acids or the proteins they encode. According to one embodiment, the ordinary skilled artisan can analyze the one or more genes for mutations including deletion mutants, insertion mutants, frame shift mutants, nonsense mutants, missense mutant, and splice mutants.

Nucleic acid used for analysis of the one or more genes can be isolated from cells in the sample according to standard methodologies (Sambrook et al., 1989). The nucleic acid, for example, may be genomic DNA or fractionated or whole cell RNA, or miRNA acquired from exosomes or cell surfaces. Where RNA is used, it may be desired to convert the RNA to a complementary DNA. In one embodiment, the RNA is whole cell RNA; in another, it is poly-A RNA; in another, it is exosomal RNA. Normally, the nucleic acid is amplified. Depending on the format of the assay for analyzing the one or more genes, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; *Bellus*, 1994).

Various types of defects are known to occur in the biomarkers as described herein. Alterations include without limitation deletions, insertions, point mutations, and duplications. Point mutations can be silent or can result in stop codons, frame shift mutations or amino acid substitutions. Mutations in and outside the coding region of the one or more genes may occur and can be analyzed according to the methods as described herein. The target site of a nucleic acid of interest can include the region wherein the sequence varies. Examples include, but are not limited to, polymorphisms which exist in different forms such as single nucleotide variations, nucleotide repeats, multibase deletion (more than one nucleotide deleted from the consensus sequence), multibase insertion (more than one nucleotide inserted from the consensus sequence), microsatellite repeats (small numbers of nucleotide repeats with a typical 5-1000 repeat units), di-nucleotide repeats, tri-nucleotide repeats, sequence rearrangements (including translocation and duplication), chimeric sequence (two sequences from different gene origins are fused together), and the like. Among sequence polymorphisms, the most frequent polymorphisms in the human genome are single-base variations, also called single-nucleotide polymorphisms (SNPs). SNPs are abundant, stable and widely distributed across the genome.

Molecular profiling includes methods for haplotyping one or more genes. The haplotype is a set of genetic determinants located on a single chromosome and it typically contains a particular combination of alleles (all the alternative sequences of a gene) in a region of a chromosome. In other words, the haplotype is phased sequence information on individual chromosomes. Very often, phased SNPs on a chromosome define a haplotype. A combination of haplotypes on chromosomes can determine a genetic profile of a cell. It is the haplotype that determines a linkage between a specific genetic marker and a disease mutation. Haplotyping can be done by any methods known in the art. Common methods of scoring SNPs include hybridization microarray or direct gel sequencing, reviewed in Landgren et al., Genome Research, 8:769-776, 1998. For example, only one copy of one or more genes can be isolated from an individual and the nucleotide at each of the variant positions is determined. Alternatively, an allele specific PCR or a similar method can be used to amplify only one copy of the one or more genes in an individual, and SNPs at the variant positions of the present disclosure are determined. The Clark method known in the art can also be employed for haplotyping. A high throughput molecular haplotyping method is also disclosed in Tost et al., Nucleic Acids Res., 30(19):e96 (2002), which is incorporated herein by reference.

Thus, additional variant(s) that are in linkage disequilibrium with the variants and/or haplotypes of the present disclosure can be identified by a haplotyping method known in the art, as will be apparent to a skilled artisan in the field of genetics and haplotyping. The additional variants that are in linkage disequilibrium with a variant or haplotype of the present disclosure can also be useful in the various applications as described below.

For purposes of genotyping and haplotyping, both genomic DNA and mRNA/cDNA can be used, and both are herein referred to generically as "gene."

Numerous techniques for detecting nucleotide variants are known in the art and can all be used for the method of this disclosure. The techniques can be protein-based or nucleic acid-based. In either case, the techniques used must be sufficiently sensitive so as to accurately detect the small nucleotide or amino acid variations. Very often, a probe is used which is labeled with a detectable marker. Unless otherwise specified in a particular technique described below, any suitable marker known in the art can be used, including but not limited to, radioactive isotopes, fluorescent compounds, biotin which is detectable using streptavidin, enzymes (e.g., alkaline phosphatase), substrates of an enzyme, ligands and antibodies, etc. See Jablonski et al., Nucleic Acids Res., 14:6115-6128 (1986); Nguyen et al., Biotechniques, 13:116-123 (1992); Rigby et al., J. Mol. Biol., 113:237-251 (1977).

In a nucleic acid-based detection method, target DNA sample, i.e., a sample containing genomic DNA, cDNA, mRNA and/or miRNA, corresponding to the one or more genes must be obtained from the individual to be tested. Any tissue or cell sample containing the genomic DNA, miRNA, mRNA, and/or cDNA (or a portion thereof) corresponding to the one or more genes can be used. For this purpose, a tissue sample containing cell nucleus and thus genomic DNA can be obtained from the individual. Blood samples can also be useful except that only white blood cells and other lymphocytes have cell nucleus, while red blood cells are without a nucleus and contain only mRNA or miRNA. Nevertheless, miRNA and mRNA are also useful as either can be analyzed for the presence of nucleotide variants in its sequence or serve as template for cDNA synthesis. The tissue or cell samples can be analyzed directly without much processing. Alternatively, nucleic acids including the target sequence can be extracted, purified, and/or amplified before they are subject to the various detecting procedures discussed below. Other than tissue or cell samples, cDNAs or genomic DNAs from a cDNA or genomic DNA library constructed using a tissue or cell sample obtained from the individual to be tested are also useful.

To determine the presence or absence of a particular nucleotide variant, sequencing of the target genomic DNA or cDNA, particularly the region encompassing the nucleotide variant locus to be detected. Various sequencing techniques are generally known and widely used in the art including the Sanger method and Gilbert chemical method. The pyrosequencing method monitors DNA synthesis in real time using a luminometric detection system. Pyrosequencing has been shown to be effective in analyzing genetic polymorphisms such as single-nucleotide polymorphisms and can also be used in the present methods. See Nordstrom et al., Biotechnol. Appl. Biochem., 31(2):107-112 (2000); Ahmadian et al., Anal. Biochem., 280:103-110 (2000).

Nucleic acid variants can be detected by a suitable detection process. Non limiting examples of methods of detection, quantification, sequencing and the like are; mass detection of mass modified amplicons (e.g., matrix-assisted laser desorption ionization (MALDI) mass spectrometry and electrospray (ES) mass spectrometry), a primer extension method (e.g., iPLEX™; Sequenom, Inc.), microsequencing methods (e.g., a modification of primer extension methodology), ligase sequence determination methods (e.g., U.S. Pat. Nos. 5,679,524 and 5,952,174, and WO 01/27326), mismatch sequence determination methods (e.g., U.S. Pat. Nos. 5,851,770; 5,958,692; 6,110,684; and 6,183,958), direct DNA sequencing, fragment analysis (FA), restriction fragment length polymorphism (RFLP analysis), allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension (e.g., microarray sequence determination methods), Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader assay, hybridization methods (e.g., hybridization using at least one probe, hybridization using at least one fluorescently labeled probe, and the like), conventional dot blot analyses, single strand conformational polymorphism analysis (SSCP, e.g., U.S. Pat. Nos. 5,891,625 and 6,013,499; Orita et al., Proc. Natl. Acad. Sci. U.S.A. 86: 27776-2770 (1989)), denaturing gradient gel electrophoresis (DGGE), heteroduplex analysis, mismatch cleavage detection, and techniques described in Sheffield et al., Proc. Natl. Acad. Sci. USA 49: 699-706 (1991), White et al., Genomics 12: 301-306 (1992), Grompe et al., Proc. Natl. Acad. Sci. USA 86: 5855-5892 (1989), and Grompe, Nature Genetics 5: 111-117 (1993), cloning and sequencing, electrophoresis, the use of hybridization probes and quantitative real time polymerase chain reaction (QRT-PCR), digital PCR, nanopore sequencing, chips and combinations thereof. The detection and quantification of alleles or paralogs can be carried out using the "closed-tube" methods described in U.S. patent application Ser. No. 11/950,395, filed on Dec. 4, 2007. In some embodiments the amount of a nucleic acid species is determined by mass spectrometry, primer extension, sequencing (e.g., any suitable method, for example nanopore or pyrosequencing), Quantitative PCR (Q-PCR or QRT-PCR), digital PCR, combinations thereof, and the like.

The term "sequence analysis" as used herein refers to determining a nucleotide sequence, e.g., that of an amplification product. The entire sequence or a partial sequence of a polynucleotide, e.g., DNA or mRNA, can be determined, and the determined nucleotide sequence can be referred to as a "read" or "sequence read." For example, linear amplification products may be analyzed directly without further amplification in some embodiments (e.g., by using single-molecule sequencing methodology). In certain embodiments, linear amplification products may be subject to further amplification and then analyzed (e.g., using sequencing by ligation or pyrosequencing methodology). Reads may be subject to different types of sequence analysis. Any suitable sequencing method can be used to detect, and determine the amount of, nucleotide sequence species, amplified nucleic acid species, or detectable products generated from the foregoing. Examples of certain sequencing methods are described hereafter.

A sequence analysis apparatus or sequence analysis component(s) includes an apparatus, and one or more components used in conjunction with such apparatus, that can be used by a person of ordinary skill to determine a nucleotide sequence resulting from processes described herein (e.g., linear and/or exponential amplification products). Examples of sequencing platforms include, without limitation, the 454 platform (Roche) (Margulies, M. et al. 2005 Nature 437, 376-380), Illumina Genomic Analyzer (or Solexa platform) or SOLID System (Applied Biosystems; see PCT patent application publications WO 06/084132 entitled "Reagents, Methods, and Libraries For Bead-Based Sequencing" and WO07/121,489 entitled "Reagents, Methods, and Libraries for Gel-Free Bead-Based Sequencing"), the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53: 1996-2001), Ion semiconductor sequencing (Ion Torrent Systems, Inc, San Francisco, CA), or DNA nanoball sequencing (Complete Genomics, Mountain View, CA), VisiGen Biotechnologies approach (Invitrogen) and polony sequencing. Such platforms allow sequencing of many nucleic acid molecules isolated from a specimen at high orders of multiplexing in a parallel manner (Dear Brief Funct Genomic Proteomic 2003; 1: 397-416; Haimovich, Methods, challenges, and promise of next-generation sequencing in cancer biology. Yale J Biol Med. 2011 December; 84(4):439-46). These non-Sanger-based sequencing technologies are sometimes referred to as NextGen sequencing, NGS, next-generation sequencing, next generation sequencing, and variations thereof. Typically they allow much higher throughput than the traditional Sanger approach. See Schuster, Next-generation sequencing transforms today's biology, Nature Methods 5:16-18 (2008); Metzker, Sequencing technologies—the next generation. Nat Rev Genet. 2010 January; 11(1):31-46; Levy and Myers, Advancements in Next-Generation Sequencing. Annu Rev Genomics Hum Genet. 2016 Aug. 31; 17:95-115. These platforms can allow sequencing of clonally expanded or non-amplified single molecules of nucleic acid fragments. Certain platforms involve, for example, sequencing by ligation of dye-modified probes (including cyclic ligation and cleavage), pyrosequencing, and single-molecule sequencing. Nucleotide sequence species, amplification nucleic acid species and detectable products generated there from can be analyzed by such sequence analysis platforms. Next-generation sequencing can be used in the methods as described herein, e.g., to determine mutations, copy number, or expression levels, as appropriate. The methods can be used to perform whole genome sequencing or sequencing of specific sequences of interest, such as a gene of interest or a fragment thereof.

Sequencing by ligation is a nucleic acid sequencing method that relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucleotides or primers, enables sequence determination by fluorescence detection. Longer sequence reads may be obtained by including primers containing cleavable linkages that can be cleaved after label identification. Cleavage at the linker removes the label and regenerates the 5' phosphate on the end of the ligated primer, preparing the primer for another round of ligation. In some embodiments primers may be labeled with more than one fluorescent label, e.g., at least 1, 2, 3, 4, or 5 fluorescent labels.

Sequencing by ligation generally involves the following steps. Clonal bead populations can be prepared in emulsion microreactors containing target nucleic acid template sequences, amplification reaction components, beads and primers. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four color dye-labeled probes competes for ligation to the sequencing primer. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in the 5' direction is laid down for another series of ligations. Primer reset and ligation rounds (5-7 ligation cycles per round) are repeated sequentially five times to generate 25-35 base pairs of sequence for a single tag. With mate-paired sequencing, this process is repeated for a second tag.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Target nucleic acids may be immobilized to a solid support, hybridized with a sequencing primer, incubated with DNA polymerase, ATP sulfurylase, luciferase, apyrase, adenosine 5' phosphosulfate and luciferin. Nucleotide solutions are sequentially added and removed. Correct incorporation of a nucleotide releases a pyrophosphate, which interacts with ATP sulfurylase and produces ATP in the presence of adenosine 5' phosphosulfate, fueling the luciferin reaction, which produces a chemiluminescent signal allowing sequence determination. The amount of light generated is proportional to the number of bases added. Accordingly, the sequence downstream of the sequencing primer can be determined. An illustrative system for pyrosequencing involves the following steps: ligating an adaptor nucleic acid to a nucleic acid under investigation and hybridizing the resulting nucleic acid to a bead; amplifying a nucleotide sequence in an emulsion; sorting beads using a picoliter multiwell solid support; and sequencing amplified nucleotide sequences by pyrosequencing methodology (e.g., Nakano et al., "Single-molecule PCR using water-in-oil emulsion;" Journal of Biotechnology 102: 117-124 (2003)).

Certain single-molecule sequencing embodiments are based on the principal of sequencing by synthesis, and use single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair" in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing a primer to a target nucleic acid sequence to generate a complex; associating the complex with a solid phase; iteratively extending the primer by a nucleotide tagged with a fluorescent molecule; and capturing an image of fluorescence resonance energy transfer signals after each iteration (e.g., U.S. Pat. No. 7,169,314; Braslaysky et al., PNAS 100(7): 3960-3964 (2003)). Such a system can be used to directly sequence amplification products (linearly or exponentially amplified products) generated by processes described herein. In some embodiments the amplification products can be hybridized to a primer that contains sequences complementary to immobilized capture sequences present on a solid support, a bead or glass slide for example. Hybridization of the primer-amplification product complexes with the immobilized capture sequences, immobilizes amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer-amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, nucleotide sequencing may be by solid phase single nucleotide sequencing methods and processes. Solid phase single nucleotide sequencing methods involve contacting target nucleic acid and solid support under conditions in which a single molecule of sample nucleic acid hybridizes to a single molecule of a solid support. Such conditions can include providing the solid support molecules and a single molecule of target nucleic acid in a "microreactor." Such conditions also can include providing a mixture in which the target nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008.

In certain embodiments, nanopore sequencing detection methods include (a) contacting a target nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53(11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the detectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known to the person of ordinary skill (e.g., Venter et al., Science 291: 1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons can be performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis can be facilitated by the use of sequence analysis apparatus and components described above.

Primer extension polymorphism detection methods, also referred to herein as "microsequencing" methods, typically are carried out by hybridizing a complementary oligonucleotide to a nucleic acid carrying the polymorphic site. In these methods, the oligonucleotide typically hybridizes adjacent to the polymorphic site. The term "adjacent" as used in reference to "microsequencing" methods, refers to the 3' end of the extension oligonucleotide being sometimes 1 nucleotide from the 5' end of the polymorphic site, often 2 or 3, and at times 4, 5, 6, 7, 8, 9, or 10 nucleotides from the 5' end of the polymorphic site, in the nucleic acid when the extension oligonucleotide is hybridized to the nucleic acid. The extension oligonucleotide then is extended by one or more nucleotides, often 1, 2, or 3 nucleotides, and the number and/or type of nucleotides that are added to the extension oligonucleotide determine which polymorphic variant or variants are present. Oligonucleotide extension methods are disclosed, for example, in U.S. Pat. Nos. 4,656,127; 4,851, 331; 5,679,524; 5,834,189; 5,876,934; 5,908,755; 5,912, 118; 5,976,802; 5,981,186; 6,004,744; 6,013,431; 6,017, 702; 6,046,005; 6,087,095; 6,210,891; and WO 01/20039. The extension products can be detected in any manner, such as by fluorescence methods (see, e.g., Chen & Kwok, Nucleic Acids Research 25: 347-353 (1997) and Chen et al., Proc. Natl. Acad. Sci. USA 94/20: 10756-10761 (1997)) or by mass spectrometric methods (e.g., MALDI-TOF mass spectrometry) and other methods described herein. Oligonucleotide extension methods using mass spectrometry are described, for example, in U.S. Pat. Nos. 5,547,835; 5,605, 798; 5,691,141; 5,849,542; 5,869,242; 5,928,906; 6,043, 031; 6,194,144; and 6,258,538.

Microsequencing detection methods often incorporate an amplification process that proceeds the extension step. The amplification process typically amplifies a region from a nucleic acid sample that comprises the polymorphic site. Amplification can be carried out using methods described above, or for example using a pair of oligonucleotide primers in a polymerase chain reaction (PCR), in which one oligonucleotide primer typically is complementary to a region 3' of the polymorphism and the other typically is complementary to a region 5' of the polymorphism. A PCR primer pair may be used in methods disclosed in U.S. Pat. Nos. 4,683,195; 4,683,202, 4,965,188; 5,656,493; 5,998, 143; 6,140,054; WO 01/27327; and WO 01/27329 for example. PCR primer pairs may also be used in any commercially available machines that perform PCR, such as any of the GeneAmp™ Systems available from Applied Biosystems.

Other appropriate sequencing methods include multiplex polony sequencing (as described in Shendure et al., Accurate Multiplex Polony Sequencing of an Evolved Bacterial Genome, Sciencexpress, Aug. 4, 2005, pg 1 available at www.sciencexpress.org/4 Aug. 2005/Page1/10.1126/science.1117389, incorporated herein by reference), which employs immobilized microbeads, and sequencing in microfabricated picoliter reactors (as described in Margulies et al., Genome Sequencing in Microfabricated High-Density Picolitre Reactors, Nature, August 2005, available at www.nature.com/nature (published online 31 Jul. 2005, doi: 10.1038/nature03959, incorporated herein by reference).

Whole genome sequencing may also be used for discriminating alleles of RNA transcripts, in some embodiments. Examples of whole genome sequencing methods include, but are not limited to, nanopore-based sequencing methods, sequencing by synthesis and sequencing by ligation, as described above.

Nucleic acid variants can also be detected using standard electrophoretic techniques. Although the detection step can sometimes be preceded by an amplification step, amplification is not required in the embodiments described herein. Examples of methods for detection and quantification of a nucleic acid using electrophoretic techniques can be found in the art. A non-limiting example comprises running a sample (e.g., mixed nucleic acid sample isolated from maternal serum, or amplification nucleic acid species, for example) in an agarose or polyacrylamide gel. The gel may be labeled (e.g., stained) with ethidium bromide (see, Sambrook and Russell, Molecular Cloning: A Laboratory Manual 3d ed., 2001). The presence of a band of the same size as the standard control is an indication of the presence of a target nucleic acid sequence, the amount of which may then be compared to the control based on the intensity of the band, thus detecting and quantifying the target sequence of interest. In some embodiments, restriction enzymes capable of distinguishing between maternal and paternal alleles may be used to detect and quantify target nucleic acid species. In certain embodiments, oligonucleotide probes specific to a sequence of interest are used to detect the presence of the target sequence of interest. The oligonucleotides can also be used to indicate the amount of the target nucleic acid molecules in comparison to the standard control, based on the intensity of signal imparted by the probe.

Sequence-specific probe hybridization can be used to detect a particular nucleic acid in a mixture or mixed population comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch. A number of hybridization formats are known in the art, which include but are not limited to, solution phase, solid phase, or mixed phase hybridization assays. The following articles provide an overview of the various hybridization assay formats: Singer et al., Biotechniques 4:230, 1986; Haase et al., Methods in Virology, pp. 189-226, 1984; Wilkinson, In situ Hybridization, Wilkinson ed., IRL Press, Oxford University Press, Oxford; and Hames and Higgins eds., Nucleic Acid Hybridization: A Practical Approach, IRL Press, 1987.

Hybridization complexes can be detected by techniques known in the art. Nucleic acid probes capable of specifically hybridizing to a target nucleic acid (e.g., mRNA or DNA) can be labeled by any suitable method, and the labeled probe used to detect the presence of hybridized nucleic acids. One commonly used method of detection is autoradiography, using probes labeled with $^3H$, $^{125}I$, $^{35}S$ $^{14}C$, $^{32}P$, $^{33}P$, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. In some embodiments, probes can be conjugated directly with labels such as fluorophores, chemiluminescent agents or enzymes. The choice of label depends on sensitivity required, ease of conjugation with the probe, stability requirements, and available instrumentation.

In embodiments, fragment analysis (referred to herein as "FA") methods are used for molecular profiling. Fragment analysis (FA) includes techniques such as restriction fragment length polymorphism (RFLP) and/or (amplified fragment length polymorphism). If a nucleotide variant in the target DNA corresponding to the one or more genes results in the elimination or creation of a restriction enzyme recognition site, then digestion of the target DNA with that particular restriction enzyme will generate an altered restriction fragment length pattern. Thus, a detected RFLP or AFLP will indicate the presence of a particular nucleotide variant.

Terminal restriction fragment length polymorphism (TRFLP) works by PCR amplification of DNA using primer pairs that have been labeled with fluorescent tags. The PCR products are digested using RFLP enzymes and the resulting patterns are visualized using a DNA sequencer. The results are analyzed either by counting and comparing bands or peaks in the TRFLP profile, or by comparing bands from one or more TRFLP runs in a database.

The sequence changes directly involved with an RFLP can also be analyzed more quickly by PCR. Amplification can be directed across the altered restriction site, and the products digested with the restriction enzyme. This method has been called Cleaved Amplified Polymorphic Sequence (CAPS). Alternatively, the amplified segment can be analyzed by Allele specific oligonucleotide (ASO) probes, a process that is sometimes assessed using a Dot blot.

A variation on AFLP is cDNA-AFLP, which can be used to quantify differences in gene expression levels.

Another useful approach is the single-stranded conformation polymorphism assay (SSCA), which is based on the altered mobility of a single-stranded target DNA spanning the nucleotide variant of interest. A single nucleotide change in the target sequence can result in different intramolecular base pairing pattern, and thus different secondary structure of the single-stranded DNA, which can be detected in a non-denaturing gel. See Orita et al., Proc. Natl. Acad. Sci. USA, 86:2776-2770 (1989). Denaturing gel-based techniques such as clamped denaturing gel electrophoresis (CDGE) and denaturing gradient gel electrophoresis (DGGE) detect differences in migration rates of mutant sequences as compared to wild-type sequences in denaturing gel. See Miller et al., Biotechniques, 5:1016-24 (1999); Sheffield et al., Am. J. Hum, Genet., 49:699-706 (1991); Wartell et al., Nucleic Acids Res., 18:2699-2705 (1990); and Sheffield et al., Proc. Natl. Acad. Sci. USA, 86:232-236 (1989). In addition, the double-strand conformation analysis (DSCA) can also be useful in the present methods. See Arguello et al., Nat. Genet., 18:192-194 (1998).

The presence or absence of a nucleotide variant at a particular locus in the one or more genes of an individual can also be detected using the amplification refractory mutation system (ARMS) technique. See e.g., European Patent No. 0,332,435; Newton et al., Nucleic Acids Res., 17:2503-2515 (1989); Fox et al., Br. J. Cancer, 77:1267-1274 (1998); Robertson et al., Eur. Respir. J., 12:477-482 (1998). In the ARMS method, a primer is synthesized matching the nucleotide sequence immediately 5' upstream from the locus being tested except that the 3'-end nucleotide which corresponds to the nucleotide at the locus is a predetermined nucleotide. For example, the 3'-end nucleotide can be the same as that in the mutated locus. The primer can be of any suitable length so long as it hybridizes to the target DNA under stringent conditions only when its 3'-end nucleotide matches the nucleotide at the locus being tested. Preferably the primer has at least 12 nucleotides, more preferably from about 18 to 50 nucleotides. If the individual tested has a mutation at the locus and the nucleotide therein matches the 3'-end nucleotide of the primer, then the primer can be further extended upon hybridizing to the target DNA template, and the primer can initiate a PCR amplification reaction in conjunction with another suitable PCR primer. In contrast, if the nucleotide at the locus is of wild type, then primer extension cannot be achieved. Various forms of ARMS techniques developed in the past few years can be used. See e.g., Gibson et al., Clin. Chem. 43:1336-1341 (1997).

Similar to the ARMS technique is the mini sequencing or single nucleotide primer extension method, which is based on the incorporation of a single nucleotide. An oligonucleotide primer matching the nucleotide sequence immediately 5' to the locus being tested is hybridized to the target DNA, mRNA or miRNA in the presence of labeled dideoxyribonucleotides. A labeled nucleotide is incorporated or linked to the primer only when the dideoxyribonucleotides matches the nucleotide at the variant locus being detected. Thus, the identity of the nucleotide at the variant locus can be revealed based on the detection label attached to the incorporated dideoxyribonucleotides. See Syvanen et al., Genomics, 8:684-692 (1990); Shumaker et al., Hum. Mutat., 7:346-354 (1996); Chen et al., Genome Res., 10:549-547 (2000).

Another set of techniques useful in the present methods is the so-called "oligonucleotide ligation assay" (OLA) in which differentiation between a wild-type locus and a mutation is based on the ability of two oligonucleotides to anneal adjacent to each other on the target DNA molecule allowing the two oligonucleotides joined together by a DNA ligase. See Landergren et al., Science, 241:1077-1080 (1988); Chen et al, Genome Res., 8:549-556 (1998); Iannone et al., Cytometry, 39:131-140 (2000). Thus, for example, to detect a single-nucleotide mutation at a particular locus in the one or more genes, two oligonucleotides can be synthesized, one having the sequence just 5' upstream from the locus with its 3' end nucleotide being identical to the nucleotide in the variant locus of the particular gene, the other having a nucleotide sequence matching the sequence immediately 3' downstream from the locus in the gene. The oligonucleotides can be labeled for the purpose of detection. Upon hybridizing to the target gene under a stringent condition, the two oligonucleotides are subject to ligation in the presence of a suitable ligase. The ligation of the two oligonucleotides would indicate that the target DNA has a nucleotide variant at the locus being detected.

Detection of small genetic variations can also be accomplished by a variety of hybridization-based approaches. Allele-specific oligonucleotides are most useful. See Conner et al., Proc. Natl. Acad. Sci. USA, 80:278-282 (1983); Saiki et al, Proc. Natl. Acad. Sci. USA, 86:6230-6234 (1989). Oligonucleotide probes (allele-specific) hybridizing specifically to a gene allele having a particular gene variant at a particular locus but not to other alleles can be designed by methods known in the art. The probes can have a length of, e.g., from 10 to about 50 nucleotide bases. The target DNA and the oligonucleotide probe can be contacted with each other under conditions sufficiently stringent such that the nucleotide variant can be distinguished from the wild-type gene based on the presence or absence of hybridization. The probe can be labeled to provide detection signals. Alternatively, the allele-specific oligonucleotide probe can be used as a PCR amplification primer in an "allele-specific PCR" and the presence or absence of a PCR product of the expected length would indicate the presence or absence of a particular nucleotide variant.

Other useful hybridization-based techniques allow two single-stranded nucleic acids annealed together even in the presence of mismatch due to nucleotide substitution, insertion or deletion. The mismatch can then be detected using various techniques. For example, the annealed duplexes can be subject to electrophoresis. The mismatched duplexes can be detected based on their electrophoretic mobility that is different from the perfectly matched duplexes. See Cariello, Human Genetics, 42:726 (1988). Alternatively, in an RNase protection assay, a RNA probe can be prepared spanning the nucleotide variant site to be detected and having a detection marker. See Giunta et al., Diagn. Mol. Path., 5:265-270 (1996); Finkelstein et al., Genomics, 7:167-172 (1990); Kinszler et al., Science 251:1366-1370 (1991). The RNA probe can be hybridized to the target DNA or mRNA forming a heteroduplex that is then subject to the ribonuclease RNase A digestion. RNase A digests the RNA probe in the heteroduplex only at the site of mismatch. The digestion can be determined on a denaturing electrophoresis gel based on size variations. In addition, mismatches can also be detected by chemical cleavage methods known in the art. See e.g., Roberts et al., Nucleic Acids Res., 25:3377-3378 (1997).

In the mutS assay, a probe can be prepared matching the gene sequence surrounding the locus at which the presence or absence of a mutation is to be detected, except that a predetermined nucleotide is used at the variant locus. Upon annealing the probe to the target DNA to form a duplex, the E. coli mutS protein is contacted with the duplex. Since the mutS protein binds only to heteroduplex sequences containing a nucleotide mismatch, the binding of the mutS protein will be indicative of the presence of a mutation. See Modrich et al., Ann. Rev. Genet., 25:229-253 (1991).

A great variety of improvements and variations have been developed in the art on the basis of the above-described basic techniques which can be useful in detecting mutations or nucleotide variants in the present methods. For example, the "sunrise probes" or "molecular beacons" use the fluorescence resonance energy transfer (FRET) property and give rise to high sensitivity. See Wolf et al., Proc. Nat. Acad. Sci. USA, 85:8790-8794 (1988). Typically, a probe spanning the nucleotide locus to be detected are designed into a hairpin-shaped structure and labeled with a quenching fluorophore at one end and a reporter fluorophore at the other end. In its natural state, the fluorescence from the reporter fluorophore is quenched by the quenching fluorophore due to the proximity of one fluorophore to the other. Upon hybridization of the probe to the target DNA, the 5' end is separated apart from the 3'-end and thus fluorescence signal is regenerated. See Nazarenko et al., Nucleic Acids Res., 25:2516-2521 (1997); Rychlik et al., Nucleic Acids Res., 17:8543-8551 (1989); Sharkey et al., Bio/Technology 12:506-509 (1994); Tyagi et al., Nat. Biotechnol., 14:303-308 (1996); Tyagi et al., Nat. Biotechnol., 16:49-53 (1998). The homo-tag assisted non-dimer system (HANDS) can be used in combination with the molecular beacon methods to suppress primer-dimer accumulation. See Brownie et al., Nucleic Acids Res., 25:3235-3241 (1997).

Dye-labeled oligonucleotide ligation assay is a FRET-based method, which combines the OLA assay and PCR. See Chen et al., Genome Res. 8:549-556 (1998). TaqMan is another FRET-based method for detecting nucleotide variants. A TaqMan probe can be oligonucleotides designed to have the nucleotide sequence of the gene spanning the variant locus of interest and to differentially hybridize with different alleles. The two ends of the probe are labeled with a quenching fluorophore and a reporter fluorophore, respectively. The TaqMan probe is incorporated into a PCR reaction for the amplification of a target gene region containing the locus of interest using Taq polymerase. As Taq polymerase exhibits 5'-3' exonuclease activity but has no 3'-5' exonuclease activity, if the TaqMan probe is annealed to the target DNA template, the 5'-end of the TaqMan probe will be degraded by Taq polymerase during the PCR reaction thus separating the reporting fluorophore from the quenching fluorophore and releasing fluorescence signals. See Holland et al., Proc. Natl. Acad. Sci. USA, 88:7276-7280 (1991); Kalinina et al., Nucleic Acids Res., 25:1999-2004 (1997); Whitcombe et al., Clin. Chem., 44:918-923 (1998).

In addition, the detection in the present methods can also employ a chemiluminescence-based technique. For example, an oligonucleotide probe can be designed to hybridize to either the wild-type or a variant gene locus but not both. The probe is labeled with a highly chemiluminescent acridinium ester. Hydrolysis of the acridinium ester destroys chemiluminescence. The hybridization of the probe to the target DNA prevents the hydrolysis of the acridinium ester. Therefore, the presence or absence of a particular mutation in the target DNA is determined by measuring chemiluminescence changes. See Nelson et al., Nucleic Acids Res., 24:4998-5003 (1996).

The detection of genetic variation in the gene in accordance with the present methods can also be based on the "base excision sequence scanning" (BESS) technique. The BESS method is a PCR-based mutation scanning method. BESS T-Scan and BESS G-Tracker are generated which are analogous to T and G ladders of dideoxy sequencing. Mutations are detected by comparing the sequence of normal and mutant DNA. See, e.g., Hawkins et al., Electrophoresis, 20:1171-1176 (1999).

Mass spectrometry can be used for molecular profiling according to the present methods. See Graber et al., Curr. Opin. Biotechnol., 9:14-18 (1998). For example, in the primer oligo base extension (PROBE™) method, a target nucleic acid is immobilized to a solid-phase support. A primer is annealed to the target immediately 5' upstream from the locus to be analyzed. Primer extension is carried out in the presence of a selected mixture of deoxyribonucleotides and dideoxyribonucleotides. The resulting mixture of newly extended primers is then analyzed by MALDI-TOF. See e.g., Monforte et al., Nat. Med., 3:360-362 (1997).

In addition, the microchip or microarray technologies are also applicable to the detection method of the present methods. Essentially, in microchips, a large number of different oligonucleotide probes are immobilized in an array on a substrate or carrier, e.g., a silicon chip or glass slide. Target nucleic acid sequences to be analyzed can be contacted with the immobilized oligonucleotide probes on the microchip. See Lipshutz et al., Biotechniques, 19:442-447 (1995); Chee et al., Science, 274:610-614 (1996); Kozal et al., Nat. Med. 2:753-759 (1996); Hacia et al., Nat. Genet., 14:441-447 (1996); Saiki et al., Proc. Natl. Acad. Sci. USA, 86:6230-6234 (1989); Gingeras et al., Genome Res., 8:435-448 (1998). Alternatively, the multiple target nucleic acid sequences to be studied are fixed onto a substrate and an array of probes is contacted with the immobilized target sequences. See Drmanac et al., Nat. Biotechnol., 16:54-58 (1998). Numerous microchip technologies have been developed incorporating one or more of the above described techniques for detecting mutations. The microchip technologies combined with computerized analysis tools allow fast screening in a large scale. The adaptation of the microchip technologies to the present methods will be apparent to a person of skill in the art apprised of the present disclosure. See, e.g., U.S. Pat. No. 5,925,525 to Fodor et al; Wilgenbus et al., J. Mol. Med., 77:761-786 (1999); Graber et al., Curr. Opin. Biotechnol., 9:14-18 (1998); Hacia et al., Nat. Genet., 14:441-447 (1996); Shoemaker et al., Nat. Genet., 14:450-456 (1996); DeRisi et al., Nat. Genet., 14:457-460 (1996); Chee et al., Nat. Genet., 14:610-614 (1996); Lockhart et al., Nat. Genet., 14:675-680 (1996); Drobyshev et al., Gene, 188:45-52 (1997).

As is apparent from the above survey of the suitable detection techniques, it may or may not be necessary to amplify the target DNA, i.e., the gene, cDNA, mRNA, miRNA, or a portion thereof to increase the number of target DNA molecule, depending on the detection techniques used. For example, most PCR-based techniques combine the amplification of a portion of the target and the detection of the mutations. PCR amplification is well known in the art and is disclosed in U.S. Pat. Nos. 4,683,195 and 4,800,159, both which are incorporated herein by reference. For non-PCR-based detection techniques, if necessary, the amplification can be achieved by, e.g., in vivo plasmid multiplication, or by purifying the target DNA from a large amount of tissue or cell samples. See generally, Sambrook et al., Molecular Cloning: A Laboratory Manual, $2^{nd}$ ed., Cold Spring Harbor Laboratory, Cold Spring Harbor, N.Y., 1989. However, even with scarce samples, many sensitive techniques have been developed in which small genetic variations such as single-nucleotide substitutions can be detected without having to amplify the target DNA in the sample. For example, techniques have been developed that amplify the signal as opposed to the target DNA by, e.g., employing branched DNA or dendrimers that can hybridize to the target DNA. The branched or dendrimer DNAs provide multiple hybridization sites for hybridization probes to attach thereto thus amplifying the detection signals. See Detmer et al., J. Clin. Microbiol., 34:901-907 (1996); Collins et al., Nucleic Acids Res., 25:2979-2984 (1997); Horn et al., Nucleic Acids Res., 25:4835-4841 (1997); Horn et al., Nucleic Acids Res., 25:4842-4849 (1997); Nilsen et al., J. Theor. Biol., 187:273-284 (1997).

The Invader™ assay is another technique for detecting single nucleotide variations that can be used for molecular profiling according to the methods. The Invader™ assay uses a novel linear signal amplification technology that improves upon the long turnaround times required of the typical PCR DNA sequenced-based analysis. See Cooksey et al., Antimicrobial Agents and Chemotherapy 44:1296-1301 (2000). This assay is based on cleavage of a unique secondary structure formed between two overlapping oligonucleotides that hybridize to the target sequence of interest to form a "flap." Each "flap" then generates thousands of signals per hour. Thus, the results of this technique can be easily read, and the methods do not require exponential amplification of the DNA target. The Invader™ system uses two short DNA probes, which are hybridized to a DNA target. The structure formed by the hybridization event is recognized by a special cleavase enzyme that cuts one of the probes to release a short DNA "flap." Each released "flap" then binds to a fluorescently-labeled probe to form another cleavage structure. When the cleavase enzyme cuts the labeled probe, the probe emits a detectable fluorescence signal. See e.g. Lyamichev et al., Nat. Biotechnol., 17:292-296 (1999).

The rolling circle method is another method that avoids exponential amplification. Lizardi et al., Nature Genetics, 19:225-232 (1998) (which is incorporated herein by reference). For example, Sniper™ a commercial embodiment of this method, is a sensitive, high-throughput SNP scoring system designed for the accurate fluorescent detection of specific variants. For each nucleotide variant, two linear, allele-specific probes are designed. The two allele-specific probes are identical with the exception of the 3'-base, which is varied to complement the variant site. In the first stage of the assay, target DNA is denatured and then hybridized with a pair of single, allele-specific, open-circle oligonucleotide probes. When the 3'-base exactly complements the target DNA, ligation of the probe will preferentially occur. Subsequent detection of the circularized oligonucleotide probes is by rolling circle amplification, whereupon the amplified probe products are detected by fluorescence. See Clark and Pickering, Life Science News 6, 2000, Amersham Pharmacia Biotech (2000).

A number of other techniques that avoid amplification all together include, e.g., surface-enhanced resonance Raman scattering (SERRS), fluorescence correlation spectroscopy, and single-molecule electrophoresis. In SERRS, a chromophore-nucleic acid conjugate is absorbed onto colloidal silver and is irradiated with laser light at a resonant frequency of the chromophore. See Graham et al., Anal. Chem., 69:4703-4707 (1997). The fluorescence correlation spectroscopy is based on the spatio-temporal correlations among fluctuating light signals and trapping single molecules in an electric field. See Eigen et al., Proc. Natl. Acad. Sci. USA, 91:5740-5747 (1994). In single-molecule electrophoresis, the electrophoretic velocity of a fluorescently tagged nucleic acid is determined by measuring the time required for the molecule to travel a predetermined distance between two laser beams. See Castro et al., Anal. Chem., 67:3181-3186 (1995).

In addition, the allele-specific oligonucleotides (ASO) can also be used in in situ hybridization using tissues or cells as samples. The oligonucleotide probes which can hybridize differentially with the wild-type gene sequence or the gene sequence harboring a mutation may be labeled with radio-active isotopes, fluorescence, or other detectable markers. In situ hybridization techniques are well known in the art and their adaptation to the present methods for detecting the presence or absence of a nucleotide variant in the one or more gene of a particular individual should be apparent to a skilled artisan apprised of this disclosure.

Accordingly, the presence or absence of one or more genes nucleotide variant or amino acid variant in an individual can be determined using any of the detection methods described above.

Typically, once the presence or absence of one or more gene nucleotide variants or amino acid variants is determined, physicians or genetic counselors or patients or other researchers may be informed of the result. Specifically the result can be cast in a transmittable form that can be communicated or transmitted to other researchers or physicians or genetic counselors or patients. Such a form can vary and can be tangible or intangible. The result with regard to the presence or absence of a nucleotide variant of the present methods in the individual tested can be embodied in descriptive statements, diagrams, photographs, charts, images or any other visual forms. For example, images of gel electrophoresis of PCR products can be used in explaining the results. Diagrams showing where a variant occurs in an individual's gene are also useful in indicating the testing results. The statements and visual forms can be recorded on a tangible media such as papers, computer readable media such as floppy disks, compact disks, etc., or on an intangible media, e.g., an electronic media in the form of email or website on internet or intranet. In addition, the result with regard to the presence or absence of a nucleotide variant or amino acid variant in the individual tested can also be recorded in a sound form and transmitted through any suitable media, e.g., analog or digital cable lines, fiber optic cables, etc., via telephone, facsimile, wireless mobile phone, internet phone and the like.

Thus, the information and data on a test result can be produced anywhere in the world and transmitted to a different location. For example, when a genotyping assay is conducted offshore, the information and data on a test result may be generated and cast in a transmittable form as described above. The test result in a transmittable form thus can be imported into the U.S. Accordingly, the present methods also encompasses a method for producing a transmittable form of information on the genotype of the two or more suspected cancer samples from an individual. The method comprises the steps of (1) determining the genotype of the DNA from the samples according to methods of the present methods; and (2) embodying the result of the determining step in a transmittable form. The transmittable form is the product of the production method.

In Situ Hybridization

In situ hybridization assays are well known and are generally described in Angerer et al., Methods Enzymol. 152:649-660 (1987). In an in situ hybridization assay, cells, e.g., from a biopsy, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled, e.g., with radioisotopes or fluorescent reporters, or enzymatically. FISH (fluorescence in situ hybridization) uses fluorescent probes that bind to only those parts of a sequence with which they show a high degree of sequence similarity. CISH (chromogenic in situ hybridization) uses conventional peroxidase or alkaline phosphatase reactions visualized under a standard bright-field microscope.

In situ hybridization can be used to detect specific gene sequences in tissue sections or cell preparations by hybridizing the complementary strand of a nucleotide probe to the sequence of interest. Fluorescent in situ hybridization (FISH) uses a fluorescent probe to increase the sensitivity of in situ hybridization.

FISH is a cytogenetic technique used to detect and localize specific polynucleotide sequences in cells. For example, FISH can be used to detect DNA sequences on chromosomes. FISH can also be used to detect and localize specific RNAs, e.g., mRNAs, within tissue samples. In FISH uses fluorescent probes that bind to specific nucleotide sequences to which they show a high degree of sequence similarity. Fluorescence microscopy can be used to find out whether and where the fluorescent probes are bound. In addition to detecting specific nucleotide sequences, e.g., translocations, fusion, breaks, duplications and other chromosomal abnormalities, FISH can help define the spatial-temporal patterns of specific gene copy number and/or gene expression within cells and tissues.

Various types of FISH probes can be used to detect chromosome translocations. Dual color, single fusion probes can be useful in detecting cells possessing a specific chromosomal translocation. The DNA probe hybridization targets are located on one side of each of the two genetic breakpoints. "Extra signal" probes can reduce the frequency of normal cells exhibiting an abnormal FISH pattern due to the random co-localization of probe signals in a normal nucleus. One large probe spans one breakpoint, while the other probe flanks the breakpoint on the other gene. Dual color, break apart probes are useful in cases where there may be multiple translocation partners associated with a known genetic breakpoint. This labeling scheme features two differently colored probes that hybridize to targets on opposite sides of a breakpoint in one gene. Dual color, dual fusion probes can reduce the number of normal nuclei exhibiting abnormal signal patterns. The probe offers advantages in detecting low levels of nuclei possessing a simple balanced translocation. Large probes span two breakpoints on different chromosomes. Such probes are available as Vysis probes from Abbott Laboratories, Abbott Park, IL.

CISH, or chromogenic in situ hybridization, is a process in which a labeled complementary DNA or RNA strand is used to localize a specific DNA or RNA sequence in a tissue specimen. CISH methodology can be used to evaluate gene amplification, gene deletion, chromosome translocation, and chromosome number. CISH can use conventional enzymatic detection methodology, e.g., horseradish peroxidase or alkaline phosphatase reactions, visualized under a standard bright-field microscope. In a common embodiment, a probe that recognizes the sequence of interest is contacted with a sample. An antibody or other binding agent that recognizes the probe, e.g., via a label carried by the probe, can be used to target an enzymatic detection system to the site of the probe. In some systems, the antibody can recognize the label of a FISH probe, thereby allowing a sample to be analyzed using both FISH and CISH detection. CISH can be used to evaluate nucleic acids in multiple settings, e.g., formalin-fixed, paraffin-embedded (FFPE) tissue, blood or bone marrow smear, metaphase chromosome spread, and/or fixed cells. In an embodiment, CISH is performed following the methodology in the SPoT-Light® HER2 CISH Kit available from Life Technologies (Carlsbad, CA) or similar CISH products available from Life Technologies. The SPoT-Light® HER2 CISH Kit itself is FDA approved for in vitro diagnostics and can be used for molecular profiling of HER2. CISH can be used in similar applications as FISH.

Thus, one of skill will appreciate that reference to molecular profiling using FISH herein can be performed using CISH, unless otherwise specified.

Silver-enhanced in situ hybridization (SISH) is similar to CISH, but with SISH the signal appears as a black coloration due to silver precipitation instead of the chromogen precipitates of CISH.

Modifications of the in situ hybridization techniques can be used for molecular profiling according to the methods. Such modifications comprise simultaneous detection of multiple targets, e.g., Dual ISH, Dual color CISH, bright field double in situ hybridization (BDISH). See e.g., the FDA approved INFORM HER2 Dual ISH DNA Probe Cocktail kit from Ventana Medical Systems, Inc. (Tucson, AZ); DuoCISH™, a dual color CISH kit developed by Dako Denmark A/S (Denmark).

Comparative Genomic Hybridization (CGH) comprises a molecular cytogenetic method of screening tumor samples for genetic changes showing characteristic patterns for copy number changes at chromosomal and subchromosomal levels. Alterations in patterns can be classified as DNA gains and losses. CGH employs the kinetics of in situ hybridization to compare the copy numbers of different DNA or RNA sequences from a sample, or the copy numbers of different DNA or RNA sequences in one sample to the copy numbers of the substantially identical sequences in another sample. In many useful applications of CGH, the DNA or RNA is isolated from a subject cell or cell population. The comparisons can be qualitative or quantitative. Procedures are described that permit determination of the absolute copy numbers of DNA sequences throughout the genome of a cell or cell population if the absolute copy number is known or determined for one or several sequences. The different sequences are discriminated from each other by the different locations of their binding sites when hybridized to a reference genome, usually metaphase chromosomes but in certain cases interphase nuclei. The copy number information originates from comparisons of the intensities of the hybridization signals among the different locations on the reference genome. The methods, techniques and applications of CGH are known, such as described in U.S. Pat. No. 6,335,167, and in U.S. App. Ser. No. 60/804,818, the relevant parts of which are herein incorporated by reference.

In an embodiment, CGH used to compare nucleic acids between diseased and healthy tissues. The method comprises isolating DNA from disease tissues (e.g., tumors) and reference tissues (e.g., healthy tissue) and labeling each with a different "color" or fluor. The two samples are mixed and hybridized to normal metaphase chromosomes. In the case of array or matrix CGH, the hybridization mixing is done on a slide with thousands of DNA probes. A variety of detection system can be used that basically determine the color ratio along the chromosomes to determine DNA regions that might be gained or lost in the diseased samples as compared to the reference.

Molecular Profiling Methods

FIG. 1G illustrates a block diagram of an illustrative embodiment of a system 10 for determining individualized medical intervention for a particular disease state that uses molecular profiling of a patient's biological specimen. System 10 includes a user interface 12, a host server 14 including a processor 16 for processing data, a memory 18 coupled to the processor, an application program 20 stored in the memory 18 and accessible by the processor 16 for directing processing of the data by the processor 16, a plurality of internal databases 22 and external databases 24, and an interface with a wired or wireless communications network 26 (such as the Internet, for example). System 10 may also include an input digitizer 28 coupled to the processor 16 for inputting digital data from data that is received from user interface 12.

User interface 12 includes an input device 30 and a display 32 for inputting data into system 10 and for displaying information derived from the data processed by processor 16. User interface 12 may also include a printer 34 for printing the information derived from the data processed by the processor 16 such as patient reports that may include test results for targets and proposed drug therapies based on the test results.

Internal databases 22 may include, but are not limited to, patient biological sample/specimen information and tracking, clinical data, patient data, patient tracking, file management, study protocols, patient test results from molecular profiling, and billing information and tracking. External databases 24 may include, but are not limited to, drug libraries, gene libraries, disease libraries, and public and private databases such as UniGene, OMIM, GO, TIGR, GenBank, KEGG and Biocarta.

Various methods may be used in accordance with system 10. FIG. 2 shows a flowchart of an illustrative embodiment of a method for determining individualized medical intervention for a particular disease state that uses molecular profiling of a patient's biological specimen that is non disease specific. In order to determine a medical intervention for a particular disease state using molecular profiling that is independent of disease lineage diagnosis (i.e. not single disease restricted), at least one molecular test is performed on the biological sample of a diseased patient. Biological samples are obtained from diseased patients by taking a biopsy of a tumor, conducting minimally invasive surgery if no recent tumor is available, obtaining a sample of the patient's blood, or a sample of any other biological fluid including, but not limited to, cell extracts, nuclear extracts, cell lysates or biological products or substances of biological origin such as excretions, blood, sera, plasma, urine, sputum, tears, feces, saliva, membrane extracts, and the like.

A target is defined as any molecular finding that may be obtained from molecular testing. For example, a target may include one or more genes or proteins. For example, the presence of a copy number variation of a gene can be determined. As shown in FIG. 2, tests for finding such targets can include, but are not limited to, NGS, IHC, fluorescent in-situ hybridization (FISH), in-situ hybridization (ISH), and other molecular tests known to those skilled in the art.

Furthermore, the methods disclosed herein also including profiling more than one target. For example, the copy number, or presence of a CNV, of a plurality of genes can be identified. Furthermore, identification of a plurality of targets in a sample can be by one method or by various means. For example, the presence of a CNV of a first gene can be determined by one method and the presence of a CNV of a second gene determined by a different method. Alternatively, the same method can be used to detect the presence of a CNV in both the first and second gene.

Accordingly, one or more of the following may be performed: CNV analysis, IHC analysis, a microanalysis, and other molecular tests know to those skilled in the art.

The test results are then compiled to determine the individual characteristics of the cancer. After determining the characteristics of the cancer, a therapeutic regimen is identified.

Finally, a patient profile report may be provided which includes the patient's test results for various targets and any proposed therapies based on those results.

The systems as described herein can be used to automate the steps of identifying a molecular profile to assess a cancer. In an aspect, the present methods can be used for generating a report comprising a molecular profile. The methods can comprise: performing molecular profiling on a sample from a subject to assess the copy number or presence of a CNV of each of the plurality of cancer biomarkers, and compiling a report comprising the assessed characteristics into a list, thereby generating a report that identifies a molecular profile for the sample. The report can further comprise a list describing the expected benefit of the plurality of treatment options based on the assessed copy number, thereby identifying candidate treatment options for the subject.

Molecular Profiling for Treatment Selection

The methods as described herein provide a candidate treatment selection for a subject in need thereof. Molecular profiling can be used to identify one or more candidate therapeutic agents for an individual suffering from a condition in which one or more of the biomarkers disclosed herein are targets for treatment. For example, the method can identify one or more chemotherapy treatments for a cancer. In an aspect, the methods provides a method comprising: performing at least one molecular profiling technique on at least one biomarker. Any relevant biomarker can be assessed using one or more of the molecular profiling techniques described herein or known in the art. The marker need only have some direct or indirect association with a treatment to be useful. Any relevant molecular profiling technique can be performed, such as those disclosed here. These can include without limitation, protein and nucleic acid analysis techniques. Protein analysis techniques include, by way of non-limiting examples, immunoassays, immunohistochemistry, and mass spectrometry. Nucleic acid analysis techniques include, by way of non-limiting examples, amplification, polymerase chain amplification, hybridization, microarrays, in situ hybridization, sequencing, dye-terminator sequencing, next generation sequencing, pyrosequencing, and restriction fragment analysis.

Molecular profiling may comprise the profiling of at least one gene (or gene product) for each assay technique that is performed. Different numbers of genes can be assayed with different techniques. Any marker disclosed herein that is associated directly or indirectly with a target therapeutic can be assessed. For example, any "druggable target" comprising a target that can be modulated with a therapeutic agent such as a small molecule or binding agent such as an antibody, is a candidate for inclusion in the molecular profiling methods as described herein. The target can also be indirectly drug associated, such as a component of a biological pathway that is affected by the associated drug. The molecular profiling can be based on either the gene, e.g., DNA sequence, and/or gene product, e.g., mRNA or protein. Such nucleic acid and/or polypeptide can be profiled as applicable as to presence or absence, level or amount, activity, mutation, sequence, haplotype, rearrangement, copy number, or other measurable characteristic. In some embodiments, a single gene and/or one or more corresponding gene products is assayed by more than one molecular profiling technique. A gene or gene product (also referred to herein as "marker" or "biomarker"), e.g., an mRNA or protein, is assessed using applicable techniques (e.g., to assess DNA, RNA, protein), including without limitation ISH, gene expression, IHC, sequencing or immunoassay. Therefore, any of the markers disclosed herein can be assayed by a single molecular profiling technique or by multiple methods disclosed herein (e.g., a single marker is profiled by one or more of IHC, ISH, sequencing, microarray, etc.). In some embodiments, at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or at least about 100 genes or gene products are profiled by at least one technique, a plurality of techniques, or using any desired combination of ISH, IHC, gene expression, gene copy, and sequencing. In some embodiments, at least about 100, 200, 300, 400, 500, 600, 700, 800, 900, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, or at least 50,000 genes or gene products are profiled using various techniques. The number of markers assayed can depend on the technique used. For example, microarray and massively parallel sequencing lend themselves to high throughput analysis. Because molecular profiling queries molecular characteristics of the tumor itself, this approach provides information on therapies that might not otherwise be considered based on the lineage of the tumor.

In some embodiments, a sample from a subject in need thereof is profiled using methods which include but are not limited to IHC analysis, gene expression analysis, ISH analysis, and/or sequencing analysis (such as by PCR, RT-PCR, pyrosequencing, NGS) for one or more of the following: ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKN1A, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNA11, GNAQ, GNRH1, GNRHR1, GSTP1, HCK, HDAC1, hENT-1, Her2/Neu, HGF, HIF1A, HIG1, HSP90, HSP90AA1, HSPCA, IGF-1R, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKBIA, NRAS, ODC1, OGFR, p16, p21, p27, p53, p95, PARP-1, PDGFC, PDGFR, PDGFRA, PDGFRB, PGP, PGR, PI3K, POLA, POLA1, PPARG, PPARGC1, PR, PTEN, PTGS2, PTPN12, RAF1, RARA, ROS1, RRM1, RRM2, RRM2B, RXRB, RXRG, SIK2, SPARC, SRC, SSTR1, SSTR2, SSTR3, SSTR4, SSTR5, Survivin, TK1, TLE3, TNF, TOP1, TOP2A, TOP2B, TS, TUBB3, TXN, TXNRD1, TYMS, VDR, VEGF, VEGFA, VEGFC, VHL, YES1, ZAP70.

As understood by those of skill in the art, genes and proteins have developed a number of alternative names in the scientific literature. Listing of gene aliases and descriptions used herein can be found using a variety of online databases, including GeneCards® (www.genecards.org), HUGO Gene Nomenclature (www.genenames.org), Entrez Gene (www.ncbi.nlm.nih.gov/entrez/query.fcgi?db=gene), UniProtKB/Swiss-Prot (www.uniprot.org), UniProtKB/TrEMBL (www.uniprot.org), OMIM (www.ncbi.nlm.nih.gov/entrez/query.fcgi?db=OMIM), GeneLoc (genecards.weizmann.ac.il/geneloc/), and Ensembl (www.ensembl.org). For example, gene symbols and names used herein can correspond to those approved by HUGO, and protein names can be those recommended by UniProtKB/Swiss-Prot. In the specification, where a protein name indicates a precursor, the mature protein is also implied. Throughout the application, gene and protein symbols may be used interchangeably and the meaning can be derived from context, e.g., ISH or NGS can be used to analyze nucleic acids whereas IHC is used to analyze protein.

The choice of genes and gene products to be assessed to provide molecular profiles as described herein can be updated over time as new treatments and new drug targets are identified. For example, once the expression or mutation of a biomarker is correlated with a treatment option, it can be assessed by molecular profiling. One of skill will appreciate that such molecular profiling is not limited to those techniques disclosed herein but comprises any methodology conventional for assessing nucleic acid or protein levels, sequence information, or both. The methods as described herein can also take advantage of any improvements to current methods or new molecular profiling techniques developed in the future. In some embodiments, a gene or gene product is assessed by a single molecular profiling technique. In other embodiments, a gene and/or gene product is assessed by multiple molecular profiling techniques. In a non-limiting example, a gene sequence can be assayed by one or more of NGS, ISH and pyrosequencing analysis, the mRNA gene product can be assayed by one or more of NGS, RT-PCR and microarray, and the protein gene product can be assayed by one or more of IHC and immunoassay. One of skill will appreciate that any combination of biomarkers and molecular profiling techniques that will benefit disease treatment are contemplated by the present methods.

Genes and gene products that are known to play a role in cancer and can be assayed by any of the molecular profiling techniques as described herein include without limitation those listed in any of International Patent Publications WO/2007/137187 (Int'l Appl. No. PCT/US2007/069286), published Nov. 29, 2007; WO/2010/045318 (Int'l Appl. No. PCT/US2009/060630), published Apr. 22, 2010; WO/2010/093465 (Int'l Appl. No. PCT/US2010/000407), published Aug. 19, 2010; WO/2012/170715 (Int'l Appl. No. PCT/US2012/041393), published Dec. 13, 2012; WO/2014/089241 (Int'l Appl. No. PCT/US2013/073184), published Jun. 12, 2014; WO/2011/056688 (Int'l Appl. No. PCT/US2010/054366), published May 12, 2011; WO/2012/092336 (Int'l Appl. No. PCT/US2011/067527), published Jul. 5, 2012; WO/2015/116868 (Int'l Appl. No. PCT/US2015/013618), published Aug. 6, 2015; WO/2017/053915 (Int'l Appl. No. PCT/US2016/053614), published Mar. 30, 2017; WO/2016/141169 (Int'l Appl. No. PCT/US2016/020657), published Sep. 9, 2016; and WO2018175501 (Int'l Appl. No. PCT/US2018/023438), published Sep. 27, 2018; each of which publications is incorporated by reference herein in its entirety.

Mutation profiling can be determined by sequencing, including Sanger sequencing, array sequencing, pyrosequencing, NextGen sequencing, etc. Sequence analysis may reveal that genes harbor activating mutations so that drugs that inhibit activity are indicated for treatment. Alternately, sequence analysis may reveal that genes harbor mutations that inhibit or eliminate activity, thereby indicating treatment for compensating therapies. In some embodiments, sequence analysis comprises that of exon 9 and 11 of c-KIT. Sequencing may also be performed on EGFR-kinase domain exons 18, 19, 20, and 21. Mutations, amplifications or misregulations of EGFR or its family members are implicated in about 30% of all epithelial cancers. Sequencing can also be performed on PI3K, encoded by the PIK3CA gene. This gene is a found mutated in many cancers. Sequencing analysis can also comprise assessing mutations in one or more ABCC1, ABCG2, ADA, AR, ASNS, BCL2, BIRC5, BRCA1, BRCA2, CD33, CD52, CDA, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1, IGFBP3, IGFBP4, IGFBP5, IL2RA, KDR, KIT, LCK, LYN, MET, MGMT, MLH1, MS4A1, MSH2, NFKB1, NFKB2, NFKBIA, NRAS, OGFR, PARP1, PDGFC, PDGFRA, PDGFRB, PGP, PGR, POLA1, PTEN, PTGS2, PTPN12, RAF1, RARA, RRM1, RRM2, RRM2B, RXRB, RXRG, SIK2, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, and ZAP70. One or more of the following genes can also be assessed by sequence analysis: ALK, EML4, hENT-1, IGF-1R, HSP90AA1, MMR, p16, p21, p27, PARP-1, PI3K and TLE3. The genes and/or gene products used for mutation or sequence analysis can be at least 1, 2, 3, 4, 5, 6, 7, 8, 9, 10, 15, 20, 25, 30, 40, 50, 60, 70, 80, 90, 100, 200, 300, 400, 500 or all of the genes and/or gene products listed in any of Tables 4-12 of WO2018175501, e.g., in any of Tables 5-10 of WO2018175501, or in any of Tables 7-10 of WO2018175501.

In embodiments, the methods as described herein are used detect gene fusions, such as those listed in any of International Patent Publications WO/2007/137187 (Int'l Appl. No. PCT/US2007/069286), published Nov. 29, 2007; WO/2010/045318 (Int'l Appl. No. PCT/US2009/060630), published Apr. 22, 2010; WO/2010/093465 (Int'l Appl. No. PCT/US2010/000407), published Aug. 19, 2010; WO/2012/170715 (Int'l Appl. No. PCT/US2012/041393), published Dec. 13, 2012; WO/2014/089241 (Int'l Appl. No. PCT/US2013/073184), published Jun. 12, 2014; WO/2011/056688 (Int'l Appl. No. PCT/US2010/054366), published May 12, 2011; WO/2012/092336 (Int'l Appl. No. PCT/US2011/067527), published Jul. 5, 2012; WO/2015/116868 (Int'l Appl. No. PCT/US2015/013618), published Aug. 6, 2015; WO/2017/053915 (Int'l Appl. No. PCT/US2016/053614), published Mar. 30, 2017; WO/2016/141169 (Int'l Appl. No. PCT/US2016/020657), published Sep. 9, 2016; and WO/2018/175501 (Int'l Appl. No. PCT/US2018/023438), published Sep. 27, 2018; each of which publications is incorporated by reference herein in its entirety. A fusion gene is a hybrid gene created by the juxtaposition of two previously separate genes. This can occur by chromosomal translocation or inversion, deletion or via trans-splicing. The resulting fusion gene can cause abnormal temporal and spatial expression of genes, leading to abnormal expression of cell growth factors, angiogenesis factors, tumor promoters or other factors contributing to the neoplastic transformation of the cell and the creation of a tumor. For example, such fusion genes can be oncogenic due to the juxtaposition of: 1) a strong promoter region of one gene next to the coding region of a cell growth factor, tumor promoter or other gene promoting oncogenesis leading to elevated gene expression, or 2) due to the fusion of coding regions of two different genes, giving rise to a chimeric gene and thus a chimeric protein with abnormal activity. Fusion genes are characteristic of many cancers. Once a therapeutic intervention is associated with a fusion, the presence of that fusion in any type of cancer identifies the therapeutic intervention as a candidate therapy for treating the cancer.

The presence of fusion genes can be used to guide therapeutic selection. For example, the BCR-ABL gene fusion is a characteristic molecular aberration in ~90% of chronic myelogenous leukemia (CML) and in a subset of acute leukemias (Kurzrock et al., Annals of Internal Medicine 2003; 138:819-830). The BCR-ABL results from a translocation between chromosomes 9 and 22, commonly referred to as the Philadelphia chromosome or Philadelphia translocation. The translocation brings together the 5' region of the BCR gene and the 3' region of ABL1, generating a chimeric BCR-ABL1 gene, which encodes a protein with constitutively active tyrosine kinase activity (Mittleman et al., Nature Reviews Cancer 2007; 7:233-245). The aberrant tyrosine kinase activity leads to de-regulated cell signaling, cell growth and cell survival, apoptosis resistance and growth factor independence, all of which contribute to the pathophysiology of leukemia (Kurzrock et al., Annals of Internal Medicine 2003; 138:819-830). Patients with the Philadelphia chromosome are treated with imatinib and other targeted therapies. Imatinib binds to the site of the constitutive tyrosine kinase activity of the fusion protein and prevents its activity. Imatinib treatment has led to molecular responses (disappearance of BCR-ABL+blood cells) and improved progression-free survival in BCR-ABL+CML patients (Kantarjian et al., Clinical Cancer Research 2007; 13:1089-1097).

Another fusion gene, IGH-MYC, is a defining feature of ~80% of Burkitt's lymphoma (Ferry et al. Oncologist 2006; 11:375-83). The causal event for this is a translocation between chromosomes 8 and 14, bringing the c-Myc oncogene adjacent to the strong promoter of the immunoglobulin heavy chain gene, causing c-myc overexpression (Mittleman et al., Nature Reviews Cancer 2007; 7:233-245). The c-myc rearrangement is a pivotal event in lymphomagenesis as it results in a perpetually proliferative state. It has wide ranging effects on progression through the cell cycle, cellular differentiation, apoptosis, and cell adhesion (Ferry et al. Oncologist 2006; 11:375-83).

A number of recurrent fusion genes have been catalogued in the Mittleman database (cgap.nci.nih.gov/Chromosomes/Mitelman). The gene fusions can be used to characterize neoplasms and cancers and guide therapy using the subject methods described herein. For example, TMPRSS2-ERG, TMPRSS2-ETV and SLC45A3-ELK4 fusions can be detected to characterize prostate cancer; and ETV6-NTRK3 and ODZ4-NRG1 can be used to characterize breast cancer. The EML4-ALK, RLF-MYCL1, TGF-ALK, or CD74-ROS1 fusions can be used to characterize a lung cancer. The ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4 fusions can be used to characterize a prostate cancer. The GOPC-ROS1 fusion can be used to characterize a brain cancer. The CHCHD7-PLAG1, CTNNB1-PLAG1, FHIT-HMGA2, HMGA2-NFIB, LIFR-PLAG1, or TCEA1-PLAG1 fusions can be used to characterize a head and neck cancer. The ALPHA-TFEB, NONO-TFE3, PRCC-TFE3, SFPQ-TFE3, CLTC-TFE3, or MALAT1-TFEB fusions can be used to characterize a renal cell carcinoma (RCC). The AKAP9-BRAF, CCDC6-RET, ERC1-RETM, GOLGAS-RET, HOOK3-RET, HRH4-RET, KTN1-RET, NCOA4-RET, PCM1-RET, PRKARA1A-RET, RFG-RET, RFG9-RET, Ria-RET, TGF-NTRK1, TPM3-NTRK1, TPM3-TPR, TPR-MET, TPR-NTRK1, TRIM24-RET, TRIM27-RET or TRIM33-RET fusions can be used to characterize a thyroid cancer and/or papillary thyroid carcinoma; and the PAX8-PPARy fusion can be analyzed to characterize a follicular thyroid cancer. Fusions that are associated with hematological malignancies include without limitation TTL-ETV6, CDK6-MLL, CDK6-TLX3, ETV6-FLT3, ETV6-RUNX1, ETV6-TTL, MLL-AFF1, MLL-AFF3, MLL-AFF4, MLL-GAS7, TCBA1-ETV6, TCF3-PBX1 or TCF3-TFPT, which are characteristic of acute lymphocytic leukemia (ALL); BCL11B-TLX3, IL2-TNFRFS17, NUP214-ABL1, NUP98-CCDC28A, TAL1-STIL, or ETV6-ABL2, which are characteristic of T-cell acute lymphocytic leukemia (T-ALL); ATIC-ALK, KIAA1618-ALK, MSN-ALK, MYH9-ALK, NPM1-ALK, TGF-ALK or TPM3-ALK, which are characteristic of anaplastic large cell lymphoma (ALCL); BCR-ABL1, BCR-JAK2, ETV6-EVI1, ETV6-MN1 or ETV6-TCBA1, characteristic of chronic myelogenous leukemia (CML); CBFB-MYH11, CHIC2-ETV6, ETV6-ABL1, ETV6-ABL2, ETV6-ARNT, ETV6-CDX2, ETV6-HLXB9, ETV6-PER1, MEF2D-DAZAP1, AML-AFF1, MLL-ARHGAP26, MLL-ARHGEF12, MLL-CASC5, MLL-CBL,MLL-CREBBP, MLL-DAB21P, MLL-ELL, MLL-EP300, MLL-EPS15, MLL-FNBP1, MLL-FOXO3A, MLL-GMPS, MLL-GPHN, MLL-MLLT1, MLL-MLLT11, MLL-MLLT3, MLL-MLLT6, MLL-MYO1F, MLL-PICALM, MLL-SEPT2, MLL-SEPT6, MLL-SORBS2, MYST3-SORBS2, MYST-CREBBP, NPM1-MLF1, NUP98-HOXA13, PRDM16-EVI1, RABEP1-PDGFRB, RUNX1-EVI1, RUNX1-MDS1, RUNX1-RPL22, RUNX1-RUNX1T1, RUNX1-SH3D19, RUNX1-USP42, RUNX1-YTHDF2, RUNX1-ZNF687, or TAF15-ZNF-384, which are characteristic of acute myeloid leukemia (AML); CCND1-FSTL3, which is characteristic of chronic lymphocytic leukemia (CLL); BCL3-MYC, MYC-BTG1, BCL7A-MYC, BRWD3-ARHGAP20 or BTG1-MYC, which are characteristic of B-cell chronic lymphocytic leukemia (B-CLL); CITTA-BCL6, CLTC-ALK, IL21R-BCL6, PIM1-BCL6, TFCR-BCL6, IKZF1-BCL6 or SEC31A-ALK, which are characteristic of diffuse large B-cell lymphomas (DLBCL); FLIP1-PDGFRA, FLT3-ETV6, KIAA1509-PDGFRA, PDE4DIP-PDGFRB, NIN-PDGFRB, TP53BP1-PDGFRB, or TPM3-PDGFRB, which are characteristic of hyper eosinophilia/chronic eosinophilia; and IGH-MYC or LCP1-BCL6, which are characteristic of Burkitt's lymphoma. One of skill will understand that additional fusions, including those yet to be identified to date, can be used to guide treatment once their presence is associated with a therapeutic intervention.

The fusion genes and gene products can be detected using one or more techniques described herein. In some embodiments, the sequence of the gene or corresponding mRNA is determined, e.g., using Sanger sequencing, NGS, pyrosequencing, DNA microarrays, etc. Chromosomal abnormalities can be assessed using ISH, NGS or PCR techniques, among others. For example, a break apart probe can be used for ISH detection of ALK fusions such as EML4-ALK, KIF5B-ALK and/or TFG-ALK. As an alternate, PCR can be used to amplify the fusion product, wherein amplification or lack thereof indicates the presence or absence of the fusion, respectively. mRNA can be sequenced, e.g., using NGS to detect such fusions. See, e.g., Table 9 or Table 12 of WO2018175501. In some embodiments, the fusion protein fusion is detected. Appropriate methods for protein analysis include without limitation mass spectroscopy, electrophoresis (e.g., 2D gel electrophoresis or SDS-PAGE) or antibody related techniques, including immunoassay, protein array or immunohistochemistry. The techniques can be combined. As a non-limiting example, indication of an ALK fusion by NGS can be confirmed by ISH or ALK expression using IHC, or vice versa.

Molecular Profiling Targets for Treatment Selection

The systems and methods described herein allow identification of one or more therapeutic regimes with projected therapeutic efficacy, based on the molecular profiling. Illustrative schemes for using molecular profiling to identify a treatment regime are provided throughout. Additional schemes are described in International Patent Publications WO/2007/137187 (Int'l Appl. No. PCT/US2007/069286), published Nov. 29, 2007; WO/2010/045318 (Int'l Appl. No. PCT/US2009/060630), published Apr. 22, 2010; WO/2010/093465 (Int'l Appl. No. PCT/US2010/000407), published Aug. 19, 2010; WO/2012/170715 (Int'l Appl. No. PCT/US2012/041393), published Dec. 13, 2012; WO/2014/089241 (Int'l Appl. No. PCT/US2013/073184), published Jun. 12, 2014; WO/2011/056688 (Int'l Appl. No. PCT/US2010/054366), published May 12, 2011; WO/2012/092336 (Int'l Appl. No. PCT/US2011/067527), published Jul. 5, 2012; WO/2015/116868 (Int'l Appl. No. PCT/US2015/013618), published Aug. 6, 2015; WO/2017/053915 (Int'l Appl. No. PCT/US2016/053614), published Mar. 30, 2017; WO/2016/141169 (Int'l Appl. No. PCT/US2016/020657), published Sep. 9, 2016; and WO2018175501 (Int'l Appl. No. PCT/US2018/023438), published Sep. 27, 2018; each of which publications is incorporated by reference herein in its entirety.

The methods described herein comprise use of molecular profiling results to suggest associations with treatment benefit. In some embodiments, rules are used to provide the suggested chemotherapy treatments based on the molecular profiling test results. The simplest rules are constructed in the format of "if biomarker positive then treatment option one, else treatment option two." Treatment options comprise no treatment with a specific drug, or treatment with a specific regimen (i.e., FOLFOX or FOLFIRI). In some embodiments, more complex rules are constructed that involve the interaction of two or more biomarkers. Finally, a report can be generated that describes the association of the predicted benefit of a treatment and the biomarker and optionally a summary statement of the best evidence supporting the treatments selected. Ultimately, the treating physician will decide on the best course of treatment.

The selection of a candidate treatment for an individual can be based on molecular profiling results from any one or more of the methods described.

As disclosed herein, molecular profiling can be performed to determine a copy number or a copy number variation of one or more genes present in a sample. The CNV of the gene or genes is used to select a regimen that is predicted to be efficacious. The methods can also include detection of mutations, indels, fusions, and the like in other genes and/or gene products, e.g., as described in International Patent Publications WO/2007/137187 (Int'l Appl. No. PCT/US2007/069286), published Nov. 29, 2007; WO/2010/045318 (Int'l Appl. No. PCT/US2009/060630), published Apr. 22, 2010; WO/2010/093465 (Int'l Appl. No. PCT/US2010/000407), published Aug. 19, 2010; WO/2012/170715 (Int'l Appl. No. PCT/US2012/041393), published Dec. 13, 2012; WO/2014/089241 (Int'l Appl. No. PCT/US2013/073184), published Jun. 12, 2014; WO/2011/056688 (Int'l Appl. No. PCT/US2010/054366), published May 12, 2011; WO/2012/092336 (Int'l Appl. No. PCT/US2011/067527), published Jul. 5, 2012; WO/2015/116868 (Int'l Appl. No. PCT/US2015/013618), published Aug. 6, 2015; WO/2017/053915 (Int'l Appl. No. PCT/US2016/053614), published Mar. 30, 2017; WO/2016/141169 (Int'l Appl. No. PCT/US2016/020657), published Sep. 9, 2016; and WO2018175501 (Int'l Appl. No. PCT/US2018/023438), published Sep. 27, 2018; each of which publications is incorporated by reference herein in its entirety.

The methods described herein are used to prolong survival of a subject with colorectal cancer by providing personalized treatment. In some embodiments, the subject has been previously treated with one or more therapeutic agents to treat the cancer. The cancer may be refractory to one of these agents, e.g., by acquiring drug resistance mutations. In some embodiments, the cancer is metastatic. In some embodiments, the subject has not previously been treated with one or more therapeutic agents identified by the method. Using molecular profiling, candidate treatments can be selected regardless of the stage, anatomical location, or anatomical origin of the cancer cells.

The present disclosure provides methods and systems for analyzing diseased tissue using molecular profiling as previously described above. Because the methods rely on analysis of the characteristics of the tumor under analysis, the methods can be applied in for any tumor or any stage of disease, such an advanced stage of disease or a metastatic tumor of unknown origin. As described herein, a tumor or cancer sample is analyzed for copy number or presence of a CNV of one or more biomarkers in order to predict or identify a candidate therapeutic treatment.

The present methods can be used for selecting a treatment of primary or metastatic colorectal cancer.

The biomarker patterns and/or biomarker signature sets can comprise pluralities of biomarkers. In yet other embodiments, the biomarker patterns or signature sets can comprise at least 6, 7, 8, 9, or 10 biomarkers. In some embodiments, the biomarker signature sets or biomarker patterns can comprise at least 15, 20, 30, 40, 50, or 60 biomarkers. In some embodiments, the biomarker signature sets or biomarker patterns can comprise at least 70, 80, 90, 100, or 200, biomarkers. Analysis of the one or more biomarkers can be by one or more methods, e.g., as described herein.

As described herein, the molecular profiling of one or more targets can be used to determine or identify a therapeutic for an individual. For example, the copy number or presence of a CNV of one or more biomarkers can be used to determine or identify a therapeutic for an individual. The one or more biomarkers, such as those disclosed herein, can be used to form a biomarker pattern or biomarker signature set, which is used to identify a therapeutic for an individual. In some embodiments, the therapeutic identified is one that the individual has not previously been treated with. For example, a reference biomarker pattern has been established for a particular therapeutic, such that individuals with the reference biomarker pattern will be responsive to that therapeutic. An individual with a biomarker pattern that differs from the reference, for example the expression of a gene in the biomarker pattern is changed or different from that of the reference, would not be administered that therapeutic. In another example, an individual exhibiting a biomarker pattern that is the same or substantially the same as the reference is advised to be treated with that therapeutic. In some embodiments, the individual has not previously been treated with that therapeutic and thus a new therapeutic has been identified for the individual.

The genes used for molecular profiling, e.g., by IHC, ISH, sequencing (e.g., NGS), and/or PCR (e.g., qPCR), can be selected from those listed in any described in WO2018175501, e.g., in Tables 5-10 therein. Assessing one or more biomarkers disclosed herein can be used for characterizing a cancer, e.g., a colorectal cancer as disclosed herein.

A cancer in a subject can be characterized by obtaining a biological sample from a subject and analyzing one or more biomarkers from the sample. For example, characterizing a cancer for a subject or individual can include identifying appropriate treatments or treatment efficacy for specific diseases, conditions, disease stages and condition stages, predictions and likelihood analysis of disease progression, particularly disease recurrence, metastatic spread or disease relapse. The products and processes described herein allow assessment of a subject on an individual basis, which can provide benefits of more efficient and economical decisions in treatment.

In an aspect, characterizing a cancer includes predicting whether a subject is likely to benefit from a treatment for the cancer. Biomarkers can be analyzed in the subject and compared to biomarker profiles of previous subjects that were known to benefit or not from a treatment. If the biomarker profile in a subject more closely aligns with that of previous subjects that were known to benefit from the treatment, the subject can be characterized, or predicted, as a one who benefits from the treatment. Similarly, if the biomarker profile in the subject more closely aligns with that of previous subjects that did not benefit from the treatment, the subject can be characterized, or predicted as one who does not benefit from the treatment. The sample used for characterizing a cancer can be any useful sample, including without limitation those disclosed herein.

The methods can further include administering the selected treatment to the subject. The FOLFOX and FOLFIRI regimens are known in the art; see, e.g., nccn.org/professionals/physician_gls/pdf/colon.pdf.

The present disclosure describes the use of a machine learning approach to analyze molecular profiling data to discover clinically relevant biosignatures for predicting benefit or lack of benefit from FOLFOX. We trained machine learning classification models on Stage III and Stage IV colorectal cancer (CRC) samples. See Examples 2-4. Here, we combined all models to develop a machine-learning approach to predict CRC patients as responders or non-responders to the FOLFOX chemotherapeutic treatment regimen. Benefit is a relative term and indicates that a treatment has a positive influence in treating a patient with cancer, but does not require complete remission. A subject that receives a benefit may be referred to as a benefiter, responder, or the like. Likewise, a subject unlikely to receive a benefit or that does not benefit may be referred to herein as a non-benefiter, non-responder, or similar.

As described in the Examples, provided herein are methods comprising: obtaining a biological sample comprising cells from a cancer in a subject; and performing an assay to assess at least one biomarker in the biological sample, wherein the biomarkers comprise at least one of the following: (a) Group 1 comprising 1, 2, 3, 4, 5 or all 6 of MYC, EP300, U2AF1, ASXL1, MAML2, and CNTRL; (b) Group 2 comprising 1, 2, 3, 4, 5, 6, 7, or all 8 of MYC, EP300, U2AF1, ASXL1, MAML2, CNTRL, WRN, and CDX2; (c) Group 3 comprising 1, 2, 3, 4, 5, 6, 7, 8, 9, 10, 11, 12, 13, or all 14 of BCL9, PBX1, PRRX1, INHBA, YWHAE, GNAS, LHFPL6, FCRL4, HOXA11, AURKA, BIRC3, IKZF1, CASP8, and EP300; (d) Group 4 comprising 1, 2, 3, 4, 5, 6, 7, 8, 9, 10, 11, 12, or all 13 of PBX1, BCL9, INHBA, PRRX1, YWHAE, GNAS, LHFPL6, FCRL4, AURKA, IKZF1, CASP8, PTEN, and EP300; (e) Group 5 comprising 1, 2, 3, 4, 5, 6, 7, 8, 9, 10, 11, or all 12 of BCL9, PBX1, PRRX1, INHBA, GNAS, YWHAE, LHFPL6, FCRL4, PTEN, HOXA11, AURKA, and BIRC3; (f) Group 6 comprising 1, 2, 3, 4, or all 5 of BCL9, PBX1, PRRX1, INHBA, and YWHAE; (g) Group 7 comprising 1, 2, 3, 4, 5, 6, 7, 8, 9, 10, 11, 12, 13, 14 or all 15 of BCL9, PBX1, GNAS, LHFPL6, CASP8, ASXL1, FH, CRKL, MLF1, TRRAP, AKT3, ACKR3, MSI2, PCM1, and MNX1; (h) Group 8 comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or all 45 of BX1, GNAS, AURKA, CASP8, ASXL1, CRKL, MLF1, GAS7, MN1, SOX10, TCL1A, LMO1, BRD3, SMARCA4, PER1, PAX7, SBDS, SEPT5, PDGFB, AKT2, TERT, KEAP1, ETV6, TOP1, TLX3, COX6C, NFIB, ARFRP1, ARID1A, MAP2K4, NFKBIA, WWTR1, ZNF217, IL2, NSD3, CREB1, BRIP1, SDC4, EWSR1, FLT3, FLT1, FAS, CCNE1, RUNX1T1, and EZR; and (i) Group 9 comprising 1, 2, 3, 4, 5, 6, 7, 8, 9, 10, or all 11 of BCL9, PBX1, PRRX1, INHBA, YWHAE, GNAS, LHFPL6, FCRL4, BIRC3, AURKA, and HOXA11. These gene identifiers are those commonly accepted in the scientific community at the time of filing and can be used to look up the genes at various well-known databases such as the HUGO Gene Nomenclature Committee (HNGC; genenames.org), NCBI's Gene database (www.ncbi.nlm.nih.gov/gene), GeneCards (genecards.org), Ensembl (ensembl.org), UniProt (uniprot.org), and others. The method may assess useful combination of the groups of biomarkers, e.g., such that provide desired information about the subject.

The biological sample can be any useful biological sample from the subject such as described herein, including without limitation formalin-fixed paraffin-embedded (FFPE) tissue, fixed tissue, a core needle biopsy, a fine needle aspirate, unstained slides, fresh frozen (FF) tissue, formalin samples, tissue comprised in a solution that preserves nucleic acid or protein molecules, a fresh sample, a malignant fluid, a bodily fluid, a tumor sample, a tissue sample, or any combination thereof. In preferred embodiments, the biological sample comprises cells from a solid tumor. The biological sample may be a bodily fluid, which bodily fluid may comprise circulating tumor cells (CTCs). In some embodiments, the bodily fluid comprises a malignant fluid, a pleural fluid, a peritoneal fluid, or any combination thereof. The bodily fluid can be any useful bodily fluid from the subject, including without limitation peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid, pre-ejaculatory fluid, female ejaculate, sweat, fecal matter, tears, cyst fluid, pleural fluid, peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyst cavity fluid, or umbilical cord blood. In preferred embodiments, the bodily fluid comprises blood or a blood derivative or fraction such as plasma or serum.

The assay used to assess the biomarkers can be chosen to provide the desired level of information about the biomarker in the biological sample and thus about the subject. In some embodiments, the assessment comprises determining a presence, level, or state of a protein or nucleic acid for each biomarker. The nucleic acid can be a deoxyribonucleic acid (DNA), ribonucleic acid (RNA), or a combination thereof. The presence, level or state of various proteins can be determined using methodology such as described herein, including without limitation immunohistochemistry (IHC), flow cytometry, an immunoassay, an antibody or functional fragment thereof, an aptamer, or any combination thereof.

Similarly, the presence, level or state of various nucleic acids can be determined using methodology such as described herein, including without limitation polymerase chain reaction (PCR), in situ hybridization, amplification, hybridization, microarray, nucleic acid sequencing, dye termination sequencing, pyrosequencing, next generation sequencing (NGS; high-throughput sequencing), or any combination thereof. The state of the nucleic acid can be any relevant state, including without limitation a sequence, mutation, polymorphism, deletion, insertion, substitution, translocation, fusion, break, duplication, amplification, repeat, copy number, copy number variation (CNV; copy number alteration; CNA), or any combination thereof. The state may be wild type or non-wild type. In some embodiments, next-generation sequencing (NGS) is used to assess the presence, level, or state in a single assay. NGS can be used to assess panels of biomarkers (see, e.g., Example 1), whole exome, whole transcriptome, or any combination thereof.

Useful groups of biomarkers for predicting response or benefit of FOLFOX in colorectal cancer patients were identified according to the machine learning modeling disclosed herein. Such groups were identified as described in Examples 2-4 by analyzing data collected from cancer patients using molecular profiling data collected as described in Example 1. Such useful groups include Group 1 (i.e., MYC, EP300, U2AF1, ASXL1, MAML2, and CNTRL), Group 2 (i.e., MYC, EP300, U2AF1, ASXL1, MAML2, CNTRL, WRN, and CDX2), Group 3 (i.e., BCL9, PBX1, PRRX1, INHBA, YWHAE, GNAS, LHFPL6, FCRL4, HOXA11, AURKA, BIRC3, IKZF1, CASP8, and EP300), Group 4 (i.e., PBX1, BCL9, INHBA, PRRX1, YWHAE, GNAS, LHFPL6, FCRL4, AURKA, IKZF1, CASP8, PTEN, and EP300), Group 5 (i.e., BCL9, PBX1, PRRX1, INHBA, GNAS, YWHAE, LHFPL6, FCRL4, PTEN, HOXA11, AURKA, and BIRC3), Group 6 (i.e., BCL9, PBX1, PRRX1, INHBA, and YWHAE), Group 7 (i.e., BCL9, PBX1, GNAS, LHFPL6, CASP8, ASXL1, FH, CRKL, MLF1, TRRAP, AKT3, ACKR3, MSI2, PCM1, and MNX1), Group 8 (i.e., BX1, GNAS, AURKA, CASP8, ASXL1, CRKL, MLF1, GAS7, MN1, SOX10, TCL1A, LMO1, BRD3, SMARCA4, PER1, PAX7, SBDS, SEPT5, PDGFB, AKT2, TERT, KEAP1, ETV6, TOP1, TLX3, COX6C, NFIB, ARFRP1, ARID1A, MAP2K4, NFKBIA, WWTR1, ZNF217, IL2, NSD3, CREB1, BRIP1, SDC4, EWSR1, FLT3, FLT1, FAS, CCNE1, RUNX1T1, and EZR), Group 9 (i.e., BCL9, PBX1, PRRX1, INHBA, YWHAE, GNAS, LHFPL6, FCRL4, BIRC3, AURKA, and HOXA11). Unless otherwise noted, the machine learning algorithms chose copy number as determined by NGS as the relevant state of the specified biomarkers.

Cells are typically diploid with two copies of each gene. However, cancer may lead to various genomic alterations which can alter copy number. In some instances, copies of genes are amplified (gained), whereas in other instances copies of genes are lost. Genomic alterations can affect different regions of a chromosome. For example, gain or loss may occur within a gene, at the gene level, or within groups of neighboring genes. Gain or loss may be observed at the level of cytogenetic bands or even larger portions of chromosomal arms. Thus, analysis of such proximate regions to a gene may provide similar or even identical information to the gene itself. Accordingly, the methods provided herein are not limited to determining copy number of the specified genes, but also expressly contemplate the analysis of proximate regions to the genes, wherein such proximate regions provide similar or the same level of information. For example, Table 11 lists the locus of each gene at the level of the cytogenetic band. Groups of genes can be observed at the level of the band, the arm, or the chromosome. There are regions where multiple genes appear, including without limitation at 1q (PAX7, BCL9, FCRL4, PBX1, PRRX1, FH, AKT3), 20q (ASXL1, TOP1, SDC4, AURKA, ZNF217, GNAS, ARFRP1) and 22q (CRKL, SEPT5, MN1, EWSR1, PDGFB, SOX10, EP300). This suggests that there are chromosomal "hotspots" for genomic alterations which our method detects when multiple genes lie with a given genetic local. Merely by way of example, the disclosure contemplates that analysis of alternate genes at 1q, 20q and 22q may be used in the FOLFOX biosignatures provided herein. Similar analysis can be applied for the locus of each gene listed in Groups 1-9.

As noted, the methods provided herein may further comprise the likely benefit of FOLFOX based on the biomarkers assessed. If the methods determine that FOLFOX is not likely to benefit the subject, an alternate treatment may be chosen, such as FOLFIRI. In some embodiments, the method comprises performing an assay to determine a copy number of: (a) at least one or all members of Group 1 and Group 2, or proximate genomic regions thereto (see Example 2); (b) at least one or all members of Group 3, or proximate genomic regions thereto (see Example 3); or (c) at least one or all members of Group 2, Group 6, Group 7, Group 8, and Group 9, or proximate genomic regions thereto (see Example 4). Based on the observed copy numbers, the likely benefit of FOLFOX can be determined using a voting module (see FIG. 1F and related text). In preferred embodiments, use of such voting module includes applying a machine learning classification model to the copy numbers obtained for each of Group 2, Group 6, Group 7, Group 8, and Group 9, including without limitation random forest model. The random forest models can be as described in Table 10 herein.

Further provided herein is a method of selecting a treatment for a subject who has a colorectal cancer, the method comprising: obtaining a biological sample comprising cells from the colorectal cancer; performing next generation sequencing on genomic DNA from the biological sample to determine a copy number for each of the following groups of genes or proximate genomic regions thereto: (a) Group 2 comprising 1, 2, 3, 4, 5, 6, 7, or all 8 of MYC, EP300, U2AF1, ASXL1, MAML2, CNTRL, WRN, and CDX2; (b) Group 6 comprising 1, 2, 3, 4, or all 5 of BCL9, PBX1, PRRX1, INHBA, and YWHAE; (c) Group 7 comprising 1, 2, 3, 4, 5, 6, 7, 8, 9, 10, 11, 12, 13, 14 or all 15 of BCL9, PBX1, GNAS, LHFPL6, CASP8, ASXL1, FH, CRKL, MLF1, TRRAP, AKT3, ACKR3, MSI2, PCM1, and MNX1; (d) Group 8 comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or all 45 of BX1, GNAS, AURKA, CASP8, ASXL1, CRKL, MLF1, GAS7, MN1, SOX10, TCL1A, LMO1, BRD3, SMARCA4, PER1, PAX7, SBDS, SEPT5, PDGFB, AKT2, TERT, KEAP1, ETV6, TOP1, TLX3, COX6C, NFIB, ARFRP1, ARID1A, MAP2K4, NFKBIA, WWTR1, ZNF217, IL2, NSD3, CREB1, BRIP1, SDC4, EWSR1, FLT3, FLT1, FAS, CCNE1, RUNX1T1, and EZR; and (e) Group 9 comprising 1, 2, 3, 4, 5, 6, 7, 8, 9, 10, or all 11 of BCL9, PBX1, PRRX1, INHBA, YWHAE, GNAS, LHFPL6, FCRL4, BIRC3, AURKA, and HOXA11; applying a machine learning classification model to the copy numbers obtained for each of Group 2, Group 6, Group 7, Group 8, and Group 9, optionally wherein each machine learning classification model is a random forest model, optionally wherein the random forest models are as described in Table 10; obtaining an indication from each machine learning classification model whether the subject is likely to benefit from treatment with 5-fluorouracil/leucovorin combined with oxaliplatin (FOLFOX); and selecting FOLFOX if the majority of the machine learning classification models indicate that the subject is likely to benefit from the treatment and selecting an alternate treatment to FOLFOX if the majority of the machine learning classification models indicate that the subject is not likely to benefit from the FOLFOX, optionally wherein the alternate treatment is 5-fluorouracil/leucovorin combined with irinotecan (FOLFIRI). In some embodiments, the method further comprises administering the selected treatment to the subject. See Example 5.

Report

In an embodiment, the methods as described herein comprise generating a molecular profile report. The report can be delivered to the treating physician or other caregiver of the subject whose cancer has been profiled. The report can comprise multiple sections of relevant information, including without limitation: 1) a list of the genes in the molecular profile; 2) a description of the molecular profile comprising copy number of CNV of the genes and/or gene products as determined for the subject; 3) a treatment associated with the molecular profile; and 4) and an indication whether each treatment is likely to benefit the patient, not benefit the patient, or has indeterminate benefit. The list of the genes in the molecular profile can be those presented herein. The description of the molecular profile of the genes as determined for the subject may include such information as the laboratory technique used to assess each biomarker (e.g., RT-PCR, FISH/CISH, PCR, FA/RFLP, NGS, etc) as well as the result and criteria used to score each technique. By way of example, the criteria for scoring a CNV may be a presence (i.e., a copy number that is greater or lower than the "normal" copy number present in a subject who does not have cancer, or statistically identified as present in the general population, typically diploid) or absence (i.e., a copy number that is the same as the "normal" copy number present in a subject who does not have cancer, or statistically identified as present in the general population, typically diploid) The treatment associated with one or more of the genes and/or gene products in the molecular profile can be determined using a biomarker-drug association rule set such as in any of International Patent Publications WO/2007/137187 (Int'l Appl. No. PCT/US2007/069286), published Nov. 29, 2007; WO/2010/045318 (Int'l Appl. No. PCT/US2009/060630), published Apr. 22, 2010; WO/2010/093465 (Int'l Appl. No. PCT/US2010/000407), published Aug. 19, 2010; WO/2012/170715 (Int'l Appl. No. PCT/US2012/041393), published Dec. 13, 2012; WO/2014/089241 (Int'l Appl. No. PCT/US2013/073184), published Jun. 12, 2014; WO/2011/056688 (Int'l Appl. No. PCT/US2010/054366), published May 12, 2011; WO/2012/092336 (Int'l Appl. No. PCT/US2011/067527), published Jul. 5, 2012; WO/2015/116868 (Int'l Appl. No. PCT/US2015/013618), published Aug. 6, 2015; WO/2017/053915 (Int'l Appl. No. PCT/US2016/053614), published Mar. 30, 2017; WO/2016/141169 (Int'l Appl. No. PCT/US2016/020657), published Sep. 9, 2016; and WO2018175501 (Int'l Appl. No. PCT/US2018/023438), published Sep. 27, 2018; each of which publications is incorporated by reference herein in its entirety. The indication whether each treatment is likely to benefit the patient, not benefit the patient, or has indeterminate benefit may be weighted. For example, a potential benefit may be a strong potential benefit or a lesser potential benefit. Such weighting can be based on any appropriate criteria, e.g., the strength of the evidence of the biomarker-treatment association, or the results of the profiling, e.g., a degree of over- or underexpression.

Various additional components can be added to the report as desired. In some embodiments, the report comprises a list having an indication of whether a copy number or CNV of one or more of the genes in the molecular profile is associated with an ongoing clinical trial. The report may include identifiers for any such trials, e.g., to facilitate the treating physician's investigation of potential enrollment of the subject in the trial. In some embodiments, the report provides a list of evidence supporting the association of the CNV in the molecular profile with the reported treatment. The list can contain citations to the evidentiary literature and/or an indication of the strength of the evidence for the particular biomarker-treatment association. In some embodiments, the report comprises a description of the genes in the molecular profile. The description of the genes in the molecular profile can comprise without limitation the biological function and/or various treatment associations.

The molecular profiling report can be delivered to the caregiver for the subject, e.g., the oncologist or other treating physician. The caregiver can use the results of the report to guide a treatment regimen for the subject. For example, the caregiver may use one or more treatments indicated as likely benefit in the report to treat the patient. Similarly, the caregiver may avoid treating the patient with one or more treatments indicated as likely lack of benefit in the report.

In some embodiments of the method of identifying at least one therapy of potential benefit, the subject has not previously been treated with the at least one therapy of potential benefit. The cancer may comprise a metastatic cancer, a recurrent cancer, or any combination thereof. In some cases, the cancer is refractory to a prior therapy, including without limitation front-line or standard of care therapy for the cancer. In some embodiments, the cancer is refractory to all known standard of care therapies. In other embodiments, the subject has not previously been treated for the cancer. The method may further comprise administering the at least one therapy of potential benefit to the individual. Progression free survival (PFS), disease free survival (DFS), or lifespan can be extended by the administration.

The report can be computer generated, and can be a printed report, a computer file or both. The report can be made accessible via a secure web portal.

In an aspect, the disclosure provides use of a reagent in carrying out the methods as described herein as described above. In a related aspect, the disclosure provides of a reagent in the manufacture of a reagent or kit for carrying out the methods as described herein. In still another related aspect, the disclosure provides a kit comprising a reagent for carrying out the methods as described herein. The reagent can be any useful and desired reagent. In preferred embodiments, the reagent comprises at least one of a reagent for extracting nucleic acid from a sample, and a reagent for performing next-generation sequencing.

In an aspect, the disclosure provides a system for identifying at least one therapy associated with a cancer in an individual, comprising: (a) at least one host server; (b) at least one user interface for accessing the at least one host server to access and input data; (c) at least one processor for processing the inputted data; (d) at least one memory coupled to the processor for storing the processed data and instructions for: i) accessing a CNV status (i.e., copy number or presence/absence of a CNV) determine by a method described herein; and ii) identifying, based on the CNV status, at least one therapy with potential benefit for treatment of the cancer; and (e) at least one display for displaying the identified therapy with potential benefit for treatment of the cancer. In some embodiments, the system further comprises at least one memory coupled to the processor for storing the processed data and instructions for identifying, based on the generated molecular profile according to the methods above, at least one therapy with potential benefit for treatment of the cancer; and at least one display for display thereof. The system may further comprise at least one database comprising references for various biomarker states, data for drug/biomarker associations, or both. The at least one display can be a report provided by the present disclosure.

EXAMPLES

The invention is further described in the following examples, which do not limit the scope as described herein described in the claims.

Example 1: Next-Generation Profiling

Comprehensive molecular profiling provides a wealth of data concerning the molecular status of patient samples. We have performed such profiling on well over 100,000 tumor patients from practically all cancer lineages using various profiling technologies as described herein, e.g., in Example 1. To date, we have tracked the benefit or lack of benefit from treatments in over 20,000 of these patients. Our molecular profiling data can thus be compared to patient benefit to treatments to identify additional biomarker signatures that predict the benefit to various treatments in additional cancer patients. We have applied this "next generation profiling" (NGP) approach to identify biomarker signatures that correlate with patient benefit (including positive, negative, or indeterminate benefit) to various cancer therapeutics.

The general approach to NGP is as follows. Over several years we have performed comprehensive molecular profiling of tens of thousands of patients using various molecular profiling techniques. As further outlined in FIG. 2C, these techniques include without limitation next generation sequencing (NGS) of DNA to assess various attributes 2301, gene expression and gene fusion analysis of RNA 2302, IHC analysis of protein expression 2303, and ISH to assess gene copy number and chromosomal aberrations such as translocations 2304. We currently have matched patient clinical outcomes data for over 20,000 patients of various cancer lineages 2305. We use cognitive computing approaches 2306 to correlate the comprehensive molecular profiling results against the actual patient outcomes data for various treatments as desired. Clinical outcome may be determined using the surrogate endpoint time-on-treatment (TOT) or time-to-next-treatment (TTNT or TNT). See, e.g., Roever L (2016) Endpoints in Clinical Trials: Advantages and Limitations. Evidence Based Medicine and Practice 1: e111. doi:10.4172/ebmp.1000e111. The results provide a biosignature comprising a panel of biomarkers 2307, wherein the biosignature is indicative of benefit or lack of benefit from the treatment under investigation. The biosignature can be applied to molecular profiling results for new patients in order to predict benefit from the applicable treatment and thus guide treatment decisions. Such personalized guidance can improve the selection of efficacious treatments and also avoid treatments with lesser clinical benefit, if any.

Table 2 lists numerous biomarkers we have profiled over the past several years. As relevant molecular profiling and patient outcomes are available, any or all of these biomarkers can serve as features to input into the cognitive computing environment to develop a biosignature of interest. The table shows molecular profiling techniques and various biomarkers assessed using those techniques. The listing is non-exhaustive, and data for all of the listed biomarkers will not be available for every patient. It will further be appreciated that various biomarker have been profiled using multiple methods. As a non-limiting example, consider the EGFR gene expressing the Epidermal Growth Factor Receptor (EGFR) protein. As shown in Table 2, expression of EGFR protein has been detected using IHC; EGFR gene amplification, gene rearrangements, mutations and alterations have been detected with ISH, Sanger sequencing, NGS, fragment analysis, and PCR such as qPCR; and EGFR RNA expression has been detected using PCR techniques, e.g., qPCR, and DNA microarray. As a further non-limiting example, molecular profiling results for the presence of the EGFR variant III (EGFRvIII) transcript has been collected using fragment analysis (e.g., RFLP) and sequencing (e.g., NGS).

Table 3 shows exemplary molecular profiles for various tumor lineages. Data from these molecular profiles may be used as the input for NGP in order to identify one or more biosignatures of interest. In the table, the cancer lineage is shown in the column "Lineage." The remaining columns show various biomarkers that can be assessed using the indicated methodology (i.e., immunohistochemistry (IHC), in situ hybridization (ISH), or other techniques). As explained above, the biomarkers are identified using symbols known to those of skill in the art. Under the IHC column, "MMR" refers to the mismatch repair proteins MLH1, MSH2, MSH6, and PMS2, which are each individually assessed using IHC. Under the NGS column "DNA," "CNA" refers to copy number alteration, which is also referred to herein as copy number variation (CNV). One of skill will appreciate that molecular profiling technologies may be substituted as desired and/or interchangeable. For example, other suitable protein analysis methods can be used instead of IHC (e.g., alternate immunoassay formats), other suitable nucleic acid analysis methods can be used instead of ISH (e.g., that assess copy number and/or rearrangements, translocations and the like), and other suitable nucleic acid analysis methods can be used instead of fragment analysis. Similarly, FISH and CISH are generally interchangeable and the choice may be made based upon probe availability and the like. Tables 4-8 present panels of genomic analysis and genes that have been assessed using Next Generation Sequencing (NGS) analysis. One of skill will appreciate that other nucleic acid analysis methods can be used instead of NGS analysis, e.g., other sequencing (e.g., Sanger), hybridization (e.g., microarray, Nanostring) and/or amplification (e.g., PCR based) methods.

Nucleic acid analysis may be performed to assess various aspects of a gene. For example, nucleic acid analysis can include, but is not limited to, mutational analysis, fusion analysis, variant analysis, splice variants, SNP analysis and gene copy number/amplification. Such analysis can be performed using any number of techniques described herein or known in the art, including without limitation sequencing (e.g., Sanger, Next Generation, pyrosequencing), PCR, variants of PCR such as RT-PCR, fragment analysis, and the like. NGS techniques may be used to detect mutations, fusions, variants and copy number of multiple genes in a single assay. Unless otherwise stated or obvious in context, a "mutation" as used herein may comprise any change in a gene or genome as compared to wild type, including without limitation a mutation, polymorphism, deletion, insertion, indels (i.e., insertions or deletions), substitution, translocation, fusion, break, duplication, amplification, repeat, or copy number variation. Different analyses may be available for different genomic alterations and/or sets of genes. For example, Table 4 lists attributes of genomic stability that can be measured with NGS, Table 5 lists various genes that may be assessed for point mutations and indels, Table 6 lists various genes that may be assessed for point mutations, indels and copy number variations, Table 7 lists various genes that may be assessed for gene fusions via RNA analysis, and similarly Table 8 lists genes that can be assessed for transcript variants via RNA. Molecular profiling results for additional genes can be used to identify an NGP biosignature as such data is available.

TABLE 2

Molecular Profiling Biomarkers

| Technique | Biomarkers |
|---|---|
| IHC | ABL1, ACPP (PAP), Actin (ACTA), ADA, AFP, AKT1, ALK, ALPP (PLAP-1), APC, AR, ASNS, ATM, BAP1, BCL2, BCRP, BRAF, BRCA1, BRCA2, CA19-9, CALCA, CCND1 (BCL1), CCR7, CD19, CD276, CD3, CD33, CD52, CD80, CD86, CD8A, CDH1 (ECAD), CDW52, CEACAM5 (CEA; CD66e), CES2, CHGA (CGA), CK 14, CK 17, CK 5/6, CK1, CK10, CK14, CK15, CK16, CK19, CK2, CK3, CK4, CK5, CK6, CK7, CK8, COX2, CSF1R, CTL4A, CTLA4, CTNNB1, Cytokeratin, DCK, DES, DNMT1, EGFR, EGFR H-score, ERBB2 (HER2), ERBB4 (HER4), ERCC1, ERCC3, ESR1 (ER), F8 (FACTOR8), FBXW7, FGFR1, FGFR2, FLT3, FOLR2, GART, GNA11, GNAQ, GNAS, Granzyme A, Granzyme B, GSTP1, HDAC1, HIF1A, HNF1A, HPL, HRAS, HSP90AA1 (HSPCA), IDH1, IDO1, IL2, IL2RA (CD25), JAK2, JAK3, KDR (VEGFR2), KI67, KIT (cKIT), KLK3 (PSA), KRAS, KRT20 (CK20), KRT7 (CK7), KRT8 (CYK8), LAG-3, MAGE-A, MAP KINASE PROTEIN (MAPK1/3), MDM2, MET (cMET), MGMT, MLH1, MPL, MRP1, MS4A1 (CD20), MSH2, MSH4, MSH6, MSI, MTAP, MUC1, MUC16, NFKB1, NFKB1A, NFKB2, NGF, NOTCH1, NPM1, NRAS, NY-ESO-1, ODC1 (ODC), OGFR, p16, p95, PARP-1, PBRM1, PD-1, PDGF, PDGFC, PDGFR, PDGFRA, PDGFRA (PDGFR2), PDGFRB (PDGFR1), PD-L1, PD-L2, PGR (PR), PIK3CA, PIP, PMEL, PMS2, POLA1 (POLA), PR, PTEN, PTGS2 (COX2), PTPN11, RAF1, RARA (RAR), RB1, RET, RHOH, ROS1, RRM1, RXR, RXRB, S100B, SETD2, SMAD4, SMARCB1, SMO, SPARC, SST, SSTR1, STK11, SYP, TAG-72, TIM-3, TK1, TLE3, TNF, TOP1 (TOPO1), TOP2A (TOP2), TOP2B (TOPO2B), TP, TP53 (p53), TRKA/B/C, TS, TUBB3, TXNRD1, TYMP (PDECGF), TYMS (TS), VDR, VEGFA (VEGF), VHL, XDH, ZAP70 |
| ISH (CISH/FISH) | 1p19q, ALK, EML4-ALK, EGFR, ERCC1, HER2, HPV (human papilloma virus), MDM2, MET, MYC, PIK3CA, ROS1, TOP2A, chromosome 17, chromosome 12 |
| Pyrosequencing | MGMT promoter methylation |
| Sanger sequencing | BRAF, EGFR, GNA11, GNAQ, HRAS, IDH2, KIT, KRAS, NRAS, PIK3CA |
| NGS | See genes and types of testing in Tables 3-8, MSI, TMB |
| Fragment Analysis | ALK, EML4-ALK, EGFR Variant III, HER2 exon 20, ROS1, MSI |
| PCR | ALK, AREG, BRAF, BRCA1, EGFR, EML4, ERBB3, ERCC1, EREG, hENT-1, HSP90AA1, IGF-1R, KRAS, MMR, p16, p21, p27, PARP-1, PGP (MDR-1), PIK3CA, RRM1, TLE3, TOPO1, TOPO2A, TS, TUBB3 |
| Microarray | ABCC1, ABCG2, ADA, AR, ASNS, BCL2, BIRC5, BRCA1, BRCA2, CD33, CD52, CDA, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1 (HSPCA), IL2RA, HSP90AA1, KDR, KIT, LCK, LYN, MGMT, MLH1, MS4A1, MSH2, NFKB1, NFKB2, OGFR, PDGFC, PDGFRA, PDGFRB, PGR, POLA1, PTEN, PTGS2, RAF1, RARA, RRM1, RRM2, RRM2B, RXRB, RXRG, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, ZAP70 |

TABLE 3

Molecular Profiles

| | | Next-Generation Sequencing (NGS) | | | |
|---|---|---|---|---|---|
| Lineage | IHC | DNA | Genomic Signatures (DNA) | RNA | Other |
| Bladder | MMR, PD-L1 | Mutation, CNA | MSI, TMB | Fusion Analysis | |
| Breast | AR, ER, Her2/Neu, MMR, PD-L1, PR, PTEN, TRKA/B/C | Mutation, CNA | MSI, TMB | | Her2, TOP2A (CISH) |
| Cancer of Unknown Primary | MMR, PD-L1, TRKA/B/C | Mutation, CNA | MSI, TMB | | |
| Cervical | ER, MMR, PD-L1, PR, TRKA/B/C | Mutation, CNA | MSI, TMB | | |
| Cholangiocarcinoma Hepatobiliary | Her2/Neu, MMR, PD-L1 | Mutation, CNA | MSI, TMB | Fusion Analysis | Her2 (CISH) |
| Colorectal and Small Intestinal | MMR, PD-L1, PTEN, TRKA/B/C | Mutation, CNA | MSI, TMB | | |

TABLE 3-continued

Molecular Profiles

| Lineage | IHC | Next-Generation Sequencing (NGS) | | | Other |
|---|---|---|---|---|---|
| | | DNA | Genomic Signatures (DNA) | RNA | |
| Endometrial | ER, MMR, PD-L1, PR, PTEN, TRKA/B/C | Mutation, CNA | MSI, TMB | | |
| Esophageal SCC | Her2/Neu, MMR, PD-L1, TRKA/B/ | Mutation, CNA | MSI, TMB | | |
| Gastric | Her2/Neu, MMR, PD-L1, TRKA/B/C | Mutation, CNA | MSI, TMB | | Her2 (CISH) |
| GIST | MMR, PD-L1, PTEN, TRKA/B/C | Mutation, CNA | MSI, TMB | | |
| Glioma | MMR, PD-L1 | Mutation, CNA | MSI, TMB | Fusion Analysis | MGMT Methylation (Pyrosequencing) |
| Head & Neck | MMR, p16, PD-L1, TRKA/B/C | Mutation, CNA | MSI, TMB | | HPV (CISH), reflex to confirm p16 result |
| Kidney | MMR, PD-L1, TRKA/B/C | Mutation, CNA | MSI, TMB | | |
| Melanoma | MMR, PD-L1, TRKA/B/C | Mutation, CNA | MSI, TMB | | |
| Merkel Cell | MMR, PD-L1, TRKA/B/C | Mutation, CNA | MSI, TMB | | |
| Neuroendocrine/Small Cell Lung | MMR, PD-L1, TRKA/B/C | Mutation, CNA | MSI, TMB | | |
| Non-Small Cell Lung | ALK, MMR, PD-L1, PTEN | Mutation, CNA | MSI, TMB | Fusion Analysis | |
| Ovarian | ER, MMR, PD-L1, PR, TRKA/B/C | Mutation, CNA | MSI, TMB | | |
| Pancreatic | MMR, PD-L1, TRKA/B/C | Mutation, CNA | MSI, TMB | | |
| Prostate | AR, MMR, PD-L1, TRKA/B/C | Mutation, CNA | MSI, TMB | | |
| Salivary Gland | AR, Her2/Neu, MMR, PD-L1 | Mutation, CNA | MSI, TMB | Fusion Analysis | |
| Sarcoma | MMR, PD-L1, TRKA/B/C | Mutation, CNA | MSI, TMB | | |
| Thyroid | MMR, PD-L1 | Mutation, CNA | MSI, TMB | Fusion Analysis | |
| Uterine Serous | ER, Her2/Neu, MMR, PD-L1, PR, PTEN, TRKA/B/C | Mutation, CNA | MSI, TMB | | Her2 (CISH) |
| Other Tumors | MMR, PD-L1, TRKA/B/C | Mutation, CNA | MSI, TMB | | |

TABLE 4

Genomic Stability Testing (DNA)

| Microsatellite Instability (MSI) | Tumor Mutational Burden (TMB) |
|---|---|

TABLE 5

Point Mutations and Indels (DNA)

| | | | | |
|---|---|---|---|---|
| ABI1 | CRLF2 | HOXC11 | MUC1 | RHOH |
| ABL1 | DDB2 | HOXC13 | MUTYH | RNF213 |
| ACKR3 | DDIT3 | HOXD11 | MYCL (MYCL1) | RPL10 |
| AKT1 | DNM2 | HOXD13 | NBN | SEPT5 |
| AMER1 (FAM123B) | DNMT3A | HRAS | NDRG1 | SEPT6 |
| AR | EIF4A2 | IKBKE | NKX2-1 | SFPQ |
| ARAF | ELF4 | INHBA | NONO | SLC45A3 |
| ATP2B3 | ELN | IRS2 | NOTCH1 | SMARCA4 |
| ATRX | ERCC1 | JUN | NRAS | SOCS1 |
| BCL11B | ETV4 | KAT6A (MYST3) | NUMA1 | SOX2 |

TABLE 5-continued

Point Mutations and Indels (DNA)

| | | | | |
|---|---|---|---|---|
| BCL2 | FAM46C | KAT6B | NUTM2B | SPOP |
| BCL2L2 | FANCF | KCNJ5 | OLIG2 | SRC |
| BCOR | FEV | KDM5C | OMD | SSX1 |
| BCORL1 | FOXL2 | KDM6A | P2RY8 | STAG2 |
| BRD3 | FOXO3 | KDSR | PAFAH1B2 | TAL1 |
| BRD4 | FOXO4 | KLF4 | PAK3 | TAL2 |
| BTG1 | FSTL3 | KLK2 | PATZ1 | TBL1XR1 |
| BTK | GATA1 | LASP1 | PAX8 | TCEA1 |
| C15orf65 | GATA2 | LMO1 | PDE4DIP | TCL1A |
| CBLC | GNA11 | LMO2 | PHF6 | TERT |
| CD79B | GPC3 | MAFB | PHOX2B | TFE3 |
| CDH1 | HEY1 | MAX | PIK3CG | TFPT |
| CDK12 | HIST1H3B | MECOM | PLAG1 | THRAP3 |
| CDKN2B | HIST1H4I | MED12 | PMS1 | TLX3 |
| CDKN2C | HLF | MKL1 | POU5F1 | TMPRSS2 |
| CEBPA | HMGN2P46 | MLLT11 | PPP2R1A | UBR5 |
| CHCHD7 | HNF1A | MN1 | PRF1 | VHL |
| CNOT3 | HOXA11 | MPL | PRKDC | WAS |
| COL1A1 | HOXA13 | MSN | RAD21 | ZBTB16 |
| COX6C | HOXA9 | MTCP1 | RECQL4 | ZRSR2 |

TABLE 6

Point Mutations, Indels and Copy Number Variations (DNA)

| | | | | |
|---|---|---|---|---|
| ABL2 | CREB1 | FUS | MYC | RUNX1 |
| ACSL3 | CREB3L1 | GAS7 | MYCN | RUNX1T1 |
| ACSL6 | CREB3L2 | GATA3 | MYD88 | SBDS |
| ADGRA2 | CREBBP | GID4 (C17orf39) | MYH11 | SDC4 |
| AFDN | CRKL | GMPS | MYH9 | SDHAF2 |
| AFF1 | CRTC1 | GNA13 | NACA | SDHB |
| AFF3 | CRTC3 | GNAQ | NCKIPSD | SDHC |
| AFF4 | CSF1R | GNAS | NCOA1 | SDHD |
| AKAP9 | CSF3R | GOLGA5 | NCOA2 | SEPT9 |
| AKT2 | CTCF | GOPC | NCOA4 | SET |
| AKT3 | CTLA4 | GPHN | NF1 | SETBP1 |
| ALDH2 | CTNNA1 | GRIN2A | NF2 | SETD2 |
| ALK | CTNNB1 | GSK3B | NFE2L2 | SF3B1 |
| APC | CYLD | H3F3A | NFIB | SH2B3 |
| ARFRP1 | CYP2D6 | H3F3B | NFKB2 | SH3GL1 |
| ARHGAP26 | DAXX | HERPUD1 | NFKBIA | SLC34A2 |
| ARHGEF12 | DDR2 | HGF | NIN | SMAD2 |
| ARID1A | DDX10 | HIP1 | NOTCH2 | SMAD4 |
| ARID2 | DDX5 | HMGA1 | NPM1 | SMARCB1 |
| ARNT | DDX6 | HMGA2 | NSD1 | SMARCE1 |
| ASPSCR1 | DEK | HNRNPA2B1 | NSD2 | SMO |
| ASXL1 | DICER1 | HOOK3 | NSD3 | SNX29 |
| ATF1 | DOT1L | H5P90AA1 | NT5C2 | SOX10 |
| ATIC | EBF1 | H5P90AB1 | NTRK1 | SPECC1 |
| ATM | ECT2L | IDH1 | NTRK2 | SPEN |
| ATP1A1 | EGFR | IDH2 | NTRK3 | SRGAP3 |
| ATR | ELK4 | IGF1R | NUP214 | SRSF2 |
| AURKA | ELL | IKZF1 | NUP93 | SRSF3 |
| AURKB | EML4 | IL2 | NUP98 | SS18 |
| AXIN1 | EMSY | IL21R | NUTM1 | SS18L1 |
| AXL | EP300 | IL6ST | PALB2 | STAT3 |
| BAP1 | EPHA3 | IL7R | PAX3 | STAT4 |
| BARD1 | EPHA5 | IRF4 | PAX5 | STAT5B |
| BCL10 | EPHB1 | ITK | PAX7 | STIL |
| BCL11A | EPS15 | JAK1 | PBRM1 | STK11 |
| BCL2L11 | ERBB2 (HER2/NEU) | JAK2 | PBX1 | SUFU |
| BCL3 | ERBB3 (HER3) | JAK3 | PCM1 | SUZ12 |
| BCL6 | ERBB4 (HER4) | JAZF1 | PCSK7 | SYK |
| BCL7A | ERC1 | KDM5A | PDCD1 (PD1) | TAF15 |
| BCL9 | ERCC2 | KDR (VEGFR2) | PDCD1LG2 (PDL2) | TCF12 |
| BCR | ERCC3 | KEAP1 | PDGFB | TCF3 |
| BIRC3 | ERCC4 | KIAA1549 | PDGFRA | TCF7L2 |
| BLM | ERCC5 | KIF5B | PDGFRB | TET1 |
| BMPR1A | ERG | KIT | PDK1 | TET2 |
| BRAF | ESR1 | KLHL6 | PER1 | TFEB |
| BRCA1 | ETV1 | KMT2A (MLL) | PICALM | TFG |
| BRCA2 | ETV5 | KMT2C (MLL3) | PIK3CA | TFRC |
| BRIP1 | ETV6 | KMT2D (MLL2) | PIK3R1 | TGFBR2 |
| BUB1B | EWSR1 | KNL1 | PIK3R2 | TLX1 |
| CACNA1D | EXT1 | KRAS | PIM1 | TNFAIP3 |
| CALR | EXT2 | KTN1 | PML | TNFRSF14 |
| CAMTA1 | EZH2 | LCK | PMS2 | TNFRSF17 |
| CANT1 | EZR | LCP1 | POLE | TOP1 |
| CARD11 | FANCA | LGR5 | POT1 | TP53 |
| CARS | FANCC | LHFPL6 | P0U2AF1 | TPM3 |
| CASP8 | FANCD2 | LIFR | PPARG | TPM4 |
| CBFA2T3 | FANCE | LPP | PRCC | TPR |
| CBFB | FANCG | LRIG3 | PRDM1 | TRAF7 |
| CBL | FANCL | LRP1B | PRDM16 | TRIM26 |
| CBLB | FAS | LYL1 | PRKAR1A | TRIM27 |
| CCDC6 | FBXO11 | MAF | PRRX1 | TRIM33 |
| CCNB1IP1 | FBXW7 | MALT1 | PSIP1 | TRIP11 |
| CCND1 | FCRL4 | MAML2 | PTCH1 | TRRAP |
| CCND2 | FGF10 | MAP2K1 (MEK1) | PTEN | TSC1 |
| CCND3 | FGF14 | MAP2K2 (MEK2) | PTPN11 | TSC2 |
| CCNE1 | FGF19 | MAP2K4 | PTPRC | TSHR |
| CD274 (PDL1) | FGF23 | MAP3K1 | RABEP1 | TTL |
| CD74 | FGF3 | MCL1 | RAC1 | U2AF1 |
| CD79A | FGF4 | MDM2 | RAD50 | USP6 |
| CDC73 | FGF6 | MDM4 | RAD51 | VEGFA |
| CDH11 | FGFR1 | MDS2 | RAD51B | VEGFB |
| CDK4 | FGFR1OP | MEF2B | RAF1 | VTI1A |
| CDK6 | FGFR2 | MEN1 | RALGDS | WDCP |
| CDK8 | FGFR3 | MET | RANBP17 | WIF1 |
| CDKN1B | FGFR4 | MITF | RAP1GDS1 | WISP3 |
| CDKN2A | FH | MLF1 | RARA | WRN |
| CDX2 | FHIT | MLH1 | RB1 | WT1 |
| CHEK1 | FIP1L1 | MLLT1 | RBM15 | WWTR1 |
| CHEK2 | FLCN | MLLT10 | REL | XPA |
| CHIC2 | FLI1 | MLLT3 | RET | XPC |
| CHN1 | FLT1 | MLLT6 | RICTOR | XPO1 |
| CIC | FLT3 | MNX1 | RMI2 | YWHAE |
| CITTA | FLT4 | MRE11 | RNF43 | ZMYM2 |
| CLP1 | FNBP1 | MSH2 | ROS1 | ZNF217 |
| CLTC | FOXA1 | MSH6 | RPL22 | ZNF331 |
| CLTCL1 | FOXO1 | MSI2 | RPL5 | ZNF384 |
| CNBP | FOXP1 | MTOR | RPN1 | ZNF521 |
| CNTRL | FUBP1 | MYB | RPTOR | ZNF703 |
| COPB1 | | | | |

TABLE 7

Gene Fusions (RNA)

| | | | | |
|---|---|---|---|---|
| AKT3 | ETV4 | MAST2 | NUMBL | RET |
| ALK | ETV5 | MET | NUTM1 | ROS1 |
| ARHGAP26 | ETV6 | MSMB | PDGFRA | RSPO2 |
| AXL | EWSR1 | MUSK | PDGFRB | RSPO3 |
| BRAF | FGFR1 | MYB | PIK3CA | TERT |
| BRD3 | FGFR2 | NOTCH1 | PKN1 | TFE3 |
| BRD4 | FGFR3 | NOTCH2 | PPARG | TFEB |
| EGFR | FGR | NRG1 | PRKCA | THADA |
| ERG | INSR | NTRK1 | PRKCB | TMPRSS2 |
| ESR1 | MAML2 | NTRK2 | RAF1 | |
| ETV1 | MAST1 | NTRK3 | RELA | |

TABLE 8

Variant Transcripts

| EGFR vIII | MET Exon 14 Skipping |
|---|---|

Abbreviations used in this Example and throughout the specification, e.g., IHC: immunohistochemistry; ISH: in situ hybridization; CISH: colorimetric in situ hybridization; FISH: fluorescent in situ hybridization; NGS: next generation sequencing; PCR: polymerase chain reaction; CNA: copy number alteration; CNV: copy number variation; MSI: microsatellite instability; TMB: tumor mutational burden.

Example 2: Molecular Profiling Analysis for Prediction of Treatment Efficacy in Colorectal Cancer In this Example, state of the art machine learning algorithms as described here (e.g., FIGS. 1A1G) were applied to comprehensive molecular profiling data (see, e.g., Example 1 above; Tables 5-12 of WO/2018/175501 (based on International Application No. PCT/US2018/023438 filed 20 Mar. 2018), as well as WO/2015/116868 (based on International Application No. PCT/US2015/013618, filed 29 Jan. 2015), WO/2017/053915 (based on International Application No. PCT/US2016/053614, filed 24 Sep. 2016), and WO/2016/141169 (based on International Application No. PCT/

US2016/020657, filed 3 Mar. 2016)) to identify biomarker signatures that differentiate patients that did and did not have a positive benefit from FOLFOX when Time-to-Next-Treatment (TNT or TTNT) is used as the outcome endpoint. The patient population included patients with stage III or stage IV colorectal cancer. The biomarkers assessed were as in Example 1.

We identified 8 biomarker (FIGS. 3A-B) and 6 biomarker (FIGS. 3C-D) signatures that accurately predict benefit or lack of benefit from FOLFOX treatment patients with Colorectal Cancer (CRC). The numbers of benefiters or non-benefiters are identified in FIGS. 3A-D. These signatures can be used to predict benefit from FOLFOX in CRC patients.

Biomarker Signature Identification

The numeric, continuous values of the selected biomarkers produced by our molecular profiling pipeline are used as feature inputs into an ensemble classifier consisting of Random Forests, Support Vector Machines, Logistic Regression, K-Nearest Neighbors, Artificial Neural Network, Naïve Bayes, Quadratic Discriminant Analysis, and Gaussian Processes models. Training data consisting of the biomarker values for each patient is assembled and labeled as either Benefiter or Non-Benefiter according to the patient's TNT. Each model in the ensemble takes as input this training data during the training process, producing a final trained model capable of making predictions of previously unseen test cases. Novel test cases not in the training data are then fed through each of the trained models in the ensemble, with each model outputting a prediction of benefit or lack of benefit for each patient in the test set.

To clarify how these biomarker results are used in the machine learning algorithms, we briefly describe the Random Forest algorithm. A Random Forest consists of multiple Decision Trees, with each decision tree producing a single Benefit/Non-Benefit prediction for each sample. Decision Trees consists of nodes and edges similar to a flowchart. At each node in the Decision Tree, the path of a particular test case takes through the Decision Tree is determined by comparing feature values of that test case with threshold values at each node, determined during the training process. If a patient's numeric biomarker value is above a given threshold, then flow continues to the first of the child nodes, otherwise flow continues to the second of the child nodes. The nodes in the bottom layer of the Decision Tree consists of the class labels, with each patient being classified according to which node in the bottom layer that patient was placed.

Random Forests obtain their final prediction by taking the majority vote of each of the Decision Trees contained within the Random Forest. The structure of each Decision Tree allows for the discovery of high non-linear and interaction effects between biomarker values that result in more accurate predictions than are possible using a univariate approach. While algorithmically and mathematically different from Random Forests, the remaining models in the ensemble all take as input the biomarker values and return as output the benefit prediction for each patient.

Descriptive statistics for each model include Hazard Ratio (HR), a measure of difference in risk between two populations. The farther the HR is from 1.0, the greater the risk one population experiences, relative to the other. Results are presented using the well-known Kaplan-Meier estimator plots. See Kaplan, E. L.; Meier, P. (1958). "Nonparametric estimation from incomplete observations." J. Amer. Statist. Assoc. 53 (282): 457-481.

Results

Figure 3A:
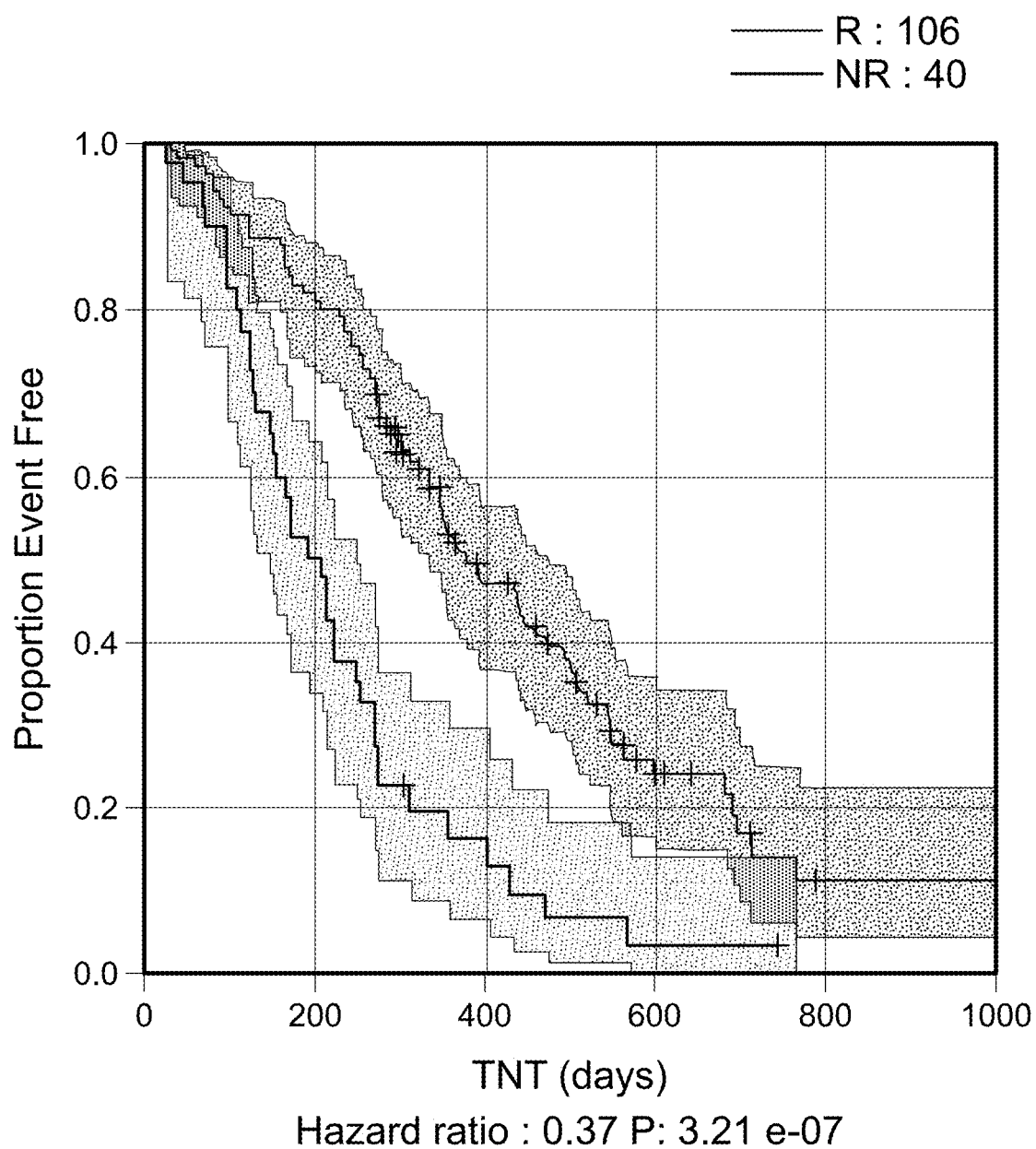
FIGS. 3A-B are a pair of Hazard Ratio Graphs showing model performance using CNV profiling of 8 markers for treatment with FOLFOX (3A) or FOLFIRI (3B). CNA=copy number alteration. The 8 markers were MYC, EP300, U2AF1, ASXL1, MAML2, CNTRL, WRN, and CDX2.
Figure 3B:
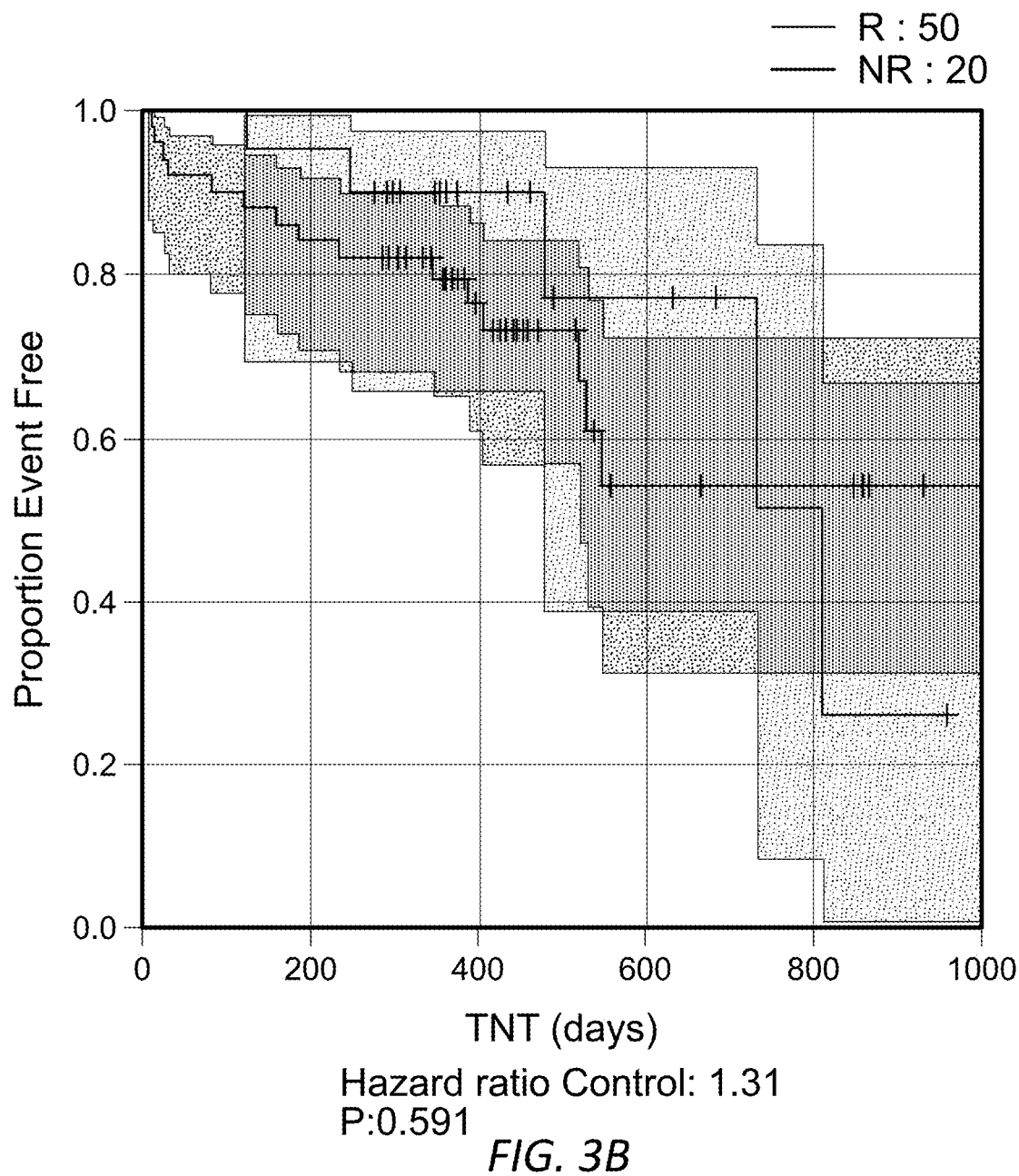
Figure 3C:
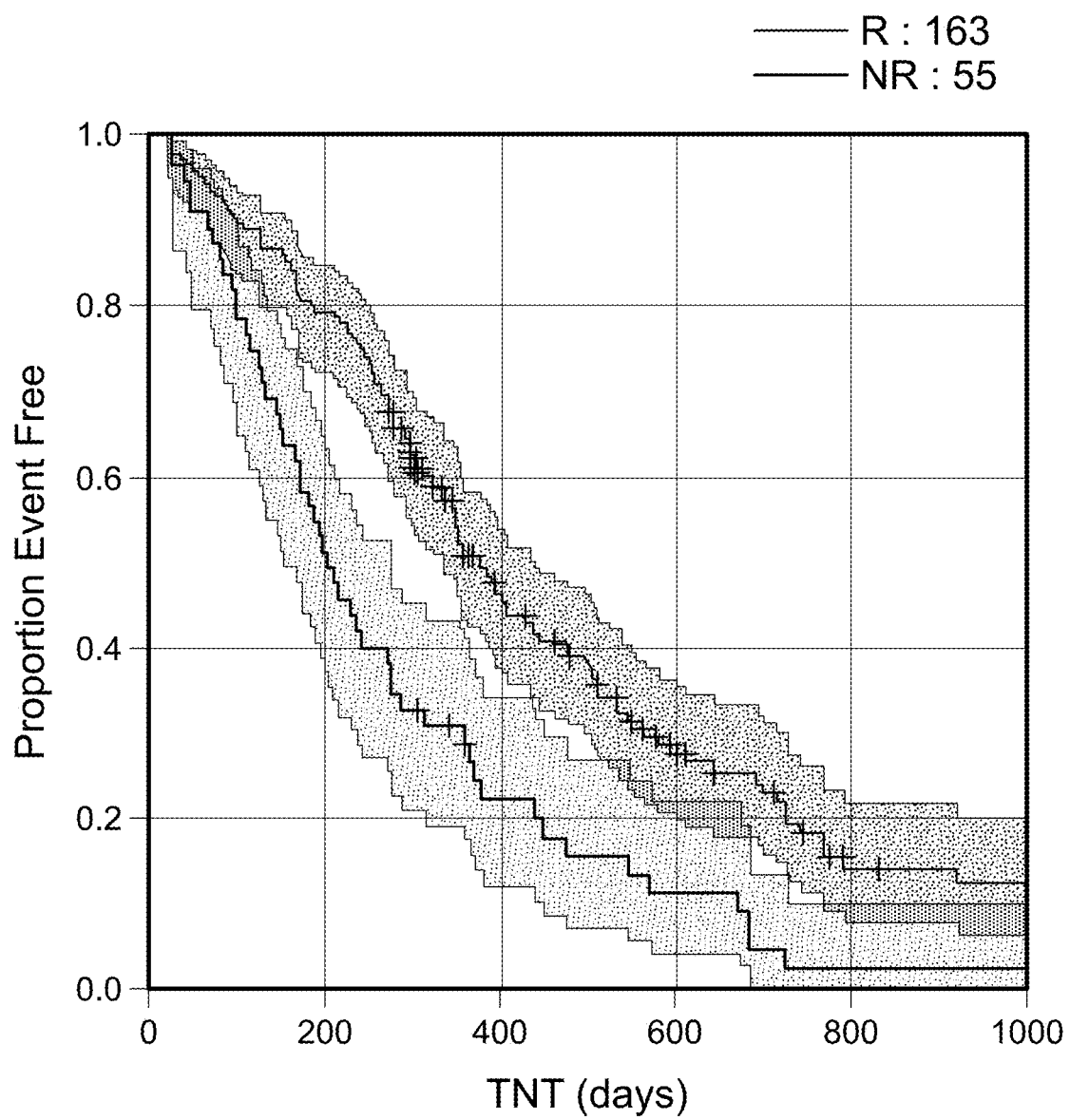
FIGS. 3C-D are a pair of Hazard Ratio Graphs showing model performance using CNV profiling of 6 markers for treatment with FOLFOX (3C) or FOLFIRI (3D). The 6 markers were MYC, EP300, U2AF1, ASXL1, MAML2, and CNTRL.
Figure 3D:
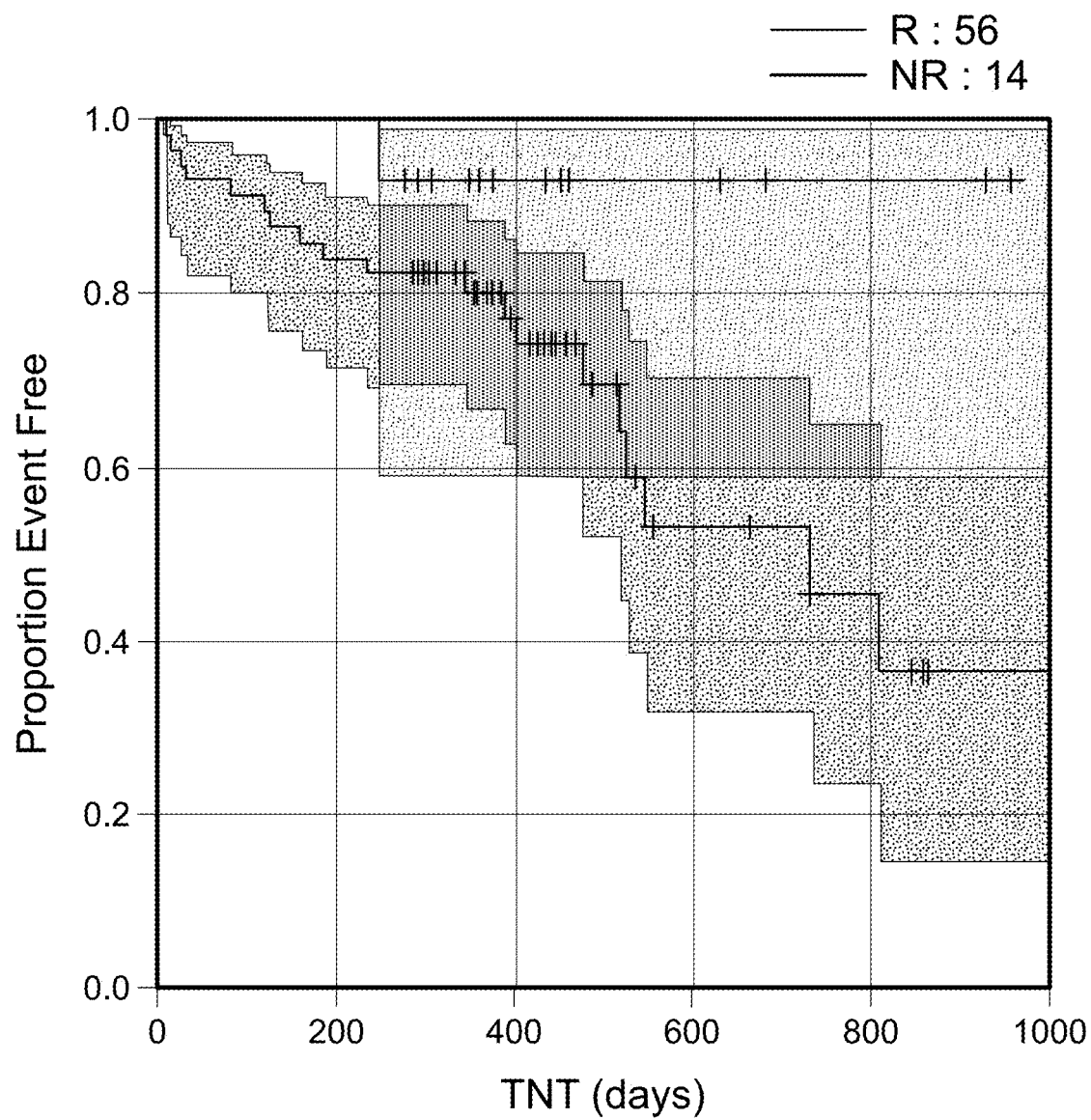
Figure 3E:
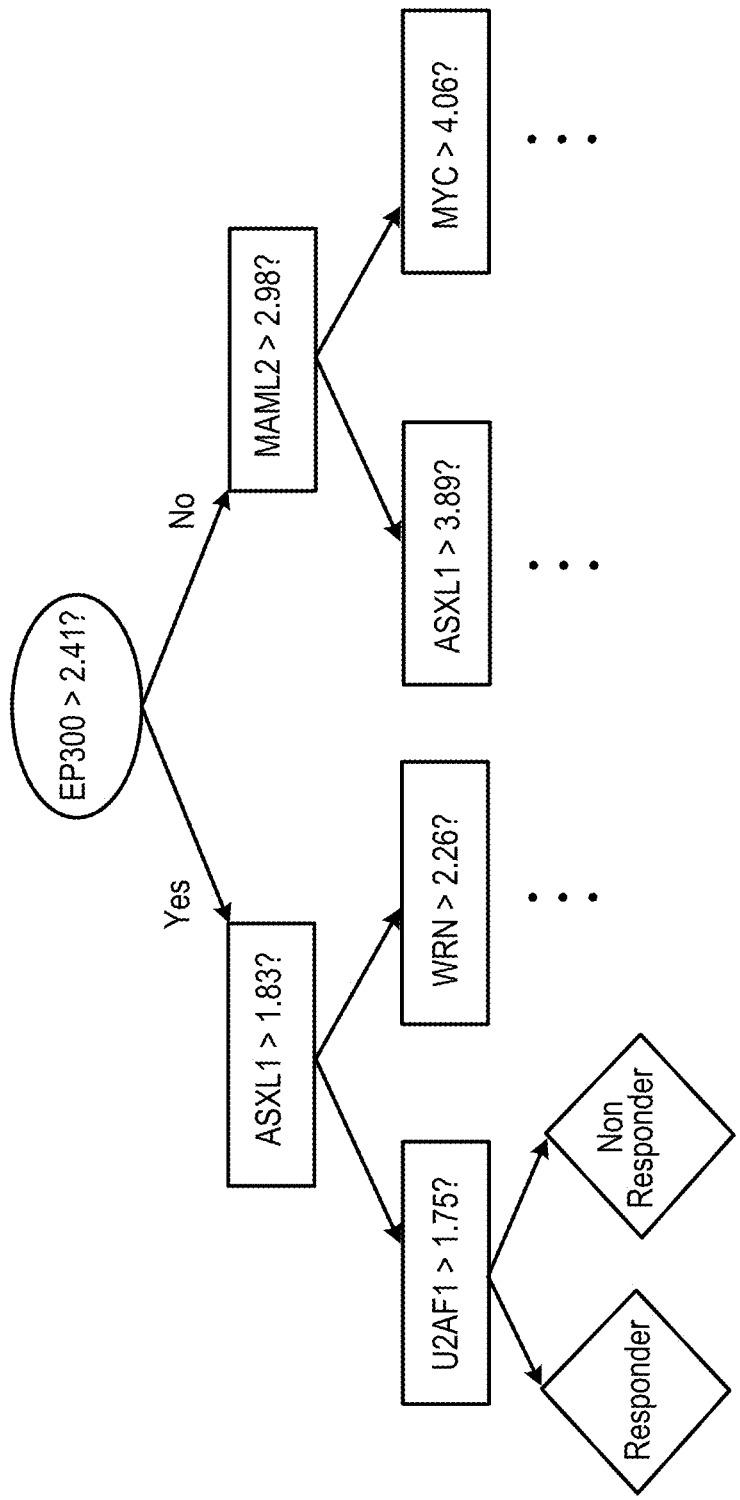
FIG. 3E shows an exemplary random forest decision tree for the 8 marker signature shown in FIGS. 3A-B.

FIG. 3E shows an illustrative random forest decision tree for the 8 marker signature (FIGS. 3A-B). The signature comprises the genes EP300, ASXL1, U2AF1, WRN, ASXL1, MAML2, MYC and CDX2. Gene identifiers are those commonly accepted in the scientific community at the time of filing and can be used to look up the genes at various well-known databases such as the HUGO Gene Nomenclature Committee (HNGC; genenames.org), NCBI's Gene database (www.ncbi.nlm.nih.gov/gene), GeneCards (genecards.org), Ensembl (ensembl.org), UniProt (uniprot.org), and others. The numbers in each box correspond to the normalized copy numbers detected using NGS. The normalized copy number variations of the members of the 8 gene biosignature are applied to the decision tree. In the figure, the vertical " . . . " beneath WRN, ASXL1 and MYC indicate that the benefit/non-benefit prediction is made in the same manner as that shown under the box corresponding to U2AF1. The tree's logic is assessed for a patient presenting with a colorectal cancer. The benefiters are predicted to benefit from FOLFOX and thus the test suggests that these patients should be administered a FOLFOX regimen. On the other hand, patients who are predicted to lack benefit from FOLFOX may be administered a different therapeutic regimen, e.g., comprising FOLFIRI.

Example 3: Molecular Profiling Analysis for Prediction of Treatment Benefit in Metastatic Colorectal Cancer In Example 2, we presented an approach to identify a biosignature for predicting benefit from the colorectal cancer treatment regimen FOLFOX. We followed the same approach in this sample to identify a biosignature for FOLFOX using a highly curated set of stage IV metastatic colorectal cancers.

FIG. 4A shows a current approach to biomarker assessment in metastatic colorectal cancer. For first line treatment, an oncologist may select a regimen consisting of FOLFOX (folinic acid (leucovorin); 5-fluorouracil (5FU) and oxaliplatin) or FOLFIRI (folinic acid (leucovorin); 5-fluorouracil (5FU) and irinotecan). 5FU is a nucleotide analog that stops DNA synthesis and folinic acid increases the efficacy of 5FU. Oxaliplatin is also believed to block DNA synthesis, whereas irinotecan is a topoisomerase inhibitor. Treatment may also rely on use of a small biomarker panel ("SP") consisting of KRAS, NRAS, BRAF and microsatellite instability (MSI). Wild type KRAS may suggest treatment with bevacizumab, an anti-VEGFA monoclonal antibody which inhibits angiogenesis and which may be given in combination with FOLFOX or FOLFIRI, and an anti-EGFR treatment such as cetuximab. Mutations in BRAF may suggest chemotherapy and a MEK inhibitor (MEKi) and EGFR inhibitor (EGFRi). Second line treatment may be similar to first line, except that the oncologist would try an alternate regimen. In addition, the presence of MSI may indicate utility of immunotherapy such as anti-PD-L1. Once these approaches have failed, third line treatment might call for regorafenib, a multi-kinase inhibitor that blocks angiogenesis, or the combination therapy trifluridine/tipiracil (trade name Lonsurf), which consists of trifluridine, a nucleoside analog, and tipiracil, a thymidine phosphorylase inhibitor. Once these options have failed, the patient typically enters into experimental treatments if available.

Figure 4B:
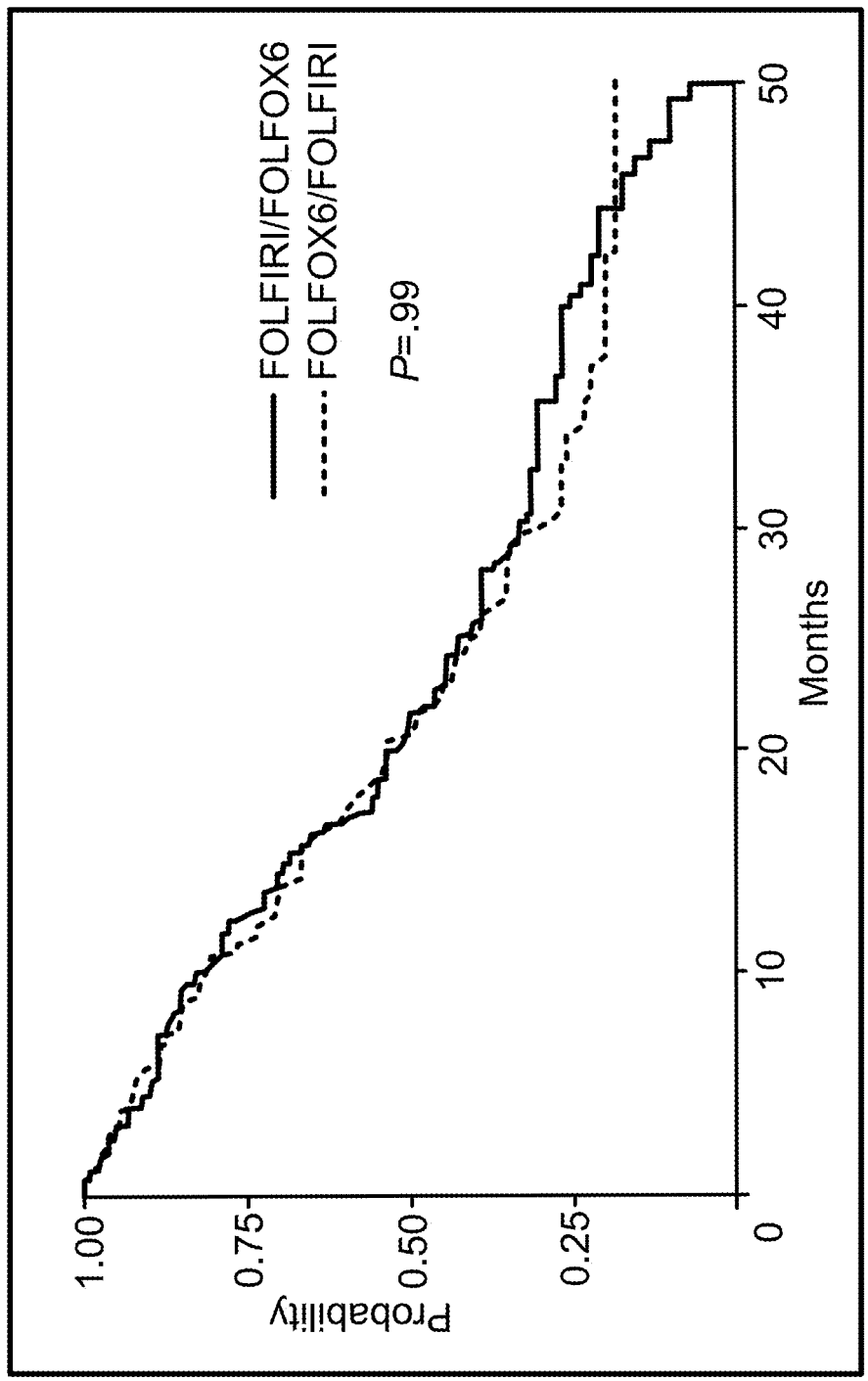
FIGS. 4A-O show development of a biosignature to predict benefit of the FOLFOX regimen in metastatic colorectal cancer patients.
Figure 4C:
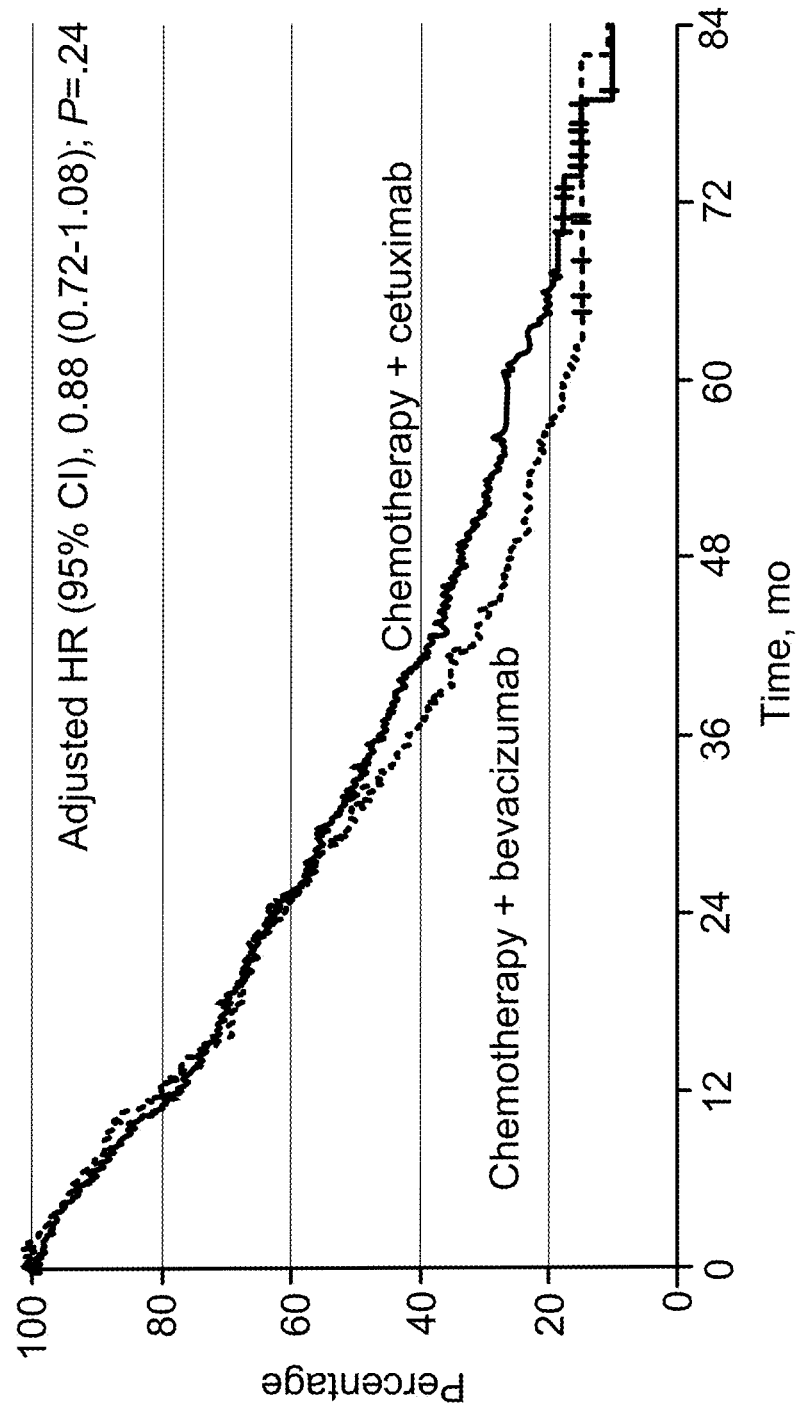

It is currently not clear which is the best approach to first line therapy. Some patients respond better to FOLFOX whereas others respond better to FOLFIRI. FIG. 4B shows survival over time in metastatic CRC patients given FOLFOX as first line therapy and FOLFIRI as second line therapy, or vice versa. See Tournigand, C. et al., FOLFIRI followed by FOLFOX6 or the reverse sequence in advanced colorectal cancer: a randomized GERCOR study. J Clin Oncol. 2004 Jan. 15; 22(2):229-37. Epub 2003 Dec. 2. No difference in efficacy was observed between groups. Similar outcomes are observed for alternate treatments in KRAS wild type CRC. FIG. 4C shows survival over time for advanced or metastatic colorectal cancer patients given first line chemotherapy plus bevacizumab or cetuximab. See Venook A P et al., Effect of First-Line Chemotherapy Combined With Cetuximab or Bevacizumab on Overall Survival in Patients With KRAS Wild-Type Advanced or Metastatic Colorectal Cancer: A Randomized Clinical Trial. JAMA. 2017 Jun. 20; 317(23):2392-2401. As seen from FIGS. 4B-C, although individual patients will respond better to certain treatments than others, there are no clear trends when looking at the overall population. Thus, there is currently little guidance for selecting first line treatment for metastatic colorectal cancer patients even though such guidance would clearly benefit individual patients.

Figure 4D:
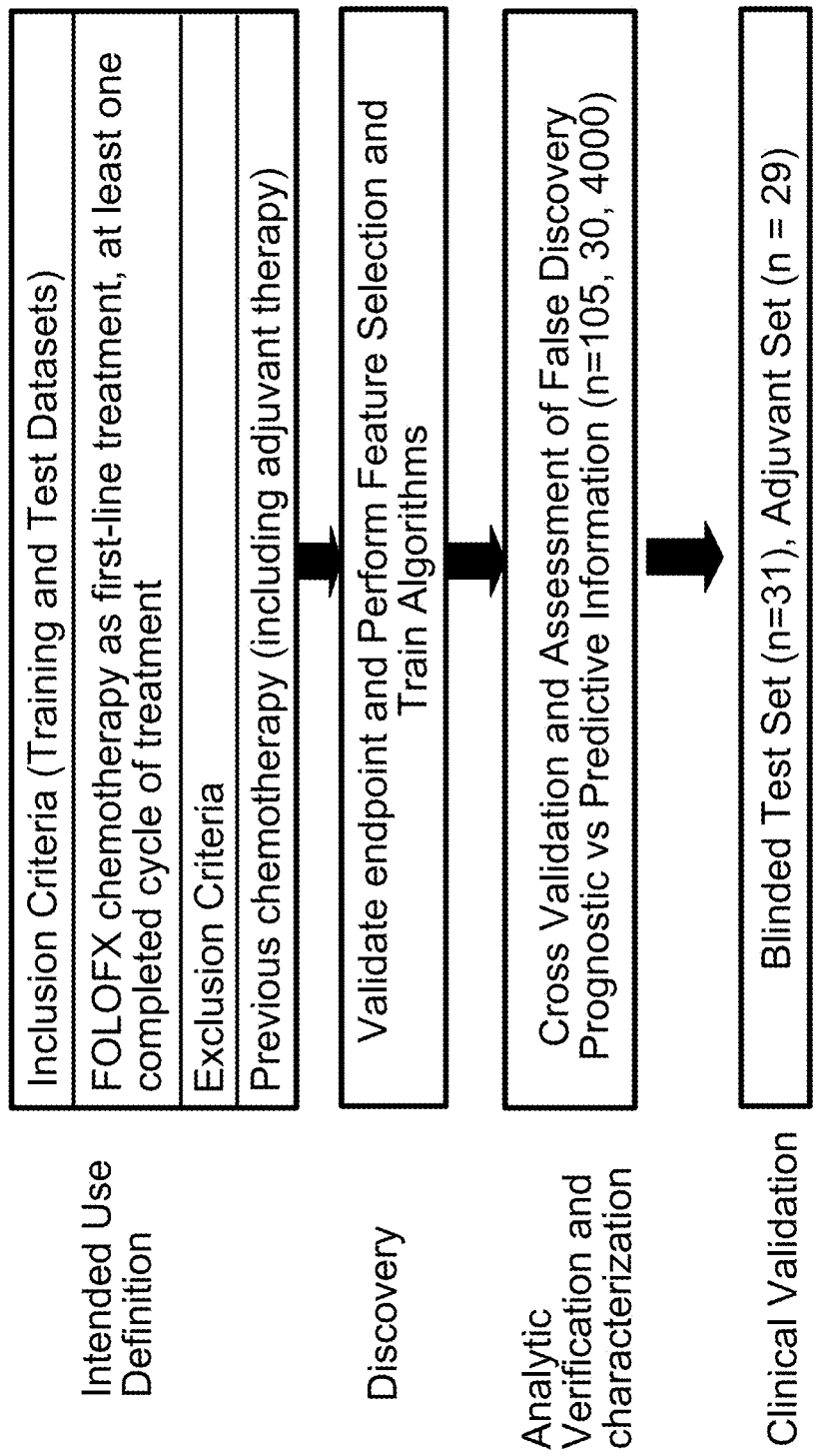

In this Example, we have employed a machine learning approach to molecular profiling data according to the methods disclosed herein to discover clinically relevant biosignatures for predicting benefit or lack of benefit from FOLFOX as first line therapy for metastatic colorectal cancer. FIG. 4D provides an outline of the application of the approach in Example 2 to this objective. First we identified a patient cohort for training and testing based on the intended use. The inclusion criteria were that patients received FOLFOX as first-line treatment, and had at least one full cycle of treatment. Patients were excluded if they had prior chemotherapy, including adjuvant therapy. Characteristics of patients chosen for the training phase are shown in FIG. 4E. For biosignature discovery, we first validated the endpoint to determine patient status as benefit or lack of benefit. A TTNT of 270 days was chosen based on the progression free survival (PFS) noted by Tournigand 2004 of ~8.5 months. Using a training set of patients, the process of biomarker (feature) selection was performed using various cognitive computing algorithms as described above. Using the selected biomarker features, algorithms were trained to identify a patient as a FOLFOX benefiter or non-benefiter. See FIG. 6 and accompanying text for an example of how the biosignature is used to make such determinations. We then performed analytic verification and characterization of the biosignature. For example, we used cross validation to assess performance. We also verified whether the biosignature was merely prognostic. Finally, clinical validation was performed on a blinded test set.

This approach discovered a biosignature comprising 14 biomarker features. The features are copy numbers of BCL9, PBX1, PRRX1, INHBA, YWHAE, GNAS, LHFPL6, FCRL4, HOXA11, AURKA, BIRC3, IKZF1, CASP8, and EP300. These gene identifiers are those commonly accepted in the scientific community at the time of filing and can be used to look up the genes at various well-known databases such as the HUGO Gene Nomenclature Committee (HNGC; genenames.org), NCBI's Gene database (www.ncbi.nlm.nih.gov/gene), GeneCards (genecards.org), Ensembl (ensembl.org), UniProt (uniprot.org), and others.

Figure 4F:
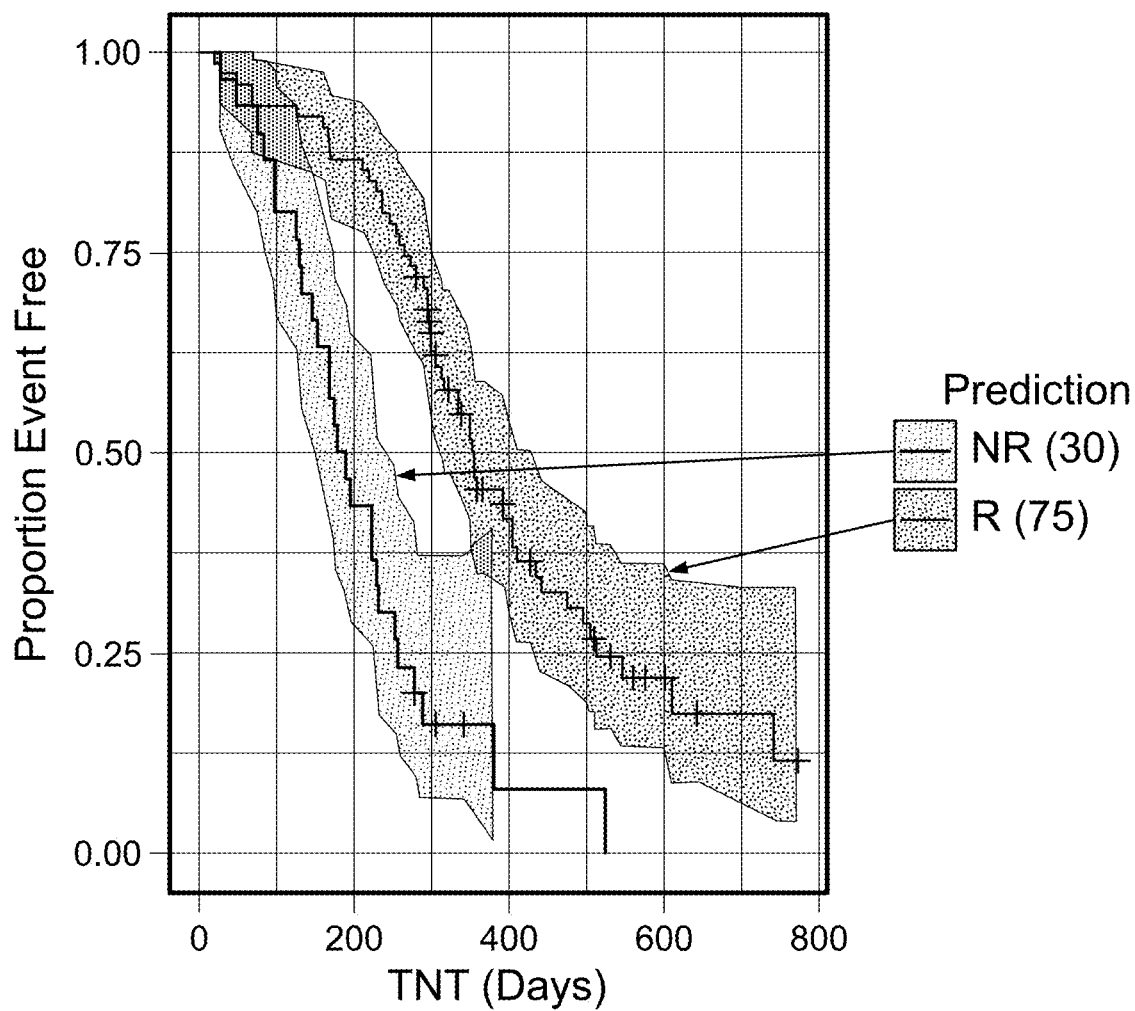
Figure 4G:
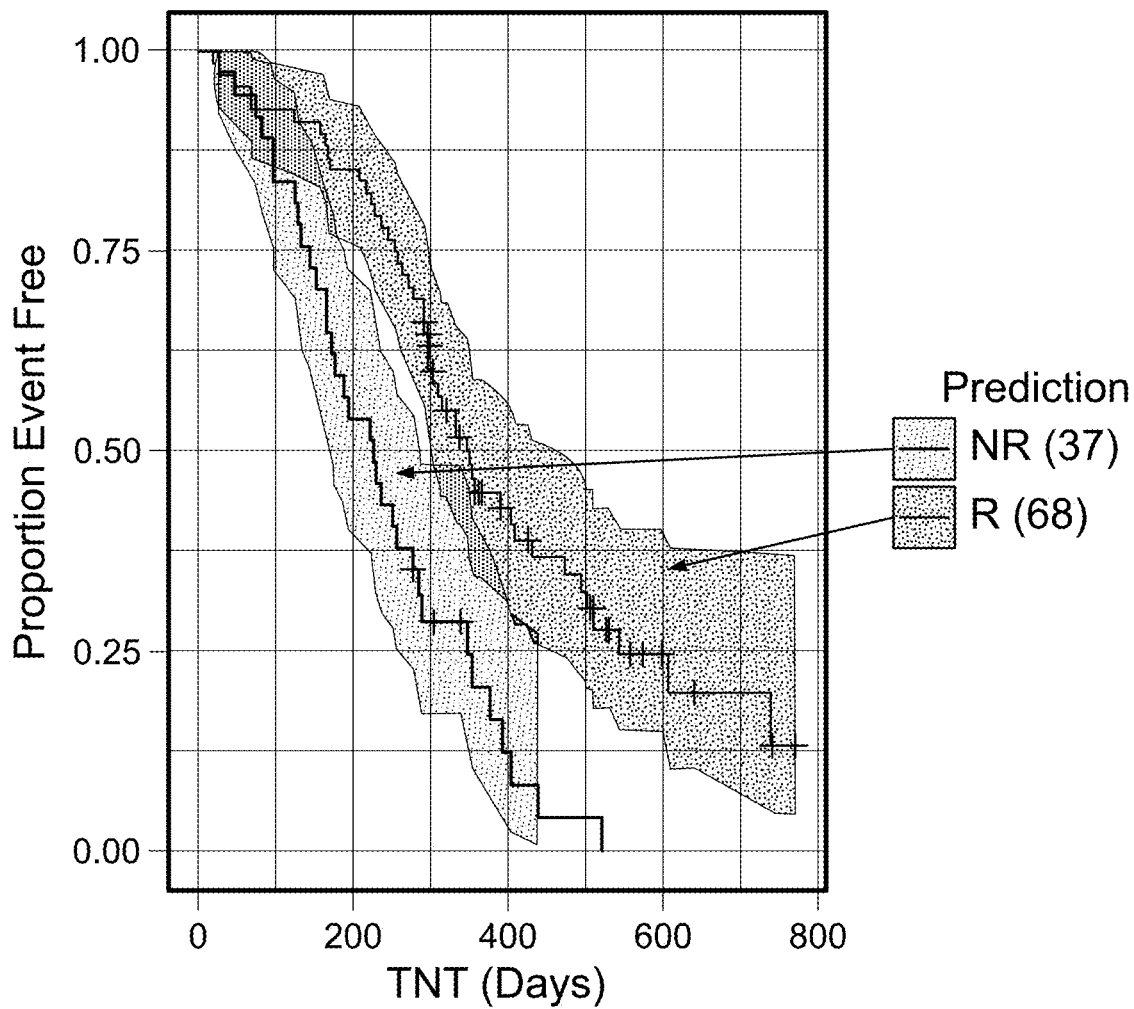

FIGS. 4F-G show results obtained using 5-fold cross validation. The top performing cross validation is shown in FIG. 4F. As shown in the figure, the hazard ratio (HR) was 0.315 and the 95% confidence interval in the HR was 0.167-0.595. The log rank p-value was highly significant at <0.0001. Similarly, the median model is shown in FIG. 4G. The observed HR of 0.407 indicates that this model predicts a subset of the population that experiences a 146% increase in risk of lack of benefit to FOLFOX relative to the remaining population. The 146% calculation was performed according to the formula $100 \times (1 - 1/HR)$ % (see Andreas Sashegy and David Ferry, On the Interpretation of the Hazard Ratio and Communication of Survival Benefit, Oncologist. 2017 April; 22(4): 484-486) but with the reciprocal of HR to give increase of risk instead of decrease in risk to conform to the goal of identifying non-responders over responders.

Figure 4H:
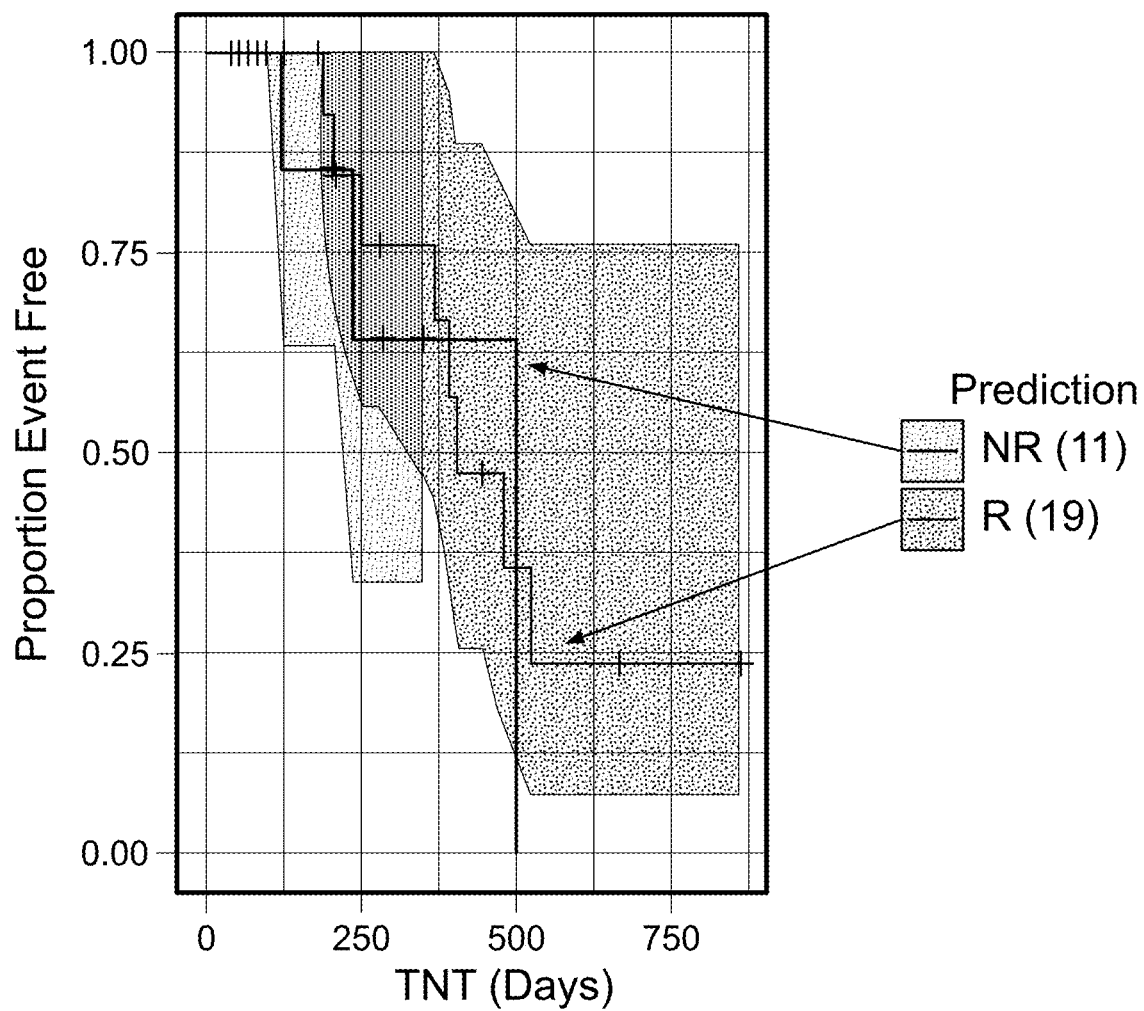
Figure 41:
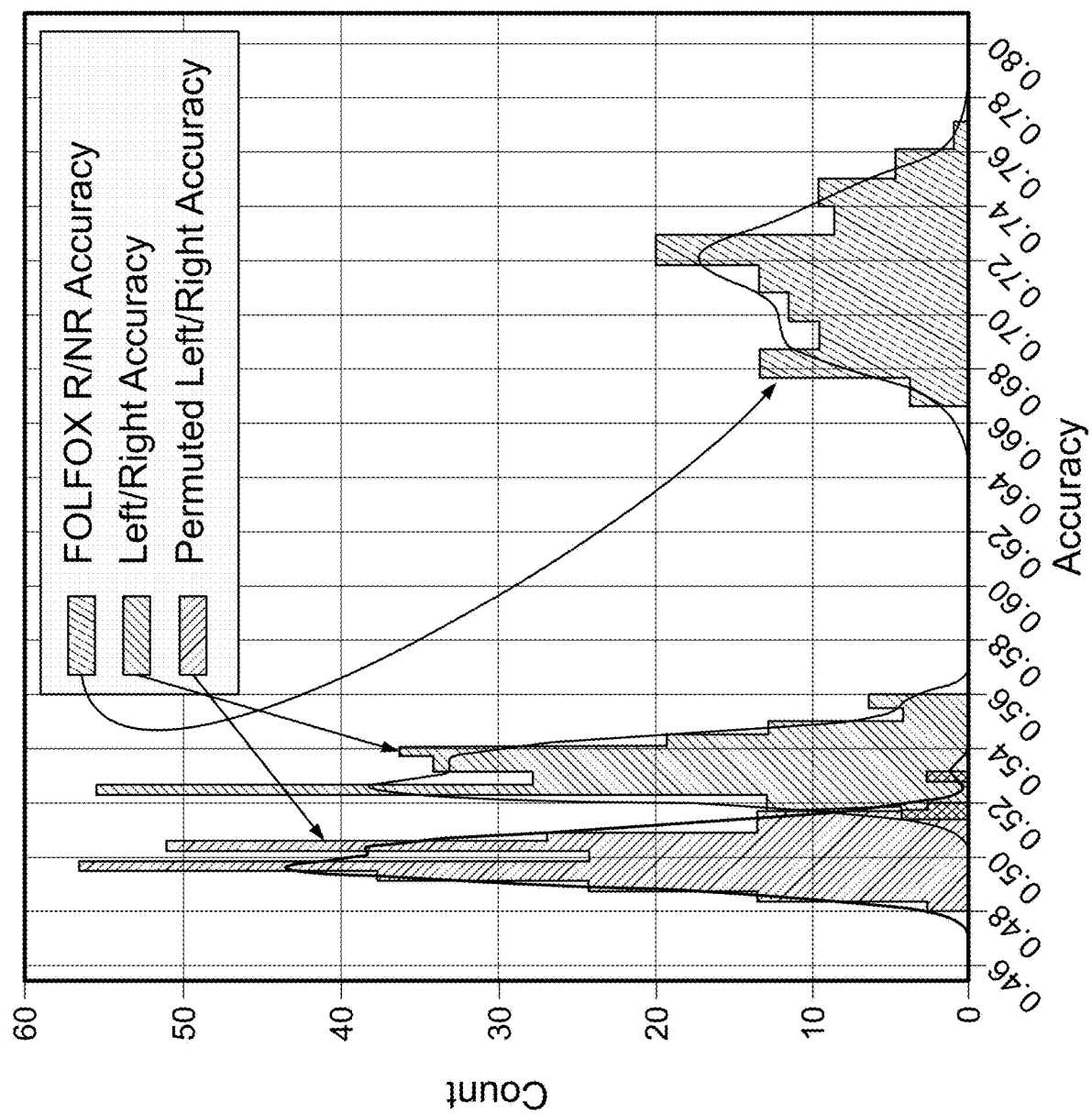

We next asked whether the biosignature was prognostic rather than predictive for benefit from FOLFOX. In other words, we wanted to know whether the biosignature merely identifies patients with better outcomes regardless of treatment. Thus, the biosignature was applied to a patient cohort who had been treated with FOLFIRI as first line treatment. Results are shown in FIG. 4H. As seen in the figure, the 95% confidence interval overlapped an HR of 1.0 and the p-value for the separation was statistically insignificant at 0.379. Because the biosignature was not able to predict benefit from FOLFIRI, these results demonstrate that the biosignature is indeed predictive for benefit from FOLFOX.

Similarly, we explored whether left/right tumor origin was a confounder in the biosignature discovery. CRC may arise on the left or right side of the colon and this origin may affect both prognosis and treatment. For example, right-sided CRC patients have worse outcomes than those with left-sided CRC. In patients with metastatic colorectal cancer, the sidedness of the primary tumor within the colon appears to affect not only survival but also the effectiveness of the commonly used biological treatments such as bevacizumab and cetuximab. See Venook A P et al., Effect of First-Line Chemotherapy Combined With Cetuximab or Bevacizumab on Overall Survival in Patients With KRAS Wild-Type Advanced or Metastatic Colorectal Cancer: A Randomized Clinical Trial. JAMA. 2017 Jun. 20; 317(23):2392-2401; see also FIG. 4A. FIG. 4I shows a histogram of accuracies calculated by 5-fold cross validation trained on detecting FOLFOX benefit/lack of benefit, and evaluated on FOLFOX benefit/lack of benefit, left/right sided CRC, and permuted left/right sidedness as a control. As observed, there was only a small increase in left/right accuracy compared to the accuracy of randomly permuted left/right side control. This stands in contrast to the high accuracies observed for predicting FOLFOX benefit. These data indicate that the biosignature is not confounded by right/left sidedness of the primary tumor.

Figure 4J:
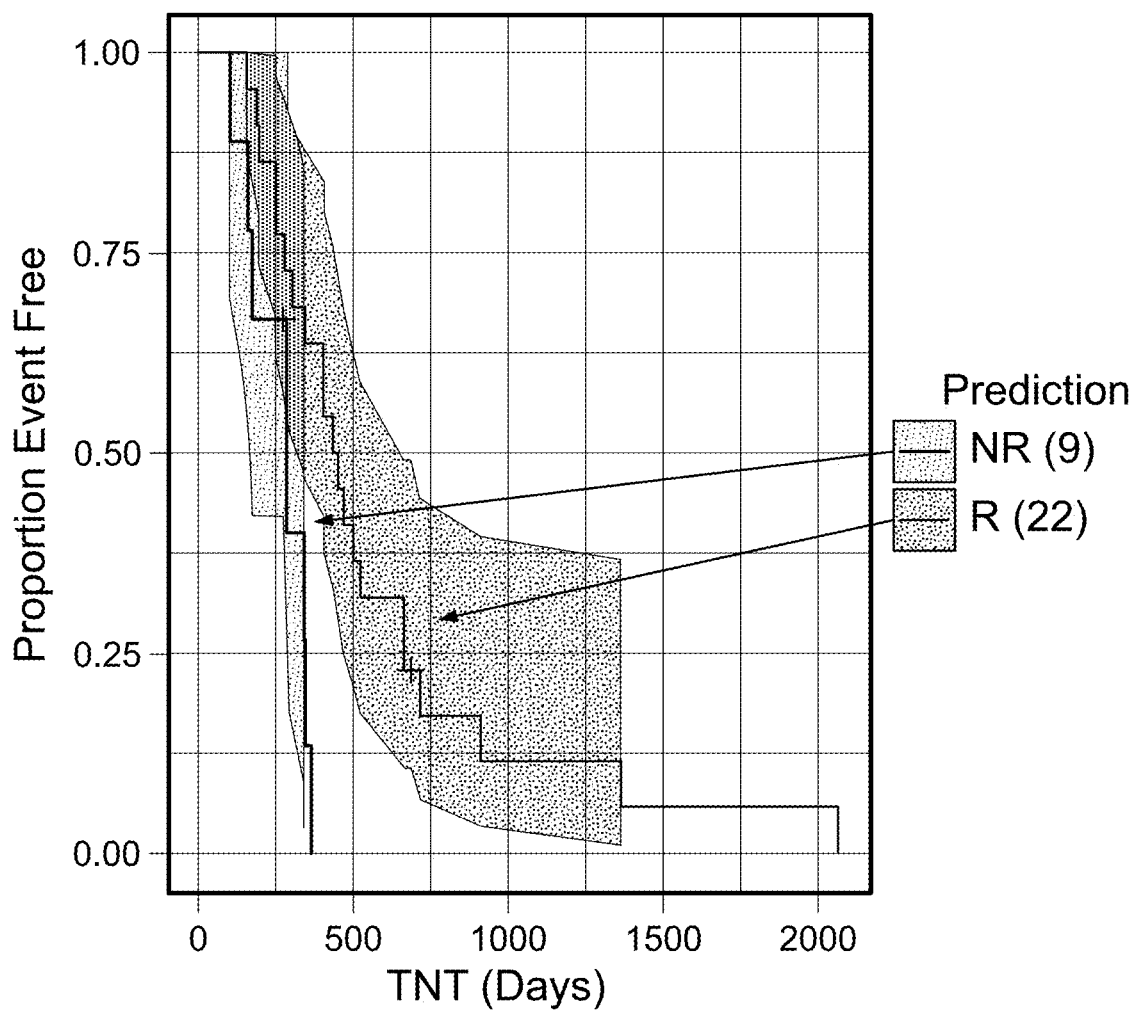
Figure 4K:
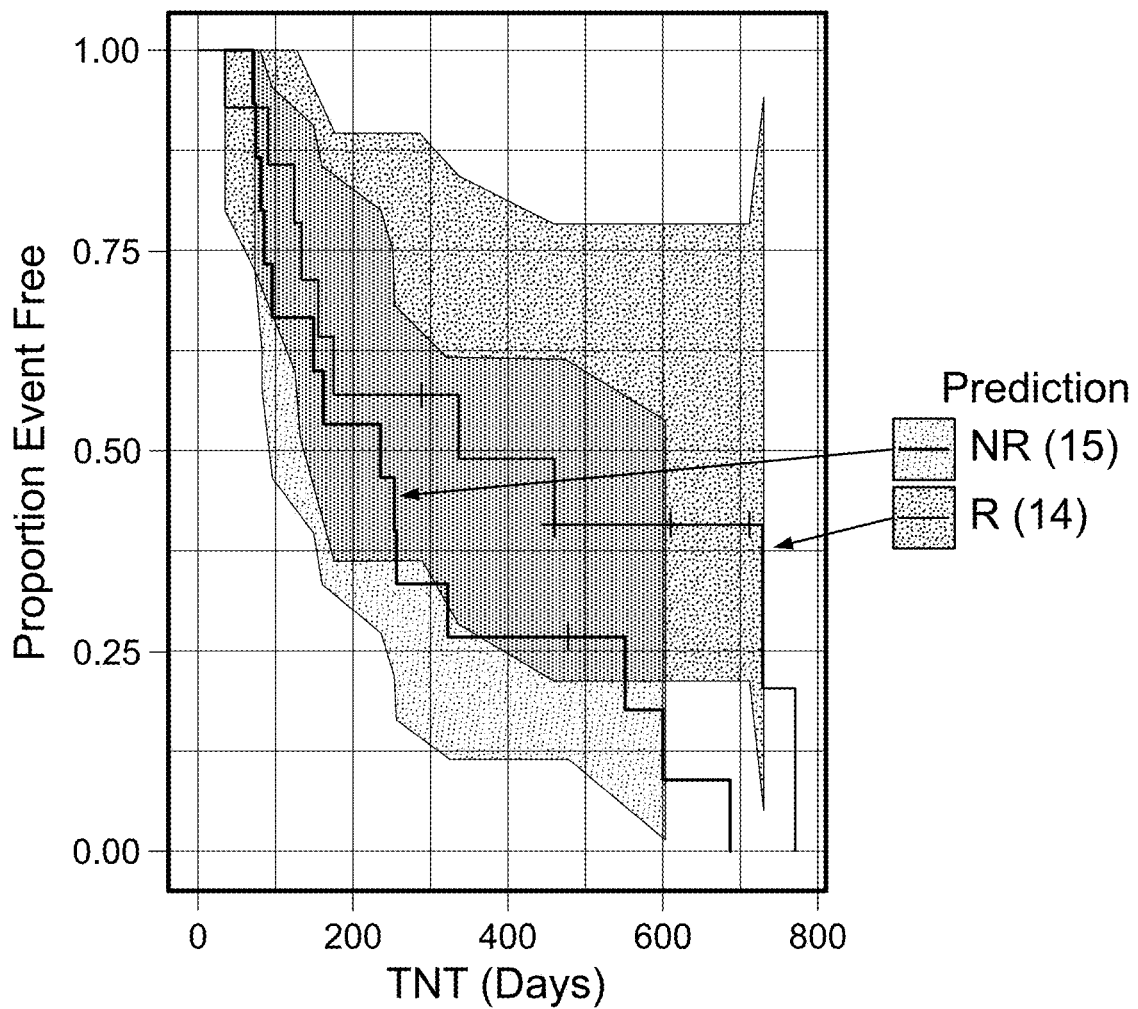
Figure 4L:
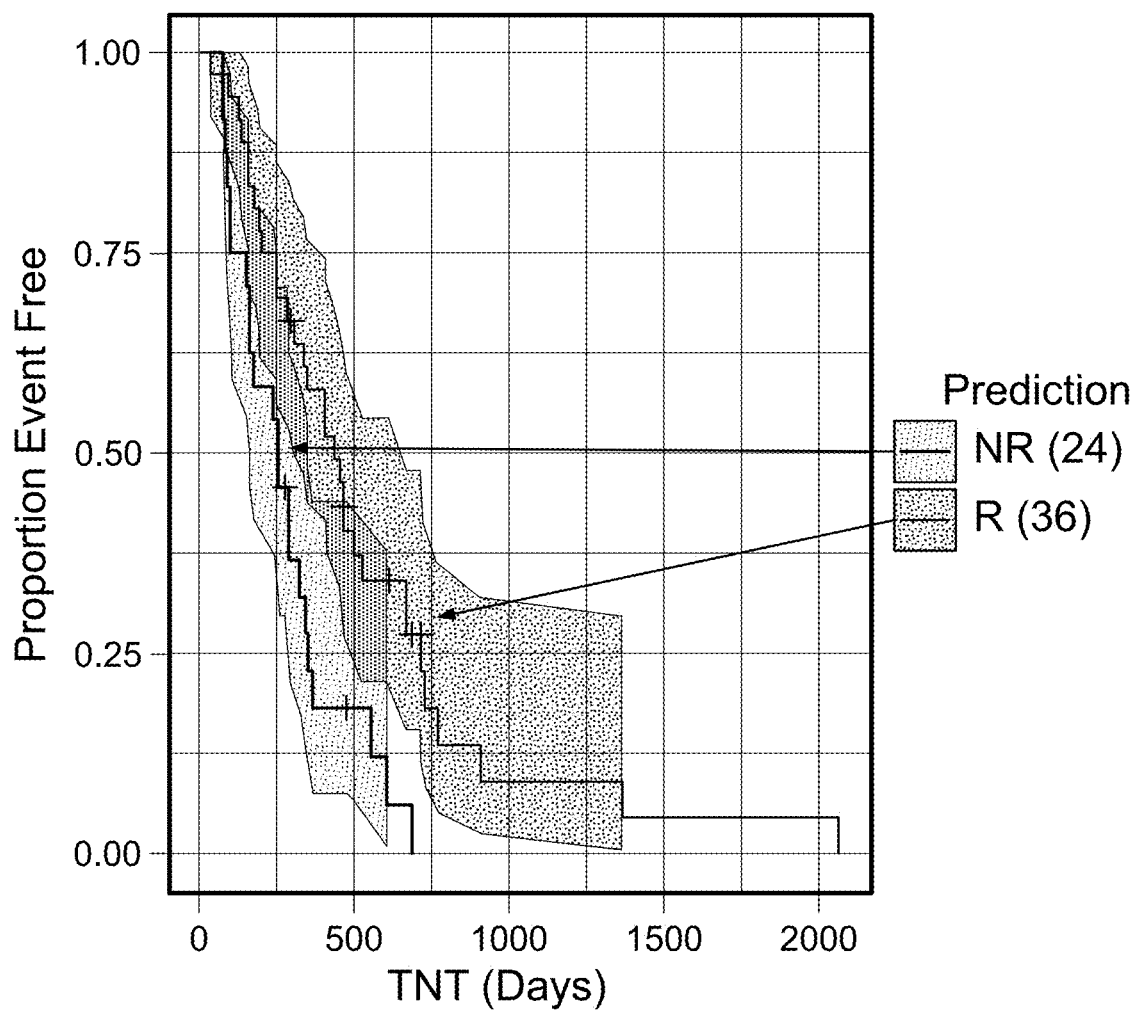

Finally we performed a clinical validation on the biosignature using an independent cohort of front line metastatic colorectal cancer patients. Results are shown in FIG. 4J. Despite the low number of non-benefiter patients available, the HR was 0.333, indicating that this model predicts a subset of the population that experiences a 200% increase in risk of lack of benefit to FOLFOX relative to the remaining population, with a highly significant p-value of 0.003. We also applied the biosignature to independent cohorts of patients from the adjuvant setting. FIG. 4K shows results obtained with a smaller cohort of Stage III CRC patients. In this setting, the HR was 0.506 and the p-value was not quite significant at 0.080. FIG. 4L shows results obtained when combining the stage III and stage IV patients from FIG. 4K and FIG. 4L, respectively. In this setting, the HR was 0.466 and the p-value was again significant at 0.003. These results suggest that the biosignature provides optimal prediction of FOLFOX with stage IV metastatic CRC patients, and may also have utility in other settings, e.g., stage III cancers or others.

Figure 4M:
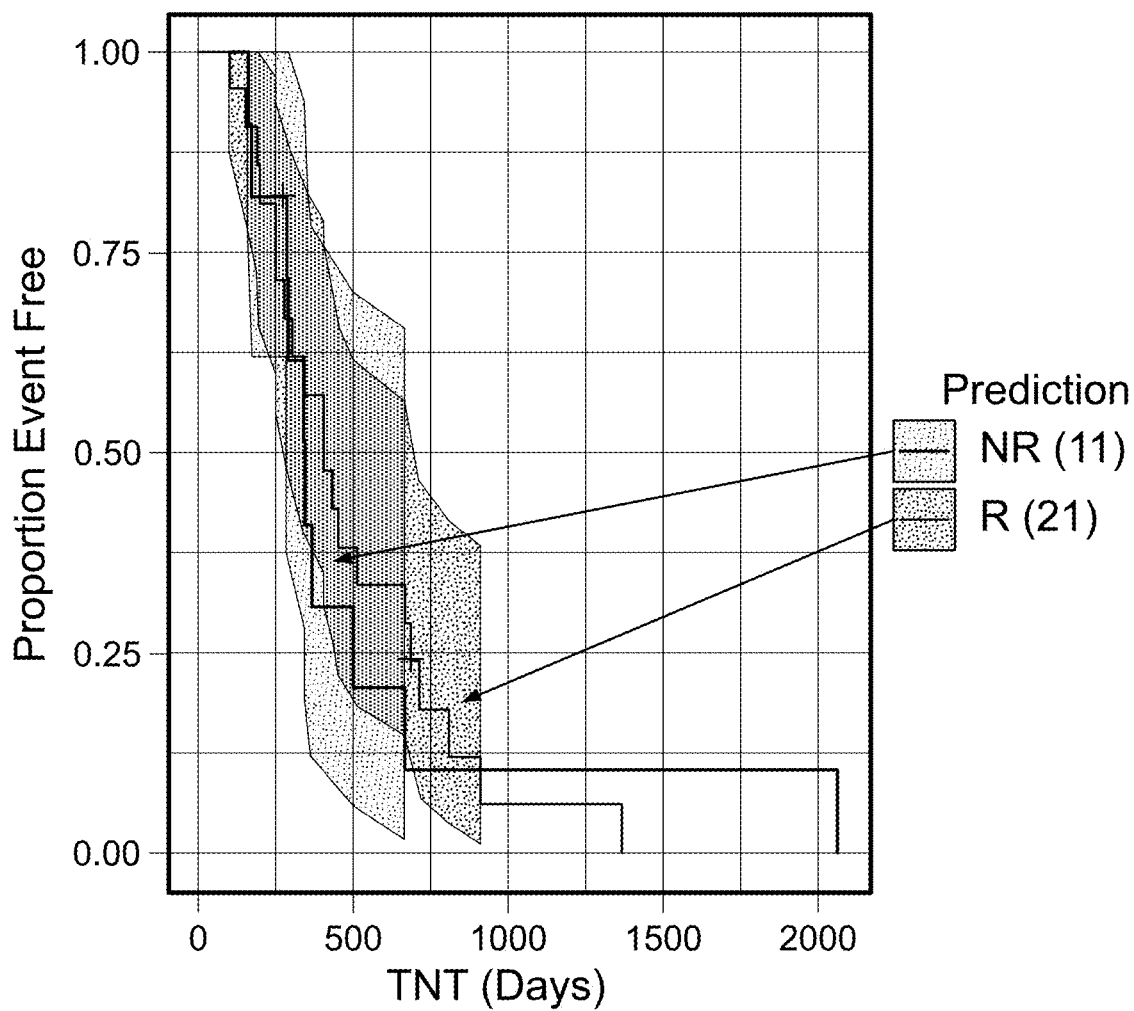
Figure 4N:
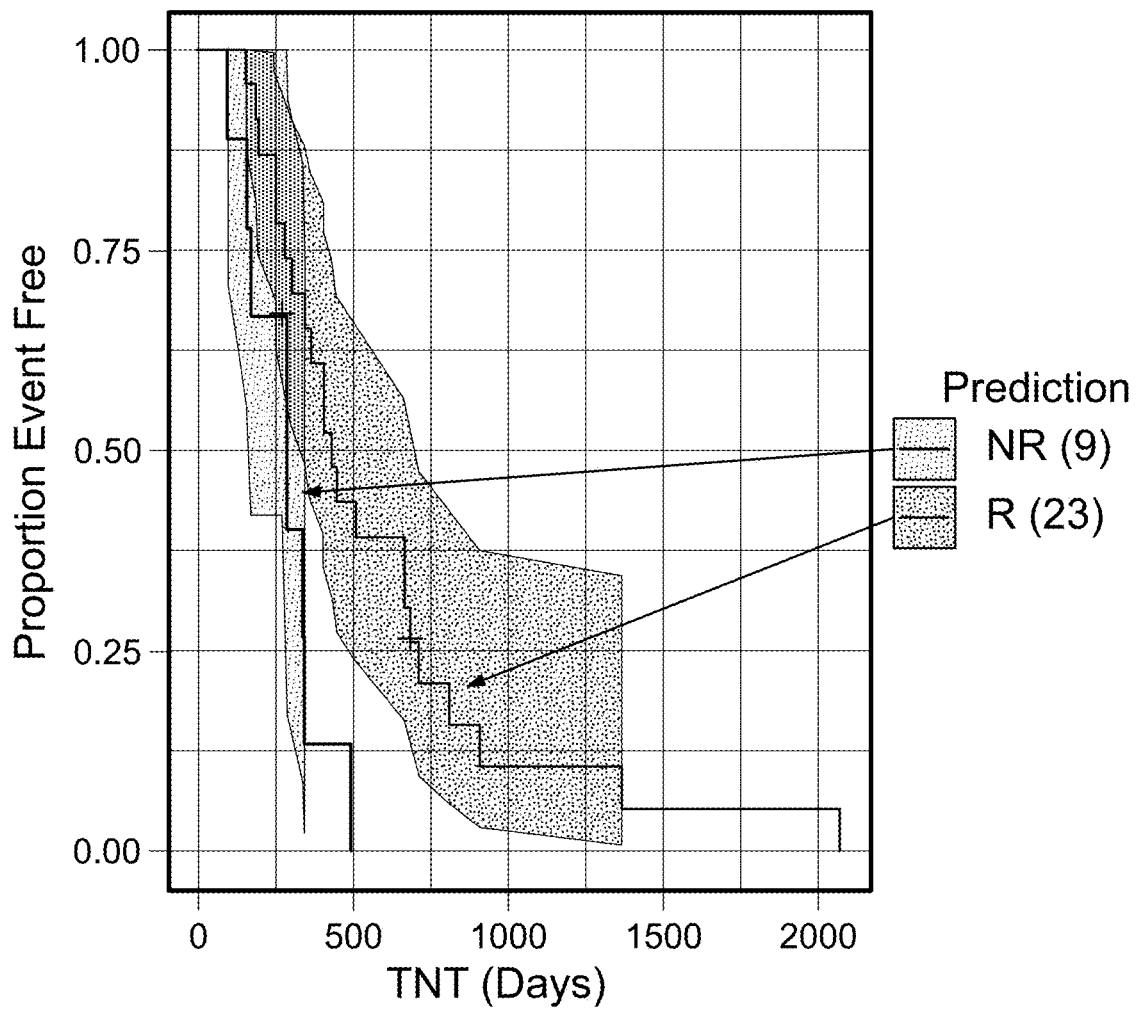
Figure 4O:
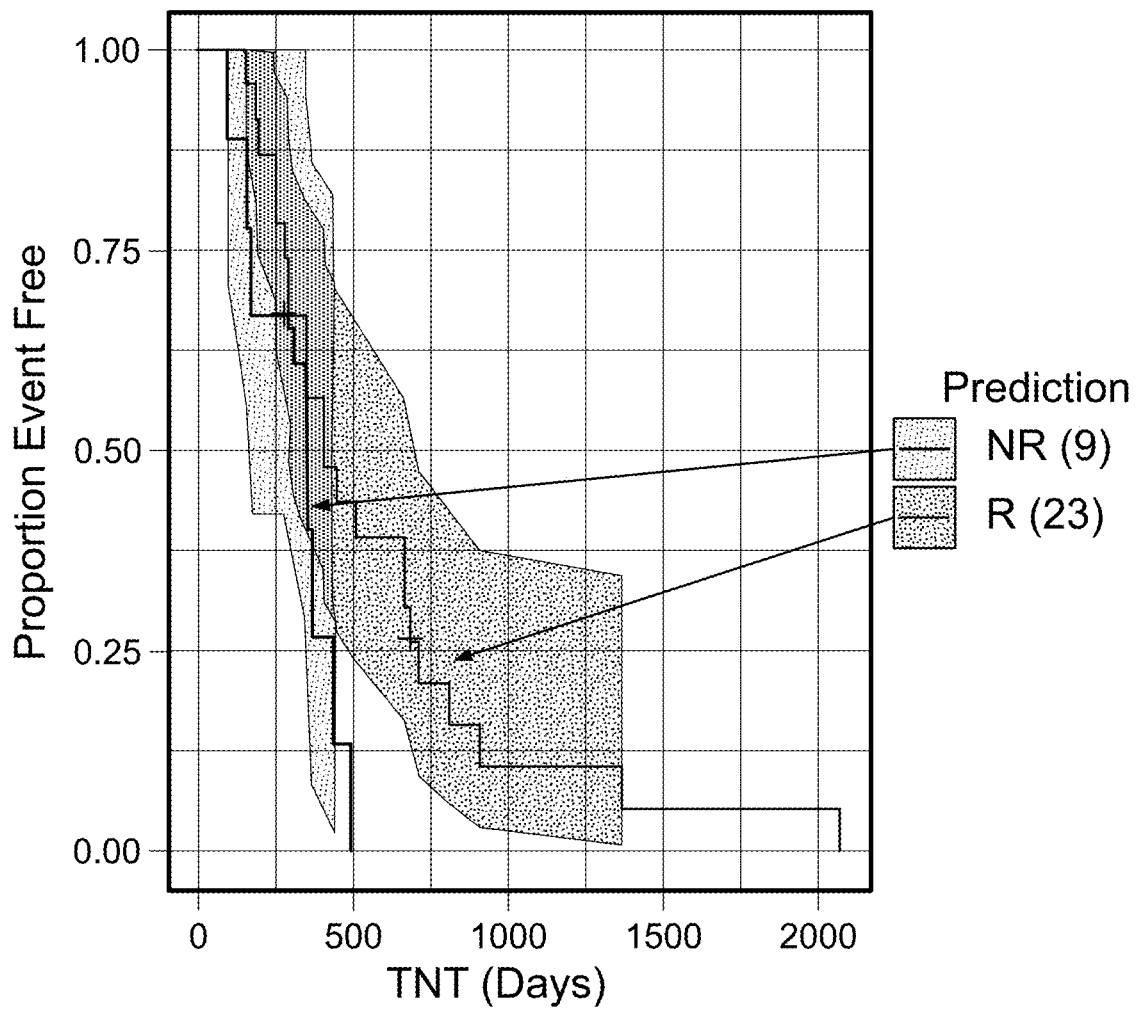

In addition to the multiple algorithm approach used to identify the biosignature above (e.g., as in FIGS. 4F-4L, we also used a single model approach to identify biosignatures of FOLFOX response. Three such random forest classifier models with parameters and results are shown in Table 9. The models were trained on the training samples above (see FIG. 4E) and tested on the samples as in FIG. 4J. KM plots for the models are as indicated in the "Model" column in Table 9. As shown in the figures, Model 1 (FIG. 4M; HR=0.917; p-value=0.814) did not significantly classify FOLFOX benefiters and non-benefiters, whereas both Model 2 (FIG. 4N; HR=0.365; p-value=0.007) and Model 3 (FIG. 4O; HR=0.465; p-value=0.047) both significantly classified the FOLFOX benefiters and non-benefiters in the test set.

TABLE 9

Random forest classifier models

| Model | Parameters | Biosignature (Biomarker Technique) |
|---|---|---|
| 1 (FIG. 4M) | Number of Trees: 2,000<br>Maximum features: square root of the number of features (i.e. sqrt (13))<br>Maximum depth: None/NULL<br>Minimum samples per leaf: 1<br>Class Weight: None/NULL | PBX1 CNA<br>BCL9 CNA<br>INHBA CNA<br>PRRX1 CNA<br>YWHAE CNA<br>GNAS CNA<br>LHFPL6 CNA<br>FCRL4 CNA<br>AURKA CNA<br>IKZF1 CNA<br>CASP8 CNA<br>PTEN IHC<br>EP300 CNA |
| 2 (FIG. 4N) | Number of Trees: 2,000<br>Maximum features: square root of the number of features (i.e. sqrt (12))<br>Maximum depth: None/NULL<br>Minimum samples per leaf: 8<br>Class Weight: None/NULL | BCL9 CNA<br>PBX1 CNA<br>PRRX1 CNA<br>INHBA CNA<br>GNAS CNA<br>YWHAE CNA<br>LHFPL6 CNA<br>FCRL4 CNA<br>PTEN IHC<br>HOXA11 CNA<br>AURKA CNA<br>BIRC3 CNA |
| 3 (FIG. 4O) | Number of Trees: 2,000<br>Maximum features: log2 of the number of features (i.e. log2 (5))<br>Maximum depth: None/NULL<br>Minimum samples per leaf: 4<br>Class Weight: None/NULL | BCL9 CNA<br>PBX1 CNA<br>PRRX1 CNA<br>INHBA CNA<br>YWHAE CNA |

Example 4: Multi-Model Prediction of Colorectal Cancer Patients as Responders or Non-Responder to FOLFOX Chemotherapeutic Treatment Regimen In the Examples above, we described the use of a machine learning approach to analyze molecular profiling data according to the methods disclosed herein to discover clinically relevant biosignatures for predicting benefit or lack of benefit from FOLFOX. The models were trained on Stage III and Stage IV colorectal cancer (CRC) samples (Example 2) or Stage IV CRC samples (Example 3). Here, we combined all models to develop a machine-learning approach to predict CRC patients as responders or non-responders to the FOLFOX chemotherapeutic treatment regimen.

Sample sets and training methodology are as described above. We identified five random forest models that together provide an optimal prediction of response. Random forest were generated using the Python language and sklearn.ensemble.RandomForestClassifier module. See Pedregosa et al., Scikit-learn: Machine Learning in Python, JMLR 12, pp. 2825-2830, 2011. The sklearn.ensemble.RandomForest-Classifier parameters used to generate the models are shown in Table 10. Model identifiers are shown in the column "Model." Each model has its own list of features as shown in column "Biosignature" in the table. Gene identifiers are those commonly accepted in the scientific community at the time of filing and can be used to look up the genes at various well-known databases such as the HUGO Gene Nomenclature Committee (HNGC; genenames.org), NCBI's Gene database (www.ncbi.nlm.nih.gov/gene), GeneCards (genecards.org), Ensembl (ensembl.org), UniProt (uniprot.org), and others. As expected, several features are used in multiple models. For example, ASXL1 is used in four of the five models, as further described below. The data for each gene feature in the biosignature consists of its copy number as determined using next generation sequencing. See Example 1 for further details.

TABLE 10

Random forest classifier models

| Model | Parameters | Biosignature |
|---|---|---|
| 1 (ARF2) | n_estimators: 2000<br>criterion: gini<br>max_depth: None<br>min_samples_split: 2<br>min_samples_leaf: 1<br>min_weight_fraction_leaf: 0<br>max_features: square root of the number of features (i.e. sqrt (15))<br>max_leaf_nodes: None<br>min_impurity_decrease: 0<br>min_impurity_split: 1e-7<br>bootstrap: True<br>oob_score: False<br>class_weight: balanced | BCL9<br>PBX1<br>GNAS<br>LHFPL6<br>CASP8<br>ASXL1<br>FH<br>CRKL<br>MLF1<br>TRRAP<br>AKT3<br>ACKR3<br>MSI2<br>PCM1<br>MNX1 |
| 2 (ARF43) | n_estimators: 2000<br>criterion: entropy<br>max_depth: 4<br>min_samples_split: 2<br>min_samples_leaf: 1<br>min_weight_fraction_leaf: 0<br>max_features: square root of the number of features (i.e. sqrt (45))<br>max_leaf_nodes: None<br>min_impurity_decrease: 0<br>min_impurity_split: 1e-7<br>bootstrap: True<br>oob_score: False<br>class_weight: None | PBX1<br>GNAS<br>AURKA<br>CASP8<br>ASXL1<br>CRKL<br>MLF1<br>GAS7<br>MN1<br>SOX10<br>TCL1A<br>LMO1<br>BRD3<br>SMARCA4<br>PER1<br>PAX7<br>SBDS<br>SEPT5<br>PDGFB<br>AKT2<br>TERT<br>KEAP1<br>ETV6<br>TOP1<br>TLX3<br>COX6C<br>NFIB<br>ARFRP1<br>ARID1A<br>MAP2K4<br>NFKBIA |

TABLE 10-continued

Random forest classifier models

| Model | Parameters | Biosignature |
|---|---|---|
| | | WWTR1 |
| | | ZNF217 |
| | | IL2 |
| | | NSD3 |
| | | CREB1 |
| | | BRIP1 |
| | | SDC4 |
| | | EWSR1 |
| | | FLT3 |
| | | FLT1 |
| | | FAS |
| | | CCNE1 |
| | | RUNX1T1 |
| | | EZR |
| 3 (DRF13) | n_estimators: 2000 | BCL9 |
| | criterion: gini | PBX1 |
| | max_depth: None | PRRX1 |
| | min_samples_split: 2 | INHBA |
| | min_samples_leaf: 8 | YWHAE |
| | min_weight_fraction_leaf: 0 | GNAS |
| | max_features: None | LHFPL6 |
| | max_leaf_nodes: None | FCRL4 |
| | min_impurity_decrease: 0 | AURKA |
| | min_impurity_split: 1e-7 | BIRC3 |
| | bootstrap: True | HOXA11 |
| | oob_score: False | |
| | class_weight: None | |
| 4 (DRF25) | n_estimators: 2000 | BCL9 |
| | criterion: gini | PBX1 |
| | max_depth: None | PRRX1 |
| | min_samples_split: 2 | INHBA |
| | min_samples_leaf: 4 | YWHAE |
| | min_weight_fraction_leaf: 0 | |
| | max_features: log2 of the number of features (i.e. log2 (5)) | |
| | max_leaf_nodes: None | |
| | min_impurity_decrease: 0 | |
| | min_impurity_split: 1e-7 | |
| | bootstrap: True | |
| | oob_score: False | |
| | class_weight: None | |
| 5 (JRF38) | n_estimators: 2000 | ASXL1 |
| | criterion: entropy | MYC |
| | max_depth: None | U2AF1 |
| | min_samples_split: 2 | EP300 |
| | min_samples_leaf: 1 | CNTRL |
| | min_weight_fraction_leaf: 0 | MAML2 |
| | max_features: None | WRN |
| | max_leaf_nodes: None | CDX2 |
| | min_impurity_decrease: 0 | |
| | min_impurity_split: 1e-7 | |
| | bootstrap: True | |
| | oob_score: False | |
| | class_weight: balanced | |

Figure 5A:
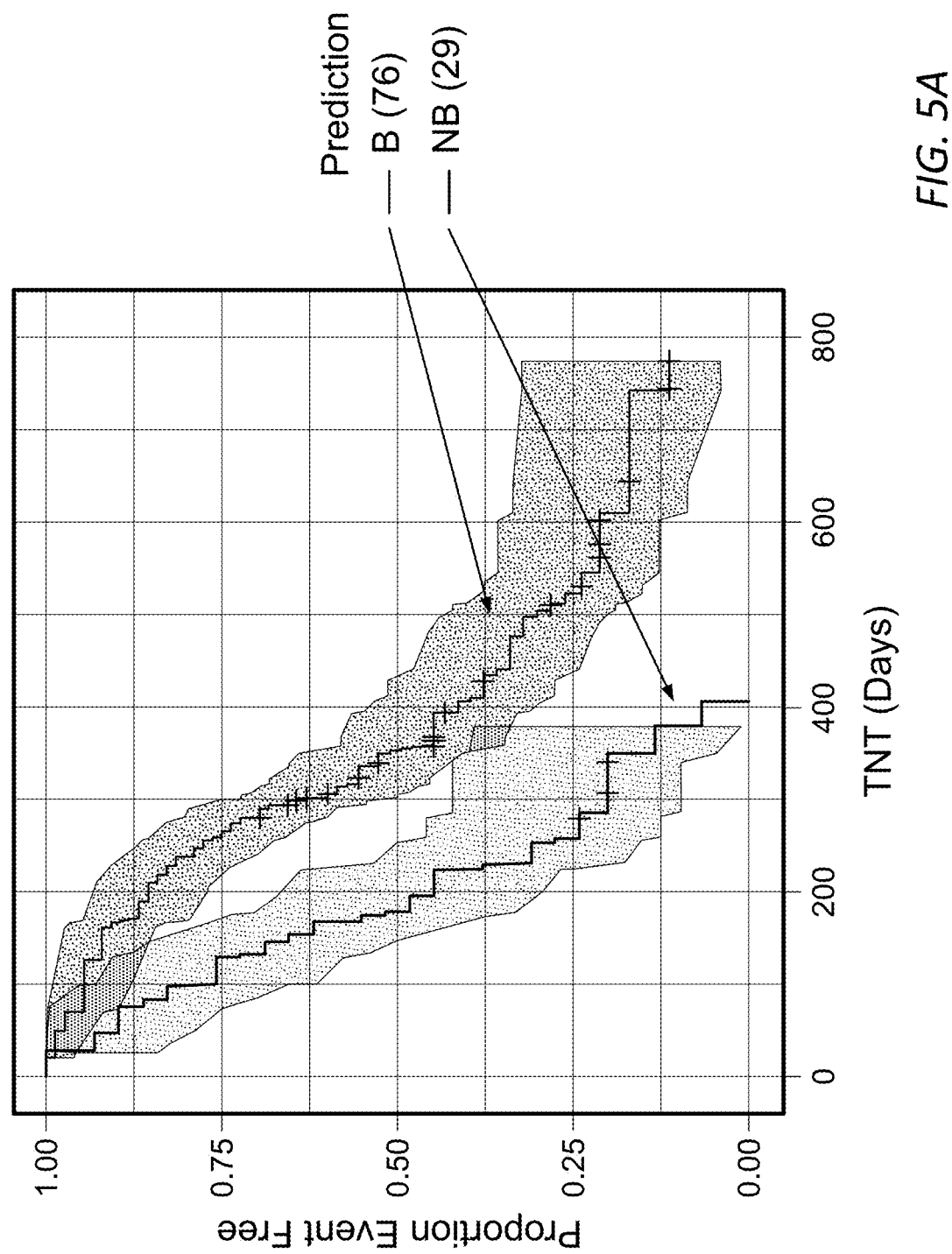
FIGS. 5A-C show development of a biosignature to predict benefit of the FOLFOX regimen in colorectal cancer patients.
Figure 5B:
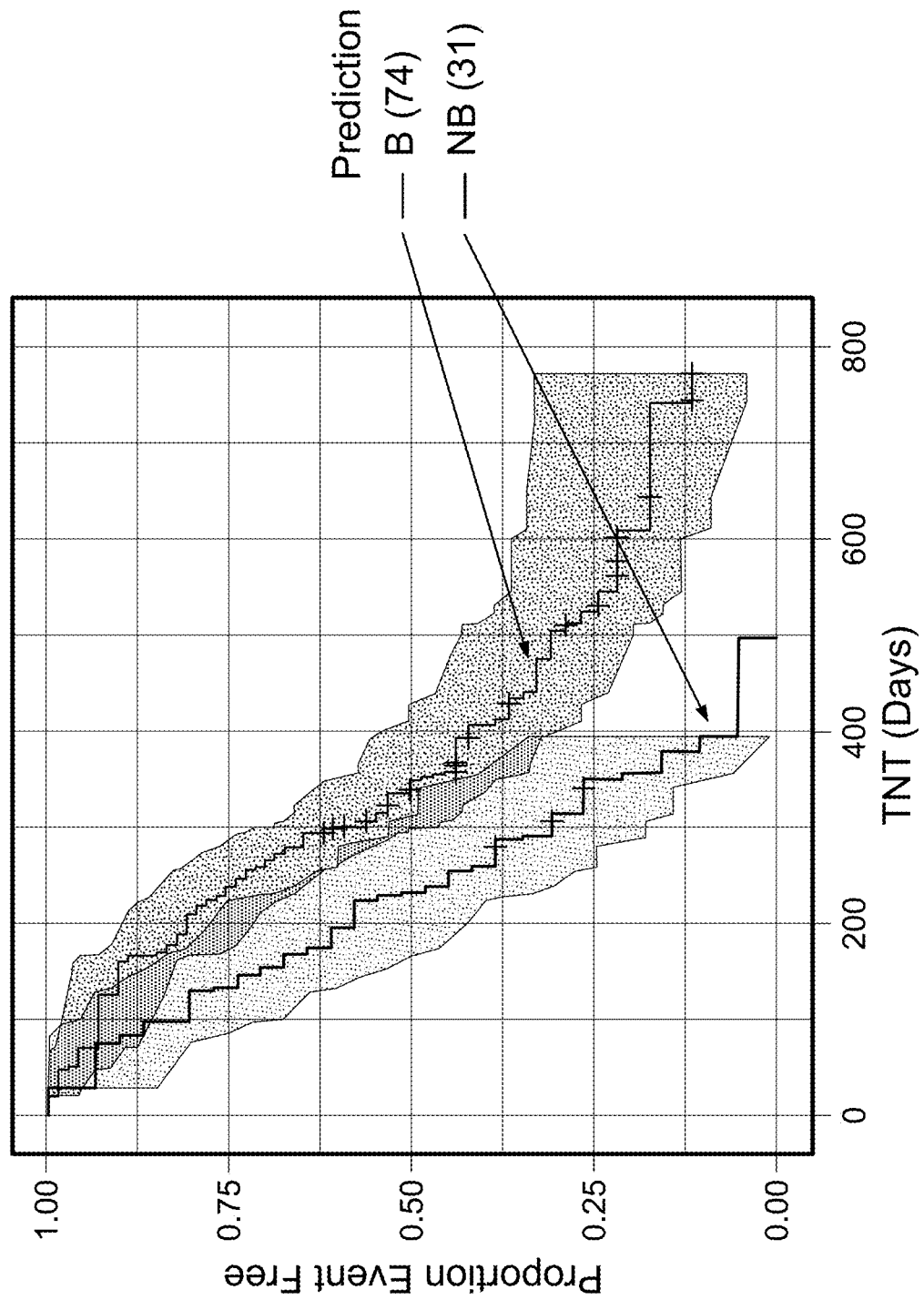

The predictions made using the models are based on 5,000 saved model instances. Each of the five models was trained 1,000 times and each specific instance results in a slightly different random forest that likewise produces slightly different results. However, the forests are saved objects and will always produce the same output given a fixed input. In order to make a prediction for a case, we run the case's copy number values for the specified gene features through each of the 1,000 saved model instances. Each individual instance produces a probability that the case is a non-responder. The case then has 1,000 probabilities for Model #1, 1,000 probabilities for Model #2, and so on. We aggregate these results down to five probabilities by taking the median probability per model (i.e., Model 1 probability=median (mode11.1, mode11.2, mode11.1000, and so on). The final prediction of the case is the median of these five median probabilities, i.e., one probability per model listed in Table 10. Since there are five models, if at least 3 of the models predict that the case is a non-responder, then the overall prediction is non-responder, or vice versa. Results this approach using 5-fold cross validation on the training sets are shown in FIGS. 5A-B. FIG. 5A shows results using all models. FIG. 5B presents representative results using one model.

Figure 5C:
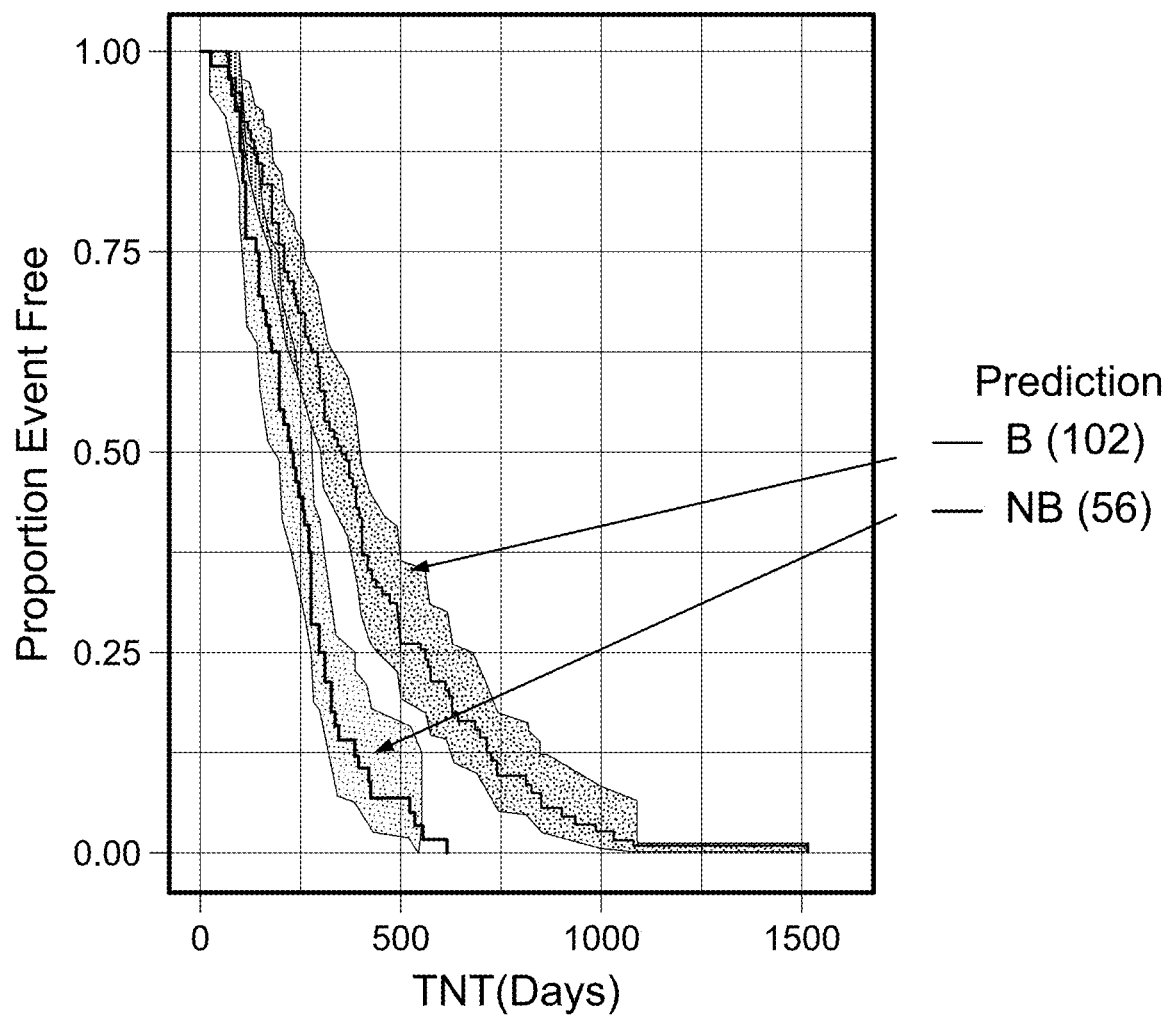

The joint five random forest model was validated using molecular profiling and outcomes data for 166 Stage IV CRC cases. Each patient had a CRC tumor that had been previously profiled using as described in Example 1, but the cases were not used in any previous FOLFOX development efforts described herein. Prediction of response to FOLFOX based on results of the joint model are show in FIG. 5C. The figure shows that our method accurately predicts response or lack of response to FOLFOX. The joint model was also applied to the validation sets used the Examples described above and achieved similar results. Data not shown. Collectively, these data indicate that the joint five random forest model can be used to predict response to FOLFOX in front line late stage CRC patients using real world patient samples from diverse sources. Our data suggest the treatment of patients that are predicted responders with FOLFOX, while predicted non-responders may be treated with FOLFIRI.

Table 11 provides more detail of the genes/features listed in Table 10. The column "Ensembl ID" lists the gene IDs from Ensembl (ensembl.org). The column "Name" lists name for the gene commonly accepted at the time of filing. The columns "R" and "NR" show the copy number for each gene detected using our NGS approach for the responder cases and non-responder cases, respectively. As a cell would be expected to be diploid, and thus harbor 2 copies of a gene per cell, numbers below 2 are suggestive of loss whereas numbers above 2 are suggestive of gain/amplification. The column "#Models" indicates how many times the gene appears in the five models in Table 10. For example, PAX7 appears in one model in Table 10, i.e., Model 2 (ARF43), whereas PBX1 appears in four of the five models, i.e., Model 1 (ARF2), Model 2 (ARF43), Model 3 (DRF13), and Model 4 (DRF25). The column "Cyto Band" is the locus of the gene given in standard nomenclature (e.g., the leading number is the chromosome, "p" indicates the short arm and "q" indicates the long arm of the chromosome, and the trailing numbers are region and band).

TABLE 11

Random forest classifier models

| Gene ID | Ensembl ID | Name | R | NR | # Models | Cyto Band |
|---|---|---|---|---|---|---|
| ARID1A | ENSG00000117713 | AT-Rich Interaction Domain 1A | 1.84 ± 0.31 | 1.84 ± 0.26 | 1 | 1p36.11 |
| PAX7 | ENSG00000009709 | Paired Box 7 | 1.94 ± 0.64 | 1.75 ± 0.67 | 1 | 1p36.13 |

TABLE 11-continued

Random forest classifier models

| Gene ID | Ensembl ID | Name | R | NR | # Models | Cyto Band |
|---|---|---|---|---|---|---|
| BCL9 | ENSG00000116128 | BCL9 Transcription Coactivator | 2.01 ± 0.41 | 1.77 ± 0.29 | 3 | 1q21.2 |
| FCRL4 | ENSG00000163518 | Fc Receptor Like 4 | 1.88 ± 0.43 | 1.72 ± 0.27 | 1 | 1q23.1 |
| PBX1 | ENSG00000185630 | PBX Homeobox 1 | 2.00 ± 0.39 | 1.77 ± 0.22 | 4 | 1q23.3 |
| PRRX1 | ENSG00000116132 | Paired Related Homeobox 1 | 2.04 ± 0.39 | 1.81 ± 0.27 | 2 | 1q24.2 |
| FH | ENSG00000091483 | Fumarate Hydratase | 1.88 ± 0.53 | 1.79 ± 0.37 | 1 | 1q43 |
| AKT3 | ENSG00000117020 | AKT Serine/Threonine Kinase 3 | 1.81 ± 0.52 | 1.77 ± 0.42 | 1 | 1q44 |
| CASP8 | ENSG00000064012 | Caspase 8 | 1.91 ± 0.50 | 2.07 ± 0.31 | 2 | 2q33.1 |
| CREB1 | ENSG00000118260 | CAMP Responsive Element Binding Protein 1 | 1.78 ± 0.61 | 2.08 ± 0.70 | 1 | 2q33.3 |
| ACKR3 | ENSG00000144476 | Atypical Chemokine Receptor 3 | 2.26 ± 0.50 | 1.94 ± 0.66 | 1 | 2q37.3 |
| WWTR1 | ENSG00000018408 | WW Domain Containing Transcription Regulator 1 | 1.90 ± 0.26 | 1.88 ± 0.22 | 1 | 3q25.1 |
| MLF1 | ENSG00000178053 | Myeloid Leukemia Factor 1 | 1.87 ± 0.41 | 1.86 ± 0.35 | 3 | 3q25.32 |
| IL2 | ENSG00000109471 | Interleukin 2 | 1.80 ± 0.63 | 1.97 ± 0.65 | 1 | 4q27 |
| TERT | ENSG00000164362 | Telomerase Reverse Transcriptase | 1.99 ± 0.81 | 2.01 ± 0.77 | 1 | 5p15.33 |
| TLX3 | ENSG00000164438 | T Cell Leukemia Homeobox 3 | 1.88 ± 0.70 | 1.74 ± 0.80 | 1 | 5q35.1 |
| EZR | ENSG00000092820 | Ezrin | 2.16 ± 0.40 | 2.05 ± 0.38 | 1 | 6q25.3 |
| INHBA | ENSG00000122641 | Inhibin Subunit Beta A | 2.29 ± 0.78 | 1.86 ± 0.43 | 2 | 7p14.1 |
| HOXA11 | EN5G00000005073 | Homeobox A11 | 2.54 ± 0.63 | 2.19 ± 0.43 | 1 | 7p15.2 |
| SBDS | EN5G00000126524 | SBDS Ribosome Maturation Factor | 2.02 ± 0.46 | 2.05 ± 0.38 | 1 | 7q11.21 |
| TRRAP | ENSG00000196367 | Transformation/Transcription Domain Associated Protein | 2.01 ± 0.43 | 1.94 ± 0.37 | 1 | 7q22.1 |
| MNX1 | EN5G00000130675 | Motor Neuron And Pancreas Homeobox 1 | 2.17 ± 0.96 | 1.96 ± 0.71 | 1 | 7q36.3 |
| NSD3 | EN5G00000147548 | Nuclear Receptor Binding SET Domain Protein 3 | 1.95 ± 1.99 | 2.06 ± 0.59 | 1 | 8p11.23 |
| WRN | EN5G00000165392 | WRN RecQ Like Helicase | 1.53 ± 0.78 | 1.87 ± 0.73 | 1 | 8p12 |
| PCM1 | EN5G00000078674 | Pericentriolar Material 1 | 1.59 ± 0.87 | 2.03 ± 0.69 | 1 | 8p22 |
| RUNX1T1 | ENSG00000079102 | RUNX1 Partner Transcriptional Co-Repressor 1 | 2.04 ± 0.43 | 2.00 ± 0.35 | 1 | 8q21.3 |
| COX6C | EN5G00000164919 | Cytochrome C Oxidase Subunit 6C | 2.00 ± 0.45 | 2.10 ± 0.46 | 1 | 8q22.2 |
| MYC | EN5G00000136997 | MYC Proto-Oncogene, BHLH Transcription Factor | 2.20 ± 0.69 | 2.13 ± 0.52 | 1 | 8q24.21 |
| NFIB | EN5G00000147862 | Nuclear Factor I B | 2.08 ± 0.62 | 2.09 ± 0.41 | 1 | 9p22.3 |
| CNTRL | EN5G00000119397 | Centriolin | 1.93 ± 0.44 | 2.11 ± 0.41 | 1 | 9q33.2 |
| BRD3 | ENSG00000169925 | Bromodomain Containing 3 | 2.14 ± 0.58 | 2.00 ± 0.65 | 2 | 9q34.2 |
| FAS | EN5G00000026103 | Fas Cell Surface Death Receptor | 1.73 ± 0.49 | 2.01 ± 0.59 | 1 | 10q23.31 |
| LMO1 | EN5G00000166407 | LIM Domain Only 1 | 2.21 ± 0.59 | 1.96 ± 0.73 | 1 | 11p15.4 |
| MAML2 | ENSG00000184384 | Mastermind Like Transcriptional Coactivator 2 | 2.13 ± 0.34 | 2.03 ± 1.30 | 1 | 11q21 |
| BIRC3 | ENSG00000023445 | Baculoviral IAP Repeat Containing 3 | 1.68 ± 0.64 | 2.15 ± 0.83 | 1 | 11q22.2 |
| ETV6 | ENSG00000139083 | ETS Variant Transcription Factor 6 | 2.10 ± 0.34 | 2.02 ± 0.42 | 1 | 12p13.2 |
| CDX2 | ENSG00000165556 | Caudal Type Homeobox 2 | 3.57 ± 2.25 | 2.75 ± 3.29 | 1 | 13q12.2 |
| FLT3 | ENSG00000122025 | Fms Related Tyrosine Kinase 3 | 2.73 ± 1.47 | 2.61 ± 1.37 | 1 | 13q12.2 |
| FLT1 | ENSG00000102755 | Fms Related Tyrosine Kinase 1 | 2.70 ± 1.18 | 2.41 ± 1.08 | 1 | 13q12.3 |

TABLE 11-continued

Random forest classifier models

| Gene ID | Ensembl ID | Name | R | NR | # Models | Cyto Band |
|---|---|---|---|---|---|---|
| LHFPL6 | ENSG00000183722 | LHFPL Tetraspan Subfamily Member 6 | 2.69 ± 0.93 | 2.16 ± 0.81 | 2 | 13q14.11 |
| NFKBIA | ENSG00000100906 | NFKB Inhibitor Alpha | 1.90 ± 0.47 | 1.96 ± 0.36 | 1 | 14q13.2 |
| TCL1A | ENSG00000100721 | T Cell Leukemia/Lymphoma 1A | 1.91 ± 0.49 | 1.84 ± 0.62 | 1 | 14q32.13 |
| MAP2K4 | ENSG00000065559 | Mitogen-Activated Protein Kinase Kinase 4 | 1.70 ± 0.56 | 1.77 ± 0.54 | 1 | 17p12 |
| PER1 | EN5G00000179094 | Period Circadian Regulator 1 | 1.91 ± 0.53 | 1.92 ± 0.59 | 1 | 17p13.1 |
| GAS7 | EN5G00000007237 | Growth Arrest Specific 7 | 1.92 ± 0.49 | 1.94 ± 0.62 | 1 | 17p13.1 |
| YWHAE | EN5G00000108953 | Tyrosine 3-Monooxygenase/Tryptophan 5-Monooxygenase Activation Protein Epsilon | 1.77 ± 0.36 | 2.11 ± 0.41 | 2 | 17p13.3 |
| MSI2 | ENSG00000153944 | Musashi RNA Binding Protein 2 | 1.95 ± 0.41 | 1.91 ± 0.28 | 1 | 17q22 |
| BRIP1 | EN5G00000136492 | BRCA1 Interacting Protein C-Terminal Helicase 1 | 1.66 ± 0.51 | 1.73 ± 0.43 | 1 | 17q23.2 |
| KEAP1 | EN5G00000079999 | Kelch Like ECH Associated Protein 1 | 2.19 ± 0.62 | 2.10 ± 0.67 | 1 | 19p13.2 |
| SMARCA4 | EN5G00000127616 | SWI/SNF Related, Matrix Associated, Actin Dependent Regulator Of Chromatin, Subfamily A, Member 4 | 2.11 ± 0.65 | 2.08 ± 0.69 | 1 | 19p13.2 |
| CCNE1 | EN5G00000105173 | Cyclin E1 | 2.01 ± 0.35 | 1.96 ± 0.27 | 1 | 19q12 |
| AKT2 | EN5G00000105221 | AKT Serine/Threonine Kinase 2 | 2.14 ± 0.65 | 1.96 ± 0.94 | 1 | 19q13.2 |
| ASXL1 | EN5G00000171456 | ASXL Transcriptional Regulator 1 | 2.47 ± 0.59 | 2.11 ± 0.69 | 4 | 20q11.21 |
| TOP1 | EN5G00000198900 | DNA Topoisomerase I | 2.20 ± 0.51 | 2.20 ± 0.53 | 1 | 20q12 |
| SDC4 | EN5G00000124145 | Syndecan 4 | 2.67 ± 0.85 | 2.18 ± 0.69 | 1 | 20q13.12 |
| AURKA | ENSG00000087586 | Aurora Kinase A | 2.37 ± 0.53 | 2.05 ± 0.47 | 3 | 20q13.2 |
| ZNF217 | ENSG00000171940 | Zinc Finger Protein 217 | 2.42 ± 0.56 | 2.28 ± 0.53 | 1 | 20q13.2 |
| GNAS | ENSG00000087460 | GNAS Complex Locus | 2.57 ± 0.59 | 2.22 ± 0.50 | 4 | 20q13.32 |
| ARFRP1 | ENSG00000101246 | ADP Ribosylation Factor Related Protein 1 | 2.68 ± 1.00 | 2.26 ± 0.81 | 1 | 20q13.33 |
| U2AF1 | ENSG00000160201 | U2 Small Nuclear RNA Auxiliary Factor 1 | 1.96 ± 0.34 | 1.97 ± 0.30 | 1 | 21q22.3 |
| CRKL | ENSG00000099942 | CRK Like Proto-Oncogene, Adaptor Protein | 1.91 ± 0.46 | 2.07 ± 0.32 | 2 | 22q11.21 |
| SEPT5 | ENSG00000184702 | Septin 5 | 1.83 ± 0.66 | 1.90 ± 0.59 | 1 | 22q11.21 |
| MN1 | ENSG00000169184 | MN1 Proto-Oncogene, Transcriptional Regulator | 1.80 ± 0.72 | 1.83 ± 0.73 | 1 | 22q12.1 |
| EWSR1 | ENSG00000182944 | EWS RNA Binding Protein 1 | 1.85 ± 0.42 | 1.98 ± 0.30 | 1 | 22q12.2 |
| PDGFB | ENSG00000100311 | Platelet Derived Growth Factor Subunit B | 1.80 ± 0.59 | 1.89 ± 0.66 | 1 | 22q13.1 |
| SOX10 | ENSG00000100146 | SRY-Box Transcription Factor 10 | 1.87 ± 0.65 | 1.85 ± 0.72 | 1 | 22q13.1 |
| EP300 | ENSG00000100393 | E1A Binding Protein P300 | 1.73 ± 0.31 | 1.94 ± 0.34 | 1 | 22q13.2 |

Without intending to be bound by theory, various observations may be made from the data in Table 11. For example, our method is highly sensitive to changes in copy number. We found the model to be robust across real world samples, but, as shown in the table, the changes in copy were often more subtle than differences that would be detected using conventional laboratory techniques. The samples that we profile using NGS are typically micro-dissected FFPE tumor samples. Thus, our method is robust given the heterogeneity between tumor cells in the sample. In addition, there are regions where multiple genes appear, including without limitation at 1q (PAX7, BCL9, FCRL4, PBX1, PRRX1, FH, AKT3), 20q (ASXL1, TOP1, SDC4, AURKA, ZNF217, GNAS, ARFRP1) and 22q (CRKL, SEPT5, MN1, EWSR1, PDGFB, SOX10, EP300). This suggests that there are chromosomal "hotspots" for genomic alterations which our method detects when multiple genes lie with a given genetic local. See, e.g., Ashktorab H et al. Distinct genetic alterations in colorectal cancer. PLoS One. 2010 Jan. 26; 5(1): e8879. doi: 10.1371/journal.pone.0008879. Moreover, in many cases assessment of neighboring chromosomal locales to those of the genes we analyzed may be expected to provide similar results.

The multiple random forest models were trained on similar if not identical molecular profiling data (see, e.g., Example 1), but with different parameters on the same sample data (see, e.g., Tables 9 and 10) or on a different sample set (cf. Examples 2 and 3). Combining the models using a "voting" scheme where essentially each model gets a vote provides superior results to any individual model. Cf. FIGS. 5A and 5B. Without being bound by theory, each model may perform optimally on cases having different characteristics, and in combination the voting scheme accounts for suboptimal performance of any given model on a certain subset or subsets of cases.

Taken together, we employed advanced machine learning algorithms to build multiple models that predict response or non-response of CRC patients to the FOLFOX chemotherapeutic treatment regimen. The multiple models are each allowed a "vote" according to the methods disclosed herein, and the majority "wins." The method is shown to provide robust results across disparate and real world samples (i.e., actual clinical samples), is not merely prognostic and is robust to sidedness. Treating physicians can use the results of our FOLFOX testing to assist in the determination whether to treat a CRC patient with FOLFOX or alternate regimen such as FOLFIRI.

Example 3: Selecting Treatment for a Colorectal Cancer Patient

An oncologist treating a colorectal cancer patient desires to determine whether to treat the patient with FOLFOX or FOLFIRI. A biological sample comprising tumor cells from the patient is collected. A molecular profile is generated for the sample according to Example 1. The five random forest models described in Table 10 are each used to classify the molecular profile as indicative of likely response or non-response to FOLFOX. The majority classification is included in a report that also describes the molecular profiling that was performed. The report is provided to the oncologist. The oncologist uses the classification in the report to assist in determining a treatment regimen for the patient. If the classification is responder, the oncologist treats that patient with FOLFOX. If the classification is responder, the oncologist treats that patient with FOLFIRI.

Other Embodiments

It is to be understood that while the invention has been described in conjunction with the detailed description thereof, the foregoing description is intended to illustrate and not limit the scope as described herein, which is defined by the scope of the appended claims. Other aspects, advantages, and modifications are within the scope of the following claims.

What is claimed is:

1. A method for classification of a test entity for a treatment, the method comprising:
    obtaining data that represents the test entity, wherein the obtained data includes data from at least one biomarker selected from the following: MYC, EP300, U2AF1, ASXL1, MAML2, CNTRL, WRN, CDX2, BCL9, PBX1, PRRX1, INHBA, YWHAE, GNAS, LHFPL6, CASP8, FH, CRKL, MLF1, TRRAP, AKT3, ACKR3, MSI2, PCM1, MNX1, BX1, AURKA, ASXL1, CRKL, GAS7, MN1, SOX10, TCL1A, LMO1, BRD3, SMARCA4, PER1, PAX7, SBDS, SEPT5, PDGFB, AKT2, TERT, KEAP1, ETV6, TOP1, TLX3, COX6C, NFIB, ARFRP1, ARID1A, MAP2K4, NFKBIA, WWTR1, ZNF217, IL2, NSD3, CREB1, BRIP1, SDC4, EWSR1, FLT3, FLT1, FAS, CCNE1, RUNX1T1, EZR, FCRL4, BIRC3, and HOXA11;
    for each machine learning model of one or more machine learning models that have each been trained on a same set of training data:
        providing the obtained data as an input to the machine learning model, wherein the machine learning model has been trained to determine a particular class of one or more training entities from multiple different entity classes based on processing of input data representing each of the one or more training entities, wherein the multiple different entity classes include (1) a responsive class for the test entity responding to the treatment that includes 5-fluorouracil and leucovorin combined with oxaliplatin (FOLFOX) and a (2) a non-responsive class for the test entity not responding to the treatment that includes 5-fluorouracil and leucovorin combined with oxaliplatin (FOLFOX);
        processing the provided data through each layer of the machine learning model to generate output data; and
        obtaining the output data generated by the machine learning model based on the machine learning model's processing of the provided data, wherein the obtained output data indicates the particular class of the multiple different entity classes as an initial classification for the test entity;
    obtaining the output data obtained for each of the one or more machine learning models, wherein the provided output data includes data representing a determination of the initial classification for the test entity by each of the one or more machine learning models; and
    determining, based on the provided output data, a most likely entity class for the test entity, the most likely entity class being the responsive class or the non-responsive class.

2. The method of claim 1, wherein determining, based on the provided output data, the most likely entity class for the test entity comprises:
    determining a number of occurrences of each initial classification of the test entity into the particular class of the multiple different entity classes; and
    selecting, as the most likely class for the test entity, a class of the multiple different entity classes having the highest number of occurrences of initial classifications.

3. The method of claim 1, wherein the one or more machine learning models are a plurality of machine learning models, the method further comprising:
    accessing a confidence score for each of the plurality of machine learning models; and
    adjusting the output data generated by each machine learning model based on the confidence score that corresponds to each respective machine learning model.

4. The method of claim 3, wherein the confidence score for each of the plurality of machine learning models is indicative of a historical accuracy of each of the plurality of machine learning models.

5. The method of claim 3, wherein adjusting the output data generated by each machine learning model based on the confidence score that corresponds to each respective machine learning model comprises:

increasing a weighted value of output data generated by a first machine learning model of the plurality of machine learning models based on the confidence score that corresponds to the first machine learning model.

6. The method of claim 3, wherein adjusting the output data generated by each machine learning model based on the confidence score that corresponds to each respective machine learning model comprises:
decreasing a weighted value of output data generated by a first machine learning model of the plurality of machine learning models based on the confidence score that corresponds to the first machine learning model.

7. The method of claim 1, wherein the one or more machine learning models are a plurality of machine learning models, and wherein at least one machine learning model of the plurality of machine learning models comprises a random forest classification algorithm, support vector machine, logistic regression, k-nearest neighbor model, artificial neural network, naïve Bayes model, quadratic discriminant analysis, or Gaussian processes model.

8. The method of claim 1, wherein the one or more machine learning models are a plurality of machine learning models, and wherein each machine learning model of the plurality of machine learning models comprises a random forest classification algorithm, support vector machine, logistic regression, k-nearest neighbor model, artificial neural network, naïve Bayes model, quadratic discriminant analysis, or Gaussian processes model.

9. The method of claim 1, wherein the one or more machine learning models are a plurality of machine learning models, and wherein at least two machine learning models of the plurality of machine learning models comprise a same type of machine learning model.

10. The method of claim 9, wherein the same type of machine learning model comprises a random forest classification algorithm, support vector machine, logistic regression, k-nearest neighbor model, artificial neural network, naïve Bayes model, quadratic discriminant analysis, or Gaussian processes model.

11. The method of claim 1, wherein the one or more machine learning models are a plurality of machine learning models, and wherein at least two machine learning models of the plurality of machine learning models comprise a different type of machine learning model.

12. The method of claim 1, wherein the test entity has colorectal carcinoma, wherein the test entity is in the responsive class, the method further comprising:
treating the test entity with 5-fluorouracil and leucovorin combined with oxaliplatin (FOLFOX).

13. The method of claim 1, wherein the test entity is in the responsive class, the method further comprising:
treating the test entity with 5-fluorouracil and leucovorin combined with oxaliplatin (FOLFOX).

14. The method of claim 13, wherein the at least one biomarker includes BCL9.

15. The method of claim 13, wherein the one or more machine learning models are a plurality of machine learning models.

16. The method of claim 15, wherein the plurality of machine learning models include at least five machine learning models, and wherein:
a first machine learning model uses at least one biomarker selected from a group consisting of MYC, EP300, U2AF1, ASXL1, MAML2, CNTRL, WRN, and CDX2;
a second machine learning model uses at least one biomarker selected from a group consisting of BCL9, PBX1, PRRX1, INHBA, and YWHAE;
a third machine learning model uses at least one biomarker selected from a group consisting of BCL9, PBX1, GNAS, LHFPL6, CASP8, ASXL1, FH, CRKL, MLF1, TRRAP, AKT3, ACKR3, MSI2, PCM1, and MNX1;
a fourth machine learning model uses at least one biomarker selected from a group consisting of BX1, GNAS, AURKA, CASP8, ASXL1, CRKL, MLF1, GAS7, MN1, SOX10, TCL1A, LMO1, BRD3, SMARCA4, PER1, PAX7, SBDS, SEPT5, PDGFB, AKT2, TERT, KEAP1, ETV6, TOP1, TLX3, COX6C, NFIB, ARFRP1, ARID1A, MAP2K4, NFKBIA, WWTR1, ZNF217, IL2, NSD3, CREB1, BRIP1, SDC4, EWSR1, FLT3, FLT1, FAS, CCNE1, RUNX1T1, and EZR; and
a fifth machine learning model uses at least one biomarker selected from a group consisting of BCL9, PBX1, PRRX1, INHBA, YWHAE, GNAS, LHFPL6, FCRL4, BIRC3, AURKA, and HOXA11.

17. A system for classification of a test entity, the system comprising:
one or more computers; and
one or more memory devices storing instructions that, when executed by the one or more computers, cause the one or more computers to perform operations, the operations comprising:
obtaining data that represents the test entity, wherein the obtained data includes data from at least one biomarker selected from the following: MYC, EP300, U2AF1, ASXL1, MAML2, CNTRL, WRN, CDX2, BCL9, PBX1, PRRX1, INHBA, YWHAE, GNAS, LHFPL6, CASP8, FH, CRKL, MLF1, TRRAP, AKT3, ACKR3, MSI2, PCM1, MNX1, BX1, AURKA, ASXL1, CRKL, GAS7, MN1, SOX10, TCL1A, LMO1, BRD3, SMARCA4, PER1, PAX7, SBDS, SEPT5, PDGFB, AKT2, TERT, KEAP1, ETV6, TOP1, TLX3, COX6C, NFIB, ARFRP1, ARID1A, MAP2K4, NFKBIA, WWTR1, ZNF217, IL2, NSD3, CREB1, BRIP1, SDC4, EWSR1, FLT3, FLT1, FAS, CCNE1, RUNX1T1, EZR, FCRL4, BIRC3, and HOXA11;
for each machine learning model of one or more machine learning models that have each been trained on a same set of training data:
providing the obtained data as an input to the machine learning model, wherein the machine learning model has been trained to determine a particular class of one or more training entities from multiple different entity classes based on processing of input data representing each of the one or more training entities, wherein the multiple different entity classes include (1) a responsive class for the test entity responding to a treatment that includes 5-fluorouracil and leucovorin combined with oxaliplatin (FOLFOX) and a (2) a non-responsive class for the test entity not responding to the treatment that includes 5-fluorouracil and leucovorin combined with oxaliplatin (FOLFOX);
processing the provided data through each layer of the machine learning model to generate output data; and
obtaining the output data generated by the machine learning model based on the machine learning model's processing of the provided data, wherein the obtained output data indicates the particular class of the multiple different entity classes as an initial classification for the test entity;

obtaining the output data obtained for each of the one or more machine learning models, wherein the provided output data includes data representing a determination of the initial classification for the test entity by each of the plurality of one or more machine learning models; and determining, based on the provided output data, a most likely entity class for the test entity, the most likely entity class being the responsive class or the non-responsive class.

18. The system of claim 17, wherein determining, based on the provided output data, the most likely entity class for the test entity comprises:

determining a number of occurrences of each initial classification of the test entity into the particular class of the multiple different entity classes; and selecting, as the most likely class for the test entity, a class of the multiple different entity classes having the highest number of occurrences of initial classifications.

19. The system of claim 17, wherein the one or more machine learning models are a plurality of machine learning models, the operations further comprising:

accessing a confidence score for each of the plurality of machine learning models; and adjusting the output data generated by each machine learning model based on the confidence score that corresponds to each respective machine learning model.

20. The system of claim 19, wherein the confidence score for each of the plurality of machine learning models is indicative of a historical accuracy of each of the plurality of machine learning models.

21. The system of claim 19, wherein adjusting the output data generated by each machine learning model based on the confidence score that corresponds to each respective machine learning model comprises:

increasing a weighted value of output data generated by a first machine learning model of the plurality of machine learning models based on the confidence score that corresponds to the first machine learning model.

22. The system of claim 19, wherein adjusting the output data generated by each machine learning model based on the confidence score that corresponds to each respective machine learning model comprises:

decreasing a weighted value of output data generated by a first machine learning model of the plurality of machine learning models based on the confidence score that corresponds to the first machine learning model.

23. The system of claim 17, wherein the one or more machine learning models are a plurality of machine learning models, and wherein at least one machine learning model of the plurality of machine learning models comprises a random forest classification algorithm, support vector machine, logistic regression, k-nearest neighbor model, artificial neural network, naïve Bayes model, quadratic discriminant analysis, or Gaussian processes model.

24. The system of claim 17, wherein the one or more machine learning models are a plurality of machine learning models, and wherein each machine learning model of the plurality of machine learning models comprises a random forest classification algorithm, support vector machine, logistic regression, k-nearest neighbor model, artificial neural network, naïve Bayes model, quadratic discriminant analysis, or Gaussian processes model.

25. The system of claim 17, wherein the one or more machine learning models are a plurality of machine learning models, and wherein at least two machine learning models of the plurality of machine learning models comprise a same type of machine learning model.

26. The system of claim 25, wherein the same type of machine learning model comprises a random forest classification algorithm, support vector machine, logistic regression, k-nearest neighbor model, artificial neural network, naïve Bayes model, quadratic discriminant analysis, or Gaussian processes model.

27. The system of claim 17, wherein the one or more machine learning models are a plurality of machine learning models, and wherein at least two machine learning models of the plurality of machine learning models comprise a different type of machine learning model.

28. One or more non-transitory computer-readable storage media storing instructions that, when executed by one or more computers, cause the one or more computers to perform operations for classification of a test entity, the operations comprising:

obtaining data that represents the test entity, wherein the obtained data includes data from at least one biomarker selected from the following: MYC, EP300, U2AF1, ASXL1, MAML2, CNTRL, WRN, CDX2, BCL9, PBX1, PRRX1, INHBA, YWHAE, GNAS, LHFPL6, CASP8, FH, CRKL, MLF1, TRRAP, AKT3, ACKR3, MSI2, PCM1, MNX1, BX1, AURKA, ASXL1, CRKL, GAS7, MN1, SOX10, TCL1A, LMO1, BRD3, SMARCA4, PER1, PAX7, SBDS, SEPT5, PDGFB, AKT2, TERT, KEAP1, ETV6, TOP1, TLX3, COX6C, NFIB, ARFRP1, ARID1A, MAP2K4, NFKBIA, WWTR1, ZNF217, IL2, NSD3, CREB1, BRIP1, SDC4, EWSR1, FLT3, FLT1, FAS, CCNE1, RUNX1T1, EZR, FCRL4, BIRC3, and HOXA11;

for each machine learning model of one or more machine learning models that have each been trained on a same set of training data:

providing the obtained data as an input to the machine learning model, wherein the machine learning model has been trained to determine a particular class of one or more training entities from multiple different entity classes based on processing of input data representing each of the one or more training entities, wherein the multiple different entity classes include (1) a responsive class for the test entity responding to a treatment that includes 5-fluorouracil and leucovorin combined with oxaliplatin (FOLFOX) and a (2) a non-responsive class for the test entity not responding to the treatment that includes 5-fluorouracil and leucovorin combined with oxaliplatin (FOLFOX);

processing the provided data through each layer of the machine learning model to generate output data; and obtaining the output data generated by the machine learning model based on the machine learning model's processing of the provided data, wherein the obtained output data indicates the particular class of the multiple different entity classes as an initial classification for the test entity;

obtaining the output data obtained for each of the one or more machine learning models, wherein the provided output data includes data representing a determination of the initial classification for the test entity by each of the one or more machine learning models; and determining, based on the provided output data, a most likely entity class for the test entity, the most likely entity class being the responsive class or the non-responsive class, wherein the obtained data includes data from at least one biomarker selected from the following: MYC, EP300, U2AF1, ASXL1, MAML2, CNTRL, WRN, CDX2, BCL9, PBX1, PRRX1, INHBA, YWHAE, GNAS, LHFPL6, CASP8, FH, CRKL, MLF1, TRRAP, AKT3, ACKR3, MSI2, PCM1, MNX1, BX1, AURKA, ASXL1, CRKL, GAS7, MN1, SOX10, TCL1A, LMO1, BRD3, SMARCA4, PER1, PAX7, SBDS, SEPT5, PDGFB, AKT2, TERT, KEAP1, ETV6, TOP1, TLX3, COX6C, NFIB, ARFRP1, ARID1A, MAP2K4, NFKBIA, WWTR1, ZNF217, IL2, NSD3, CREB1, BRIP1, SDC4, EWSR1, FLT3, FLT1, FAS, CCNE1, RUNX1T1, EZR, FCRL4, BIRC3, and HOXA11.

29. The computer-readable storage media of claim 28, wherein determining, based on the provided output data, the most likely entity class for the test entity comprises:
   determining a number of occurrences of each initial classification of the test entity into the particular class of the multiple different entity classes; and
   selecting, as the most likely class for the test entity, a class of the multiple different entity classes having the highest number of occurrences of initial classifications.

30. The computer-readable storage media of claim 28, wherein the one or more machine learning models are a plurality of machine learning models, the operations further comprising:
   accessing a confidence score for each of the plurality of machine learning models; and
   adjusting the output data generated by each machine learning model based on the confidence score that corresponds to each respective machine learning model.

31. The computer-readable storage media of claim 30, wherein the confidence score for each of the plurality of machine learning models is indicative of a historical accuracy of each of the plurality of machine learning models.

* * * * *

UNITED STATES PATENT AND TRADEMARK OFFICE
CERTIFICATE OF CORRECTION

PATENT NO. : 12,165,759 B2
APPLICATION NO. : 17/727681
DATED : December 10, 2024
INVENTOR(S) : Jim Abraham et al.

It is certified that error appears in the above-identified patent and that said Letters Patent is hereby corrected as shown below:

In the Claims

In Column 123, Line 66 of Claim 1, please delete "BX1," and "ASXL1, CRKL,"

In Column 126, Line 10 of Claim 16, please delete "BX1" and insert --PBX1--

In Column 126, Line 37 of Claim 17, please delete "BX1," and "ASXL1, CRKL,"

In Column 128, Line 28 of Claim 28, please delete "BX1," and "ASXL1, CRKL,"

In Column 129, Line 8 of Claim 28, please delete "BX1," and "ASXL1, CRKL,"

Signed and Sealed this
Thirteenth Day of May, 2025

Coke Morgan Stewart
*Acting Director of the United States Patent and Trademark Office*